US007834039B2

(12) United States Patent
Hobson et al.

(10) Patent No.: US 7,834,039 B2
(45) Date of Patent: Nov. 16, 2010

(54) OXADIAZOLE COMPOUNDS

(75) Inventors: Adrian D. Hobson, Shrewsbury, MA (US); Shannon R. Fix-Stenzel, Shrewsbury, MA (US); Kevin P. Cusack, Holden, MA (US); Eric C. Breinlinger, Charlton, MA (US); Graham K. Ansell, Millbury, MA (US); Robert H. Stoffel, Harvard, MA (US); Kevin R. Woller, Antioch, IL (US); Pintipa Grongsaard, Whippany, NJ (US)

(73) Assignee: Abbott Laboratories, Abbott Park, IL (US)

(*) Notice: Subject to any disclaimer, the term of this patent is extended or adjusted under 35 U.S.C. 154(b) by 0 days.

(21) Appl. No.: 12/002,196

(22) Filed: Dec. 14, 2007

(65) Prior Publication Data
US 2008/0280876 A1 Nov. 13, 2008

Related U.S. Application Data

(60) Provisional application No. 60/875,251, filed on Dec. 15, 2006.

(51) Int. Cl.
A61K 31/4245 (2006.01)
C07D 271/06 (2006.01)
(52) U.S. Cl. ........................ 514/364; 548/131
(58) Field of Classification Search ................ 548/131; 514/364, 326; 546/209
See application file for complete search history.

(56) References Cited

U.S. PATENT DOCUMENTS

| 4,003,909 | A | 1/1977 | Narayanan et al. |
| 6,211,234 | B1 | 4/2001 | Astles et al. |
| 6,277,872 | B1* | 8/2001 | Brenner et al. .............. 514/364 |
| 6,579,880 | B2 | 6/2003 | Weidner-Wells et al. |
| 6,992,096 | B2 | 1/2006 | Karp et al. |
| 7,220,745 | B2 | 5/2007 | Singh et al. |
| 2001/0049367 | A1 | 12/2001 | Bennani et al. |
| 2004/0024024 | A1 | 2/2004 | Freskos et al. |
| 2005/0124675 | A1 | 6/2005 | Hsieh et al. |
| 2006/0122397 | A1 | 6/2006 | Arora et al. |
| 2006/0148863 | A1 | 7/2006 | Karp et al. |
| 2008/0113961 | A1 | 5/2008 | Nishi et al. |
| 2008/0200535 | A1 | 8/2008 | Ohmori et al. |
| 2008/0269236 | A1 | 10/2008 | Ji et al. |

FOREIGN PATENT DOCUMENTS

| CA | 962684 | 2/1975 |
| EP | 0504574 | 9/1992 |
| EP | 1845097 A1 | 10/2007 |
| WO | WO 00/25768 | 5/2000 |
| WO | WO 01/19822 | 3/2001 |
| WO | WO 01/54507 | 8/2001 |
| WO | WO 01/66534 | 9/2001 |
| WO | 02/068417 A2 | 9/2002 |
| WO | WO 02/092588 | 11/2002 |
| WO | 03/053986 A1 | 7/2003 |
| WO | 03/059871 A1 | 7/2003 |
| WO | 03/087044 A2 | 10/2003 |
| WO | 03/087045 A1 | 10/2003 |
| WO | 03/105771 A2 | 12/2003 |
| WO | WO 03/105771 | 12/2003 |
| WO | 2004/035538 A1 | 4/2004 |
| WO | WO 2004/035538 | 4/2004 |
| WO | 2004/048319 A1 | 6/2004 |
| WO | 2005/032465 A2 | 4/2005 |
| WO | 2005/058848 A1 | 6/2005 |
| WO | WO 2005/048953 | 6/2005 |
| WO | 2005/070925 A1 | 8/2005 |
| WO | 2005/082898 A1 | 9/2005 |
| WO | WO 2005/051932 A1 * | 9/2005 |
| WO | WO 2006/008260 | 1/2006 |
| WO | WO2006/016724 | 2/2006 |
| WO | 2006/047195 A2 | 5/2006 |
| WO | 2006/066126 A2 | 6/2006 |
| WO | 2006/131336 A1 | 12/2006 |
| WO | WO 2007/003960 | 1/2007 |
| WO | 2007/013830 A1 | 2/2007 |
| WO | 2007/043400 A1 | 4/2007 |
| WO | WO 2007/039781 | 4/2007 |
| WO | WO 2007/076055 | 7/2007 |
| WO | WO2007/080542 | 7/2007 |
| WO | 2007/085451 A2 | 8/2007 |
| WO | 2007/098474 A1 | 8/2007 |

(Continued)

OTHER PUBLICATIONS

Vippagunta et al., Crystalline solids, 2001, Advanced Drug Delivery Reviews, 48, pp. 3 and 18.*
Wolff et al., Burger's Medicinal Chemistry and Drug Discovery, 1994, Wiley-Interscience, Fifth Edition, vol. I: Principles and Practice, pp. 975-977.*
Kwon et al., Handbook of Essential Pharmacokinetics, Pharmacodynamics and Drug Metabolism for Industrial Scientists, 2001, http://www.myilibrary.com/Browse/open.asp?ID=4284 &loc=1, Retrieved from the Internet Jun. 16, 2008, p. 213.*

(Continued)

Primary Examiner—Kamal A Saeed
Assistant Examiner—Kristin Bianchi
(74) Attorney, Agent, or Firm—Gayle B. O'Brien; Kenneth P. Lwicker

(57) ABSTRACT

Novel oxadiazole compounds, pharmaceutical compositions containing such compounds and the use of those compounds or compositions as agonists or antagonists of the S1P family of G protein-coupled receptors for treating diseases associated with modulation of S1P family receptor activity, in particular by affording a beneficial immunosuppressive effect are disclosed.

13 Claims, No Drawings

FOREIGN PATENT DOCUMENTS

| | | |
|---|---|---|
| WO | WO 2007/098474 | 8/2007 |
| WO | 2007/132307 A1 | 11/2007 |
| WO | WO2008/016692 | 2/2008 |
| WO | 2008/029370 A1 | 3/2008 |
| WO | 2008/029371 A1 | 3/2008 |
| WO | 2008/035239 A1 | 3/2008 |
| WO | 2008/037476 A1 | 4/2008 |
| WO | 2008/073942 A2 | 6/2008 |
| WO | 2008/094053 A1 | 8/2008 |
| WO | WO2008/114157 | 9/2008 |
| WO | 2008/131148 A1 | 10/2008 |
| WO | 2008/151184 A1 | 12/2008 |

OTHER PUBLICATIONS

Metabolomics [online], Retrieved from the Internet Jun. 16, 2008, URL: http://www.en.wikipedia.org/wiki/Metabolomics, p. 1.*

Barrett, et al. "Chromatography-Free Synthesis of 1,2,4-Oxadiazoles Using ROMPGEL-Supported Acylating Reagents", (2000), Combinatorial Chemistry & High Throughput Screening. (3): 131-138.

Deegan, et al. "Parallel Synthesis of 1,2,4-Oxadiazoles Using CDI Activation", (1999), Bioorganic & Medicinal Chemistry Letters. (9): 209-212.

Antunes, et al. "Synthesis, characterization and interaction mechanism of new oxadiazolo-phthalimides as peripheral analgesics. IV", (2003), Journal of Molecular Structure. (660): 1-13.

Antunes, et al. "New Phthalimide Derivatives with Potent Analgesic Activity: II", (1998), Bioorganic & Medicinal Chemistry Letters. (8): 3071-3076.

Arakawa, et al. "Morphological and Enzymatic Alterations in the Rat Liver caused by Administration of a Hypocholesterolemic Agent at-308 and its Related Compounds", (1978), Biochemical Pharmacology. (27): 167-171.

Nakai, et al. "Metabolic Disposition of 3-[4-(1-Ethoxycarbony 1-1 methylethoxy)phenyl]-5(3 pyridy)-1,2,4-oxadiazole (AT-308), a Hypocholesterolemic Agent, in Rats)", (1977), J. Takeda Res. Lab. 36(½): 46-52.

Asahi, et al. "Properties and Stabilities of 3-[4-(1-Ethoxycarbony-1-Methylethoxy)phenyl]-5-(3-pyridy1)-1,2,4-oxadiazole (AT-308)", (1976), J. Takeda Res. Lab. 35(¾): 151-158.

Yurugi, et al. "Studies on the Syntheses of N-Heterocyclic Compounds. IV.[1]) Hypocholesterolemic 1,2,4-Oxadiazole Derivatives. (2)", (1973), Chem. Pharm. Bull. 21(9): 1885-1893.

Yurugi, et al. "Studies on the Synthesis of N-Heterocyclic Compounds. III.1) Hypocholesterolemic 1,2,4-Oxadiazole Derivatives (1)", (1973), Chem. Parm. Bull. 21(8): 1641-1650.

Imai, et al. "Biological Studies of AT-308, Part 1 Hypocholesterolemic Effect of 1,2,4-Oxadiazole Derivatives in Rats", (1973), Atherosclerosis. (17): 121-129.

Krippner, et al. "Synthesis and Antiviral Activity of Dimeric Capsid-Binding Inhibitors of Human Rhinovirus (HRV)", (2004), Aust. J. Chem. (57): 553-564.

Neidlein et al. "Syntheses of 1,2,4-Oxadiazole substituted Pyrazole, Isoxazole and Pyrimidine Heterocycles", (1996), J. Heterocyclic Chem. (33): 1943.

Bailey, et al "Acetylfurans as bio-isosteres for 3-methylisoxazole. The effect of acetylfuran positional isomers on antirhinoviral activity", (1996), Antiviral Chemistry & Chemotherapy. 7(1): 46-52.

Giranda, et al. "Structures of Four Methyltetrazole-Containing Antiviral Compounds in Human Rhinovirus Serotpe 14", (1995), Acta Cryst. (D51): 496-503.

Diana, et al. "Picornavirus Inhibitors: Triflouromethyl Substitution Provides a Globall Protective Effect against Hepatic Metabolism", (1995), J. Med. Chem. (38) 1355-1371.

Bailey, et al. "An Evaluation of the Antirhinoviral Activity of Acylfuran Replacements for 3-Methylisoxazoles. Are 2-Acetylfurans Bioisosteres for 3-Methylisoxazoles?", (1994), J. Med. Chem. (37) 4177-4184.

Bailey, et al. "Additions and Corrections—1994, vol. 37", (1995), J. Med. Chem. (38):1416.

Yan, et al. "Discovery of 3-arylpropionic acids as potent agonists of sphingosine-1-phosphate receptor-1 ($S1P_1$) with high selectivity against all other known S1P receptor subtypes", (2006), Bioorganic & Medicinal Chemistry Letter. (16) 3679-3683.

Li, et al. "Discovery of Potent 3,5-Diphenyl-1,2,4-oxadiazole Sphingosine-1-phosphate-1 S1P1) Receptor Agonists with Exceptional Selectivity against $S1P_2$, and $S1P_3$", (2005), Journal of Medicinal Chemistry. 48(5): 6179-6173.

Torgova, et al. "Influence of Chemical Structure on the Mesomorphic Behaviour of 3,5-Disubstituted 1,2,4-Oxadiazoles", (2002), Brazilian Journal of Physics. 32(2B): 593-601.

Karamysheva, et al. "Dependence of Mesomorphic Properties of 3,5-Disubstituted 1,2,4-Oxadiazoles on Geometric and Electronic Factors", (1995), Mol. Cryst. Liq. Cryst. (260): 217-225.

Karamysheva, et al. "3,5-Disubstituded 1,2,4-Oxadiazoles—New Class of Liquid Crystalline Compounds", (1994), Mol. Mat. (4): 289-293.

Guy D. Diana, et al., "Picornavirus Inhibitors: Trifluoromethyl Substitution Provides a Global Protective Effect against Hepatic Metabolism", J. Med. Chem., 1995 vol. 38:1355-1371.

* cited by examiner

OXADIAZOLE COMPOUNDS

CROSS REFERENCE TO RELATED APPLICATION

This application claims priority to U.S. Provisional Application Ser. No. 60/875,251 filed on Dec. 15, 2006.

BACKGROUND OF THE INVENTION

Sphingosine-1-phosphate (S1P) is part of sphingomyelin biosynthetic pathway and is known to affect multiple biological processes. S1P is formed through phosphorylation of sphingosine by sphingosine kinases (SK1 and SK2) and it is degraded through cleavage by sphingosine lyase to form palmitaldehyde and phosphoethanolamine or through dephosphorylation by phospholipid phosphatases. It is present at high levels (~500 nM) in serum and it is found in most tissues. It can be synthesized in a wide variety of cells in response to several stimuli, which include cytokines, growth factors and G protein-coupled receptor (GPCR) ligands. The GPCRs that bind S1P (currently know as the S1P receptors S1P1-5), couple through pertussis toxin sensitive (Gi) pathways as well as pertusis toxin insensitive pathways to stimulate a variety of processes. The individual receptors of the S1P family are both tissue and response specific and so are attractive as therapeutic targets.

S1P evokes many responses from cells and tissues. In particular, S1P has been shown to be an agonist at all five GPCRs, S1P1 (Edg-1), S1P2 (Edg-5), S1P3 (Edg-3), S1P4 (Edg-6) and S1P5 (Edg-8). The action of S1P at the S1P receptors has been linked to resistance to apoptosis, changes in cellular morphology, cell migration, growth, differentiation, cell division, angiogenesis and modulation of the immune system via alterations of lymphocyte trafficking. Therefore, S1P receptors are targets for therapy of, for example, neoplastic diseases, autoimmune disorders and tissue rejection in transplantation. These receptors also share 50-55% amino acid identity with three other lysophospholipid receptors, LPA1, LPA2, and LPA3 of the structurally related lysophosphatidic acid (LPA).

GPCRs are excellent drug targets with numerous examples of marketed drugs across multiple disease areas. GPCRs are cell surface receptors that bind hormones on the extracellular surface of the cell and transduce a signal across the cellular membrane to the inside of the cell. The internal signal is amplified through interaction with G proteins which in turn interact with various second messenger pathways. This transduction pathway is manifested in downstream cellular responses that include cytoskeletal changes, cell motility, proliferation, apoptosis, secretion and regulation of protein expression to name a few. SIP receptors make good drug targets because individual receptors are expressed in different tissues and signal through different pathways making the individual receptors both tissue and response specific. Tissue specificity of the SIP receptors is desirable because development of an agonist or antagonist selective for one receptor localizes the cellular response to tissues containing that receptor, limiting unwanted side effects. Response specificity of the SIP receptors is also of importance because it allows for the development of agonists or antagonists that initiate or suppress certain cellular responses without affecting other responses. For example, the response specificity of the SIP receptors could allow for an SIP mimetic that initiates platelet aggregation without affecting cell morphology.

The physiologic implications of stimulating individual SIP receptors are largely unknown due in part to a lack of receptor type selective ligands. Isolation and characterization of SIP analogs that have potent agonist or antagonist activity for SIP receptors have been limited.

S1P1 for example is widely expressed and the knockout causes embryonic lethality due to large vessel rupture. Adoptive cell transfer experiments using lymphocytes from SIP1 knockout mice have shown that S1P1 deficient lymphocytes sequester to secondary lymph organs. Conversely, T cells overexpressing S1P1 partition preferentially into the blood compartment rather than secondary lymph organs. These experiments provide evidence that S1P1 is the main sphingosine receptor involved in lymphocyte homing and trafficking to secondary lymphoid compartments Currently, there is a need for novel, potent, and selective agents, which are agonists or antagonists of the individual receptors of the S1P receptor family in order to address unmet medical needs associated with agonism or antagonism of the individual receptors of the S1P receptor family.

SUMMARY OF THE INVENTION

The present invention provides novel compounds described by general Formula (I), (Ia), (II), (III), (IV), (IVa) and (IVb) as agonists of the G protein-coupled receptor S1P1. These compounds reduce the number of circulating and infiltrating T- and B-lymphocytes affording a beneficial immunosuppressive effect. The compounds also exhibit activity within the S1P receptor family.

In a first embodiment, the invention provides compound of Formula I

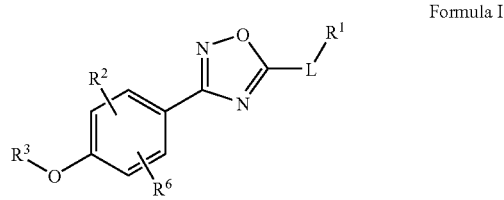

Formula I pharmaceutically acceptable salts, biologically active metabolites, solvates, hydrates, prodrugs, enantiomers or stereoisomers thereof, wherein L is a bond or optionally substituted ($C_1$-$C_3$)alkyl;

$R^1$ is —C(O)—NH-phenyl, —NH—C(O)-furanyl, —NH—S(O)$_2$-optionally substituted phenyl, —O-optionally substituted ($C_1$-$C_3$)alkyl, —S-optionally substituted ($C_1$-$C_3$)alkyl, optionally substituted ($C_2$-$C_6$)alkyl, optionally substituted amino, optionally substituted ($C_3$-$C_6$)cycloalkyl, —(CH$_2$)($C_3$)alkyl, tetrahydrobenzofuranyl, furanyl, tetrahydrofuranyl, optionally substituted 2,3-dihydroisoindolyl, optionally substituted imidazolyl, optionally substituted indolyl, optionally substituted isoxazolyl, optionally substituted morpholinyl, optionally substituted naphthyl, optionally substituted phenyl, —O—CH$_2$-phenyl, —O-phenyl, —O-optionally substituted phenyl, optionally substituted piperidinyl, optionally substituted pyrazolyl, optionally substituted pyridinyl, optionally substituted pyrimidinyl, optionally substituted pyrrolidinyl, optionally substituted 1,2,3,4-tetrahydroisoquinolinyl, optionally substituted quinolinyl, optionally substituted 5,6,7,8-tetrahydroimidazo[1,2-a]pyrazinyl, optionally substituted pyrrolyl, optionally substituted quinolinyl, optionally substituted thiazolyl or optionally substituted thienyl;

R² is Br, C₁, CF₃, CN, or —O—(C₁-C₂)alkyl;

R³ is optionally substituted-(C₃-C₈)alkyl, (C₄-C₅)alkenyl, (C₄-C₅)alkynyl, optionally substituted-(C₃-C₆)cycloalkyl, —(C₂-C₃)alkyl-O-optionally substituted (C₁-C₃)alkyl, —(C₁-C₃)alkyl-imidazolyl, —(C₁-C₃)alkyl-morpholinyl, —(C₁-C₃)alkyl-optionally substituted phenyl, —(C₁-C₃)alkyl-optionally substituted piperazinyl, —(C₁-C₃)alkyl-pyrrolidinyl, —(C₁-C₃)alkyl-piperidinyl, —(C₁-C₃)alkyl-thienyl, tetrahydrofuranyl or thiazolyl; and R⁶ is H;

provided that

R¹ is not substituted by optionally substituted cyclohexyl, —C(O)-cyclohexyl or —NH-cyclohexyl;

when L is (C₁-C₃)alkyl, R¹ is not optionally substituted isoxazolyl;

when R³ is optionally substituted (C₁)alkyl, L-R¹ is not cyclohexyl or —CH₂-cyclohexyl; and provided that the compound is not

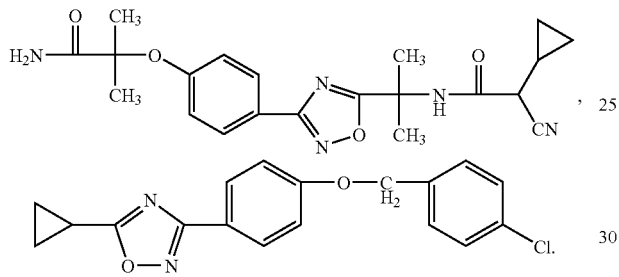

In a second embodiment the invention provides a compound of embodiment 1 wherein R¹ is optionally substituted by one or more substituents independently selected from Br, Cl, F, CF₃, CN, oxo, optionally substituted (C₁-C₆)alkyl, optionally substituted (C₂-C₆)alkenyl, optionally substituted amino, optionally substituted (C₃-C₆)cycloalkyl, —CH₂-optionally substituted piperidinyl, —C(O)— optionally substituted (C₁-C₆)alkyl, —C(O)—NR—(C₁-C₆)alkyl, —C(O)—O-optionally substituted (C₁-C₆)alkyl, —O— optionally substituted (C₁-C₆)alkyl, —NH—(C₃-C₆)cycloalkyl, —NH—C(O)—O—(C₁-C₃)alkyl, —S(O)₂—N(R⁹)₂, —S(O)₂—NH-optionally substituted (C₁-C₄)alkyl, —NH-optionally substituted (C₁-C₆)alkyl, —NH—C(O)-furanyl, —NH—S(O)₂-optionally substituted phenyl, optionally substituted pyridinyl,

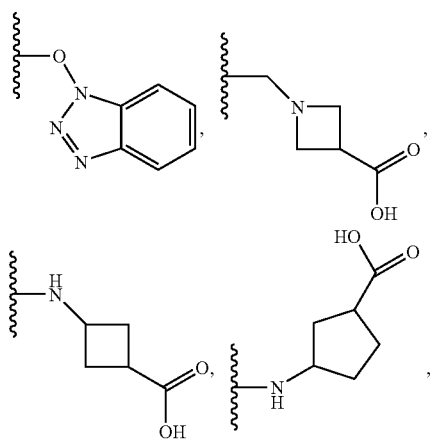

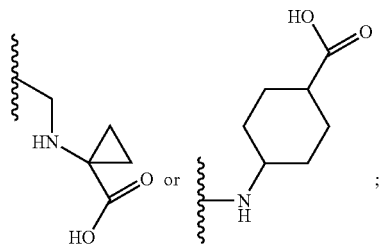

wherein R is H or (C₁-C₃)alkyl; and wherein each R⁹ is independently selected from H or optionally substituted (C₁-C₆)alkyl.

In a third embodiment, the invention provides compounds of any of the foregoing embodiments wherein the compound is a compound of Formula Ia

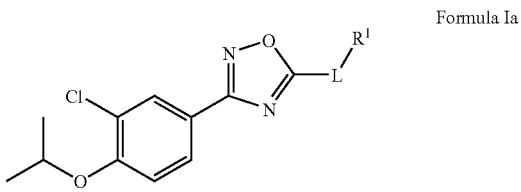

Formula Ia wherein L is a bond.

In a fourth embodiment the invention provides compounds of any of the foregoing embodiments wherein R¹ is optionally substituted phenyl or optionally substituted indolyl.

In a fifth embodiment the invention provides compounds of any of the foregoing embodiments wherein the compound is

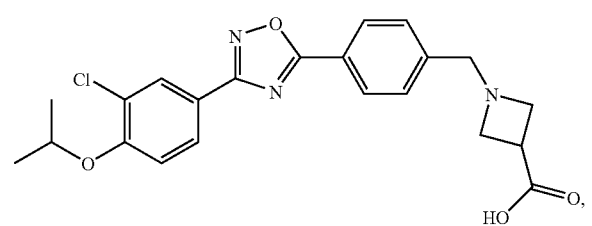

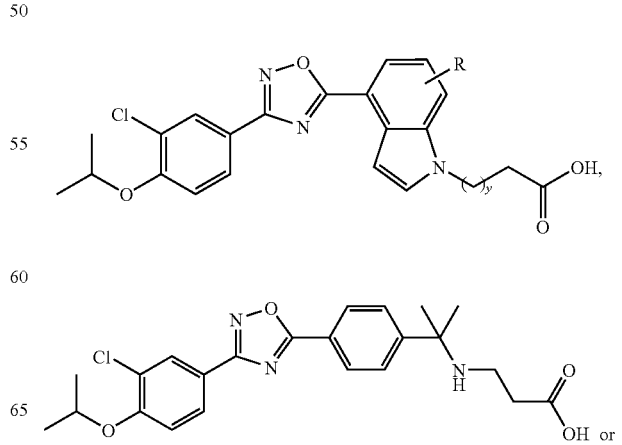

or

-continued

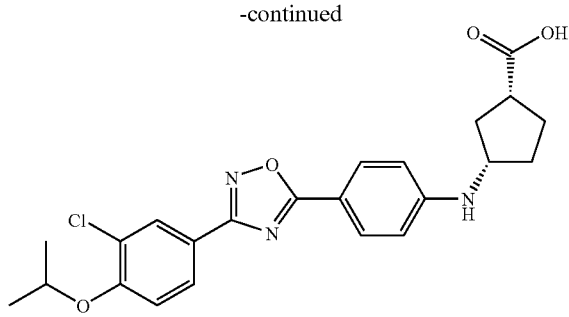

wherein y is 1 or 2.

In a sixth embodiment the invention provides a compound according to any of the foregoing embodiments wherein L is optionally substituted $(C_1-C_3)$alkyl;
$R^1$ is —C(O)—NH-phenyl, —NH—C(O)-furanyl, —NH—S(O)$_2$-optionally substituted phenyl, optionally substituted —$(C_1-C_3)$alkyl, —S—$(C_1-C_3)$alkyl, benzyloxy, optionally substituted $(C_3-C_6)$cycloalkyl, optionally substituted imidazolyl, morpholinyl, optionally substituted naphthyl, optionally substituted phenyl, optionally substituted phenoxy, optionally substituted piperazinyl, optionally substituted piperidinyl, optionally substituted pyridinyl, optionally substituted pyrrolidinyl or optionally substituted thienyl;
$R^2$ is Cl;
$R^3$ is isopropyl; and
$R^6$ is H.

In a seventh embodiment the invention provides compounds according to any of the foregoing embodiments wherein L is $CH_2$ and $R^1$ is optionally substituted phenyl or optionally substituted $(C_3-C_6)$cycloalkyl.

In an eighth embodiment the invention provides compounds according to claim 7 wherein $R^1$ is substituted by one or more substituents independently selected from F, dimethylamino and phenoxy.

In a ninth embodiment the invention provides compounds of formula II

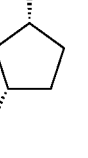 Formula II

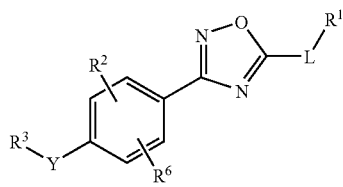

pharmaceutically acceptable salts, biologically active metabolites, solvates, hydrates, prodrugs, enantiomers or stereoisomers thereof, wherein Y is a bond;
L is a bond or $CH_2$;
$R^1$ is optionally substituted $(C_1-C_4)$alkyl, optionally substituted indolyl or optionally substituted phenyl;
$R^2$ is $CF_3$;
$R^3$ is H, morpholinyl or $(C_3-C_5)$cycloalkyl; and
$R^6$ is H.

In a tenth embodiment the invention provides compounds according to the ninth embodiment wherein $R^1$ is optionally substituted phenyl and $R^3$ is morpholinyl.

In an eleventh embodiment the invention provides compounds of according to embodiments nine and ten wherein $R^1$ is optionally substituted by one or more substituents independently selected from Cl, optionally substituted $(C_1-C_3)$alkyl,

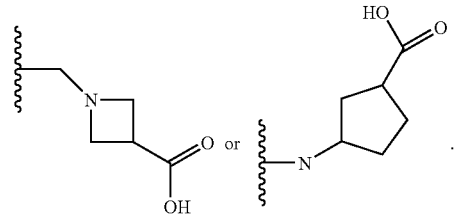

In a twelfth embodiment the invention provides compounds of Formula III

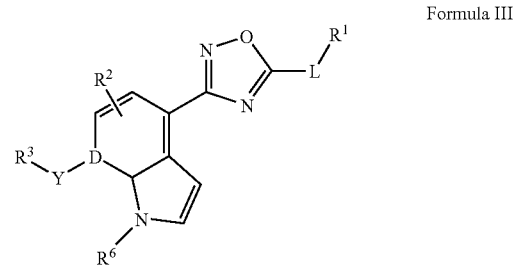

Formula III pharmaceutically acceptable salts, biologically active metabolites, solvates, hydrates, prodrugs, enantiomers or stereoisomers thereof, wherein D is CH or N;
Y is a bond;
L is a bond;
$R^1$ is optionally substituted phenyl;
$R^2$ is H;
$R^3$ is H; and
$R^6$ is optionally substituted $(C_1-C_3)$alkyl.

In a thirteenth embodiment the invention provides compounds according to the twelfth embodiment wherein $R^1$ is substituted with Cl and isopropoxy.

In a fourteenth embodiment the invention provides compounds having formula (IV):

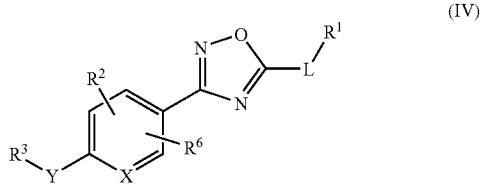

(IV)

or a pharmaceutically acceptable salt, solvate, hydrate, metabolite, prodrug, enantiomer or stereoisomer thereof,
wherein:
X is N or $CR^4$;
L is a bond, —$CH_2CH_2$—, $(C_3-C_6)$cycloalkyl, or —$CHR^5$;
Y is —O—, —$NR^7$— or —$C(R^7)(R^7)$—;
$R^1$ is optionally substituted aryl, optionally substituted heteroaryl, optionally substituted heterocyclyl, optionally substituted —$(C_1-C_6)$alkyl-O—$(C_1-C_3)$alkyl, optionally substituted —$(C_1-C_6)$alkyl-O—$(C_1-C_6)$alkyl —O—$(C_1-C_3)$alkyl, optionally substituted —$(C_1-C_6)$alkyl-O-aryl, alkylsulfanylalkyl, unsubstituted (C$_2$-C$_5$)alkyl, substituted (C$_1$-C$_6$)alkyl, —COR$^9$, optionally substituted —O—(C$_1$-C$_3$)alkyl, —N(R$^7$)(R$^8$), —N(R$^7$)SO$_2$—R$^9$ or optionally substituted (C$_3$-C$_6$)cycloalkyl, and wherein R$^1$ is not substituted cyclopentathiophene, halothiophene, substituted indan or substituted chromenone;

R$^2$ and R$^6$ may be the same or different and are independently H, —(C$_1$-C$_4$)alkyl, —O—(C$_1$-C$_3$)alkyl, —CF$_3$, —CN, halo or —COO—(C$_1$-C$_4$)alkyl;

R$^3$ is optionally substituted aryl, optionally substituted heterocyclyl, optionally substituted heteroaryl, optionally substituted (C$_3$-C$_6$)cycloalkyl, —(CH$_2$)$_n$—R$^9$, —CO—OR$^9$, —CO—R$^9$, —CON(R$^7$)(R$^9$), —N(R$^7$)(R$^9$), —SOR$^9$, —SO$_2$R$^9$ and optionally substituted straight or branched (C$_1$-C$_8$)alkyl chain optionally including —CO—, —COO—, —SO—, —SO$_2$—, —CONH—, —NHCO—, —N— or —O— groups embedded within the alkyl chain; and when Y is O, R$^3$ is not alkyldiazeapane, —C(CH$_3$)$_2$COOCH$_2$CH$_3$ or —CH$_2$CH$_2$N(CH$_2$CH$_3$)$_2$ and when Y is —CH$_2$—, R$^3$ is not —CH$_2$COOH;

or Y is a bond and R$^3$ is optionally substituted morpholino;

R$^4$ is H, —(C$_1$-C$_4$)alkyl, —O—(C$_1$-C$_3$)alkyl, —CF$_3$, —CN or halo;

R$^5$ is H, O—(C$_1$-C$_3$)alkyl or (C$_1$-C$_3$)alkyl; each occurrence of R$^7$ or R$^{7'}$ is independently H or optionally substituted (C$_1$-C$_3$)alkyl;

R$^8$ is H, optionally substituted CH$_3$, or —COR$^9$;

R$^9$ is hydrogen, optionally substituted (C$_1$-C$_3$)alkyl, optionally substituted alkynyl, optionally substituted aryl, optionally substituted heteroaryl, optionally substituted heterocyclyl or optionally substituted (C$_3$-C$_6$)cycloalkyl; and n is 1, 2, 3 or 4;

provided that

R$^1$ is not optionally substituted furanyl or —C(O)-optionally substituted furanyl;

R$^3$ is not optionally substituted quinolinyl;

R$^9$ is not optionally substituted cyclopropyl, optionally substituted cyclohexyl, optionally substituted furanyl, optionally substituted imidazolyl, optionally substituted indolyl, optionally substituted naphthyl, optionally substituted piperazinyl, optionally substituted pyrazolyl, optionally substituted pyridazinyl or optionally substituted quinolinyl;

R$^1$ is not substituted by —C(O)-cyclopentyl, optionally substituted cyclopentyl, —C(O)-cyclobutyl, cyclobutyl, —C(O)-cyclohexyl or optionally substituted cyclohexyl;

R$^3$ is not substituted by —C(O)-cyclopropyl;

when R$^3$ is CH$_3$ or 4-chlorophenylmethyl, L-R' is not cyclopropyl, cyclopentyl, optionally substituted cyclohexyl, —CH$_2$-cyclohexyl, —NH-cyclohexyl, —CH$_2$CH$_2$-cyclohexyl or optionally substituted pyrazolyl;

when Y is O, R$^3$ is not —(C$_0$-C$_4$)alkyl-optionally substituted isoxazolyl or optionally substituted pyrazolyl;

when L is (C$_1$-C$_3$)alkyl, R$^1$ is not optionally substituted isoxazolyl;

when L is a bond, R$^1$ is not optionally substituted cyclobutyl, optionally substituted cyclohexyl, optionally substituted naphthyl, —CH$_2$-optionally substituted naphthyl, —CH$_2$—O-optionally substituted naphthyl, optionally substituted pyrazolyl or tetrahydrobenzofuranyl;

the compound is not

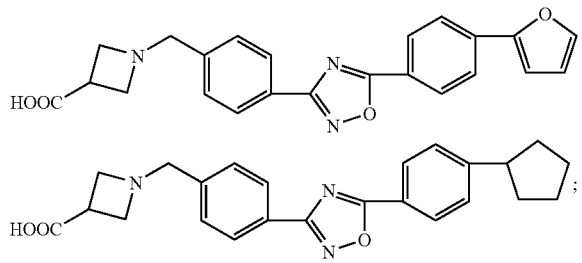

the compound is not

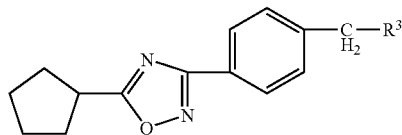

wherein R$^3$ is optionally substituted piperazinyl or optionally substituted phenyl;

the compound is not

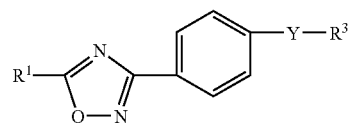

wherein R$^1$ is optionally substituted pyridine or 3-chlorophenyl and —Y—R$^3$ is —NH—C(O)-optionally substituted phenyl;

—O-optionally substituted pyridinyl;

—NH—C(O)—OCH$_3$;

—CH$_2$-optionally substituted piperazinyl;

—O-optionally substituted (C$_1$-C$_9$)alkyl;

—CH$_2$-morpholinyl; or

—O—C(O)-optionally substituted pyridinyl;

provided the compound is not

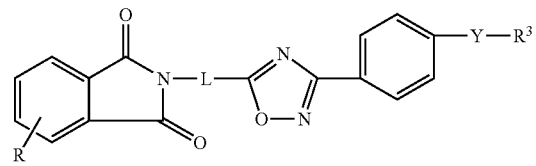

wherein

L is CH$_2$, CH(CH$_3$) or CH$_2$CH$_2$;

Y is O or CH$_2$;

R$^2$ is H or OCH$_3$;

R$^3$ is CH$_3$ or OCF$_3$; and

R is H or NO$_2$;

provided the compound is not

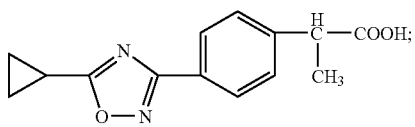

provided the compound is not

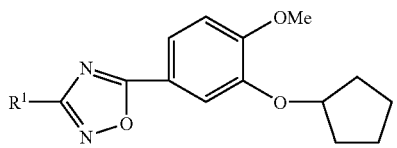

wherein R¹ is phenyl, 4-chlorophenyl, piperidinyl or thienyl.

In a fifteenth embodiment the invention provides compounds according to the fourteenth embodiment wherein each substituent or optional substitutent is independently one or more $R^{10}$ groups wherein $R^{10}$ is optionally substituted alkyl, alkenyl, optionally substituted alkoxy groups, alkoxyalkoxy, alkoxyalkyl, alkoxycarbonyl, alkoxycarbonylheterocycloalkoxy, alkyl, alkylamino, alkylcarbonyl, alkylester, alkyl-O—C(O)-alkyl-heterocyclyl, alkyl-cycloalkyl, alkylnitrile, alkylsulfonyl, alkynyl, amido groups, amino, aminoalkyl, aminoalkoxy, aminocarbonyl, carbonitrile, carbonylalkoxy, carboxamido, $CF_3$, CN, —C(O)OH, —C(O)H, —C(O)—C(CH_3)_3, —OH, —C(O)O-alkyl, —C(O)O-cycloalkyl, —C(O)O-heterocyclyl, —C(O)-alkyl, —C(O)-cycloalkyl, —C(O)-heterocyclyl, CN, cycloalkyl, dialkylamino, dialkylaminoalkoxy, dialkylaminocarbonylalkoxy, dialkylaminocarbonyl, dialkylaminosulfonyl, —C(O)—$OR^a$, halogen, heterocyclyl, heterocyclylalkyl, heterocycyloxy, hydroxy, hydroxyalkyl, nitro, oxo, phenyl, —$SO_2CH_3$, —$SO_2CF_3$, sulfonyl, tetrazolyl, thienylalkoxy, trifluoromethylcarbonylamino, trifluoromethylsulfonamido, heterocycylalkoxy, heterocyclyl-$S(O)_p$, cycloalkyl-$S(O)_p$, alkyl-S—, heterocyclyl-S, heterocycloalkyl, cycloalkylalkyl, heterocycolthio, cycloalkylthio, N-alkylamino and N,N-dialkylamino where $R^a$ is alkyl, heterocycloalkyl, or heterocyclyl and p is 1 or 2.

In a sixteenth embodiment the invention provides compounds according to embodiments fourteen and fifteen having formula (IVa):

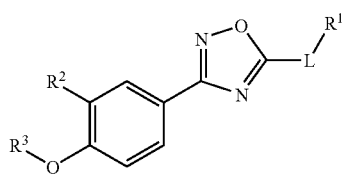

or a physiologically acceptable salt, solvate, hydrate or stereoisomer thereof, wherein:

L is a bond, —$CH_2CH_2$— or $(C_3-C_6)$cycloalkyl;

R¹ is optionally substituted aryl, optionally substituted heteroaryl or optionally substituted —O—$(C_1-C_3)$alkyl;

R² is a halogen or $CF_3$; and $R^3$ is straight or branched optionally substituted $(C_2-C_8)$ alkyl, or optionally substituted $(C_3-C_6)$cycloalkyl.

In a seventeenth embodiment the invention provides compounds according to embodiments fourteen through sixteen wherein $R^2$ is $C_1$ or $CF_3$.

In an eighteenth embodiment the invention provides compounds according to embodiments fourteen through seventeen wherein $R^2$ is Cl.

In an nineteenth embodiment the invention provides compounds according to embodiments fourteen through eighteen having formula (IVb):

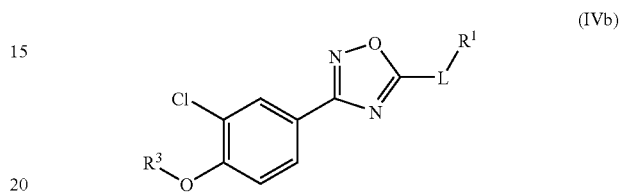

or a physiologically acceptable salt, solvate, hydrate, prodrug, enantiomer or stereoisomer thereof, wherein:

L is a bond, —$CH_2CH_2$—, or $(C_3-C_6)$cycloalkyl;

R¹ is tolyl, pyridinyl, isoxazolyl, pyrazinyl, methylpyrazinyl, ethanonylphenyl, phenyl carbamic acid tert-butyl ester, benzonitrile, diethylaminophenyl, thiophenyl, N-methylpyrrolyl, halopyridinyl, or methylpyridinyl; and $R^3$ is isobutyl, cyclopropylmethyl, 3-methoxypropyl, 1-ethylpropyl, sec-butyl, isopropyl, tertbutyl, or trifluoroethyl.

In a twentieth embodiment the invention provides compounds according to embodiment fourteen having formula (IVc):

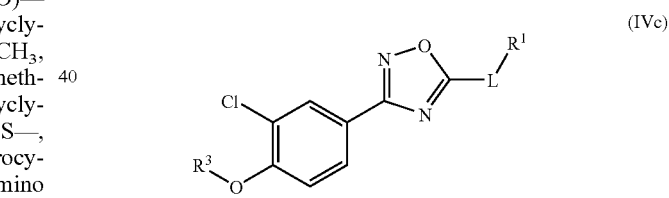

or a physiologically acceptable salt, solvate, hydrate or stereoisomer thereof, wherein:

L is a bond or —$CH_2CH_2$—;

R¹ is tolyl, pyridinyl, methylpyrazinyl, phenyl carbamic acid tert-butyl ester, benzonitrile, thiophenyl, N-methylpyrrolyl, or halopyridinyl; and $R^3$ is isobutyl, isopropyl, cyclopropylmethyl, 3-methoxypropyl, 1-ethylpropyl, sec-butyl, or isopropyl.

In a twenty-first embodiment the invention provides compounds according to the twentieth embodiment, wherein $R^3$ is isopropyl.

In a twenty-second embodiment the invention provides compounds according to the twentieth and twenty-first embodiments wherein R¹ is tolyl or halopyridinyl.

In a twenty-third embodiment the invention provides compounds according to the twentieth through twenty-second embodiments wherein R¹ is chloropyridinyl or fluoropyridinyl.

In a twenty-fourth embodiment the invention provides a pharmaceutical composition comprising a compound according any of the foregoing embodiments or a pharmaceutically acceptable salt, solvate, hydrate, metabolite, prodrug, enantiomer or stereoisomer thereof and a pharmaceutically acceptable diluent or carrier.

In a twenty-fifth embodiment the invention provides a method of treating an immune disorder comprising administering to a subject in need thereof a therapeutically effective amount of any of the foregoing embodiments or a pharmaceutically acceptable salt, solvate, hydrate, metabolite, prodrug or stereoisomer thereof for treating an immune disorder of one or more compounds.

In a twenty-sixth embodiment the invention provides a method according to the twenty-fifth embodiment wherein the immune disorder is an autoimmune disorder.

In a twenty-seventh embodiment the invention provides a method according to the twenty-sixth embodiment wherein the autoimmune disorder is active chronic hepatitis, Addison's Disease, anti-phospholipid syndrome, atopic allergy, autoimmune atrophic gastritis, achlorhydra autoimmune, Celiac Disease, Crohn's Disease, Cushing's Syndrome, dermatomyositis, Goodpasture's Syndrome, Grave's Disease, Hashimoto's thyroiditis, idiopathic adrenal atrophy, idiopathic thrombocytopenia, Lambert-Eaton Syndrome, lupoid hepatitis, mixed connective tissue disease, pemphigoid, pemphigus vulgaris, pernicious anemia, phacogenic uveitis, polyarteritis nodosa, primary biliary cirrhosis, primary sclerosing cholangitis, psoriasis, Raynauds, Reiter's Syndrome, relapsing polychondritis, Schmidt's Syndrome, Sjogren's Syndrome, sympathetic ophthalmia, Takayasu's Arteritis, temporal arteritis, thyrotoxicosis, lupus, rheumatoid arthritis, Type B Insulin Resistance, ulcerative colitis, or Wegener's granulomatosis.

In a twenty-eighth embodiment the invention provides a method of treating a central nervous system disorder comprising administering to a patient in need thereof one or more compounds of embodiments one through twenty-three or a pharmaceutically acceptable salt, solvate, hydrate, metabolite, prodrug, enantiomer or stereoisomer thereof.

In a twenty-ninth embodiment the invention provides a method of treating multiple sclerosis comprising administering to a patient in need thereof one or more compounds of embodiments one through twenty-three or a pharmaceutically acceptable salt, solvate, hydrate, metabolite, prodrug, enantiomer or stereoisomer thereof for the manufacture of a medicament for.

In specific embodiments, the invention provides the compounds:

3-(3-Chloro-4-cyclopropylmethoxy-phenyl)-5-o-tolyl-[1,2,4]oxadiazole;
3-(4-Butoxy-3-chloro-phenyl)-5-o-tolyl-[1,2,4]oxadiazole;
3-[3-Chloro-4-(1-methyl-cyclopropylmethoxy)-phenyl]-5-o-tolyl-[1,2,4]oxadiazole;
3-[3-Chloro-4-(1-methyl-cyclopropylmethoxy)-phenyl]-5-o-tolyl-[1,2,4]oxadiazole;
3-(3-Chloro-4-pentyloxy-phenyl)-5-o-tolyl-[1,2,4]oxadiazole;
3-[3-Chloro-4-(3,3-dimethyl-butoxy)-phenyl]-5-o-tolyl-[1,2,4]oxadiazole;
3-(3-Chloro-4-cyclopentylmethoxy-phenyl)-5-o-tolyl-[1,2,4]oxadiazole;
3-[3-Chloro-4-(2-ethyl-butoxy)-phenyl]-5-o-tolyl-[1,2,4]oxadiazole;
3-(3-Chloro-4-octyloxy-phenyl)-5-o-tolyl-[1,2,4]oxadiazole;
3-[3-Chloro-4-(3-methoxy-propoxy)-phenyl]-5-o-tolyl-[1,2,4]oxadiazole;
3-[3-Chloro-4-(3-ethoxy-propoxy)-phenyl]-5-o-tolyl-[1,2,4]oxadiazole;
1-{2-[2-Chloro-4-(5-o-tolyl-[1,2,4]oxadiazol-3-yl)-phenoxy]-ethyl}-piperidine;
4-{(2-[2-Chloro-4-(5-o-tolyl-[1,2,4]oxadiazol-3-yl)-phenoxy]-ethyl}-morpholine;
3-(3-Chloro-4-cyclopentyloxy-phenyl)-5-o-tolyl-[1,2,4]oxadiazole;
3-[3-Chloro-4-(1-ethyl-propoxy)-phenyl]-5-o-tolyl-[1,2,4]oxadiazole;
3-(3-Chloro-4-cyclohexyloxy-phenyl)-5-o-tolyl-[1,2,4]oxadiazole;
3-(3-Chloro-4-phenethyloxy-phenyl)-5-o-tolyl-[1,2,4]oxadiazole;
3-[3-Chloro-4-(3-methyl-butoxy)-phenyl]-5-o-tolyl-[1,2,4]oxadiazole;
3-(3-Chloro-4-cyclohexylmethoxy-phenyl)-5-o-tolyl-[1,2,4]oxadiazole;
3-[3-Chloro-4-(2-isopropoxy-ethoxy)-phenyl]-5-o-tolyl-[1,2,4]oxadiazole;
3-(3-Chloro-4-pent-3-ynyloxy-phenyl)-5-o-tolyl-[1,2,4]oxadiazole;
3-[3-Chloro-4-(2-thiophen-2-yl-ethoxy)-phenyl]-5-o-tolyl-[1,2,4]oxadiazole;
3-(4-sec-Butoxy-3-chloro-phenyl)-5-o-tolyl-[1,2,4]oxadiazole;
{2-[2-Chloro-4-(5-o-tolyl-[1,2,4]oxadiazol-3-yl)-phenoxy]-propyl}-dimethyl-amine;
{2-[2-Chloro-4-(5-o-tolyl-[1,2,4]oxadiazol-3-yl)-phenoxy]-ethyl}-dimethyl-amine;
3-(3-Chloro-4-cyclobutylmethoxy-phenyl)-5-o-tolyl-[1,2,4]oxadiazole;
3-{4-[((E)-But-2-enyl)oxy]-3-chloro-phenyl}-5-o-tolyl-[1,2,4]oxadiazole;
3-[3-Chloro-4-(4,4,4-trifluoro-butoxy)-phenyl]-5-o-tolyl-[1,2,4]oxadiazole;
3-[3-Chloro-4-(4-methyl-cyclohexylmethoxy)-phenyl]-5-o-tolyl-[1,2,4]oxadiazole;
2-[3-(3-Chloro-4-isopropoxy-phenyl)-[1,2,4]oxadiazol-5-yl]-pyrazine;
3-(3-Chloro-4-isopropoxy-phenyl)-5-isoxazol-3-yl-[1,2,4]oxadiazole;
3-(3-Chloro-4-isopropoxy-phenyl)-5-(2-methoxy-ethyl)-[1,2,4]oxadiazole;
4-[3-(3-Chloro-4-isopropoxy-phenyl)-[1,2,4]oxadiazol-5-yl]-pyridine;
3-(3-Chloro-4-isopropoxy-phenyl)-5-cyclopropylmethyl-[1,2,4]oxadiazole;
3-[3-(3-Chloro-4-isopropoxy-phenyl)-[1,2,4]oxadiazol-5-yl]-pyridine;
2-[3-(3-Chloro-4-isopropoxy-phenyl)-[1,2,4]oxadiazol-5-yl]-pyridine;
3-(3-Chloro-4-isopropoxy-phenyl)-5-o-tolyl-[1,2,4]oxadiazole;
4-[3-(3-Chloro-4-isopropoxy-phenyl)-[1,2,4]oxadiazol-5-yl]-3-methyl-pyridine;
3,5-Bis-(3-chloro-4-isopropoxy-phenyl)-[1,2,4]oxadiazole;
[3-(3-Chloro-4-isopropoxy-phenyl)-[1,2,4]oxadiazol-5-yl]-dimethyl-amine;
5-Benzyl-3-(3-chloro-4-isopropoxy-phenyl)-[1,2,4]oxadiazole;
3-(3-Chloro-4-isopropoxy-phenyl)-5-phenyl-[1,2,4]oxadiazole;
3-[3-(3-Chloro-4-isopropoxy-phenyl)-[1,2,4]oxadiazol-5-ylmethyl]-pyridine;

4-{2-[3-(3-Chloro-4-isopropoxy-phenyl)-[1,2,4]oxadiazol-5-yl]-ethyl}-pyridine;
3-(3-Chloro-4-isopropoxy-phenyl)-5-(3-trifluoromethyl-phenyl)-[1,2,4]oxadiazole;
3-(3-Chloro-4-isopropoxy-phenyl)-5-(3-methyl-butyl)-[1,2,4]oxadiazole;
3-(3-Chloro-4-isopropoxy-phenyl)-5-(2,2-dimethyl-propyl)-[1,2,4]oxadiazole;
3-(3-Chloro-4-isopropoxy-phenyl)-5-hexyl-[1,2,4]oxadiazole;
3-(3-Chloro-4-isopropoxy-phenyl)-5-(3,3,3-trifluoro-propyl)-[1,2,4]oxadiazole;
3-(3-Chloro-4-isopropoxy-phenyl)-5-methoxymethyl-[1,2,4]oxadiazole;
3-(3-Chloro-4-isopropoxy-phenyl)-5-methylsulfanylmethyl-[1,2,4]oxadiazole;
3-(3-Chloro-4-isopropoxy-phenyl)-5-ethoxymethyl-[1,2,4]oxadiazole;
3-(3-Chloro-4-isopropoxy-phenyl)-5-(2-methoxy-ethoxymethyl)-[1,2,4]oxadiazole;
3-(3-Chloro-4-isopropoxy-phenyl)-5-(tetrahydro-furan-2-yl)-[1,2,4]oxadiazole;
3-(3-Chloro-4-isopropoxy-phenyl)-5-(tetrahydro-furan-3-yl)-[1,2,4]oxadiazole;
3-(3-Chloro-4-isopropoxy-phenyl)-5-cyclopropyl-[1,2,4]oxadiazole;
3-(3-Chloro-4-isopropoxy-phenyl)-5-cyclobutyl-[1,2,4]oxadiazole;
3-(3-Chloro-4-isopropoxy-phenyl)-5-cyclopentyl-[1,2,4]oxadiazole;
3-(3-Chloro-4-isopropoxy-phenyl)-5-cyclopentylmethyl-[1,2,4]oxadiazole;
3-(3-Chloro-4-isopropoxy-phenyl)-5-cyclohexyl-[1,2,4]oxadiazole;
3-(3-Chloro-4-isopropoxy-phenyl)-5-cyclohexylmethyl-[1,2,4]oxadiazole;
3-(3-Chloro-4-isopropoxy-phenyl)-5-(1-methyl-cyclopropyl)-[1,2,4]oxadiazole;
3-(3-Chloro-4-isopropoxy-phenyl)-5-(2-methyl-cyclopropyl)-[1,2,4]oxadiazole;
3-(3-Chloro-4-isopropoxy-phenyl)-5-(2-ethoxy-ethyl)-[1,2,4]oxadiazole;
(S)-5-[3-(3-Chloro-4-isopropoxy-phenyl)-[1,2,4]oxadiazol-5-yl]-pyrrolidin-2-one;
(R)-5-[3-(3-Chloro-4-isopropoxy-phenyl)-[1,2,4]oxadiazol-5-yl]-pyrrolidin-2-one;
5-Benzyloxymethyl-3-(3-chloro-4-isopropoxy-phenyl)-[1,2,4]oxadiazole;
3-(3-Chloro-4-isopropoxy-phenyl)-5-(1-phenyl-cyclopropyl)-[1,2,4]oxadiazole;
3-(3-Chloro-4-isopropoxy-phenyl)-5-((S)-1-phenyl-propyl)-[1,2,4]oxadiazole;
3-(3-Chloro-4-isopropoxy-phenyl)-5-(3-phenyl-propyl)-[1,2,4]oxadiazole;
3-(3-Chloro-4-isopropoxy-phenyl)-5-((R)-methoxy-phenyl-methyl)-[1,2,4]oxadiazole;
3-(3-Chloro-4-isopropoxy-phenyl)-5-((S)-methoxy-phenyl-methyl)-[1,2,4]oxadiazole;
3-(3-Chloro-4-isopropoxy-phenyl)-5-(2-phenoxy-ethyl)-[1,2,4]oxadiazole;
Furan-2-carboxylic acid [3-(3-chloro-4-isopropoxy-phenyl)-[1,2,4]oxadiazol-5-ylmethyl]-amide;
3-(3-Chloro-4-isopropoxy-phenyl)-5-(3-thiophen-2-yl-propyl)-[1,2,4]oxadiazole;
1-{4-[3-(3-Chloro-4-isopropoxy-phenyl)-[1,2,4]oxadiazol-5-yl]-piperidin-1-yl}-ethanone;
3-(3-Chloro-4-isopropoxy-phenyl)-5-(3,5-difluoro-benzyl)-[1,2,4]oxadiazole;
3-[3-(3-Chloro-4-isopropoxy-phenyl)-[1,2,4]oxadiazol-5-yl]-1-phenyl-propan-1-one;
3-(3-Chloro-4-isopropoxy-phenyl)-5-(3-phenoxy-propyl)-[1,2,4]oxadiazole;
3-[3-(3-Chloro-4-isopropoxy-phenyl)-[1,2,4]oxadiazol-5-yl]-1-thiophen-2-yl-propan-1-one;
4-[3-(3-Chloro-4-isopropoxy-phenyl)-[1,2,4]oxadiazol-5-yl]-N-phenyl-butyramide;
N-[3-(3-Chloro-4-isopropoxy-phenyl)-[1,2,4]oxadiazol-5-ylmethyl]-4-methyl-benzenesulfonamide;
1-{4-[3-(3-Chloro-4-isopropoxy-phenyl)-[1,2,4]oxadiazol-5-yl]-phenyl}-ethanone;
{4-[3-(3-Chloro-4-isopropoxy-phenyl)-[1,2,4]oxadiazol-5-yl]-phenyl}-diethyl-amine; compound with trifluoroacetic acid;
3-(3-Chloro-4-isopropoxy-phenyl)-5-ethyl-[1,2,4]oxadiazole;
3-(3-Chloro-4-isopropoxy-phenyl)-5-propyl-[1,2,4]oxadiazole;
3-(3-Chloro-4-isopropoxy-phenyl)-5-isopropyl-[1,2,4]oxadiazole;
5-Butyl-3-(3-chloro-4-isopropoxy-phenyl)-[1,2,4]oxadiazole;
5-sec-Butyl-3-(3-chloro-4-isopropoxy-phenyl)-[1,2,4]oxadiazole;
3-(3-Chloro-4-isopropoxy-phenyl)-5-isobutyl-[1,2,4]oxadiazole;
3-(3-Chloro-4-isopropoxy-phenyl)-5-pentyl-[1,2,4]oxadiazole;
{4-[3-(3-Chloro-4-isopropoxy-phenyl)-[1,2,4]oxadiazol-5-yl]-phenyl}-carbamic acid tert-butyl ester;
3-[3-(3-Chloro-4-isopropoxy-phenyl)-[1,2,4]oxadiazol-5-yl]-benzonitrile;
4-[3-(3-Chloro-4-isopropoxy-phenyl)-[1,2,4]oxadiazol-5-yl]-benzonitrile;
{3-[3-(3-Chloro-4-isopropoxy-phenyl)-[1,2,4]oxadiazol-5-yl]-phenyl}-dimethyl-amine;
5-Biphenyl-4-ylmethyl-3-(3-chloro-4-isopropoxy-phenyl)-[1,2,4]oxadiazole;
{4-[3-(3-Chloro-4-isopropoxy-phenyl)-[1,2,4]oxadiazol-5-ylmethyl]-phenyl}-dimethyl-amine;
3-(3-Chloro-4-isopropoxy-phenyl)-5-(4-phenoxy-benzyl)-[1,2,4]oxadiazole;
5-(4-Benzyloxy-benzyl)-3-(3-chloro-4-isopropoxy-phenyl)-[1,2,4]oxadiazole;
3-(3-Chloro-4-isopropoxy-phenyl)-5-naphthalen-1-ylmethyl-[1,2,4]oxadiazole;
3-(3-Chloro-4-isopropoxy-phenyl)-5-naphthalen-2-ylmethyl-[1,2,4]oxadiazole;
3-(3-Chloro-4-isopropoxy-phenyl)-5-furan-2-yl-[1,2,4]oxadiazole;
3-(3-Chloro-4-isopropoxy-phenyl)-5-furan-3-yl-[1,2,4]oxadiazole;
3-(3-Chloro-4-isopropoxy-phenyl)-5-thiophen-2-yl-[1,2,4]oxadiazole;
3-(3-Chloro-4-isopropoxy-phenyl)-5-thiophen-3-yl-[1,2,4]oxadiazole;
3-(3-Chloro-4-isopropoxy-phenyl)-5-(1-methyl-1H-pyrrol-2-yl)-[1,2,4]oxadiazole;
3-(3-Chloro-4-isopropoxy-phenyl)-5-thiazol-4-yl-[1,2,4]oxadiazole;
3-(3-Chloro-4-isopropoxy-phenyl)-5-(3,5-dimethyl-isoxazol-4-yl)-[1,2,4]oxadiazole;
2-[3-(3-Chloro-4-isopropoxy-phenyl)-[1,2,4]oxadiazol-5-yl]-5-methyl-pyrazine;

3-[3-(3-Chloro-4-isopropoxy-phenyl)-[1,2,4]oxadiazol-5-yl]-6,7-dihydro-5H-benzofuran-4-one;
4-[3-(3-Chloro-4-isopropoxy-phenyl)-[1,2,4]oxadiazol-5-ylmethyl]-morpholine;
3-Chloro-4-[3-(3-chloro-4-isopropoxy-phenyl)-[1,2,4]oxadiazol-5-yl]-pyridine;
3-(3-Chloro-4-isopropoxy-phenyl)-5-(3-chloro-phenyl)-[1,2,4]oxadiazole;
4-[3-(3-Chloro-4-isopropoxy-phenyl)-[1,2,4]oxadiazol-5-yl]-3-fluoro-pyridine;
2-Chloro-4-[3-(3-chloro-4-isopropoxy-phenyl)-[1,2,4]oxadiazol-5-yl]-pyridine;
4-[3-(3-Chloro-4-isopropoxy-phenyl)-[1,2,4]oxadiazol-5-yl]-2-fluoro-pyridine;
4-[3-(3-Chloro-4-isopropoxy-phenyl)-[1,2,4]oxadiazol-5-yl]quinoline;
2,6-Dichloro-4-[3-(3-chloro-4-isopropoxy-phenyl)-[1,2,4]oxadiazol-5-yl]-pyridine;
3-(3-Chloro-4-isopropoxy-5-methoxy-phenyl)-5-phenyl-[1,2,4]oxadiazole;
4-[3-(3-Chloro-4-isopropoxy-5-methoxy-phenyl)-[1,2,4]oxadiazol-5-yl]-pyridine;
2-Methoxy-5-(5-phenyl-[1,2,4]oxadiazol-3-yl)-pyridine;
5-(5-Pyridin-4-yl-[1,2,4]oxadiazol-3-yl)-2-(2,2,2-trifluoro-ethoxy)-pyridine;
5-(5-Phenyl-[1,2,4]oxadiazol-3-yl)-2-(2,2,2-trifluoro-ethoxy)-pyridine;
5-(3-chloropyridin-4-yl)-3-(6-(2,2,2-trifluoroethoxy)pyridin-3-yl)-1,2,4-oxadiazole;
5-(3-methylpyridin-4-yl)-3-(6-(2,2,2-trifluoroethoxy)pyridin-3-yl)-1,2,4-oxadiazole;
3-(4-tert-Butyl-phenyl)-5-o-tolyl-[1,2,4]oxadiazole;
3-(3-Chloro-4-methyl-phenyl)-5-o-tolyl-[1,2,4]oxadiazole;
3-(4-Ethyl-phenyl)-5-o-tolyl-[1,2,4]oxadiazole;
3-(4-Butyl-phenyl)-5-o-tolyl-[1,2,4]oxadiazole;
3-(4-Isopropyl-phenyl)-5-o-tolyl-[1,2,4]oxadiazole;
4-(3-Phenyl-[1,2,4]oxadiazol-5-yl)-pyridine;
4-[3-(3-Chloro-phenyl)-[1,2,4]oxadiazol-5-yl]-pyridine;
4-(5-Pyridin-4-yl-[1,2,4]oxadiazol-3-yl)-phenol;
3-Benzofuran-5-yl-5-o-tolyl-[1,2,4]oxadiazole;
3-(4-Methoxy-3-trifluoromethyl-phenyl)-5-o-tolyl-[1,2,4]oxadiazole;
3-Biphenyl-4-yl-5-o-tolyl-[1,2,4]oxadiazole;
3-(3-Chloro-4-isopropoxy-phenyl)-5-(2,4-dichloro-phenyl)-[1,2,4]oxadiazole;

or a pharmaceutically acceptable salt, solvate, hydrate, metabolite, prodrug, enantiomer or stereoisomer thereof.

In another aspect, the invention provides a pharmaceutical composition comprising one or more compounds according to Formula (I), (Ia), (II), (III), (IV), (IVa) and (IVb), or pharmaceutically acceptable salts, solvates, hydrates, metabolites, prodrugs or stereoisomers thereof and a pharmaceutically acceptable diluent or carrier. In a preferred aspect, the invention provides a pharmaceutical composition wherein the compound or compounds are present in a therapeutically effective amount. In a related aspect, the invention provides a pharmaceutical composition wherein the compound or compounds are present in a prophylactically effective amount.

In still another aspect, the invention provides a packaged pharmaceutical comprising a one or more compounds according to Formula (I), (Ia), (II), (III), (IV), (IVa) and (IVb), or pharmaceutically acceptable salts, solvates, hydrates, metabolites, prodrugs or stereoisomers thereof and instructions for use. In one embodiment, the invention provides a packaged pharmaceutical wherein the compound or compounds are present in a therapeutically effective amount. In another embodiment, the invention provides a packaged pharmaceutical wherein the compound or compounds are present in a prophylactically effective amount.

DETAILED DESCRIPTION OF THE INVENTION

Definitions

In this invention, the following definitions are applicable:

A "therapeutically effective amount" is an amount of a compound of Formula (I), (Ia), (Ib), or (Ic) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Physiologically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of Formula (I), (Ia), (II), (III), (IV), (IVa) or (IVb) which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of Formula (I), (Ia), (II), (III), (IV), (IVa) or (IVb) and their salts may exist in more than one crystal form and the present invention includes each crystal form and mixtures thereof.

Certain compounds of Formula (I), (Ia), (II), (III), (IV), (IVa) or (IVb) and their salts may also exist in the form of solvates, for example hydrates, and the present invention includes each solvate and mixtures thereof.

Certain compounds of Formula (I), (Ia), (II), (III), (IV), (IVa) or (IVb) may contain one or more chiral centers, and exist in different optically active forms. When compounds of Formula (I), (Ia), (II), (III), (IV), (IVa) or (IVb) contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step may be used to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of Formula (I), (Ia), (II), (III), (IV), (IVa) or (IVb) contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of Formula (I), (Ia), (II), (III), (IV), (IVa) or (IVb) and mixtures thereof.

Certain compounds of Formula (I), (Ia), (II), (III), (IV), (IVa) or (IVb) may exist in different tautomeric forms or as different geometric isomers, and the present invention includes each tautomer and/or geometric isomer of compounds of Formula (I), (Ia), (II), (III), (IV), (IVa) or (IVb) and mixtures thereof.

Certain compounds of Formula (I), (Ia), (II), (III), (IV), (IVa) or (IVb) may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Formula (I), (Ia), (II), (III), (IV), (IVa) or (IVb) and mixtures thereof.

Certain compounds of Formula (I), (Ia), (II), (III), (IV), (IVa) or (IVb) may exist in zwitterionic form and the present invention includes each zwitterionic form of compounds of Formula (I), (Ia), (II), (III), (IV), (IVa) or (IVb) and mixtures thereof.

As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., —$CH_2$C(O) OH or a moiety that contains a carboxylic acid) wherein the free hydrogen is replaced by ($C_1$-$C_4$)alkyl, ($C_2$-$C_{12}$)alkanoyloxymethyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)-alkylcarbamoyl-($C_1$-$C_2$)alkyl and piperidino-, pyrrolidino- or morpholino ($C_2$-$C_3$) alkyl.

Other exemplary pro-drugs release an alcohol of Formula (I), (Ia), (II), (III), (IV), (IVa) or (IVb) wherein the free hydrogen of the hydroxyl substituent (e.g., $R^1$ contains hydroxyl) is replaced by ($C_1$-$C_6$)alkanoyloxymethyl, 1-(($C_1$-$C_6$)alkanoyloxy)ethyl, 1-methyl-1-(($C_1$-$C_6$)alkanoyloxy) ethyl, ($C_1$-$C_6$)alkoxycarbonyloxymethyl, N—($C_1$-$C_6$) alkoxycarbonylamino-methyl, succinoyl, ($C_1$-$C_6$)alkanoyl, α-amino($C_1$-$C_4$)alkanoyl, arylacyl and α-aminoacyl, or α-aminoacyl-α-aminoacyl wherein said α-aminoacyl moieties are independently any of the naturally occurring L-amino acids found in proteins, P(O)(OH)$_2$, —P(O)(O($C_1$-$C_6$)alkyl)$_2$ or glycosyl (the radical resulting from detachment of the hydroxyl of the hemiacetal of a carbohydrate).

The term "heterocyclic" or "heterocyclyl", as used herein, include non-aromatic, ring systems, including, but not limited to, monocyclic, bicyclic and tricyclic rings, which can be completely saturated or which can contain one or more units of unsaturation, for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl.

The term "heteroaryl" as used herein, include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b) thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl.

When the term "substituted heterocyclic" (or heterocyclyl) or "substituted heteroaryl" or "substituted aryl" is used, what is meant is that the heterocyclic, heteroaryl or aryl group is substituted with one or more substituents that can be made by one of ordinary skill in the art and results in a molecule that is an agonist or antagonist of the sphingosine receptor family. For purposes of exemplification, which should not be construed as limiting the scope of this invention, preferred substituents for the heterocycle, heteroaryl or aryl group of this invention are each independently selected from the optionally substituted group consisting of alkenyl, alkoxy, alkoxyalkoxy, alkoxyalkyl, alkoxycarbonyl, alkoxycarbonylheterocycloalkoxy, alkyl, alkylamino, alkylcarbonyl, alkylester, alkyl-NH-alkyl, -alkyl-NH-cycloalkyl, alkyl-O—C(O)—, -alkyl-heterocyclyl, -alkyl-cycloalkyl, alkyl-nitrile, alkynyl, amido groups, amino, aminoalkyl, aminocarbonyl, carbonitrile, carbonylalkoxy, carboxamido, $CF_3$, CN, —C(O)OH, —C(O)H, —C(O)—C(CH$_3$)$_3$, —OH, —C(O)O-alkyl, —C(O)O-cycloalkyl, —C(O)O-heterocyclyl, —C(O)O-alkyl-aryl, —C(O)-alkyl, —C(O)-cycloalkyl, —C(O)-heterocyclyl, cycloalkyl, dialkylaminoalkoxy, dialkylaminocarbonylalkoxy, dialkylaminocarbonyl, halogen, heterocyclyl, a heterocycloalkyl group, heterocyclyloxy, hydroxy, hydroxyalkyl, nitro, $OCF_3$, oxo, —O-alkyl, —O-heteroaryl, —O-heterocyclyl, —SO$_2$CH$_3$, —SO$_2$NH$_2$, —SO$_2$NH-alkyl, —SO$_2$N(alkyl)$_2$, tetrazolyl, thienylalkoxy, trifluoromethylcarbonylamino, trifluoromethylsulfonamido, heterocyclylalkoxy, heterocyclyl-S(O)$_p$, cycloalkyl-S(O)$_p$, alkyl-S—, heterocyclyl-S, heterocycloalkyl, cycloalkylalkyl, heterocycolthio, cycloalkylthio, -Z$^{105}$-C(O)N(R)$_2$, -Z$^{105}$-N(R)—C(O)-Z$^{200}$, -Z$^{105}$-N(R)—S(O)$_2$-Z$^{200}$, -Z$^{105}$-N(R)—C(O)—N(R)-Z$^{200}$, —N(R), —N(H)-alkyl, —N(H)-cycloalkyl, —C(O)R, —N(R)—C(O)OR, OR—C(O)-heterocyclyl-OR, R$^c$ and —CH$_2$OR$^c$;

wherein p is 0, 1 or 2;

where R$_c$ for each occurrence is independently hydrogen, optionally substituted alkyl, optionally substituted aryl, —(C$_1$-C$_6$)—NR$_d$R$_e$, -E-(CH$_2$)$_t$—NR$_d$R$_e$, -E-(CH$_2$)$_t$—O-alkyl, -E-(CH$_2$)$_t$—S-alkyl, or -E-(CH$_2$)$_t$, —OH;

wherein t is an integer from about 1 to about 6;

Z$^{105}$ for each occurrence is independently a covalent bond, alkyl, alkenyl or alkynyl; and Z$^{200}$ for each occurrence is independently selected from an optionally substituted group selected from the group consisting of alkyl, alkenyl, alkynyl, phenyl, alkyl-phenyl, alkenyl-phenyl or alkynyl-phenyl;

E is a direct bond, O, S, S(O), S(O)$_2$, or NR$_f$, wherein R$_f$ is H or alkyl and R$_d$ and R$_e$ are independently H, alkyl, alkanoyl or SO$_2$-alkyl; or R$_d$, R$_e$ and the nitrogen atom to which they are attached together to form a five- or six-membered heterocyclic ring.

An "heterocycloalkyl" group, as used herein, is a heterocyclic group that is linked to a compound by an aliphatic group having from one to about eight carbon atoms. For example, a preferred heterocycloalkyl group is a morpholinomethyl group.

As used herein, "aliphatic" or "an aliphatic group" or notations such as "(C$_0$-C$_8$)" include straight chained or branched hydrocarbons which are completely saturated or which contain one or more units of unsaturation, and, thus, includes alkyl, alkenyl, alkynyl and hydrocarbons comprising a mixture of single, double and triple bonds. When the group is a Co it means that the moiety is not present or in other words, it is a bond. As used herein, "alkyl" means C$_1$-C$_8$ and includes straight chained or branched hydrocarbons, which are completely saturated. Preferred alkyls are methyl, ethyl, propyl, butyl, pentyl, hexyl and isomers thereof. As used herein, "alkenyl" and "alkynyl" means C$_2$-C$_8$ and includes straight chained or branched hydrocarbons which contain one or more units of unsaturation, one or more double bonds for alkenyl and one or more triple bonds for alkynyl.

As used herein, aromatic groups (or aryl groups) include aromatic carbocyclic ring systems (e.g. phenyl and cyclopentyldienyl) and fused polycyclic aromatic ring systems (e.g. naphthyl, biphenylenyl and 1,2,3,4-tetrahydronaphthyl).

As used herein, cycloalkyl means C$_3$-C$_{12}$ monocyclic or multicyclic (e.g., bicyclic, tricyclic, etc.) hydrocarbons that is completely saturated or has one or more unsaturated bonds but does not amount to an aromatic group. Preferred examples of a cycloalkyl group are cyclopropyl, cyclobutyl, cyclopentyl, cyclopentenyl, cyclohexyl and cyclohexenyl.

As used herein, many moieties or substituents are termed as being either "substituted" or "optionally substituted". When a moiety is modified by one of these terms, unless otherwise noted, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: alkenyl groups, alkoxy group (which itself can be substituted, such as —O—C$_1$-C$_6$-alkyl-OR, —O—C$_1$-C$_6$-alkyl-N(R)$_2$, and OCF$_3$), alkoxyalkoxy, alkoxycarbonyl, alkoxycarbonylpiperidinyl-alkoxy, alkyl groups (which itself can also be substituted, such as —C$_1$-C$_6$-alkyl-OR, —C$_1$-C$_6$-alkyl-N(R)$_2$, COOH, and —CF$_3$), alkylamino, alkylcarbonyl, alkylester, alkylnitrile, alkylsulfonyl, amino, aminoalkoxy, CF$_3$, COH, COOH, CN, cycloalkyl, dialkylamino, dialkylaminoalkoxy, dialkylaminocarbonyl, dialkylaminocarbonylalkoxy, dialkylaminosulfonyl, esters (—C(O)—OR, where R is groups such as alkyl, heterocycloalkyl (which can be substituted), heterocyclyl, etc., which can be substituted), halogen or halo group (F, Cl, Br, I), hydroxy, morpholinoalkoxy, morpholinoalkyl, —NH—C$_1$-C$_6$-alkyl-COOH, nitro, oxo, OCF$_3$, S(O)$_2$CH$_3$, S(O)$_2$CF$_3$, and sulfonyl, N-alkylamino or N,N-dialkylamino (in which the alkyl groups can also be substituted).

Methods of Use

The present invention provides compounds described by general Formula (I), (Ia), (II), (III), (IV), (IVa) or (IVb), which are effective as antagonists or agonists of the G protein-coupled S1P receptor family. These compounds reduce the number of circulating and infiltrating T- and B-lymphocytes affording a beneficial immunosuppressive effect.

The present invention also provides compounds that exhibit activity within the S1P receptor family.

In a related aspect the invention provides a method for modulating receptors of the S1P family in a human subject suffering from a disorder in which modulation of S1P activity is beneficial, comprising administering to the human subject a compound of Formula (I), (Ia), (II), (III), (IV), (IVa) or (IVb) such that modulation of S1P activity in the human subject is triggered and treatment is achieved.

In another related aspect the invention provides a method of modulating sphingosine 1-phosphate receptor 1 activity comprising contacting a cell with one or more compounds of Formula (I), (Ia), (II), (III), (IV), (IVa) or (IVb).

A compound of Formula (I), (Ia), (II), (III), (IV), (IVa) or (IVb) or a salt thereof or pharmaceutical compositions containing a therapeutically effective amount thereof is useful in the treatment of a disorder selected from the group comprising CNS system disorders, arthritis, rheumatoid arthritis, osteoarthritis, juvenile chronic arthritis, Lyme arthritis, psoriatic arthritis, reactive arthritis, and septic arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection (including but not limited to bone marrow and solid organ rejection), acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia areata, seronegative arthropathy, arthropathy, Reiter's disease, psoriatic arthropathy, ulcerative colitic arthropathy, enteropathic synovitis, chlamydia, *yersinia* and *salmonella* associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaernia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma), and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aortic and peripheral aneurysms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chromic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic arteriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, epstein-barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallerrorden-Spatz disease, hashimoto's thyroiditis, hay fever, heart transplant rejection, hemachromatosis, hemodialysis, hemolytic uremic syndrome/thrombolytic thrombocytopenic purpura, hemorrhage, hepatitis (A), His bundle arrhythmias, HIV infection/HIV neuropathy, Hodgkin's disease, hyperkinetic movement disorders, hypersensitivity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, *legionella*, leishmaniasis, leprosy, lesions of the corticospinal system, lipedema, liver transplant rejection, lymphederma, malaria, malignant Lymphoma, malignant histiocytosis, malignant melanoma, meningitis, meningococcemia, metabolic/idiopathic, migraine headache, mitochondrial multi.system disorder, mixed connective tissue disease, monoclonal gammopathy, multiple myeloma, multiple systems degenerations (Mencel Dejerine-Thomas Shi-Drager and Machado-Joseph), myasthenia gravis, *mycobacterium avium intracellulare, mycobacterium tuberculosis*, myelodysplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-hodgkins lymphoma, occlusion of the abdominal aorta and its branches, occulsive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherlosclerotic disease, peripheral vascular disorders, peritonitis, pernicious anemia, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preclampsia, Progressive supranucleo Palsy, primary pulmonary hypertension, radiation therapy, Raynaud's phenomenon and disease, Raynaud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as, edema, ascites, effusions, and exudates, including for example macular edema, cerebral edema, acute lung injury, adult respiratory distress syndrome (ARDS), proliferative disorders such as restenosis, fibrotic disorders such as hepatic cirrhosis and atherosclerosis, mesangial cell proliferative disorders such as glomerulonephritis, diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, Crow-Fukase syndrome (POEMS), preeclampsia, menometrorrhagia, cat scratch fever, rubeosis, neovascular glaucoma and retinopathies such as those associated with diabetic retinopathy, retinopathy of prematurity, age-related macular degeneration or a central nervous system disorder. In addition, these compounds can be used as active agents against solid tumors, malignant ascites, von Hippel Lindau disease, hematopoietic cancers and hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

Combination Therapy

Compounds of Formula (I), (Ia), (II), (III), (IV), (IVa) or (IVb) of the invention can be used alone or in combination with another therapeutic agent to treat such diseases. It should be understood that the compounds of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the compound of the present invention. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the S1P receptor agonists or antagonists of this invention. Non-limiting examples of therapeutic agents for rheumatoid arthritis with which a compound of Formula (I), (Ia), (II), (III), (IV), (IVa) or (IVb) of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. S/T kinase inhibitors of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7 (HUMIRA™), (PCT Publication No. WO 97/29131), CA2 (REMICADE™), CDP 571, and soluble p55 or p75 TNF receptors, derivatives, thereof, (p75TNFR1gG (ENBREL™) or p55TNFR1gG (Lenercept), and also TNFα converting enzyme (TACE) inhibitors; similarly IL-1 inhibitors (Interleukin-1-converting enzyme inhibitors, IL-IRA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of Formula (I), (Ia), (II), (III), (IV), (IVa) or (IVb) of the invention may also be combined with agents, such as methotrexate, 6-MP, azathioprine sulphasalazine, mesalazine, olsalazine chloroquinine/hydroxychloroquine, penicillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen; corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™ and p55TNFRIgG (Lenercept)), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC$_{485}$, CDC-801, and Mesopram. Preferred combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of Formula (I), (Ia), (II), (III), (IV), (IVa) or (IVb) of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. IRAK, NIK, IKK, or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of Formula (I), (Ia), (II), (III), (IV), (IVa) or (IVb) can be combined include the following: TNF antagonists, for example, anti-TNF antibodies, D2E7 (PCT Publication No. WO 97/29131; HUMIRA™), CA2 (REMICADE™), CDP 571, TNFR-Ig constructs, (p75TNFRIgG (ENBREL™) and p55TNFRIgG (Lenercept™)) inhibitors and PDE4 inhibitors. A compound of Formula (I), (Ia), (II), (III), (IV), (IVa) or (IVb) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors 6-mercaptopurines; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimetoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I), (Ia), (II), (III), (IV), (IVa) or (IVb) can be combined include the following: corticosteroids; prednisolone; methylprednisolone; azathioprine; cyclophosphamide; cyclosporine; methotrexate; 4-aminopyridine; tizanidine; interferon-β1a (Avonex®; Biogen); interferon-β1b (Betaseron®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; Copaxone®; Teva Pharmaceutical Industries, Inc.); hyperbaric oxygen; intravenous immunoglobulin; clabribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I), (Ia), (II), (III), (IV), (IVa) or (IVb) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I), (Ia), (II), (III), (IV), (IVa) or (IVb) may also be combined with agents such as methotrexate, cyclosporine, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, TACE inhibitors, T-cell signalling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

Preferred examples of therapeutic agents for multiple sclerosis in which a compound of Formula (I), (Ia), (II), (III), (IV), (IVa) or (IVb) can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

A compound of Formula (I), (Ia), (II), (III), (IV), (IVa) or (IVb) may also be combined with agents, such as alemtuzumab, dronabinol, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL4 agonists.

Non-limiting examples of therapeutic agents for angina with which a compound of Formula (I), (Ia), (II), (III), (IV), (IVa) or (IVb) of the invention can be combined include the following: aspirin, nitroglycerin, isosorbide mononitrate, metoprolol succinate, atenolol, metoprolol tartrate, amlodipine besylate, diltiazem hydrochloride, isosorbide dinitrate, clopidogrel bisulfate, nifedipine, atorvastatin calcium, potassium chloride, furosemide, simvastatin, verapamil HCl, digoxin, propranolol hydrochloride, carvedilol, lisinopril, spironolactone, hydrochlorothiazide, enalapril maleate, nadolol, ramipril, enoxaparin sodium, heparin sodium, valsartan, sotalol hydrochloride, fenofibrate, ezetimibe, bumetanide, losartan potassium, lisinopril/hydrochlorothiazide, felodipine, captopril and bisoprolol fumarate.

Non-limiting examples of therapeutic agents for ankylosing spondylitis with which a compound of Formula (I), (Ia), (II), (III), (IV), (IVa) or (IVb) can be combined include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, etanercept, and infliximab.

Non-limiting examples of therapeutic agents for asthma with which a compound of Formula (I), (Ia), (II), (III), (IV), (IVa) or (IVb) can be combined include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone and metaproterenol sulfate.

Non-limiting examples of therapeutic agents for COPD with which a compound of Formula (I), (Ia), (II), (III), (IV), (IVa) or (IVb) can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for HCV with which a compound of Formula (I), (Ia), (II), (III), (IV), (IVa) or (IVb) can be combined include the following: Interferon-alpha-2a, Interferon-alpha-2b, Interferon-alpha con 1, Interferon-alpha-n1, pegylated interferon-alpha-2a, pegylated interferon-alpha-2b, ribavirin, peginterferon alfa-2b+ribavirin, ursodeoxycholic acid, glycyrrhizic acid, thymalfasin, Maxamine, VX-497 and any compounds that are used to treat HCV through intervention with the following targets: HCV polymerase, HCV protease, HCV helicase, and HCV IRES (internal ribosome entry site).

Non-limiting examples of therapeutic agents for Idiopathic Pulmonary Fibrosis with which a compound of Formula (I), (Ia), (II), (III), (IV), (IVa) or (IVb) can be combined include the following: prednisone, azathioprine, albuterol, colchicine, albuterol sulfate, digoxin, gamma interferon, methylprednisolone sod succ, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone HCl, potassium chloride, triamcinolone acetonide, tacrolimus anhydrous, calcium, interferon-alpha, methotrexate, mycophenolate mofetil and interferon-gamma-1β.

Non-limiting examples of therapeutic agents for myocardial infarction with which a compound of Formula (I), (Ia), (II), (III), (IV), (IVa) or (IVb) can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril HCl/mag carb, bumetanide, alteplase, enalaprilat, amiodarone hydrochloride, tirofiban HCl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine HCl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, and cariporide.

Non-limiting examples of therapeutic agents for psoriasis with which a compound of Formula (I), (Ia), (II), (III), (IV), (IVa) or (IVb) can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, and sulfasalazine.

Non-limiting examples of therapeutic agents for psoriatic arthritis with which a compound of Formula (I), (Ia), (II), (III), (IV), (IVa) or (IVb) can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept and efalizumab.

Non-limiting examples of therapeutic agents for restenosis with which a compound of Formula (I), (Ia), (II), (III), (IV), (IVa) or (IVb) can be combined include the following: sirolimus, paclitaxel, everolimus, tacrolimus, ABT-578, and acetaminophen.

Non-limiting examples of therapeutic agents for sciatica with which a compound of Formula (I), (Ia), (II), (III), (IV), (IVa) or (IVb) can be combined include the following: hydrocodone bitartrate/apap, rofecoxib, cyclobenzaprine HCl, methylprednisolone, naproxen, ibuprofen, oxycodone HCl/acetaminophen, celecoxib, valdecoxib, methylprednisolone acetate, prednisone, codeine phosphate/apap, tramadol hcl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone HCl, tizanidine HCl, diclofenac sodium/misoprostol, propoxyphene napsylate/apap, asa/oxycod/oxycodone ter, ibuprofen/hydrocodone bit, tramadol HCl, etodolac, propoxyphene HCl, amitriptyline HCl, carisoprodol/codeine phos/asa, morphine sulfate, multivitamins, naproxen sodium, orphenadrine citrate, and temazepam.

Preferred examples of therapeutic agents for SLE (Lupus) with which a compound of Formula (I), (Ia), (II), (III), (IV), (IVa) or (IVb) can be combined include the following: NSAIDS, for example, diclofenac, naproxen, ibuprofen, piroxicam, indomethacin; COX2 inhibitors, for example, celecoxib, rofecoxib, valdecoxib; anti-materials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I), (Ia), (II), (III), (IV), (IVa) or (IVb) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-Ira. A compound of Formula (I), (Ia), (II), (III), (IV), (IVa) or (IVb) may also be used with T cell signaling inhibitors, for example, tyrosine kinase inhibitors; or molecules that target T cell activation molecules, for example, CTLA4-IgG or anti-B7 family antibodies, anti-PD-1 family antibodies. A compound of Formula (I), (Ia), (II), (II), (IV), (IVa) or (IVb) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I), (Ia), (II), (III), (IV), (IVa) or (IVb) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (PCT Publication No. WO 97/29131; HUMIRA™), CA2 (REMICADE™), CDP 571, TNFR-Ig constructs, (p75TNFRIgG (ENBREL™) and p55TNFRIgG (LENERCEPT™)).

In the compositions of the present invention the active compound may, if desired, be associated with other compatible pharmacologically active ingredients. For example, the compounds of this invention can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors, PI3 kinase inhibitors, calcineurin inhibitors and immunosuppressants. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deleterious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present invention.

One or more compounds of the invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Pharmaceutical Compositions and Modes of Administration

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 400, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

Dosage

For any compound used in a method of the present invention, the therapeutically effective dose can be estimated initially from cellular assays. For example, a dose can be formulated in cellular and animal models to achieve a circulating concentration range that includes the $EC_{50}$ as determined in cellular assays (i.e., the concentration of the test compound which achieves a half-maximal inhibition of a given receptor activity). In some cases it is appropriate to determine the $EC_{50}$ in the presence of 3 to 5% serum albumin since such a determination approximates the binding effects of plasma protein on the compound. Such information can be used to more accurately determine useful doses in humans. Further, advantageous compounds for systemic administration effectively modulate receptors of the S1P family in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 µl). In the treatment of crises, the administration of an acute bolus or an infusion approaching the MTD may be advantageous to obtain a rapid response.

Dosage amount and interval may be adjusted individually to provide plasma levels of the active moiety which are sufficient to modulate receptors of the S1P family, or minimal effective concentration (MEC). The MEC will vary for each compound but can be estimated from in vitro data; e.g. the concentration necessary to achieve 50-90% inhibition of binding of the natural ligand using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and more preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

EXEMPLARY FORMULATIONS

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients:

| | Parts by weight |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

The present invention also comprises the use of a compound of Formula (I), (Ia), (II), (III), (IV), (IVa) or (IVb) as a medicament.

A further aspect of the present invention provides the use of a compound of Formula (I), (Ia), (II), (III), (IV), (IVa) or (IVb) or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of Formula (I), (Ia), (II), (III), (IV), (IVa) or (IVb) to a mammal, particularly a human being, in need thereof.

The teachings of all references, including journal articles, patents and published patent applications, are incorporated herein by reference in their entirety.

S1P Receptor GTPγS Assays

The [$^{35}$S]GTPγS binding assay can be run using both scintillation proximity assay (SPA) and filtration methods. Both formats are in 96 well plates and utilize membranes from a stable or transient CHO human cell lines overexpressing S1P$_1$, S1P$_2$, S1P$_3$, S1P$_4$ or S1P$_5$. Compound stocks were made up to 10 mM using DMSO and serial dilutions were carried out using 100% DMSO. Compounds were transferred to 96 well plates to yield a final DMSO concentration of 1% for all assays (1 ul for a 100 ul assay volume). Frozen membranes were thawed and diluted in assay buffer containing of 20 mM HEPES pH 7.4, 0.1% fatty acid-free BSA, 100 mM NaCl, 5 mM MgCl$_2$ and 10 μM GDP. For the SPA assay membranes are premixed with WGA-SPA beads to yield a final concentration per well of 5 ug membrane and 500 ug of bead. For the filtration assay, membranes are added directly to the incubation plate at 5 ug per well. The assay begins with the addition of 50 ul of the membrane or membrane/bead mixture to each well of the assay plate. Next, 50 ul of 0.4 nM [$^{35}$S] GTPγS is added to each well and incubated for 30 minutes. Nonspecific binding is measured using 10 uM unlabeled GTPγS. For the SPA assay the plates are spun and then read on the Topcount. For the filtration assay the plate is harvested onto GF-C filtration plates using a Packard 96 well harvester.

Inhibition of [$^{33}$P]S1P Binding to S1P Receptors

Radio ligand binding was carried out using membranes from transiently transfected HEK cells overexpressing S1P$_1$, S1P$_2$, S1P$_3$, S1P4 or S1P$_5$. All compounds are dissolved in DMSO and serial dilutions were carried out in DMSO prior to addition to assay buffer. Final assay DMSO concentrations are 1% (v/v). [$^{33}$P]S1P is purchased from Perkin Elmer and used at 50 pM in all assays. Frozen membranes are thawed and resuspended in assay buffer containing 50 mM HEPES pH7.4, 10 mM NaCl, 10 mM MgCl$_2$ and 0.1% fatty acid free BSA. Membrane is added to give 5-10 μg of membrane per well. Non-specific binding is determined in the presence of cold 1 uM S1P. Incubations are carried out at room temperature for 45-60 minutes before filtering onto GF/C filtration plates using a Packard 96 well harvester. Plates are dried before adding Microscint to each well, sealed and counted on a Topcount.

Abbreviations
ACN Acetonitrile
CHCl$_3$ Chloroform
CO$_2$ Carbon dioxide
DBAD Di-tert-butyl azodicarboxylate
DBU 1,8-Diazabicyclo(5.4.0)undec-7-ene
DCC N,N'-Dicyclohexylcarbodiimide
DIAD Diisopropyl azodicarboxylate
Dibal-H Diisobutylaluminum hydride
DIC N,N'-Diisopropylcarbodiimide
DIEA N,N-Diisopropylethylamine
DMA N,N-Dimethylacetamide DMF N,N-Dimethylformamide
DMSO Dimethyl sulfoxide
EDCI 1-(3-Dimethylaminopropyl)-3-ethylcarbodiimide
EtOAc Ethyl acetate
Et$_3$N Triethylamine
HBTU O-Benzotriazol-1-yl-N N,N',N'-tetramethyluronium hexafluorophosphate
HATU O-(7-Azabenzotriazol-1-yl)-N,N,N',N'-tetramethyluronium hexafluorophosphate
HCl Hydrochloric acid
HOBt 1-Hydroxybenzotriazole
HOAT 1-Hydroxy-7-azabenzotriazole
HPLC High Performance Liquid Chromatography
MeOH Methanol
NaOH Sodium hydroxide
PS-DCC Polymer-supported carbodiimide
PS-PPh$_3$ Polymer-supported triphenylphosphine
RBF Round bottom flask
RP Reverse Phase
R$_t$ Retention time
THF Tetrahydrofuran
i-PrOH 2-Propanol
PPh$_3$ Triphenylphosphine
SFC Super critical fluid chromatography
SOCl$_2$ Thionyl chloride Analytical Methods Analytical data is defined either within the general procedures or in the tables of examples. Unless otherwise stated, all $^1$H or $^{13}$C NMR data were collected on a Varian Mercury Plus 400 MHz or a Bruker DRX 400 MHz instrument; chemical shifts are quoted in parts per million (ppm). High-pressure liquid chromatography (HPLC) analytical data are either detailed within the experimental or referenced to the table of HPLC conditions, using the lower case method letter, in Table 1.

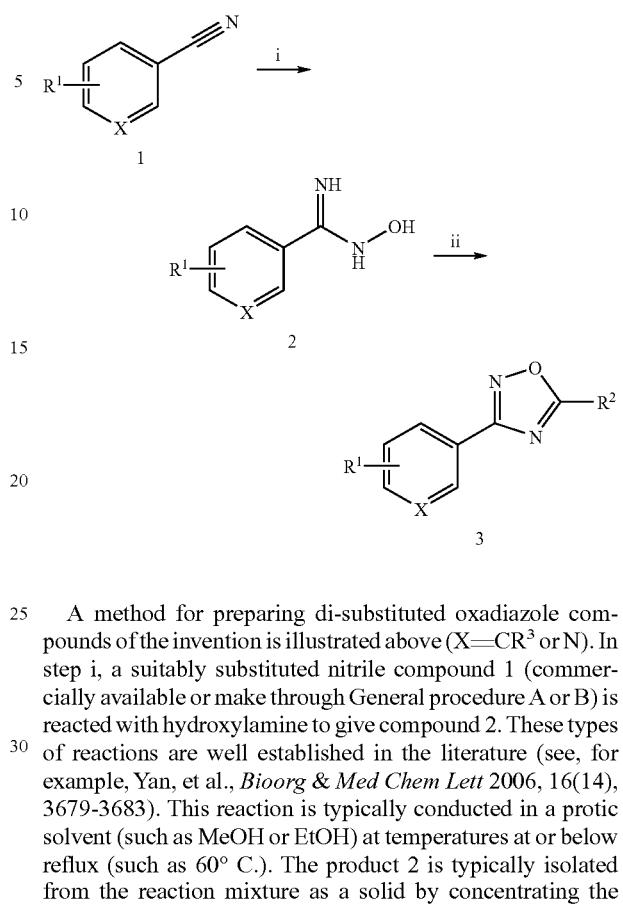

A method for preparing di-substituted oxadiazole compounds of the invention is illustrated above (X=CR$^3$ or N). In step i, a suitably substituted nitrile compound 1 (commercially available or make through General procedure A or B) is reacted with hydroxylamine to give compound 2. These types of reactions are well established in the literature (see, for example, Yan, et al., *Bioorg & Med Chem Lett* 2006, 16(14), 3679-3683). This reaction is typically conducted in a protic solvent (such as MeOH or EtOH) at temperatures at or below reflux (such as 60° C.). The product 2 is typically isolated from the reaction mixture as a solid by concentrating the

TABLE 1

List of HPLC methods

HPLC Conditions
Unless indicated otherwise mobile phase A was 10 mM ammonium acetate, mobile phase B was HPLC grade acetonitrile.

| Method | |
|---|---|
| a | 5-95% B over 3.7 min with a hold at 95% B for 1 min (1.3 mL/min flow rate). 4.6 × 50 mm Zorbax XDB C18 column (5 µm particles). Detection methods are diode array (DAD) and evaporative light scattering (ELSD) detection as well as pos/neg electrospray ionization. |
| b | 5-60% B over 1.5 min then 60-95% B to 2.5 min with a hold at 95% B for 1.2 min (1.3 mL/min flow rate). 4.6 × 30 mm Vydac Genesis C8 column (4 µm particles). Detection methods are diode array (DAD) and evaporative light scattering (ELSD) detection as well as pos/neg electrospray ionization. |
| c | 30-95% B over 2.0 min with a hold at 95% B for 1.7 min (1.0 mL/min flow rate). 4.6 × 30 mm Vydac Genesis C8 column (4 µm particles). Detection methods are diode array (DAD) and evaporative light scattering (ELSD) detection as well as pos/neg electrospray ionization. |
| d | 30-95% B over 2.0 min with a hold at 95% B for 1.5 min (1.0 mL/min flow rate). UV λ = 210-360 nm; Genesis C8, 4 µm, 30 × 4.6 mm column; ESI +ve/−ve) |
| e | A gradient of 10-100% acetonitrile (B) and 0.1% trifluoroacetic acid in water (A) is used, at a flow rate of 1.5 mL/min (0-0.1 min 10% A, 0.1-3.1 min 10-100% B, 3.1-3.9 min 100-10% B, 3.9-4.0 min 100-10% B). 2.1 mm × 30 mm Phenomenex Luna Combi-HTS C8 (5 µm particles). Detection methods are diode array (DAD) and evaporative light scattering (ELSD) detection as well as APCI ionization. |
| f | Gradient was 5-35% B in 4 min then 35-95% B to 6 min with a hold at 95% B for 1.7 min (1.3 mL/min flow rate). Mobile phase A was water with 0.1% formic acid, mobile phase B was HPLC grade acetonitrile. The column used for the chromatography was a 4.6 × 30 mm Vydac Genesis C8 column (4 µm particles). Detection methods are diode array (DAD) and evaporative light scattering (ELSD) detection as well as pos/neg electrospray ionization. | mixture. Compound 2 can be used as it is. Coupling of compound 2 with a suitable acid or acid chloride followed by ring closure to produce compound 3 is shown in step ii. The coupling reaction is typically carried out with carboxylic acids in the presence of a coupling reagent (such as HOBt, DCC) or with acid chlorides in the presence of an organic base (such as DIEA, Et$_3$N) at room temperature or elevated temperature (for example, 20-180° C.) in a solvent such as DMF or DMA. The subsequent ring closure reaction is complete in situ at elevated temperature (for example 160° C.) (see, for example, Wang, et al., *Org Lett* 2005 7(5), 925-928). The compounds 3 can then be isolated and purified using standard techniques (such as reverse-phase liquid chromatography or SFC).

General Synthetic Schemes

The general synthetic schemes that were utilized to construct the majority of compounds disclosed in this application are described below in (Schemes 1-3).

Scheme 1. General synthetic route to 4-alkoxy-benzonitrile (general procedure A, B)

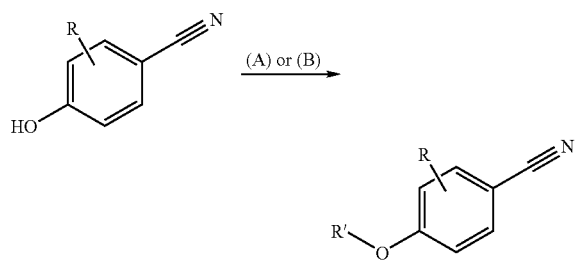

Scheme 2. General synthetic route to 3,5-disubstituted oxadiazole (general procedure C, D, and E)

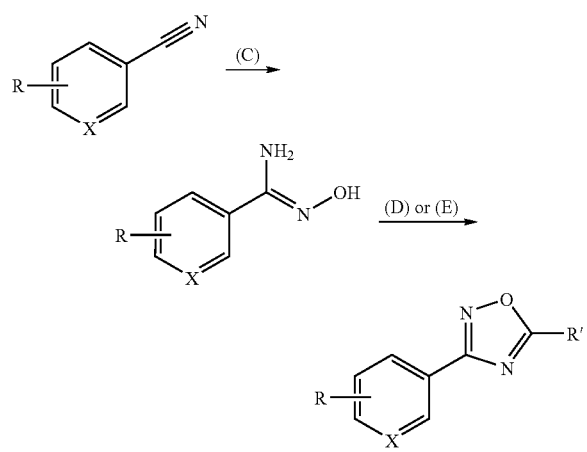

Scheme 3. General synthetic route to an acid chloride (general procedure F)

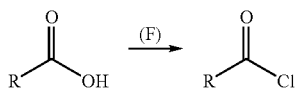

List of General Procedures
General Procedure A: Preparation of 4-alkoxy-benzonitrile Using Triphenylphosphine
General Procedure B: Preparation of 4-alkoxy-benzonitrile Using Polymer-bound Triphenylphosphine
General Procedure C: Preparation of Hydroxyamidine
General Procedure D: Oxadiazole Formation from an Acid
General Procedure E: Oxadiazole Formation from an Acid Chloride
General Procedure F: Formation of an Acid Chloride from an Acid
General Procedure G: Formation of Aldehyde from Nitrile
General Procedure H: Amination of Aldehyde
General Procedure I: Alkylation of Indole with Acrylate
General Procedure J: Alkylation of Indole with Bromide
General Procedure K: Deprotection of Tert-butyl Ester
General Procedure L: Amination of Aryl Halide
General Procedure M: Reaction of an Alkyl Bromide and a Phenol
General Procedure N: Debenzylation
General Procedure O: Deprotection of Protected 1,2-diol Example of use of General Procedures The general procedure letter codes constitute a synthetic route to the final product. A worked example of how the route is determined is given below using Example A.33 as a non-limiting illustration. Example A.33, 4-[3-(3-chloro-4-isopropoxy-phenyl)-[1,2,4]oxadiazol-5-yl]-pyridine was prepared from 3-chloro-N-hydroxy-4-isopropoxy-benzamidine using general procedure D, as represented in the following synthetic scheme:

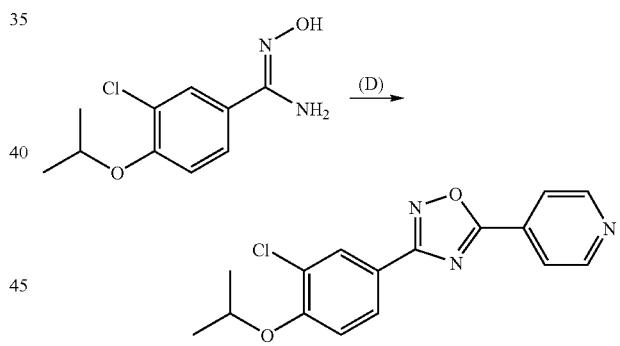

The precursor to Example A.33, 3-chloro-N-hydroxy-4-isopropoxy-benzamidine was prepared using the route (A, C). This translates into the following synthetic sequence, where the hydroxyamidine starting material used in general procedure D is the product by the following the procedure A and C, in the given order.

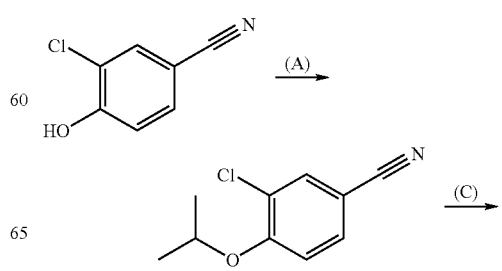

-continued

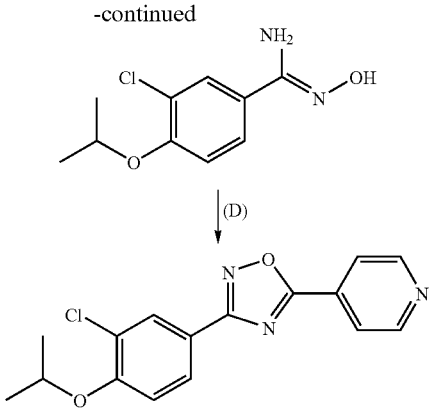

General Procedure A: Preparation of 4-alkoxy-benzonitrile using triphenylphosphine Triphenylphosphine (1-3 equivalents, preferably 1.6 equivalents) and 4-hydroxy-benzonitrile (preferably 1 equivalent) are dissolved in an anhydrous organic solvent such as dichloromethane, toluene, or tetrahydrofuran (preferably tetrahydrofuran) under an atmosphere of nitrogen. After a brief stirring, an azodicarboxylate such as diethyl azodicarboxylate, diisopropyl azodicarboxylate, or di-tert-butyl azodicarboxylate (preferably di-tert-butyl azodicarboxylate) (1-3 equivalents, preferably 1.6 equivalents) is added to the solution and the mixture is stirred for a few minutes before addition of an anhydrous alcohol (1-3 equivalents, preferably 1.25 equivalents). The reaction mixture is stirred at 0-100° C. (preferably about 23° C.) under an atmosphere of nitrogen for a period of about 2-24 hours (preferably 16 hours). The solvent is removed under reduced pressure. The crude product can be further purified by flash column chromatography.

Exemplification of General Procedure A

Preparation of 3-chloro-4-isopropoxy-benzonitrile

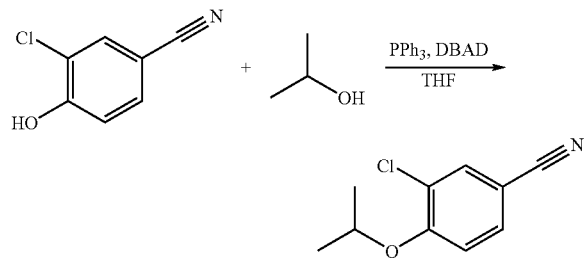

Into a round bottom flask containing triphenylphosphine (27.3 g, 104 mmol) and 3-chloro-4-hydroxy-benzonitrile (10 g, 65 mmol) was added anhydrous tetrahydrofuran (600 mL). The mixture was stirred briefly under nitrogen, di-tert-butyl azodicarboxylate (24 g, 104 mmol) was then added. The mixture was stirred for a few minutes, followed by addition of anhydrous isopropanol (6.23 mL, 81.4 mmol). The reaction mixture was stirred at room temperature overnight under nitrogen. The crude product was purified by flash chromatography using 1:4 (v/v) ethyl acetate/heptane as eluent. Fractions were dried to give 3-chloro-4-isopropoxy-benzonitrile (12.2 g, 91%) as a red-orange semi-solid.

LCMS (Table 1, Method d) $R_f$=2.36 min, m/z 152.1 $(M+H)^+$; $^1H$ NMR (400 MHz, DMSO-$d_6$) δ 7.74 (d, 1H), 7.61 (dd, 1H), 7.14 (d, 1H), 4.75 (sept., 1H), 1.34 (d, 6H)

General Procedure B: Preparation of 4-alkoxy-benzonitrile Using Polymer-bound Triphenylphosphine To an alcohol (preferably 1 equivalent) and 4-hydroxy-benzonitrile (preferably 1 equivalent) dissolved in a suitable solvent such as dichloromethane, dichloroethane, tetrahydrofuran, or 1,4-dioxane (preferable tetrahydrofuran) is added polymer-bound triphenylphosphine (1-3 equivalents, preferably 2 equivalents) and an azodicarboxylate such as diethyl azodicarboxylate, diisopropyl azodicarboxylate, or di-tert-butyl azodicarboxylate (preferably diisopropyl azodicarboxylate) (1-2 equivalents, preferably 1.5 equivalents). The mixture is shaken at about 0-100° C. (preferably about 23° C.) for a period of 4-24 hours (preferably 16 hours). The crude mixture is filtered and the resin is washed with a suitable solvent such as dichloromethane, dichloroethane, tetrahydrofuran, or 1,4-dioxane (preferably tetrahydrofuran). The filtrate is concentrated to dryness under reduced pressure and the residue is subject to General Procedure C.

Exemplification of General Procedure B

Preparation of 3-chloro-4-(1-ethyl-propoxy)-benzonitrile

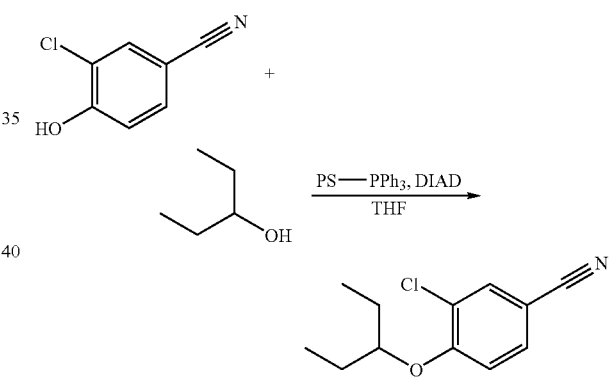

Into a scintillation vial containing a solution of pentan-3-ol (22 mg, 0.25 mmol) dissolved in THF (2 mL) was added a solution of 3-chloro-4-hydroxy-benzonitrile (38 mg, 0.25 mmol) in THF (2 mL) followed by PS-PPh$_3$ resin (357 mg, 0.5 mmol, loading 1.4 mmol/g) and a solution of DIAD (76 mg, 0.375 mmol) in THF (2 mL). The vial was capped and shaken at room temperature overnight. The reaction mixture was filtered and the resin was washed with THF (4 mL). The filtrate was concentrated to dryness to give 3-chloro-4-(1-ethyl-propoxy)-benzonitrile.

General Procedure C: Preparation of Hydroxyamidine

To a solution of benzonitrile (1 equivalent) in a suitable solvent such as methanol, ethanol, isopropanol, or water (preferably ethanol) is added (1-50 equivalents, preferably 1.1 equivalents). The reaction mixture is heated at about 25-100° C. (preferably 60° C.) for a period of about 2-24 hours (preferably 16 hours). The solvents are removed under reduced pressure. The crude product is dried under vacuum and then subjected to General Procedure D or E.

Exemplification of General Procedure C

Preparation of 3-chloro-N-hydroxy-4-isopropoxy-benzamidine

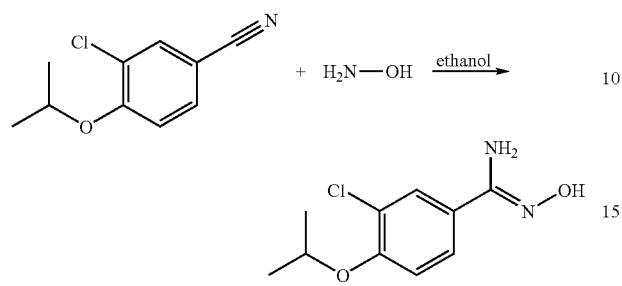

Into a round bottom flask was added 3-chloro-4-isopropoxy-benzonitrile (5.00 g, 25.6 mmol), hydroxylamine (50% by weight in water, 1.86 mL, 28.1 mmol) and ethanol (150 mL). The mixture was heated at about 60° C. overnight. Upon completion of the reaction, the mixture was concentrated to dryness under reduced pressure to give 3-chloro-N-hydroxy-4-isopropoxy-benzamidine (5.76 g, 94%) as a light yellow solid.

LCMS (Table 1, Method a) $R_f$=2.09 min, m/z 229 (M+H)$^+$; $^1$H NMR (400 MHz, DMSO-d$_6$) δ 9.58 (s, 1H), 7.70 (d, 1H), 7.59 (dd, 1H), 7.15 (d, 1H), 5.81 (s, 2H), 4.69 (sept., 1H), 1.29 (d, 6H)

General Procedure D: Oxadiazole Formation from an Acid

To a reaction vial is added a hydroxyamidine (0.9-1.5 equivalents, preferably 1.1 equivalent), an acid (0.9-1.5 equivalents, preferably 1 equivalent), a coupling reagent such as HBTU, HATU, HOBt, or polymer-bound HOBt (preferably HOBt) (1-2 equivalents, preferably 1 equivalent), a carbodiimide such as EDCI, DIC, DCC or polymer-bound DCC (preferably polymer-bound DCC) (1.5-3 equivalents, preferably 3 equivalents), a base such as diisopropylethylamine, triethylamine, or N-methylmorpholine (preferably diisopropylamine) (1-3 equivalents, preferably 3 equivalents) and a suitable solvent such as DMF, DMA, or acetonitrile (preferably acetonitrile). The reaction vial is capped and heated (conventional heating or microwave heating, preferably microwave heating) at 100-200° C. (preferably 160° C.) for a period of 15-45 minutes (preferably 30 minutes). After cooling down to room temperature, the crude reaction mixture is filtered, washed with a suitable solvent such as DMF, DMA, or acetonitrile (preferably acetonitrile), and the filtrate is concentrated to dryness under reduced pressure. The crude product is further purified by chromatography.

Exemplification of General Procedure D

Preparation of 4-[3-(3-chloro-4-isopropoxy-phenyl)-[1,2,4]oxadiazol-5-yl]-3-methyl-pyridine

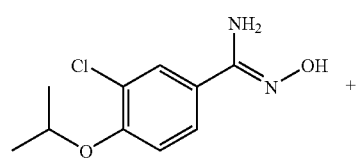

-continued

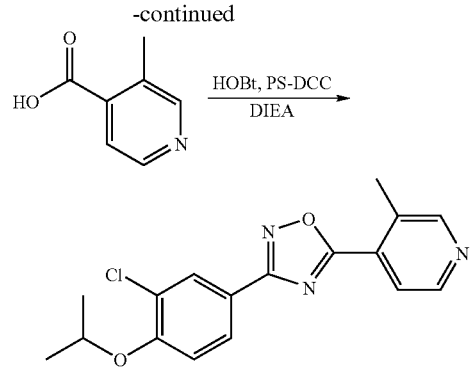

To a microwave vial charged with 3-chloro-N-hydroxy-4-isopropoxy-benzamidine (75 mg, 0.328 mmol), 3-methyl-isonicotinic acid (41 mg, 0.298 mmol), HOBt (46 mg, 0.298 mmol), PS-carbodiimide (720 mg, 0.894 mmol, loading 1.24 mmol/g) was added acetonitrile (3.5 mL) and diisopropylethylamine (156 µL, 0.894 mmol). The reaction vial was capped and heated at about 160° C. for about 30 minutes in a Biotage microwave. The reaction mixture was filtered and the resin was washed with acetonitrile (4 mL). Filtrate was concentrated to dryness. The crude product was purified via reverse phase HPLC (30-90% acetonitrile, 30 minute ramp) to give 10.2 mg (10%) of 4-[3-(3-chloro-4-isopropoxy-phenyl)-[1,2,4]oxadiazol-5-yl]-3-methyl-pyridine.

LCMS (Table 1, Method c) $R_f$=2.70 min, m/z 330 (M+H)$^+$; $^1$H NMR (400 MHz, DMSO-d$_6$) δ 8.77 (s, 1H), 8.69 (d, 1H), 8.06 (d, 1H), 8.01 (dd, 2H), 7.39 (d, 1H), 4.83 (sept., 1H), 2.70 (s, 3H), 1.35 (d, 6H)

General Procedure E: Oxadiazole Formation from an Acid Chloride

To a solution of 3-chloro-N-hydroxy-4-alkoxy-benzamidine (preferably 1 equivalent) in pyridine is added a solution of an acid chloride (1-3 equivalents, preferably 2 equivalent) in pyridine. The reaction mixture is heated at 60-100° C. (preferably 100° C.) for a period of 8-24 hours (preferably 20 hours). The solvent is removed under reduced pressure and the residue is further purified by chromatography.

Exemplification of General Procedure E

Preparation of 3-[3-chloro-4-(1-ethyl-propoxy)-phenyl]-5-o-tolyl-[1,2,4]oxadiazole

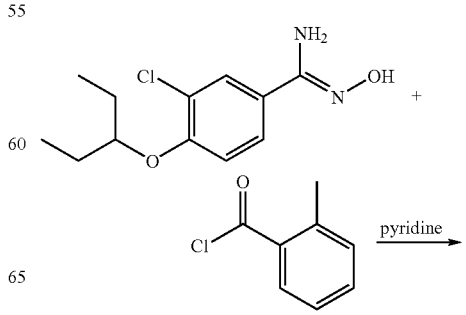

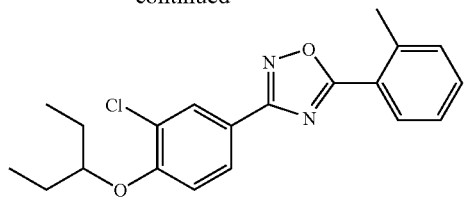

To a solution of 3-chloro-4-(1-ethyl-propoxy)-N-hydroxy-benzamidine (64 mg, 0.25 mmol) (prepared by General procedure B) in pyridine (1 mL) was added a solution of 2-methylbenzoyl chloride (77 mg, 0.5 mmol) in pyridine (1 mL). The mixture was heated at about 100° C. overnight. The solvent was removed under reduced pressure and the crude product was purified via SFC(CO$_2$/pure MeOH; gradient: 5% hold for 0.5 min, ramp at 7.3% to 50% over 6.5 min, hold at 50% for 1 min) to give 3-[3-chloro-4-(1-ethyl-propoxy)-phenyl]-5-o-tolyl-[1,2,4]oxadiazole (16.5 mg, 18.5%).

LCMS (Table 1, Method b) R$_f$=3.18 min, m/z 356.13 (M−H)$^-$; $^1$H NMR (400 MHz, CHCl$_3$) δ 8.19 (d, 1H), 8.16 (dd, 1H), 8.01 (dd, 1H), 7.48 (m, 1H), 7.37 (d, 1H), 7.01 (d, 1H), 4.28 (m, 1H), 1.77 (m, 4H), 1.01 (t, 6H)

Preparation of 3-(3-chloro-4-isopropoxyphenyl)-5-(3-chloropyridin-4-yl)-[1,2,4]-oxadiazole

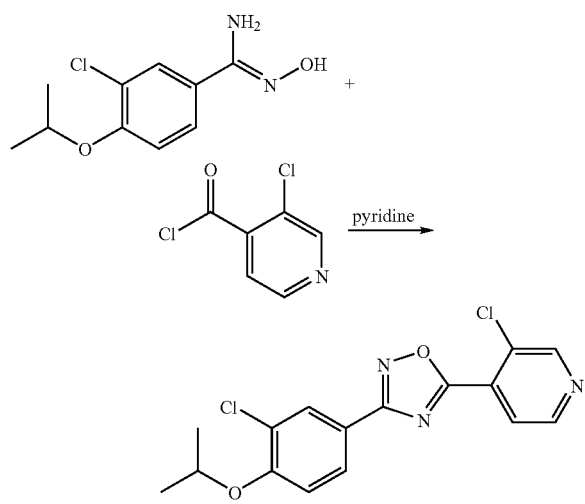

To a solution of 3-chloroisonicotinoyl chloride (about 2.6 mmol) (prepared by General procedure F) in pyridine (5 mL) was added 3-chloro-4-isopropoxy-N-hydroxy-benzamidine (300 mg, 1.31 mmol) (prepared by General procedure B). The mixture was heated at 100° C. overnight. The solvent was removed under reduced pressure and the crude product was purified via normal phase silica gel chromatography (0-50% ethyl acetate/heptane gradient over 30 min) to give 3-(3-chloro-4-isopropoxyphenyl)-5-(3-chloropyridin-4-yl)-[1,2,4]-oxadiazole (323 mg, 70.3%).

LCMS (Table 1, Method b) R$_f$=3.88 min, m/z 349.04 (M−H)$^-$; $^1$H NMR (400 MHz, CHCl$_3$) δ=8.84 (d, 1H), 8.69 (d, 1H), 8.11 (d, 1H), 8.02 (d, 1H), 7.99 (dd, 1H), 7.02, (d, 1H), 4.69 (m, 1H), 1.44 (d, 6H)

General Procedure F: Formation of an acid chloride from an acid

To an acid (preferably 1 equivalent) in a suitable solvent, such as dichloromethane, dichloroethane (preferably dichloromethane) is added a chlorinating reagent such as thionyl chloride, oxalyl chloride (preferably thionyl chloride) (1-100 equivalents, preferably 3 equivalents). The reaction mixture is stirred at 20-80° C. (preferably at about 23° C.) for a period of 1-24 hours (preferably 3 hours). The solvent is removed under reduced pressure. The crude product is dried under vacuum and then subjected General Procedure E.

Exemplification of General Procedure F

Preparation of 3-methyl-isonicotinoyl Chloride

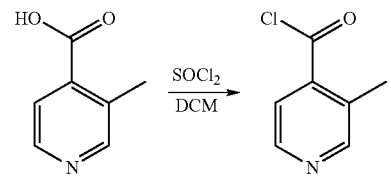

To 3-methylisonicotinic acid (100 mg, 0.729 mmol) suspended in DCM (2.5 mL) was added thionyl chloride (260 mg, 2.188 mmol). The reaction mixture was stirred at room temperature for about 3 hours. The solvent was removed under reduced pressure and the residue was dried under high vacuum for 1 hour to give 3-methyl-isonicotinoyl chloride.

Preparation of 3-methyl-isonicotinoyl Chloride

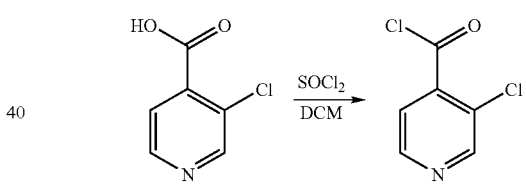

To 3-chloroisonicotinic acid (413 mg, 2.62 mmol) was added thionyl chloride (5 mL, 68.5 mmol). The reaction mixture was stirred at room temperature for about 20 hours. The solution was concentrated under reduced pressure and the residue was dried under high vacuum for 1 hour to give 3-chloro-isonicotinoyl chloride.

General Procedure G: Formation of Aldehyde from Nitrile

A mixture of a nitrile in a round bottom flask containing (0.9-1.2 equivalents, preferably 1.0 equivalents) in a suitable solvent such as dichloromethane or dichloroethane (preferably dichloromethane) was cooled to between 0° C. and −60° C. (preferably 40° C.). A solution of DIBAL (0.9-2.5 equivalents, preferably 2.0 equivalents) was added dropwise and then stirred for 15-45 minutes (preferably 30 minutes), quenched with methanol, warmed to ambient temperature and treated with a 10% solution of Rochelle's salt. After extraction with DCM the combined organic layers were stirred with dilute aqueous acid (preferably 1M aqueous HCl). The layers were separated and the aqueous layer extracted with DCM. The combined organic layers were washed with brine, dried over MgSO$_4$ or Na$_2$SO$_4$, filtered and evaporated to dryness. The crude product is further purified by chromatography.

Exemplification of General Procedure G

Preparation of 3-chloro-4-(3-(3-chloro-4-isopropoxyphenyl)-1,2,4-oxadiazol-5-yl)benzonitrile

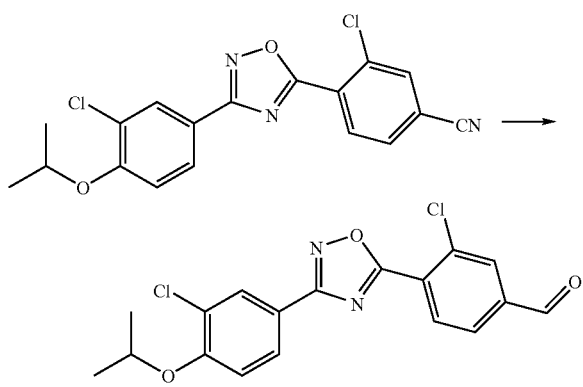

To a 100 mL RBF equipped with septa cap outfitted with nitrogen inlet needle was charged with 3-chloro-4-(3-(3-chloro-4-isopropoxyphenyl)-1,2,4-oxadiazol-5-yl)benzonitrile (1.529 g, 3.27 mmol) in DCM (65.4 ml) to give an orange solution. The reaction mixture was cooled to about −40° C. via acetonitrile-dry ice bath. DIBAL-H (3.60 ml, 3.60 mmol) was then added dropwise at about −40° C. The resulting mixture was stirred for about 2 hrs at about −40° C. Methanol (0.5 ml, 12.36 mmol) was then added dropwise to the reaction mixture at about −40° C. The ice bath was removed and the reaction was left to warm to ambient temperature then Rochelle's salt solution (60 mL) was added. The resulting mixture was stirred vigorously for about 3 hrs. The aqueous layer was separated. The organic phase was washed with brine, dried (MgSO$_4$) and concentrated to give crude yellow oil. The residue was purified via Analogix FC system using RediSep RS 120 g column, with a gradient of 0-15% EtOAc/Heptane over 40 min. at 40 mL/min then hold at 15% until all peaks eluted. Fractions containing product were combined and concentrated to yield 3-chloro-4-(3-(3-chloro-4-isopropoxyphenyl)-1,2,4-oxadiazol-5-yl)benzonitrile (0.791 g, 2.09 mmol). $^1$H NMR (400 MHz, CDCl$_3$) δ ppm 10.09 (s, 1H), 8.35 (d, J=8.02 Hz, 1H), 8.21 (d, J=1.90 Hz, 1H), 8.09 (s, 1H), 8.03 (dd, J=8.56, 1.86 Hz, 1H), 7.94 (dd, J=8.04, 0.79 Hz, 1H), 7.05 (d, J=8.62 Hz, 1H), 4.69 (td, J=12.05, 6.04 Hz, 1H), 1.45 (t, J=6.80 Hz, 6H).

General Procedure H: Amination of Aldehyde

A mixture of an amine (0.9-1.2 equivalents, preferably 1.1 equivalents), an aldehyde (0.9-1.2 equivalents, preferably 1.0 equivalents), a suitable reducing agent, such as polymer supported sodium cyanoborohydride or sodium cyanoborohydride (preferably polymer supported sodium cyanoborohydride)(1.5-3.0 equivalents, preferably 2.0 equivalents), acetic acid (2-24 drops, preferably 6 drops) and a suitable solvent such as DCM or methanol (preferably DCM) was stirred at ambient temperature for 4-72 hours, preferably 24 hours. The crude product is further purified by chromatography.

Exemplification of General Procedure H

Preparation of 1-(3-chloro-4-(3-(3-chloro-4-isopropoxyphenyl)-1,2,4-oxadiazol-5-yl)benzyl)-3-methylazetidin-3-carboxylic acid

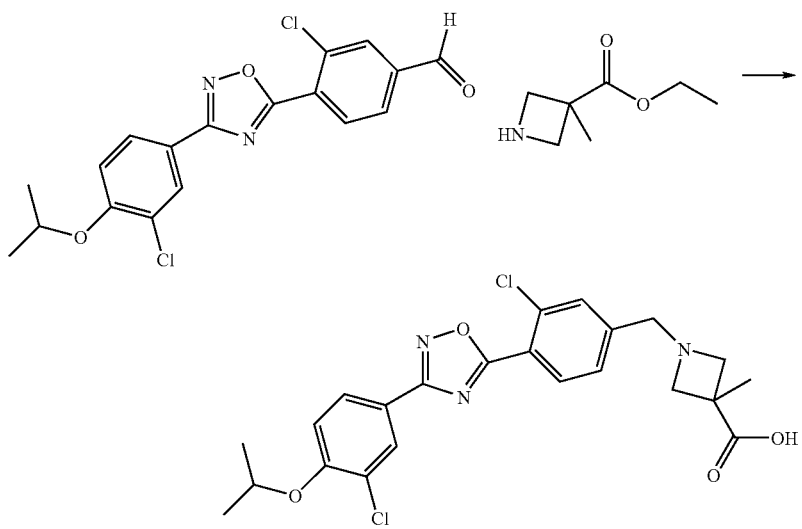

A 500-mL RBF was charged with 3-chloro-4-(3-(3-chloro-4-isopropoxyphenyl)-1,2,4-oxadiazol-5-yl)benzaldehyde (0.745 g, 1.975 mmol), ethyl 3-methylazetidine-3-carboxylate (0.566 g, 3.95 mmol) (*Tetrahedron Letter* 1991, 32, 36, 4795-4798) and methanol (197 ml). To this was added acetic acid (0.904 ml, 15.80 mmol). The resulting mixture was stirred at ambient temperature for about 1 hr then sodium cyanoborohydride (0.095 g, 1.512 mmol) was added in one portion. The reaction was stirred for about 17 hrs at ambient temperature. The progress of the reaction was monitored by LCMS. The reaction was concentrated in vacuo to give crude dark yellow oil. The residue was purified via Analogix FCC system using 120 g Redi-Sep column, with a gradient of 0-40% EtOAc/Heptane over 45 min. at 50 mL/min then held at 40% EtOAc until all peaks eluted. Fractions containing product were combined and concentrated to yield 0.820 g (1.626 mmol) of colorless oil. The material was dissolved in THF (80 ml). To this was added NaOH (9.0 ml, 9.00 mmol) as 1N solution, followed by MeOH (about 25 ml). The reaction was stirred at ambient temperature for about 3 hrs, after which the LCMS showed that hydrolysis was complete. To the reaction mixture was added HCl (9.0 ml, 9.00 mmol) as 1N solution dropwise to neutralize the pH. The reaction mixture was concentrated in vacuo then lyophilized to dryness. The crude white solid was triturated in diethyl ether and DCM then filtered. The resulting solid was washed with copious amount of water then oven-dried overnight to give 1-(3-chloro-4-(3-(3-chloro-4-isopropoxyphenyl)-1,2,4-oxadiazol-5-yl)benzyl)-3-methylazetidine-3-carboxylic acid (0.377 g, 0.75 mmol) as white solid. LCMS (Table 1, Method a) $R_t$=1.81 min.; MS m/z: 476.15 (M+H)$^+$. $^1$H NMR (400 MHz, DMSO) δ ppm 12.67-12.25 (m, 1H), 8.24-7.93 (m, 3H), 7.73-7.32 (m, 3H), 4.90-4.76 (m, 1H), 3.69 (s, 2H), 3.43 (d, J=6.51 Hz, 2H), 3.09 (d, J=6.43 Hz, 2H), 1.45 (s, 3H), 1.35 (d, J=5.75 Hz, 6H).

General Procedure I: Alkylation of Indole with Acrylate

To a solution of an indole (0.9-1.2 equivalents, preferably 1.0 equivalents) in a suitable solvent such as acetonitrile at 60° C. was added an acrylate (1.0-2.0 equivalents, preferably 1.5 equivalents) and a base such as DBU (0.3-1.0 equivalents, preferably 0.5 equivalents). The mixture was stirred at about 50° C. overnight. The solvent was removed under reduced pressure and the crude product was dissolved in DCM, washed with brine, dried over MgSO$_4$ or Na$_2$SO$_4$, filtered and solvent removed under reduced pressure. The crude product is further purified by chromatography or recrystallization.

Exemplification of General Procedure I

Preparation of tert-butyl 3-(4-(3-(3-chloro-4-isopropoxyphenyl)-1,2,4-oxadiazol-5-yl)-1H-indol-1-yl)propanoate

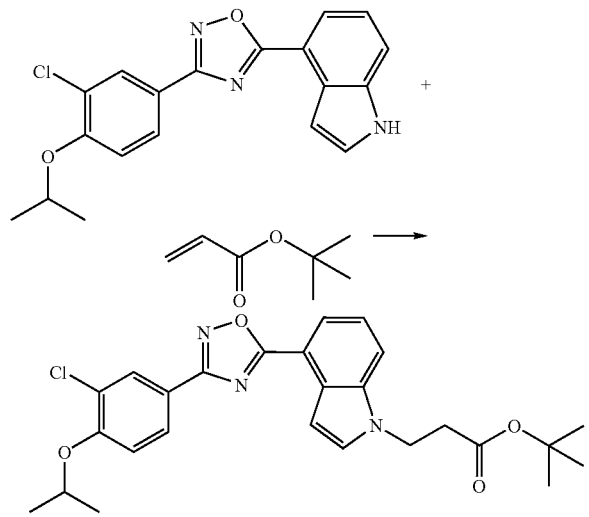

To a solution of 3-(3-chloro-4-isopropoxyphenyl)-5-(1H-indol-4-yl)-1,2,4-oxadiazole (5.6 g, 15.83 mmol) in acetonitrile (55.9 ml) at about 60° C. was added tert-butyl acrylate (3.45 ml, 23.74 mmol) drop wise, followed by DBU (1.193 ml, 7.91 mmol). The mixture was stirred at about 50° C. overnight. The solvent was removed under reduced pressure and the crude product was dissolved in DCM (150 mL), washed with brine (3×100 mL) dried over MgSO$_4$, filtered and solvent removed under reduced pressure. Re-crystallization from 30-60° C. petroleum ether gave tert-butyl 3-(4-(3-(3-chloro-4-isopropoxyphenyl)-1,2,4-oxadiazol-5-yl)-1H-indol-1-yl) propanoate (5.42 g, 69.6%). LCMS (Table 1, Method b) $R_t$=3.03 min, m/z 482.26 (M+H)$^+$.

General Procedure J: Alkylation of Indole with Bromide

To a solution of an indole (0.9-1.2 equivalents, preferably 1.0 equivalents) in a suitable solvent such as DMF was added NaH (0.9-1.2 equivalents, preferably 1.1 equivalents). After about 15 min an alkyl bromide (0.9-2.0 equivalents, preferably 1.5 equivalents) was added and the reaction mixture was heated to about 50° C. After about 24 h the reaction mixture was cooled to ambient temperature, evaporated to dryness and the crude product is further purified by chromatography.

Exemplification of General Procedure J

Preparation of tert-butyl 4-(4-(3-(3-chloro-4-isopropoxyphenyl)-1,2,4-oxadiazol-5-yl)-1H-indol-1-yl)butanoate

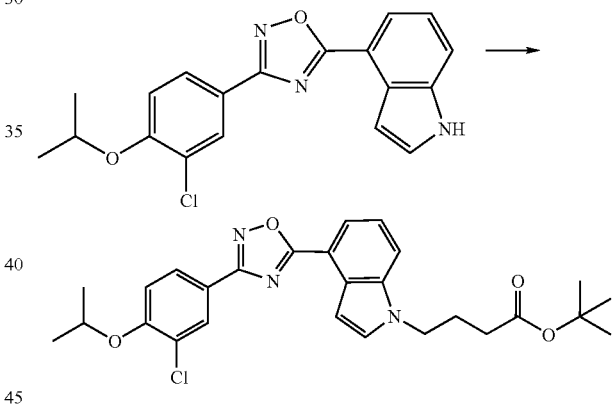

To a solution of 3-(3-chloro-4-isopropoxyphenyl)-5-(1H-indol-4-yl)-1,2,4-oxadiazole (0.100 g, 0.283 mmol) in DMF (0.999 ml) was added NaH (0.012 g, 0.311 mmol). After about 15 min tert-butyl 4-bromobutanoate (0.095 g, 0.424 mmol) was added and the reaction mixture was heated to about 50° C. After about 24 h the reaction mixture was cooled to ambient temperature, concentrated in vacuo and purified by chromatography on silica gel (eluting with EtOAc/Hep) to provide tert-butyl 4-(4-(3-(3-chloro-4-isopropoxyphenyl)-1,2,4-oxadiazol-5-yl)-1H-indol-1-yl)butanoate (0.135 g, 93%) as a colorless oil that solidified on standing.

LCMS (Table 1, Method c) $R_t$=3.50 min, m/z 496 (M+H)$^+$.

General Procedure K: Deprotection of tert-butyl Ester

To a solution of a tert-butyl ester (0.9-1.2 equivalents, preferably 1.0 equivalents) in a suitable solvent such as DCM was added trifluoroacetic acid (15-25 equivalents, preferably 20 equivalents). The mixture was stirred at ambient temperature for about 8 hr. The solvent was removed under reduced pressure and crude product is further purified by chromatography or recrystallization.

Exemplification of General Procedure K:

Preparation of 3-(4-(3-(3-chloro-4-isopropoxyphenyl)-1,2,4-oxadiazol-5-yl)-1H-indol-1-yl)propanoic acid

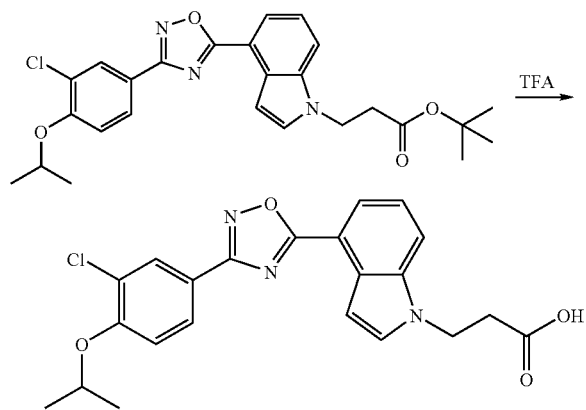

To a solution of tert-butyl 3-(4-(3-(3-chloro-4-isopropoxyphenyl)-1,2,4-oxadiazol-5-yl)-1H-indol-1-yl) propanoate oxadiazole (5.25 g, 10.89 mmol) in DCM (136 ml) was added trifluoroacetic acid (16.78 ml, 218 mmol). The mixture was stirred at ambient temperature for about 8 hr. The solvent was removed under reduced pressure and the solid residue was triturated with ether to give 3-(4-(3-(3-chloro-4-isopropoxyphenyl)-1,2,4-oxadiazol-5-yl)-1H-indol-1-yl) propanoic acid (4.35 g, 93.0%). LCMS (Table 1, Method b) $R_t$=3.03 min, m/z 356.13 (M–H)⁻; ¹H NMR (400 MHz, DMSO) δ 12.39 (s, 1H), 8.13 (m, 1H), 8.07 (m, 1H), 8.00 (d, 1H), 7.94 (d, 1H), 7.7 (d, 1H), 7.41 (m, 2H), 7.18 (d, 1H), 4.84 (s, 1H), 4.53 (td, 2H), 2.82 (td, 2H), 1.36 (d, 6H).

General Procedure L: Amination of Aryl Halide

To a microwave reaction vial is added an aryl fluoride or bromide (preferably fluoride) (0.9-1.2 equivalents, preferably 1.0 equivalents), an amine (0.9-1.5 equivalents, preferably 1.1 equivalents) potassium carbonate (1.5-3.0 equivalents, preferably 2.0 equivalents) and a suitable solvent such as DMF or DMA (preferably DMF). The reaction vial is capped and heated with cooling at 140-200° C. (preferably 160° C. for (15-45 minutes (preferably 30 minutes). The crude product is further purified by chromatography.

Exemplification of General Procedure L

Preparation of (1R,3S)-3-(4-(3-(3-chloro-4-isopropoxyphenyl)-1,2,4-oxadiazol-5-yl)phenylamino) cyclopentanecarboxylic acid

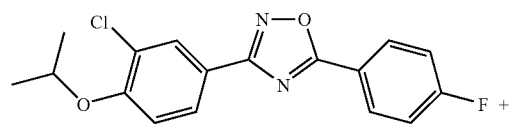

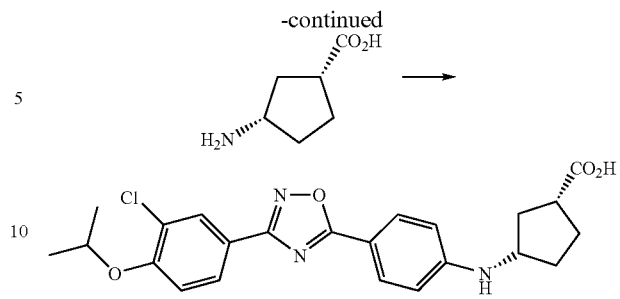

3-(3-Chloro-4-isopropoxyphenyl)-5-(4-fluorophenyl)-1,2,4-oxadiazole (360 mg, 1.082 mmol), (1R,3S)-3-aminocyclopentanecarboxylic acid (154 mg, 1.190 mmol), potassium carbonate (329 mg, 2.380 mmol) and DMF (2 ml) was heated with cooling at 160° C. on the Biotage microwave for 30 minutes. The mixture was diluted with DMSO (6 ml) and MeCN (8 ml), filtered and divided into 8 aliquots for purification by molecular ion directed LCMS. The fractions were combined and evaporated to afford a pale brown solid that was dried in vacuo at about 60° C. for about 3 hours. This gave (1R,3S)-3-(4-(3-(3-chloro-4-isopropoxyphenyl)-1,2,4-oxadiazol-5-yl)phenylamino)cyclopentanecarboxylic acid (212 mg, 0.480 mmol, 44.3% yield) as a pale brown solid. LCMS (Table 1, Method a) $R_t$=3.49 min, m/z 440.20 (M–H)⁻. ¹H NMR (400 MHz, DMSO δ ppm 4.81 (s, 1H), 3.96-3.76 (m, 1H), 2.78 (s, 1H), 2.42-2.25 (m, 1H), 2.12-1.95 (m, 1H), 1.89 (d, J=7.72 Hz, 2H), 1.73-1.61 (m, 1H), 1.61-1.48 (m, 1H), 1.39-1.30 (m, 7H), 12.22-12.07 (m, 1H), 6.73 (d, J=8.82 Hz, 2H), 6.87-6.79 (m, 1H), 7.36 (d, J=8.63 Hz, 1H), 7.87 (d, J=8.59 Hz, 2H), 7.98 (ddd, J=9.78, 1.97, 1.06 Hz, 2H).

General Procedure M: Reaction of an alkyl bromide and a phenol

Triphenylphosphine (0.9-1.2 equivalents, preferably 1.0 equivalents) in a suitable solvent such as THF was cooled to 0° C. by ice-bath. After stirring for 15 min, diisopropyl azodicarboxylate (0.9-1.2 equivalents, preferably 1.0 equivalents) was added dropwise over 5 min. The reaction mixture was stirred at 0° C. for 30 min. Then a phenol (0.9-1.2 equivalents, preferably 1.0 equivalents) and an alkyl bromide (0.9-1.2 equivalents, preferably 0.9 equivalents) in a suitable solvent such as THF were added to the mixture, keeping the temperature at or below 0° C. The mixture is stirred for 2 hr at 0° C. then slowly warmed to ambient temperature and stirred over the weekend. The mixture was concentrated in vacuo and the crude product is further purified by chromatography.

Preparation of benzyl 4-(2-tert-butoxy-2-oxoethoxy)benzoate

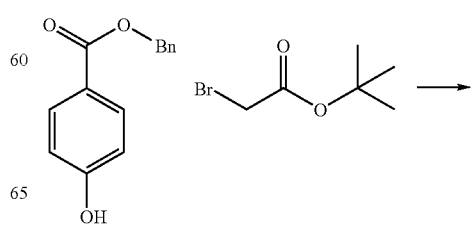

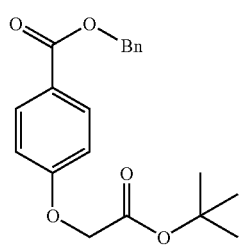

In a 100 mL round bottomed flask benzyl 4-hydroxybenzoate (1.445 g, 6.33 mmol) and potassium carbonate (4.17 g, 30.1 mmol) in acetone (100 ml) were combined. Tert-butyl 2-bromoacetate (0.908 ml, 6.03 mmol) was added dropwise. The solution was stirred at 65° C. overnight. The solution was cooled then, the reaction mixture was filtered through a sintered glass funnel. The filtrate was concentrated to afford pale yellow oil, which was purified via silica gel chromatography (40 g, 30% EtOAc:Heptane) to afford benzyl 4-(2-tert-butoxy-2-oxoethoxy)benzoate (2.06 g, 5.90 mmol, 98% yield) as colorless oil. LC/MS (Table 1, Method a) $R_f$=4.31 min.

General Procedure N: Debenzylation

A high-pressure flask was charged with palladium on carbon (0.9-1.2 equivalents, preferably 1.0 equivalents), then a suitable solvent such as MeOH (200 ml), then a benzoate ester (50-70 equivalents, preferably 60 equivalents) were added. The resulting suspension was allowed to shake under an atmosphere of hydrogen (35 Psi) at ambient temperature for 2 hrs. The mixture was filtered through Celite® and the colorless filtrate was concentrated to afford the product.

Exemplification of General Procedure N

Preparation of 4-(2-tert-butoxy-2-oxoethoxy)benzoic acid

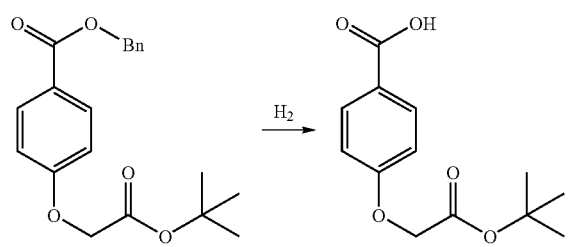

A 500 mL high-pressure flask was charged with benzyl 4-(2-tert-butoxy-2-oxoethoxy)benzoate (2.06 g, 6.02 mmol) in methanol (100 ml). Palladium on carbon (0.320 g, 0.301 mmol) was added, the resulting suspension was allowed to shake under an atmosphere of hydrogen (47 Psi) at room temperature for 6 h. The mixture was filtered through Celite®), the colorless filtrate was concentrated to afford 4-(2-tert-butoxy-2-oxoethoxy)benzoic acid (1.5 g, 5.95 mmol, 99% yield) as pale yellow solid. LC/MS (Table 1, Method a) $R_f$=3.03 min.; MS m/z: 251.30 (M−H)⁻. $^1$H NMR (400 MHz, Solvent d-DMSO) ppm 7.88 (d, J=8.99 Hz, 2H), 6.98 (d, J=9.00 Hz, 2H), 4.75 (s, 2H), 1.43 (s, 9H).

General Procedure O: Deprotection of a Protected 1,2 diol

To a solution of protected diol (0.9-1.2 equivalents, preferably 1.0 equivalents) in a suitable solvent such as THF was added a solution of 1M HCl (1.5-2.5 equivalents, preferably 2.0 equivalents). The mixture was heated to 70° C. for about 2 h. After cooling to ambient temperature a solution of an aqueous base such as 1M NaOH was added and the reaction mixture was concentrated in vacuo. The resulting solid was washed with copious amounts of water and dried in vacuo to provide afford the product.

Exemplification of General Procedure O

Preparation of 3-(4-(3-(3-chloro-4-isopropoxyphenyl)-1,2,4-oxadiazol-5-yl)phenoxy)propane-1,2-diol

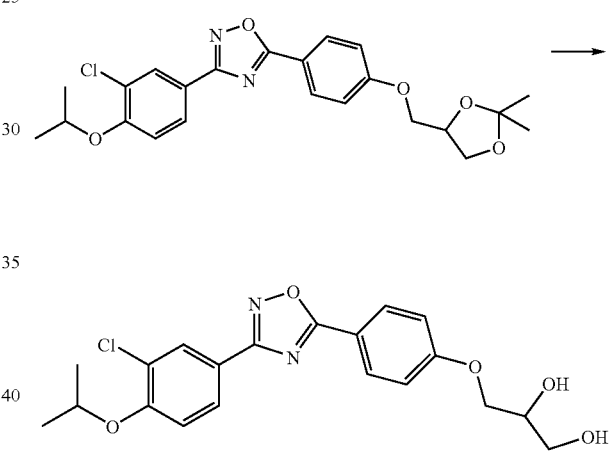

3-(3-chloro-4-isopropoxyphenyl)-5-(4-((2,2-dimethyl-1,3-dioxolan-4-yl)methoxy)phenyl)-1,2,4-oxadiazole (0.1 g, 0.225 mmol) and p-toluenesulfonic acid monohydrate (8.55 mg, 0.045 mmol) were added in methanol (2.4 mL). The reaction mixture was heated at 70° C. for 16 hr. The solution was cooled, methanol (1.5 mL) was added to the mixture and recrystallized, the resulted suspension was filtered, the solid was washed by abundant water to afford 3-(4-(3-(3-chloro-4-isopropoxyphenyl)-1,2,4-oxadiazol-5-yl)phenoxy)propane-1,2-diol (0.08 g, 0.198 mmol, 88% yield) as white solid. LC/MS (Purity QC) $R_f$=2.97 min.; MS m/z: 405.18 (M+H)⁺. $^1$H NMR (400 MHz, Solvent d-DMSO) ppm 8.16-8.09 (m, 2H), 8.05 (d, J=2.13 Hz, 1H), 7.99 (dd, J=8.64, 2.15 Hz, 1H), 7.38 (d, J=9.05 Hz, 1H), 7.25-7.16 (m, 2H), 5.03 (d, J=5.19 Hz, 1H), 4.87-4.78 (m, 1H), 4.72 (t, J=5.68 Hz, 1H), 4.15 (dd, J=3.97, 10.01 Hz, 1H), 4.01 (dd, J=6.20, 10.03 Hz, 1H), 3.84 (dt, J=4.04, 5.69, 5.91 Hz, 1H), 3.47 (t, J=5.84 Hz, 2H), 1.35 (d, J=6.03 Hz, 6H).

Tables Utilizing General Procedures

TABLE A

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R_t/min (method) | m/z |
|---|---|---|---|---|---|---|
| A.1 | 3-Chloro-4-cyclopropyl-methoxy-benzonitrile (B) | 2-Methyl-benzoyl chloride | | 3-(3-Chloro-4-cyclopropylmethoxy-phenyl)-5-o-tolyl-[1,2,4]oxadiazole | 2.94 (b) | 340 (M − H)⁻ |
| A.2 | 4-Butoxy-3-chloro-benzonitrile (B) | 2-Methyl-benzoyl chloride | | 3-(4-Butoxy-3-chloro-phenyl)-5-o-tolyl-[1,2,4]oxadiazole | 3.10 (b) | 342 (M − H)⁻ |
| A.3 | 3-Chloro-4-isobutoxy-benzonitrile (B) | 2-Methyl-benzoyl chloride | | 3-[3-Chloro-4-(1-methyl-cyclopropylmethyoxy)-phenyl]-5-o-tolyl-[1,2,4]oxadiazole | 3.11 (b) | 342 (M − H)⁻ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.4 | 3-Chloro-4-(1-methyl-cyclopropylmethoxy)-benzonitrile (B) | 2-Methyl-benzoyl chloride | | 3-[3-Chloro-4-(1-methyl-cyclopropylmethoxy)-phenyl]-5-o-tolyl-[1,2,4]oxadiazole | 3.08 (b) | 354 (M − H)− |
| A.5 | 3-Chloro-4-pentyloxy-benzonitrile (B) | 2-Methyl-benzoyl chloride | | 3-(3-Chloro-4-pentyloxy-phenyl)-5-o-tolyl-[1,2,4]oxadiazole | 3.20 (b) | 356 (M − H)− |
| A.6 | 3-Chloro-4-(3,3-dimethyl-butyoxy)-benzonitrile (B) | 2-Methyl-benzoyl chloride | | 3-[3-Chloro-4-(3,3-dimethyl-butoxy)-phenyl]-5-o-tolyl-[1,2,4]oxadiazole | 3.27 (b) | 370 (M − H)− |

TABLE A-continued

Examples made using General Procedures C, D, E (Scheme 2)
The letter in parentheses below the nitrile precursors indicates the General Procedure by which the nitrile precursor was made.

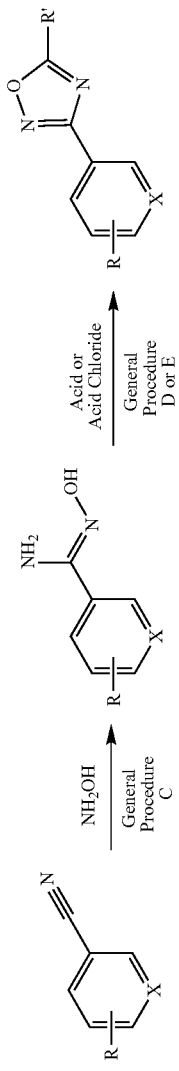

| Ex # | Nitrile precursor | Acid or acid chloride | Product | Name | R$_t$/min (method) | m/z |
|---|---|---|---|---|---|---|
| A.7 | 3-Chloro-4-cyclopentyl-methoxy-benzonitrile (B) | 2-Methyl-benzoyl chloride | | 3-(3-Chloro-4-cyclopentylmethoxy-phenyl)-5-o-tolyl-[1,2,4]oxadiazole | 3.26 (b) | 368 (M − H)$^-$ |
| A.8 | 3-Chloro-4-(2-ethyl-butoxy)-benzonitrile (B) | 2-Methyl-benzoyl chloride | | 3-[3-Chloro-4-(2-ethyl-butoxy)-phenyl]-5-o-tolyl-[1,2,4]oxadiazole | 3.34 (b) | 370 (M − H)$^-$ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.9 | 3-Chloro-4-octyloxy-benzonitrile (B) | 2-Methyl-benzoyl chloride | | 3-(3-Chloro-4-octyloxy-phenyl)-5-o-tolyl-[1,2,4]oxadiazole | 3.60 (b) | 398 (M − H)⁻ |
| A.10 | 3-Chloro-4-(3-methoxy-propoxy)-benzonitrile (B) | 2-Methyl-benzoyl chloride | | 3-[3-Chloro-4-(3-methoxy-propoxy)-phenyl]-5-o-tolyl-[1,2,4]oxadiazole | 2.86 (b) | 358 (M − H)⁻ |
| A.11 | 3-Chloro-4-(3-ethoxy-propoxy)-benzonitrile (B) | 2-Methyl-benzoyl chloride | | 3-[3-Chloro-4-(3-ethoxy-propoxy)-phenyl]-5-o-tolyl-[1,2,4]oxadiazole | 2.95 (b) | 372 (M − H)⁻ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.12 | 3-Chloro-4-(2-piperidin-1-yl-ethoxy)-benzonitrile (B) | 2-Methyl-benzoyl chloride | | 1-{2-[2-Chloro-4-(5-o-tolyl-[1,2,4]oxadiazol-3-yl)-phenoxy]-ethyl}-piperidine | 2.32 (b) | 397 (M − H)$^-$ |
| A.13 | 3-Chloro-4-(2-morpholin-4-yl-ethoxy)-benzonitrile (B) | 2-Methyl-benzoyl chloride | | 4-{2-[2-Chloro-4-(5-o-tolyl-[1,2,4]oxadiazol-3-yl)-phenoxy]-ethyl}-morpholine | 2.59 (b) | 399 (M − H)$^-$ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.14 | 3-Chloro-4-cyclopentyl-oxy-benzonitrile (B) | 2-Methyl-benzoyl chloride | | 3-(3-Chloro-4-cyclopentyloxy-phenyl)-5-o-tolyl-[1,2,4]oxadiazole | 3.14 (b) | 354 (M − H)⁻ |
| A.15 | 3-Chloro-4-(1-ethyl-propoxy)-benzonitrile (B) | 2-Methyl-benzoyl chloride | | 3-[3-Chloro-4-(1-ethyl-propoxy)-phenyl]-5-o-tolyl-[1,2,4]oxadiazole | 3.18 (b) | 356 (M − H)⁻ |
| A.16 | 3-Chloro-4-cyclohexyl-oxy-benzonitrile (B) | 2-Methyl-benzoyl chloride | | 3-(3-Chloro-4-cyclohexyloxy-phenyl)-5-o-tolyl-[1,2,4]oxadiazole | 3.22 (b) | 368 (M − H)⁻ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.17 | 3-Chloro-4-phenylethyl-oxy-benzonitrile (B) | 2-Methyl-benzoyl chloride | | 3-(3-Chloro-4-phenylethyloxy-phenyl)-5-o-tolyl-[1,2,4]oxadiazole | 3.04 (b) | 390 (M − H)⁻ |
| A.18 | 3-Chloro-4-(3-methyl-butoxy)-benzonitrile (B) | 2-Methyl-benzoyl chloride | | 3-[3-Chloro-4-(3-methyl-butoxy)-phenyl]-5-o-tolyl-[1,2,4]oxadiazole | 3.19 (b) | 356 (M − H)⁻ |
| A.19 | 3-Chloro-4-cyclohexyl-methoxy-benzonitrile (B) | 2-Methyl-benzoyl chloride | | 3-(3-Chloro-4-cyclohexylmethoxy-Phenyl)-5-o-tolyl-[1,2,4]oxadiazole | 3.39 (b) | 382 (M − H)⁻ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R_t/min (method) | m/z |
|---|---|---|---|---|---|---|
| A.20 | 3-Chloro-4-(2-isopropoxy-ethoxy)-benzonitrile (B) | 2-Methyl-benzoyl chloride | | 3-[3-Chloro-4-(2-isopropoxy-ethoxy)-phenyl]-5-o-tolyl-[1,2,4]oxadiazole | 2.91 (b) | 372 (M − H)⁻ |
| A.21 | 3-Chloro-4-pent-3-ynyloxy-benzonitrile (B) | 2-Methyl-benzoyl chloride | | 3-(3-Chloro-4-pent-3-ynyloxy-phenyl)-5-o-tolyl-[1,2,4]oxadiazole | 2.90 (b) | 352 (M − H)⁻ |
| A.22 | 3-Chloro-4-thiophen-2-yl-ethoxy)-benzonitrile (B) | 2-Methyl-benzoyl chloride | | 3-[3-Chloro-4-(2-thiophen-2-yl-ethoxy)-phenyl]-5-o-tolyl-[1,2,4]oxadiazole | 3.00 (b) | 396 (M − H)⁻ |

TABLE A-continued

Examples made using General Procedures C, D, E (Scheme 2)
The letter in parentheses below the nitrile precursors indicates the General Procedure by which the nitrile precursor was made.

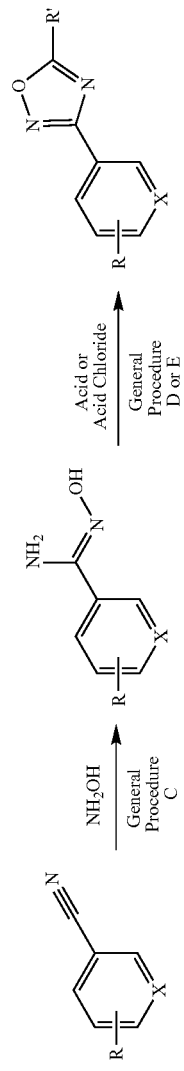

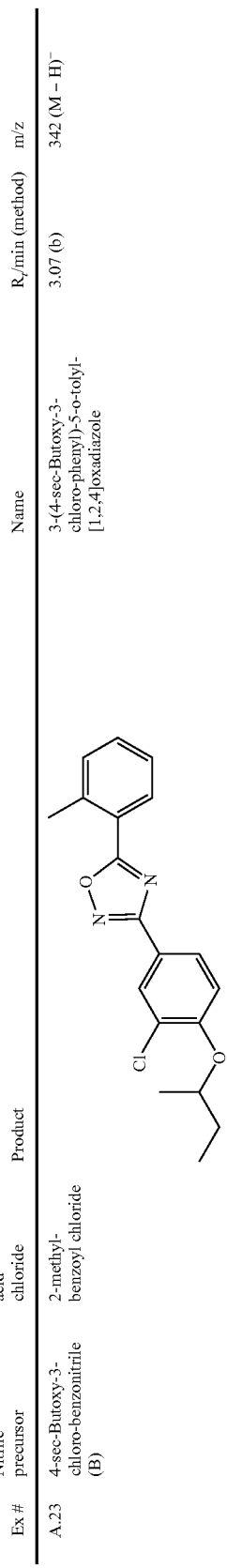

| Ex # | Nitrile precursor | Acid or acid chloride | Product | Name | R$_t$/min (method) | m/z |
|---|---|---|---|---|---|---|
| A.23 | 4-sec-Butoxy-3-chloro-benzonitrile (B) | 2-methyl-benzoyl chloride | | 3-(4-sec-Butoxy-3-chloro-phenyl)-5-o-tolyl-[1,2,4]oxadiazole | 3.07 (b) | 342 (M − H)$^-$ |
| A.24 | 3-Chloro-4-(2-dimethylamino-1-methyl-ethoxy)-benzonitrile (B) | 2-Methyl-benzoyl chloride | | {2-[2-Chloro-4-(5-o-tolyl-[1,2,4]oxadiazol-3-yl)-phenoxy]-propyl}-dimethyl-amine | 2.21 (b) | 371 (M − H)$^-$ |
| A.25 | 3-Chloro-4-(2-dimethylamino-ethoxy)-benzonitrile (B) | 2-Methyl-benzoyl chloride | | {2-[2-Chloro-4-(5-o-tolyl-[1,2,4]oxadiazol-3-yl)-phenoxy]-ethyl}-dimethyl-amine | 2.18 (b) | 357 (M − H)$^-$ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.26 | 3-Chloro-4-cyclobutyl methoxy-benzonitrile (B) | 2-Methyl-benzoyl chloride | | 3-(3-Chloro-4-cyclobutylmethoxy-phenyl)-5-o-tolyl-[1,2,4]oxadiazole | 3.15 (b) | 354 (M − H)⁻ |
| A.27 | 4-[((E)-But-2-enyl)oxy]-3-chloro-benzonitrile (B) | 2-Methyl-benzoyl chloride | | 3-{4-[((E)-But-2-enyl)oxy]-3-chloro-phenyl}-5-o-tolyl-[1,2,4]oxadiazole | 2.96 (b) | 340 (M − H)⁻ |
| A.28 | 3-Chloro-4-(4,4,4-trifluoro-butoxy)-benzonitrile (B) | 2-Methyl-benzoyl chloride | | 3-[3-Chloro-4-(4,4,4-trifluoro-butoxy)-phenyl]-5-o-tolyl-[1,2,4]oxadiazole | 2.97 (b) | 396 (M − H)⁻ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product Name | R_t/min (method) | m/z |
|---|---|---|---|---|---|
| A.29 | 3-Chloro-4-(4-methyl-cyclohexylmethoxy)-benzonitrile (B) | 2-Methyl-benzoyl chloride | 3-[3-Chloro-4-(4-methyl-cyclohexylmethoxy)-phenyl]-5-o-tolyl-[1,2,4]oxadiazole | 3.50 (b) | 396 (M − H)⁻ |
| A.30 | 3-Chloro-4-isopropoxy-benzonitrile (A) | Pyrazine-2-carboxylic acid | 2-[3-(3-Chloro-4-isopropoxy-phenyl)-[1,2,4]oxadiazol-5-yl]pyrazine | 3.48 (a) | 317 (M + H)⁺ |
| A.31 | 3-Chloro-4-isopropoxy-benzonitrile (A) | Isoxazole-3-carboxylic acid | 3-(3-Chloro-4-isopropoxy-phenyl)-5-isoxazol-3-yl-[1,2,4]oxadiazole | 3.57 (a) | 306 (M + H)⁺ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.32 | 3-Chloro-4-isopropoxy-benzonitrile (A) | 3-Methoxy-propionic acid | | 3-(3-Chloro-4-isopropoxy-phenyl)-5-(2-methoxy-ethyl)-[1,2,4]oxadiazole | 3.43 (a) | 297 (M + H)$^+$ |
| A.33 | 3-Chloro-4-isopropoxy-benzonitrile (A) | Isonicotinic acid | | 4-[3-(3-Chloro-4-isopropoxy-phenyl)-[1,2,4]oxadiazol-5-yl]-pyridine | 3.76 (a) | 316 (M + H)$^+$ |
| A.34 | 3-Chloro-4-isopropoxy-benzonitrile (A) | Cyclopropyl-acetic acid | | 3-(3-Chloro-4-isopropoxy-phenyl)-5-cyclopropylmethyl-[1,2,4]oxadiazole | 3.88 (a) | 293 (M + H)$^+$ |
| A.35 | 3-Chloro-4-isopropoxy-benzonitrile (A) | Nicotinic acid | | 3-[3-(3-Chloro-4-isopropoxy-phenyl)-[1,2,4]oxadiazol-5-yl]-pyridine | 2.37 (f) | 316 (M + H)$^+$ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R₁/min (method) | m/z |
|---|---|---|---|---|---|---|
| A.36 | 3-Chloro-4-isopropoxy-benzonitrile (A) | Pyridine-2-carboxylic acid | | 2-[3-(3-Chloro-4-isopropoxy-phenyl)-[1,2,4]oxadiazol-5-yl]-pyridine | 2.10 (f) | 316 (M + H)⁺ |
| A.37 | 3-Chloro-4-isopropoxy-benzonitrile (A) | 2-Methyl-benzoic acid | | 3-(3-Chloro-4-isopropoxy-phenyl)-5-o-tolyl-[1,2,4]oxadiazole | 2.62 (f) | 329 (M + H)⁺ |
| A.38 | 3-Chloro-4-isopropoxy-benzonitrile (A) | 3-Methyl-isonicotinic acid | | 4-[3-(3-Chloro-4-isopropoxy-phenyl)-[1,2,4]oxadi-azol-5-yl]-3-methyl-pyridine | 2.70 (f) | 330 (M + H)⁺ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.39 | 3-Chloro-4-isopropoxy-benzonitrile (A) | 3-Chloro-4-isopropoxy-benzoic acid | | 3,5-Bis-(3-chloro-4-isopropoxy-phenyl)-[1,2,4]oxadiazole | 2.81 (f) | 407 (M + H)$^+$ |
| A.40 | 3-Chloro-4-isopropoxy-benzonitrile (A) | Note a | | [3-(3-Chloro-4-isopropoxy-phenyl)-[1,2,4]oxadiazol-5-yl]-dimethyl-amine | 2.03 (f) | 282 (M + H)$^+$ |
| A.41 | 3-Chloro-4-isopropoxy-benzonitrile (A) | Phenyl-acetic acid | | 5-Benzyl-3-(3-chloro-4-isopropoxy-phenyl)-[1,2,4]oxadiazole | 2.37 (f) | 329 (M + H)$^+$ |
| A.42 | 3-Chloro-4-isopropoxy-benzonitrile (A) | Benzoic acid | | 3-(3-Chloro-4-isopropoxy-phenyl)-5-phenyl-[1,2,4]oxadiazole | 2.50 (f) | 315 (M + H)$^+$ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R_t/min (method) | m/z |
|---|---|---|---|---|---|---|
| A.43 | 3-Chloro-4-isopropoxy-benzonitrile (A) | Pyridin-3-yl-acetic acid | | 3-[3-(3-Chloro-4-isopropoxy-phenyl)-[1,2,4]oxadiazol-5-ylmethyl]-pyridine | 2.03 (f) | 330 (M + H)+ |
| A.44 | 3-Chloro-4-isopropoxy-benzonitrile (A) | 3-Pyridin-3-yl-propionic acid | | 4-{2-[3-(3-Chloro-4-isopropoxy-phenyl)-[1,2,4]oxadiazol-5-yl]-ethyl}-pyridine | 2.15 (f) | 344 (M + H)+ |
| A.45 | 3-Chloro-4-isopropoxy-benzonitrile (A) | 3-Trifluoro methyl-benzoic acid | | 3-(3-Chloro-4-isopropoxy-phenyl)-5-(3-trifluoromethyl-phenyl)-[1,2,4]oxadiazole | 4.33 (g) | 382 (M)+ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R_t/min (method) | m/z |
|---|---|---|---|---|---|---|
| A.46 | 3-Chloro-4-isopropoxy-benzonitrile (A) | 4-Methyl-pentanoic acid | 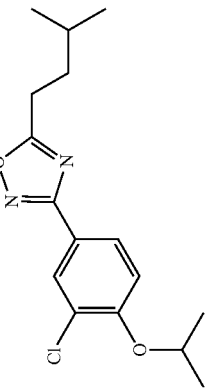 | 3-(3-Chloro-4-isopropoxy-phenyl)-5-(3-methyl-butyl)-[1,2,4]oxadiazole | 2.90 (b) | 309 (M + H)+ |
| A.47 | 3-Chloro-4-isopropoxy-benzonitrile (A) | 3,3-Dimethyl-butyric acid | 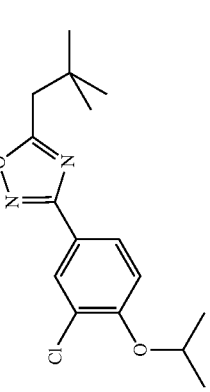 | 3-(3-Chloro-4-isopropoxy-phenyl)-5-(2,2-dimethyl-propyl)-[1,2,4]oxadiazole | 2.88 (b) | 309 (M + H)+ |
| A.48 | 3-Chloro-4-isopropoxy-benzonitrile (A) | Heptanoic acid | 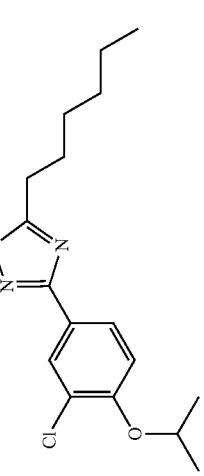 | 3-(3-Chloro-4-isopropoxy-phenyl)-5-hexyl-[1,2,4]oxadiazole | 3.01 (b) | 323.20 (M + H)+ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.49 | 3-Chloro-4-isopropoxy-benzonitrile (A) | 4,4,4-Trifluoro-butyric acid | | 3-(3-Chloro-4-isopropoxy-phenyl)-5-(3,3,3-trifluoro-propyl)-[1,2,4]oxadiazole | 2.68 (e) | 334 (M − H)⁻ |
| A.50 | 3-Chloro-4-isopropoxy-benzonitrile (A) | Methoxy-acetic acid | | 3-(3-Chloro-4-isopropoxy-phenyl)-5-methoxymethyl-[1,2,4]oxadiazole | 2.40 (b) | 283 (M + H)⁺ |
| A.51 | 3-Chloro-4-isopropoxy-benzonitrile (A) | Methylsulfanyl-acetic acid | | 3-(3-Chloro-4-isopropoxy-phenyl)-5-methylsulfanyl methyl-[1,2,4]oxadiazole | 2.55 (b) | 299 (M + H)⁺ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.52 | 3-Chloro-4-isopropoxy-benzonitrile (A) | Ethoxy-acetic acid | 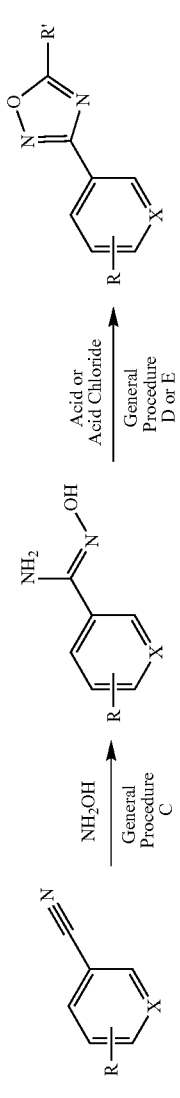 | 3-(3-Chloro-4-isopropoxyphenyl)-5-ethoxymethyl-[1,2,4]oxadiazole | 2.51 (b) | 297 (M + H)$^+$ |
| A.53 | 3-Chloro-4-isopropoxy-benzonitrile (A) | (2-Methoxy-ethoxy)-acetic acid | 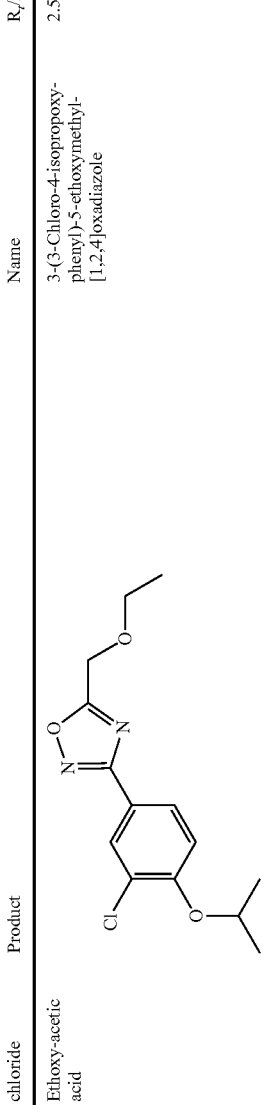 | 3-(3-Chloro-4-isopropoxyphenyl)-5-(2-methoxyethoxymethyl)-[1,2,4]oxadiazole | 2.35 (b) | 327 (M + H)$^+$ |
| A.54 | 3-Chloro-4-isopropoxy-benzonitrile (A) | Tetrahydro-furan-2-carboxylic acid |  | 3-(3-Chloro-4-isopropoxyphenyl)-5-(tetrahydrofuran-2-yl)-[1,2,4]oxadiazole | 2.37 (e) | 308 (M − H)$^−$ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.55 | 3-Chloro-4-isopropoxy-benzonitrile (A) | Tetrahydro-furan-3-carboxylic acid | | 3-(3-Chloro-4-isopropoxy-phenyl)-5-(tetrahydro-furan-3-yl)-[1,2,4]oxadiazole | 2.43 (b) | 309 (M + H)⁺ |
| A.56 | 3-Chloro-4-isopropoxy-benzonitrile (A) | Cyclopropanecar-boxylic acid | | 3-(3-Chloro-4-isopropoxy-phenyl)-5-cyclopropyl-[1,2,4]oxadiazole | 2.61 (b) | 279 (M + H)⁺ |
| A.57 | 3-Chloro-4-isopropoxy-benzonitrile (A) | Cyclobutanecar-boxylic acid | | 3-(3-Chloro-4-isopropoxy-phenyl)-5-cyclobutyl-[1,2,4]oxadiazole | 2.75 (b) | 293 (M + H)⁺ |
| A.58 | 3-Chloro-4-isopropoxy-benzonitrile (A) | Cyclopentanecar-boxylic acid | | 3-(3-Chloro-4-isopropoxy-phenyl)-5-cyclopentyl-[1,2,4]oxadiazole | 2.86 (b) | 307 (M + H)⁺ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.59 | 3-Chloro-4-isopropoxy-benzonitrile (A) | Cyclopentyl-acetic acid | 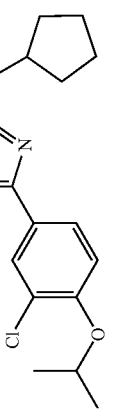 | 3-(3-Chloro-4-isopropoxy-phenyl)-5-cyclopentylmethyl-[1,2,4]oxadiazole | 2.95 (b) | 321 (M + H)$^+$ |
| A.60 | 3-Chloro-4-isopropoxy-benzonitrile (A) | Cyclohexanecarboxylic acid | 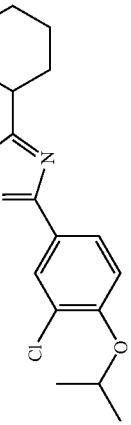 | 3-(3-Chloro-4-isopropoxy-phenyl)-5-cyclohexyl-[1,2,4]oxadiazole | 2.96 (b) | 321 (M + H)$^+$ |
| A.61 | 3-Chloro-4-isopropoxy-benzonitrile (A) | Cyclohexyl-acetic acid | 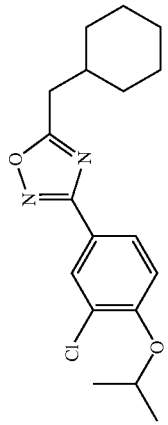 | 3-(3-Chloro-4-isopropoxy-phenyl)-5-cyclohexylmethyl-[1,2,4]oxadiazole | 3.04 (b) | 335 (M + H)$^+$ |
| A.62 | 3-Chloro-4-isopropoxy-benzonitrile (A) | 1-Methyl-cyclopropanecarboxylic acid | 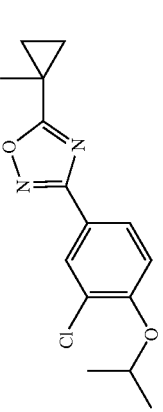 | 3-(3-Chloro-4-isopropoxy-phenyl)-5-(1-methylcyclopropyl)-[1,2,4]oxadiazole | 2.76 (b) | 293 (M + H)$^+$ |

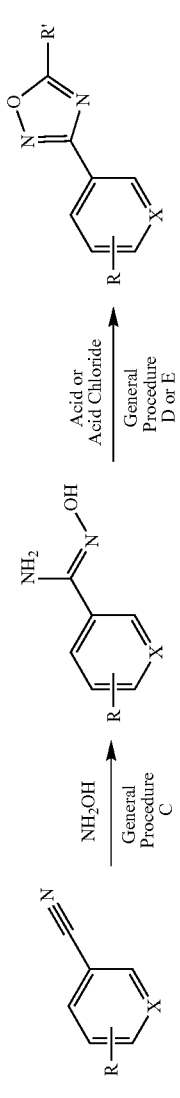

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R<sub>t</sub>/min (method) | m/z |
|------|------|------|------|------|------|------|
| A.63 | 3-Chloro-4-isopropoxy-benzonitrile (A) | 2-Methyl-cyclopropanecarboxylic acid | | 3-(3-Chloro-4-isopropoxy-phenyl)-5-(2-methyl-cyclopropyl)-[1,2,4]oxadiazole | 2.73 (b) | 293 (M + H)<sup>+</sup> |
| A.64 | 3-Chloro-4-isopropoxy-benzonitrile (A) | 3-Ethoxy-propionic acid | | 3-(3-Chloro-4-isopropoxy-phenyl)-5-(2-ethoxy-ethyl)-[1,2,4]oxadiazole | 2.53 (b) | 311 (M + H)<sup>+</sup> |
| A.65 | 3-Chloro-4-isopropoxy-benzonitrile (A) | (S)-5-Oxo-pyrrolidine-2-carboxylic acid | Chiral | (S)-5-[3-(3-Chloro-4-isopropoxy-phenyl)-[1,2,4]oxadiazol-5-yl]-pyrrolidin-2-one | 1.88 (e) | 321 (M − H)<sup>−</sup> |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.66 | 3-Chloro-4-isopropoxy-benzonitrile (A) | (R)-5-Oxo-pyrrolidine-2-carboxylic acid | 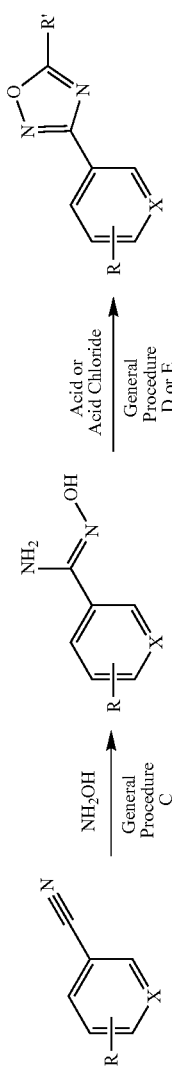 Chiral | (R)-5-[3-(3-Chloro-4-isopropoxy-phenyl)-[1,2,4]oxadiazol-5-yl]-pyrrolidin-2-one | 1.90 (e) | 321 (M − H)− |
| A.67 | 3-Chloro-4-isopropoxy-benzonitrile (A) | Benzyloxy-acetic acid | 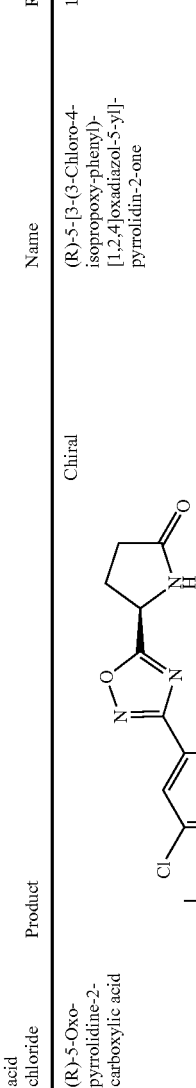 | 5-Benzyloxymethyl-3-(3-chloro-4-isopropoxy-phenyl)-[1,2,4]oxadiazole | 2.70 (b) | 359 (M + H)+ |
| A.68 | 3-Chloro-4-isopropoxy-benzonitrile (A) | 1-Phenyl-cyclopropanecarboxylic acid | 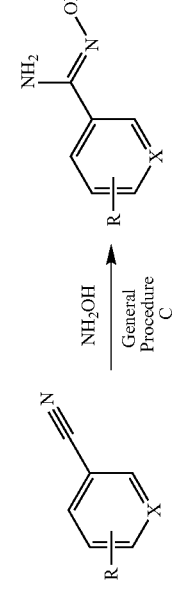 | 3-(3-Chloro-4-isopropoxy-phenyl)-5-(1-phenyl-cyclopropyl)-[1,2,4]oxadiazole | 2.88 (b) | 355 (M + H)+ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R_t/min (method) | m/z |
|---|---|---|---|---|---|---|
| A.69 | 3-Chloro-4-isopropoxy-benzonitrile (A) | (S)-2-Phenyl-butyric acid | Chiral | 3-(3-Chloro-4-isopropoxy-phenyl)-5-((S)-1-phenyl-propyl)-[1,2,4]oxadiazole | 2.94 (b) | 357 (M + H)+ |
| A.70 | 3-Chloro-4-isopropoxy-benzonitrile (A) | 4-Phenyl-butyric acid | | 3-(3-Chloro-4-isopropoxy-phenyl)-5-(3-phenyl-propyl)-[1,2,4]oxadiazole | 2.88 (b) | 357 (M + H)+ |
| A.71 | 3-Chloro-4-isopropoxy-benzonitrile (A) | (R)-Methoxy-phenyl-acetic acid | Chiral | 3-(3-Chloro-4-isopropoxy-phenyl)-5-((R)-methoxy-phenyl-methyl)-[1,2,4]oxadiazole | 2.72 (b) | 359 (M + H)+ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.72 | 3-Chloro-4-isopropoxy-benzonitrile (A) | (S)-Methoxy-phenyl-acetic acid | Chiral 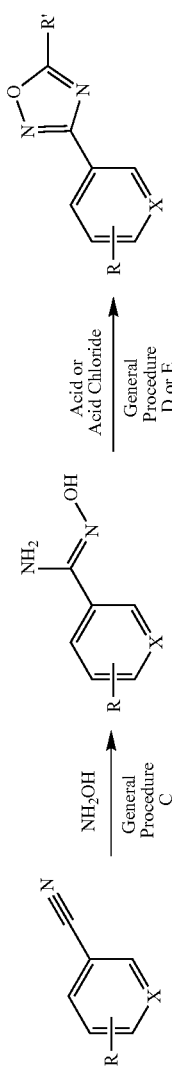 | 3-(3-Chloro-4-isopropoxy-phenyl)-5-((S)-methoxy-phenyl-methyl)-[1,2,4]oxadiazole | 2.72 (b) | 359 (M + H)$^+$ |
| A.73 | 3-Chloro-4-isopropoxy-benzonitrile (A) | 3-Phenoxy-propionic acid | 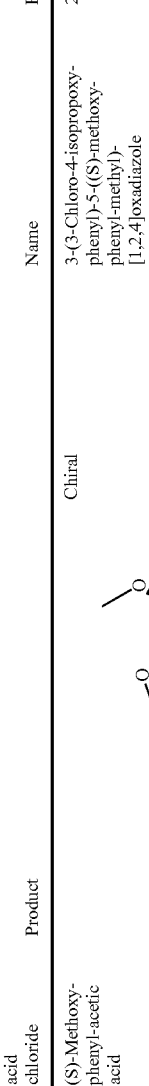 | 3-(3-Chloro-4-isopropoxy-phenyl)-5-(2-phenoxy-ethyl)-[1,2,4]oxadiazole | 2.72 (e) | 358 (M − H)$^-$ |
| A.74 | 3-Chloro-4-isopropoxy-benzonitrile (A) | [(Furan-2-carbonyl)-amino]-acetic acid | 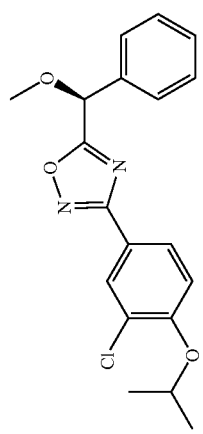 | Furan-2-carboxylic acid [3-(3-chloro-4-isopropoxy-phenyl)-[1,2,4]oxadi-azol-5-ylmethyl]-amide | 2.20 (b) | 362 (M + H)$^+$ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R₁/min (method) | m/z |
|---|---|---|---|---|---|---|
| A.75 | 3-Chloro-4-isopropoxy-benzonitrile (A) | 4-Thiophen-2-yl-butyric acid | 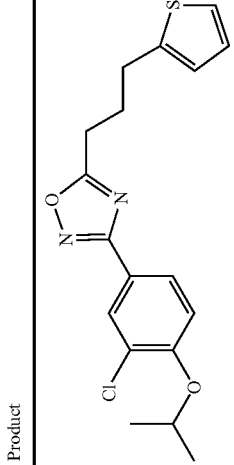 | 3-(3-Chloro-4-isopropoxy-phenyl)-5-(3-thiophen-2-yl-propyl)-[1,2,4]oxadiazole | 2.84 (b) | 363 (M + H)⁺ |
| A.76 | 3-Chloro-4-isopropoxy-benzonitrile (A) | 1-Acetyl-piperidine-4-carboxylic acid | 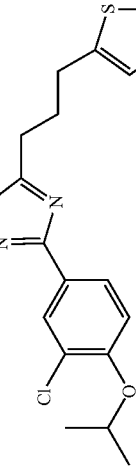 | 1-{4-[3-(3-Chloro-4-isopropoxy-phenyl)-[1,2,4]oxadiazol-5-yl]-piperidin-1-yl}-ethanone | 2.26 (b) | 364 (M + H)⁺ |
| A.77 | 3-Chloro-4-isopropoxy-benzonitrile (A) | (3,5-Difluoro-phenyl)-acetic acid | 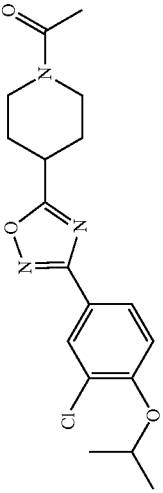 | 3-(3-Chloro-4-isopropoxy-phenyl)-5-(3,5-difluoro-benzyl)-[1,2,4]oxadiazole | 2.75 (b) | 365 (M + H)⁺ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.79 | 3-Chloro-4-isopropoxy-benzonitrile (A) | 4-Oxo-4-phenyl-butyric acid | | 3-[3-(3-Chloro-4-isopropoxy-phenyl)-[1,2,4]oxadi-azol-5-yl]-1-phenyl-propan-1-one | 2.64 (b) | 371 (M + H)+ |
| A.79 | 3-Chloro-4-isopropoxy-benzonitrile (A) | 4-Phenoxy-butyric acid | | 3-(3-Chloro-4-isopropoxy-phenyl)-5-(3-phenoxy-propyl)-[1,2,4]oxadi-azole | 2.79 (b) | 373 (M + H)+ |
| A.80 | 3-Chloro-4-isopropoxy-benzonitrile (A) | 4-Oxo-4-thiophen-2-yl-butyric acid | | 3-[3-(3-Chloro-4-isopropoxy-phenyl)-[1,2,4]oxadi-azol-5-yl]-1-thiophen-2-yl-propan-1-one | 2.57 (b) | 377 (M + H)+ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.81 | 3-Chloro-4-isopropoxy-benzonitrile (A) | 4-Phenylcarbamoyl-butyric acid | | 4-[3-(3-Chloro-4-isopropoxy-phenyl)-[1,2,4]oxadiazol-5-yl]-N-phenyl-butyramide | 2.45 (b) | 400 (M + H)$^+$ |
| A.82 | 3-Chloro-4-isopropoxy-benzonitrile (A) | (Toluene-4-sulfonylamino)-acetic acid | | N-[3-(3-Chloro-4-isopropoxy-phenyl)-[1,2,4]oxadiazol-5-ylmethyl]-4-methyl-benzenesulfonamide | 2.44 (b) | 422 (M + H)$^+$ |
| A.83 | 3-Chloro-4-isopropoxy-benzonitrile (A) | 4-Acetyl-benzoic acid | | 1-{4-[3-(3-Chloro-4-isopropoxy-phenyl)-[1,2,4]oxadiazol-5-yl]-phenyl}-ethanone | 2.72 (b) | 357 (M + H)$^+$ |

TABLE A-continued

Examples made using General Procedures C, D, E (Scheme 2)
The letter in parentheses below the nitrile precursors indicates the General Procedure by which the nitrile precursor was made.

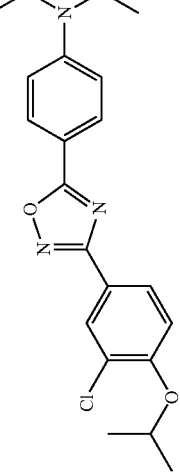

| Ex # | Nitrile precursor | Acid or acid chloride | Product | Name | R$_t$/min (method) | m/z |
|---|---|---|---|---|---|---|
| A.84 | 3-Chloro-4-isopropoxy-benzonitrile (A) | 4-Diethylamino-benzoic acid | 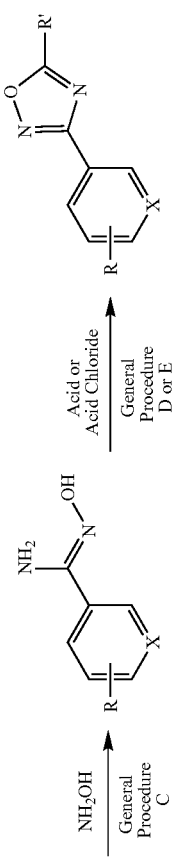 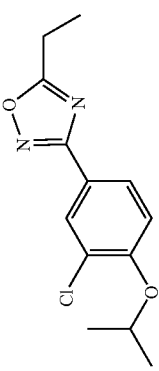 | {4-[3-(3-Chloro-4-isopropoxy-phenyl)-[1,2,4]oxadiazol-5-yl]-phenyl}-diethyl-amine; compound with trifluoro-acetic acid | 3.00 (b) | 386 (M + H)$^+$ |
| A.85 | 3-Chloro-4-isopropoxy-benzonitrile (A) | Propionic acid | 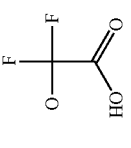 | 3-(3-Chloro-4-isopropoxy-phenyl)-5-ethyl-[1,2,4]oxadiazole | 2.55 (b) | 267 (M + H)$^+$ |
| A.86 | 3-Chloro-4-isopropoxy-benzonitrile (A) | Butyric acid |  | 3-(3-Chloro-4-isopropoxy-phenyl)-5-propyl-[1,2,4]oxadiazole | 2.69 (b) | 281 (M + H)$^+$ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R_t/min (method) | m/z |
|---|---|---|---|---|---|---|
| A.87 | 3-Chloro-4-isopropoxy-benzonitrile (A) | Isobutyric acid | | 3-(3-Chloro-4-isopropoxy-phenyl)-5-isopropyl-[1,2,4]oxadiazole | 2.70 (b) | 281 (M + H)+ |
| A.88 | 3-Chloro-4-isopropoxy-benzonitrile (A) | Pentanoic acid | | 5-Butyl-3-(3-chloro-4-isopropoxy-phenyl)-[1,2,4]oxadiazole | 2.81 (b) | 295 (M + H)+ |
| A.89 | 3-Chloro-4-isopropoxy-benzonitrile (A) | 2-Methyl-butyric acid | | 5-sec-Butyl-3-(3-chloro-4-isopropoxy-phenyl)-[1,2,4]oxadiazole | 2.82 (b) | 295 (M + H)+ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.90 | 3-Chloro-4-isopropoxy-benzonitrile (A) | 3-Methyl-butyric acid | | 3-(3-Chloro-4-isopropoxy-phenyl)-5-isobutyl-[1,2,4]oxadiazole | 2.80 (b) | 295 (M + H)$^+$ |
| A.91 | 3-Chloro-4-isopropoxy-benzonitrile (A) | Hexanoic acid | | 3-(3-Chloro-4-isopropoxy-phenyl)-5-pentyl-[1,2,4]oxadiazole | 2.92 (b) | 309 (M + H)$^+$ |
| A.92 | 3-Chloro-4-isopropoxy-benzonitrile (A) | 4-tert-Butoxycarbonylamino-benzoic acid | | {4-[3-(3-Chloro-4-isopropoxy-phenyl)-[1,2,4]oxadiazol-5-yl]-phenyl}-carbamic acid tert-butyl ester | 2.90 (b) | 430 (M + H)$^+$ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R_t/min (method) | m/z |
|---|---|---|---|---|---|---|
| A.93 | 3-Chloro-4-isopropoxy-benzonitrile (A) | 3-Cyano-benzoic acid | | 3-[3-(3-Chloro-4-isopropoxy-phenyl)-[1,2,4]oxadiazol-5-yl]-benzonitrile | 2.71 (b) | Note b |
| A.94 | 3-Chloro-4-isopropoxy-benzonitrile (A) | 4-Cyano-benzoic acid | | 4-[3-(3-Chloro-4-isopropoxy-phenyl)-[1,2,4]oxadiazol-5-yl]-benzonitrile | 2.71 (b) | Note C |
| A.95 | 3-Chloro-4-isopropoxy-benzonitrile (A) | 3-Dimethyl amino-benzoic acid | | {3-[3-(3-Chloro-4-isopropoxy-phenyl)-[1,2,4]oxadiazol-5-yl]-phenyl}-dimethyl-amine | 2.94 (b) | 358 (M + H)+ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R₁/min (method) | m/z |
|---|---|---|---|---|---|---|
| A.96 | 3-Chloro-4-isopropoxy-benzonitrile (A) | Biphenyl-4-yl-acetic acid | | 5-Biphenyl-4-ylmethyl-3-(3-chloro-4-isopropoxy-phenyl)-[1,2,4]oxadiazole | 2.93 (b) | 405 (M + H)⁺ |
| A.97 | 3-Chloro-4-isopropoxy-benzonitrile (A) | (4-Dimethyl amino-phenyl)-acetic acid | | {4-[3-(3-Chloro-4-isopropoxy-phenyl)-[1,2,4]oxadiazol-5-ylmethyl]-phenyl}-dimethyl-amine | 2.78 (b) | 372 (M + H)⁺ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R_t/min (method) | m/z |
|---|---|---|---|---|---|---|
| A.98 | 3-Chloro-4-isopropoxy-benzonitrile (A) | (4-Phenoxy-phenyl)-acetic acid | | 3-(3-Chloro-4-isopropoxy-phenyl)-5-(4-phenoxy-benzyl)-[1,2,4]oxadiazole | 2.92 (b) | 421 (M + H)+ |
| A.99 | 3-Chloro-4-isopropoxy-benzonitrile (A) | (4-Benzyloxy-phenyl)-acetic acid | | 5-(4-Benzyloxy-benzyl)-3-(3-chloro-4-isopropoxy-phenyl)-[1,2,4]oxadiazole | 2.89 (b) | 435 (M + H)+ |
| A.100 | 3-Chloro-4-isopropoxy-benzonitrile (A) | Napthhalen-1-yl-acetic acid | | 3-(3-Chloro-4-isopropoxy-phenyl)-5-napthhalen-1-ylmethyl-[1,2,4]oxadiazole | 2.85 (b) | 379 (M + H)+ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R_t/min (method) | m/z |
|---|---|---|---|---|---|---|
| A.101 | 3-Chloro-4-isopropoxy-benzonitrile (A) | Napthalen-2-yl-acetic acid | | 3-(3-Chloro-4-isopropoxy-phenyl)-5-napthalen-2-ylmethyl-[1,2,4]oxadiazole | 2.87 (b) | 379 (M + H)+ |
| A.102 | 3-Chloro-4-isopropoxy-benzonitrile (A) | Furan-2-carboxylic acid | | 3-(3-Chloro-4-isopropoxy-phenyl)-5-furan-2-yl-[1,2,4]oxadiazole | 2.62 (b) | 305 (M + H)+ |
| A.103 | 3-Chloro-4-isopropoxy-benzonitrile (A) | Furan-3-carboxylic acid | | 3-(3-Chloro-4-isopropoxy-phenyl)-5-furan-3-yl-[1,2,4]oxadiazole | 2.64 (b) | 305 (M + H)+ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.104 | 3-Chloro-4-isopropoxy-benzonitrile (A) | Thiophene-2-carboxylic acid | | 3-(3-Chloro-4-isopropoxy-phenyl)-5-thiophen-2-yl-[1,2,4]oxadiazole | 2.78 (b) | 321 (M + H)$^+$ |
| A.105 | 3-Chloro-4-isopropoxy-benzonitrile (A) | Thiophene-3-carboxylic acid | | 3-(3-Chloro-4-isopropoxy-phenyl)-5-thiophen-3-yl-[1,2,4]oxadiazole | 2.75 (b) | 321 (M + H)$^+$ |
| A.106 | 3-Chloro-4-isopropoxy-benzonitrile (A) | 1-Methyl-1H-pyrrole-2-carboxylic acid | | 3-(3-Chloro-4-isopropoxy-phenyl)-5-(1-methyl-1H-pyrrol-2-yl)-[1,2,4]oxadiazole | 2.75 (b) | 318 (M + H)$^+$ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.107 | 3-Chloro-4-isopropoxy-benzonitrile (A) | Thiazole-4-carboxylic acid | | 3-(3-Chloro-4-isopropoxy-phenyl)-5-thiazol-4-yl-[1,2,4]oxadiazole | 2.42 (b) | 322 (M + H)$^+$ |
| A.108 | 3-Chloro-4-isopropoxy-benzonitrile (A) | 3,5-Dimethyl-isoxazole-4-carboxylic acid | | 3-(3-Chloro-4-isopropoxy-phenyl)-5-(3,5-dimethyl-isoxazol-4-yl)-[1,2,4]oxadiazole | 2.72 (b) | 334 (M + H)$^+$ |
| A.109 | 3-Chloro-4-isopropoxy-benzonitrile (A) | 5-Methyl-pyrazine-2-carboxylic acid | | 2-[3-(3-Chloro-4-isopropoxy-phenyl)-[1,2,4]oxadiazol-5-yl]-5-methyl-pyrazine | 2.50 (b) | 331 (M + H)$^+$ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R<sub>t</sub>/min (method) | m/z |
|---|---|---|---|---|---|---|
| A.110 | 3-Chloro-4-isopropoxy-benzonitrile (A) | 4-Oxo-4,5,6,7-tetrahydro-benzofuran-3-carboxylic acid | 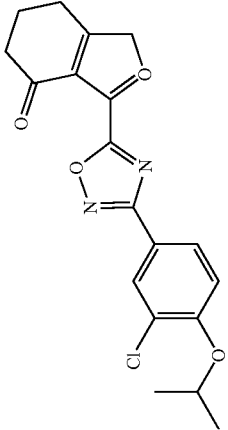 | 3-[3-(3-Chloro-4-isopropoxy-phenyl)-[1,2,4]oxadi-azol-5-yl]-6,7-dihydro-5H-benzofuran-4-one | 2.48 (b) | 373 (M + H)<sup>+</sup> |
| A.111 | 3-Chloro-4-isopropoxy-benzonitrile (A) | Morpholin-4-yl-acetic acid | 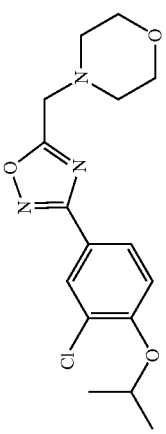 | 4-[3-(3-Chloro-4-isopropoxy-phenyl)-[1,2,4]oxadi-azol-5-ylmethyl]-morpholine | 2.70 (b) | Note d |
| A.112 | 3-Chloro-4-isopropoxy-benzonitrile (A) | 3-Chloro-isonico-tinic acid | 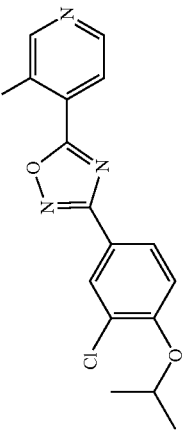 | 3-Chloro-4-[3-(3-chloro-4-isopropoxy-phenyl)-[1,2,4]oxadiazol-5-yl]-pyridine | 3.02 (f) | 350 (M + H)<sup>+</sup> |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R_t/min (method) | m/z |
|---|---|---|---|---|---|---|
| A.113 | 3-Chloro-4-isopropoxy-benzonitrile (A) | 3-Chloro-benzoic acid | | 3-(3-Chloro-4-isopropoxy-phenyl)-5-(3-chloro-phenyl)-[1,2,4]oxadiazole | 3.22 (f) | 349 (M + H)+ |
| A.114 | 3-Chloro-4-isopropoxy-benzonitrile (A) | 3-Fluoro-isonicotinic acid | | 4-[3-(3-Chloro-4-isopropoxy-phenyl)-[1,2,4]oxadiazol-5-yl]-3-fluoro-pyridine | 2.93 (f) | 334 (M + H)+ |
| A.115 | 3-Chloro-4-isopropoxy-benzonitrile (A) | 2-Chloro-isonicotinic acid | | 2-Chloro-4-[3-(3-chloro-4-isopropoxy-phenyl)-[1,2,4]oxadiazol-5-yl]-pyridine | 3.05 (f) | 351 (M + H)+ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.116 | 3-Chloro-4-isopropoxy-benzonitrile (A) | 2-Fluoro-isonicotinic acid | | 4-[3-(3-Chloro-4-isopropoxy-phenyl)-[1,2,4]oxadiazol-5-yl]-2-fluoro-pyridine | 2.95 (f) | 334 (M + H)⁺ |
| A.117 | 3-Chloro-4-isopropoxy-benzonitrile (A) | Quinoline-4-carboxylic acid | | 4-[3-(3-Chloro-4-isopropoxy-phenyl)-[1,2,4]oxadiazol-5-yl]-quinoline | 3.27 (f) | 366 (M + H)⁺ |
| A.118 | 3-Chloro-4-isopropoxy-benzonitrile (A) | 2,6-Dichloro-isonicotinic acid | | 2,6-Dichloro-4-[3-(3-chloro-4-isopropoxy-phenyl)-[1,2,4]oxadiazol-5-yl]-pyridine | 3.18 (f) | Note e |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R_t/min (method) | m/z |
|------|-------------------|----------------------|---------|------|------------------|-----|
| A.119 | 3-Chloro-4-isopropoxy-5-methoxy-benzonitrile | Benzoyl chloride | | 3-(3-Chloro-4-isopropoxy-5-methoxy-phenyl)-5-phenyl-[1,2,4]oxadiazole | 3.17 (b) | 345 (M + H)+ |
| A.120 | 3-Chloro-4-isopropoxy-5-methoxy-benzonitrile | Isonicotinoyl chloride | | 4-[3-(3-Chloro-4-isopropoxy-5-methoxy-phenyl)-[1,2,4]oxadiazol-5-yl]-pyridine | 3.14 (b) | 346 (M + H)+ |
| A.121 | 6-Methoxy-nicotinonitrile | Benzoyl chloride | | 2-Methoxy-5-(5-phenyl-[1,2,4]oxadiazol-3-yl)-pyridine | 2.28 (b) | 254 (M + H)+ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.122 | 6-(2,2,2-Trifluoro-ethoxy)-nicotinonitrile | Isonicotinoyl chloride | | 5-(5-Pyridin-4-yl-[1,2,4]oxadi-azol-3-yl)-2-(2,2,2-trifluoro-ethoxy)-pyridine | 2.81 (b) | 323 (M + H)$^+$ |
| A.123 | 6-(2,2,2-Trifluoro-ethoxy)-nicotinonitrile | Benzoyl chloride | | 5-(5-Phenyl-[1,2,4]oxadi-azol-3-yl)-2-(2,2,2-trifluoro-ethoxy)-pyrridine | 2.95 (b) | 322 (M + H)$^+$ |
| A.124 | 6-(2,2,2-Trifluoro-ethoxy)-nicotinonitrile | 3-Chloro-isonicoti-noyl chloride (F) | | 5-(3-chloropyridin-4-yl)-3-(6-(2,2,2-trifluoroethoxy)pyridin-3-yl)-1,2,4-oxadiazole | 2.46 (b) | 357 (M + H)$^+$ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R<sub>t</sub>/min (method) | m/z |
|---|---|---|---|---|---|---|
| A.125 | 6-(2,2,2-Trifluoro-ethoxy)-nicotinonitrile | 3-Methyl-isonicotinoyl chloride (F) | 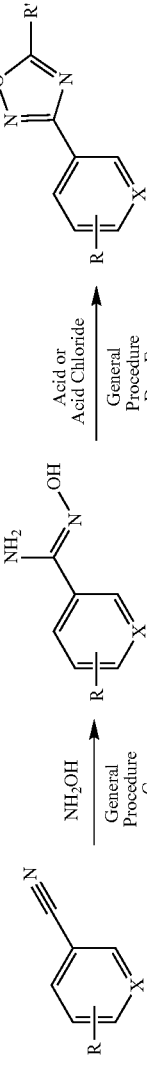 | 5-(3-methylpyridin-4-yl)-3-(6-(2,2,2-trifluoroethoxy)pyridin-3-yl)-1,2,4-oxadiazole | 2.96 (b) | 337 (M + H)<sup>+</sup> |
| A.126 | 4-tert-Butyl-benzonitrile | 2-Methyl-benzoyl chloride | 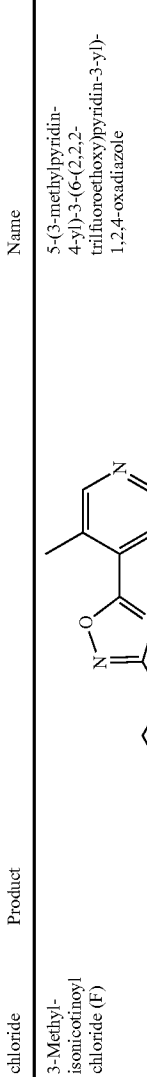 | 3-(4-tert-Butyl-phenyl)-5-o-tolyl-[1,2,4]oxadiazole | 3.46 (b) | 293 (M + H)<sup>+</sup> |
| A.127 | 3-Chloro-4-methyl-benzonitrile | 2-Methyl-benzoyl chloride | 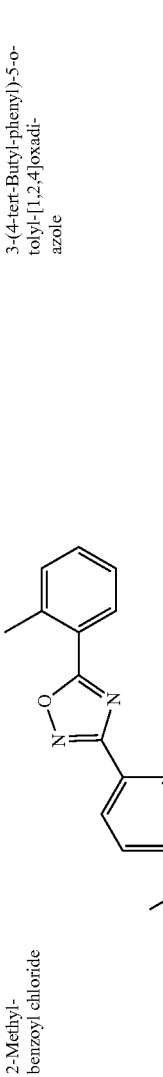 | 3-(3-Chloro-4-methyl-phenyl)-5-o-tolyl-[1,2,4]oxadiazole | 3.40 (b) | 285 (M + H)<sup>+</sup> |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.128 | 4-Ethyl-benzonitrile | 2-Methyl-benzoyl chloride | | 3-(4-Ethyl-phenyl)-5-o-tolyl-[1,2,4]oxadi-azole | 3.39 (b) | 265 (M + H)$^+$ |
| A.129 | 4-Butyl-benzonitrile | 2-Methyl-benzoyl chloride | | 3-(4-Butyl-phenyl)-5-o-tolyl-[1,2,4]oxadi-azole | 3.55 (b) | 293 (M + H)$^+$ |
| A.130 | 4-Isopropyl-benzonitrile | 2-Methyl-benzoyl chloride | | 3-(4-Isopropyl-phenyl)-5-o-tolyl-[1,2,4]oxadi-azole | 3.44 (b) | 279 (M + H)$^+$ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R_t/min (method) | m/z |
|---|---|---|---|---|---|---|
| A.131 | Benzonitrile | Isonicotinoyl chloride | 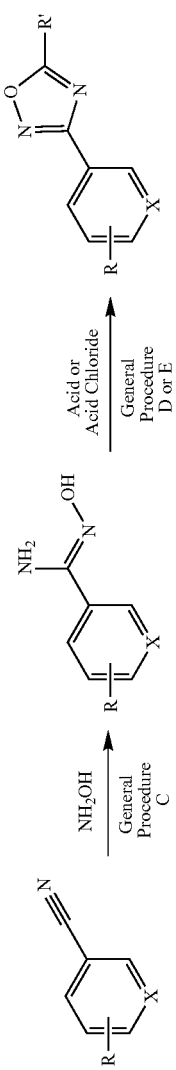 | 4-(3-Phenyl-[1,2,4]oxadiazol-5-yl)-pyridine | 2.48 (f) | 223 (M + H)+ |
| A.132 | 3-Chloro-benzonitrile | Isonicotinoyl chloride | 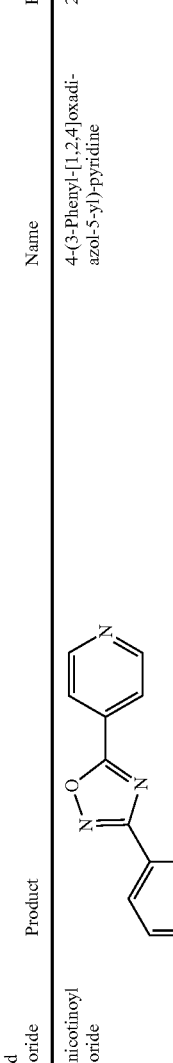 | 4-[3-(3-Chloro-phenyl)-[1,2,4]oxadiazol-5-yl]-pyridine | 2.75 (f) | 258 (M + H)+ |
| A.133 | 4-Hydroxy-benzonitrile | Isonicotinoyl chloride | 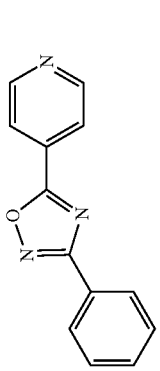 | 4-(5-Pyridin-4-yl-[1,2,4]oxadiazol-3-yl)-phenol | 1.95 (f) | 240 (M + H)+ |
| A.134 | Benzofuran-5-carbonitrile | 2-Methyl-benzoyl chloride | 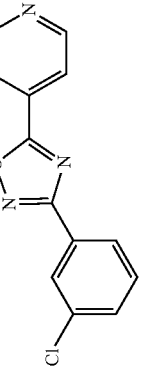 | 3-Benzofuran-5-yl-o-tolyl-[1,2,4]oxadiazole | 3.83 (a) | 277 (M + H)+ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.135 | 4-Methoxy-3-trifluoromethyl-benzonitrile | 2-Methyl-benzoyl chloride | 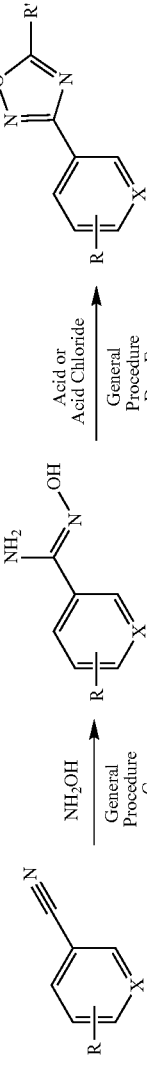 | 3-(4-Methoxy-3-trifluoromethyl-phenyl)-5-o-tolyl-[1,2,4]oxadiazole | 3.31 (f) | 335 (M + H)$^+$ |
| A.136 | Biphenyl-4-carbonitrile | 2-Methyl-benzoyl chloride | 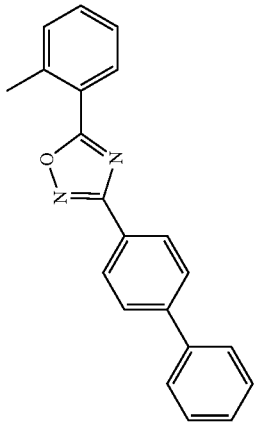 | 3-Biphenyl-4-yl-5-o-tolyl-[1,2,4]oxadiazole | 3.38 (f) | 313 (M + H)$^+$ |
| A.137 | 3-Chloro-4-isopropoxy-benzonitrile (A) | 2,4-Dichloro-benzoyl chloride (F) | 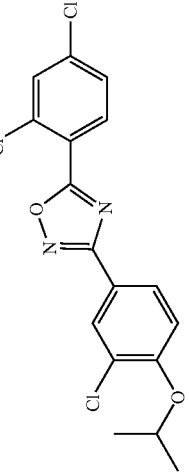 | 3-(3-Chloro-4-isopropoxy-phenyl)-5-(2,4-dichloro-phenyl)-[1,2,4]oxadiazole | 3.48 (f) | 385 (M + H)$^+$ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R_t/min (method) | m/z |
|---|---|---|---|---|---|---|
| A.138 | 3-Chloro-4-cyclopropyl methoxy-benzonitrile (B) | 4-amino-2-chlorobenzoic acid | 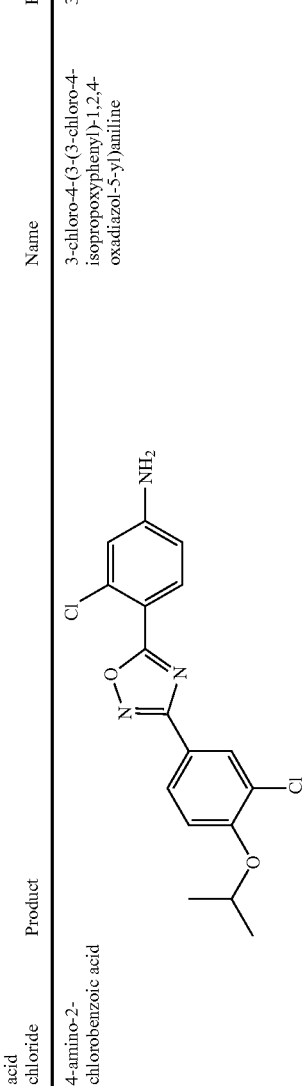 | 3-chloro-4-(3-chloro-4-isopropoxyphenyl)-1,2,4-oxadiazol-5-yl)aniline | 3.08 (c) | 364.09 (M + H)+ |
| A.139 | 3-Chloro-4-cyclopropyl methoxy-benzonitrile (B) | 1-methyl-1H-pyrazole-5-carboxylic acid | 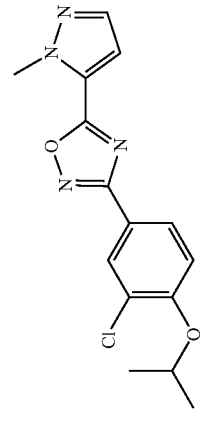 | 3-(3-chloro-4-isopropoxyphenyl)-5-(1-methyl-1H-pyrazol-5-yl)-1,2,4-oxadiazole | 3.08 (a) | 319.25 (M + H)+ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.140 | 3-Chloro-4-cyclopropyl-methoxy-benzonitrile (B) | 1-isopropyl-indoline-4-carboxylic acid | | 3-(3-chloro-4-isopropoxyphenyl)-5-(1-isopropyl-1H-indol-4-yl)-1,2,4-oxadiazole | 2.40 (c) | 396.22 (M + H)$^+$ |
| A.141 | 3-Chloro-4-cyclopropyl-methoxy-benzonitrile (B) | 6-bromonico-tinic acid | | 5-(6-bromopyridin-3-yl)-3-(3-chloro-4-isopropoxyphenyl)-1,2,4-oxadiazole | 3.99 (a) | 396.03 (M + H)$^+$ |
| A.142 | 3-Chloro-4-cyclopropyl-methoxy-benzonitrile (B) | 4-(1-cyano-cyclopropyl)ben-zoic acid | | 1-(4-(3-(3-chloro-4-isopropoxyphenyl)-1,2,4-oxadiazol-5-yl)phenyl)cyclo-propanecarbonitrile | 3.19 (c) | 380.43 (M + H)$^+$ |

TABLE A-continued

Examples made using General Procedures C, D, E (Scheme 2)
The letter in parentheses below the nitrile precursors indicates the General Procedure by which the nitrile precursor was made.

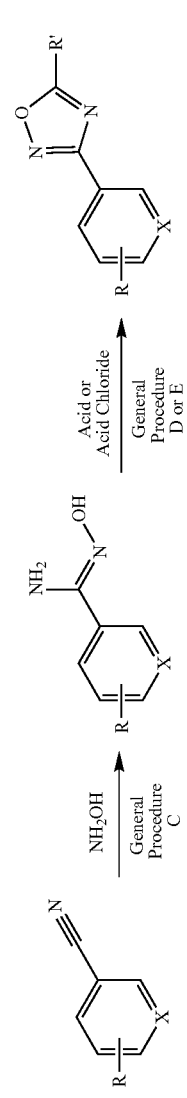

| Ex # | Nitrile precursor | Acid or acid chloride | Product | Name | m/z | R$_t$/min (method) |
|---|---|---|---|---|---|---|
| A.143 | 3-Chloro-4-cyclopropyl methoxy-benzonitrile (B) | 6-bromonico-tinoyl chloride | 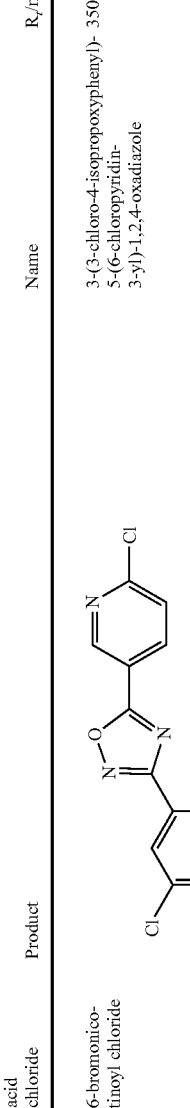 | 3-(3-chloro-4-isopropoxyphenyl)-5-(6-chloropyridin-3-yl)-1,2,4-oxadiazole | 350.08 (M + H)$^+$ | 3.92 (a) |
| A.144 | 3-Chloro-4-cyclopropyl methoxy-benzonitrile (B) | 1-isopropyl indoline-4-carboxylic acid | 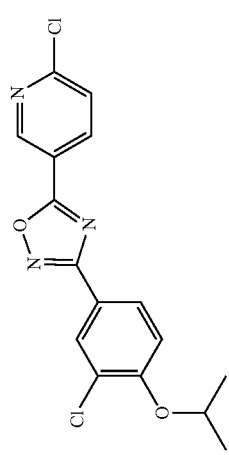 | 3-(3-chloro-4-isopropoxyphenyl)-5-(1-isopropylindolin-4-yl)-1,2,4-oxadiazole | 398.20 (M + H)$^+$ | 3.56 (c) |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R$_t$/min (method) | m/z |
|---|---|---|---|---|---|---|
| A.145 | 3-Chloro-4-cyclopropyl methoxy-benzonitrile (B) | 1-(2,4-dichloro-phenyl)cyclopropane carboxylic acid | 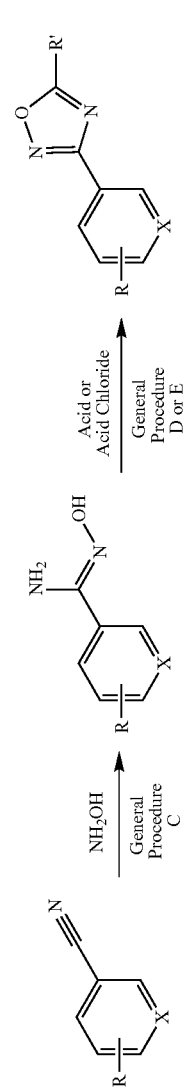 | 3-(3-chloro-4-isopropoxyphenyl)-5-(1-(2,4-dichlorophenyl) cyclopropyl)-1,2,4-oxadiazole | 3.48 (c) | 425.04 (M + H)+ |
| A.146 | 3-Chloro-4-cyclopropyl methoxy-benzonitrile (B) | 4-(pyridin-4-yl)butanoic acid | 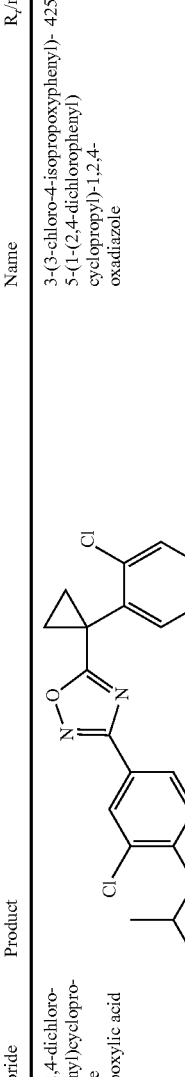 | 3-(3-chloro-4-isopropoxyphenyl)-5-(3-(pyridin-4-yl)propyl)-1,2,4-oxadiazole HCl salt | 3.11 (c) | 358.27 (M + H)+ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | R,/min (method) | m/z |
|---|---|---|---|---|---|---|
| A.147 | 3-Chloro-4-cyclopropyl methoxy-benzonitrile (B) | 1H-indole-4-carboxylic acid | 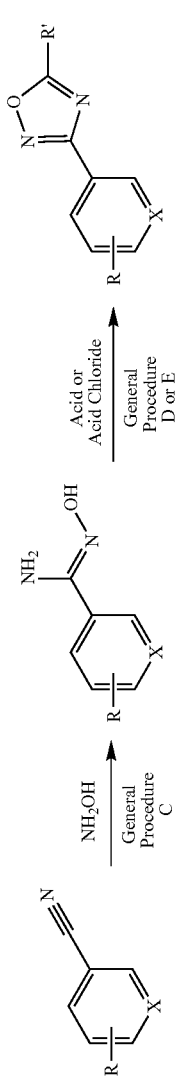 | 3-(3-chloro-4-isopropoxyphenyl)-5-(1H-indol-4-yl)-1,2,4-oxadiazole | 2.69 (h) | 354.17 (M + H)+ |
| A.148 | 3-Chloro-4-cyclopropyl methoxy-benzonitrile (B) | 4-sulfamoyl benzoic acid | 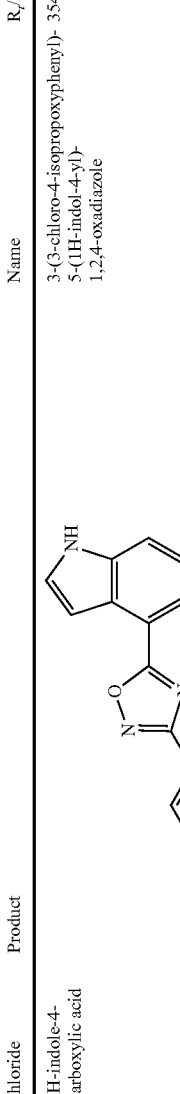 | 4-(3-(3-chloro-4-isopropoxyphenyl)-1,2,4-oxadiazol-5-yl)benzenesulfonamide | 2.77 (c) | 394.18 (M + H)+ |
| A.149 | 3-Chloro-4-cyclopropyl methoxy-benzonitrile (B) | 4-(hydroxymethyl)benzoic acid | 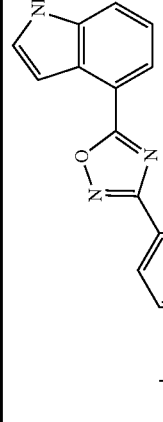 | (4-(3-(3-chloro-4-isopropoxyphenyl)-1,2,4-oxadiazol-5-yl)phenyl)methanol | 2.80 (c) | 345.16 (M + H)+ |

TABLE A-continued

Examples made using General Procedures C, D, E (Scheme 2)
The letter in parentheses below the nitrile precursors indicates the General Procedure by which the nitrile precursor was made.

| Ex # | Nitrile precursor | Acid or acid chloride | Product | Name | $R_t$/min (method) | m/z |
|---|---|---|---|---|---|---|
| A.150 | 3-Chloro-4-cyclopropyl methoxy-benzonitrile (B) | 1,2,3,4-tetrahydro-quinoline-6-carboxylic acid | | 3-(3-chloro-4-isopropoxyphenyl)-5-(1,2,3,4-tetrahydroquinolin-6-yl)-1,2,4-oxadiazole | 3.22 (c) | 370.18 (M + H)+ |

Note a: No acid or acid chloride is available. The product is a byproduct in preparation of 4-[3-(3-Chloro-4-isopropoxy-phenyl)-[1,2,4]oxadi-azol-5-yl]-pyridine.
Note b: Compound did not ionize under LCMS conditions. ¹H NMR (Varia Inova 500 NMR Spectrometer (i499), DMSO-d6) δ 8.56-8.71(m, 1H), 8.44-8.54(m, 1H), 8.14-8.24(m, 1H), 8.06-8.11(m, 1H), 7.84-7.93(m, 1H), 7.34-7.47(m, 1H), 4.67-5.00(m, 1H), 1.36(d, 6H)
Note c: Compound did not ionize under LCMS conditions. ¹H NMR (Varia Inova 500 NMR Spectrometer (i499), DMSO-d6) δ 8.28-8.44(m, 2H), 8.10-8.20(m, 2H), 8.06-8.10(m, 1H), 7.99-8.04(m, 1H), 7.30-7.51(m, 1H), 4.71-4.97(m, 1H), 1.37(d, 6H)
Note d: Compound did not ionize under LCMS conditions. ¹H NMR (Varia Inova 500 NMR Spectrometer (i499), DMSO-d6) δ 8.32-8.57(m, 1H), 7.82-7.90(m, 1H), 7.74-7.82(m, 1H), 7.20-7.40(m, 1H), 4.67-4.95(m, 1H), 1.85-2.13(m, 2H), 1.67-1.82(m, 2H), 1.53-1.63(m, 1H), 1.25-1.42(m, 9H)
Note e: Compound did not ionize under LCMS conditions. ¹H NMR (400 MHz, DMSO-d6) δ 8.24(s, 2H), 8.08(d, 1H), 8.01(dd, 1H), 7.40(d, 1H), 4.83(sept, 1H), 1.35(d, 6H)

TABLE B

Examples made using General Procedures C, D or E, G and H

| Ex # | Nitrile precursor | Acid or acid chloride | Amine | Structure | Name | m/z | Rt/min (method) |
|---|---|---|---|---|---|---|---|
| B.1 | 3-bromo-4-isopropoxybenzonitrile | 2-chloro-4-cyanobenzoic acid | azetidine-3-carboxylic acid | 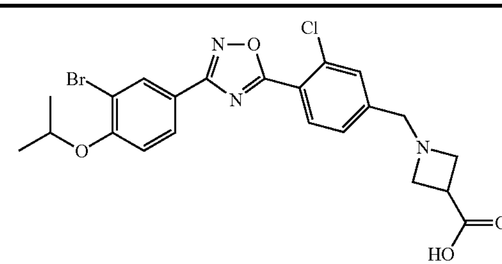 | 1-(4-(3-bromo-4-isopropoxyphenyl)-1,2,4-oxadiazol-5-yl)-3-chlorobenzyl)azetidine-3-carboxylic acid | 508.05 (M + H)+ | 3.16 (a) |
| B.2 | 3-chloro-4-isopropoxybenzonitrile | 3-cyanobenzoic acid | azetidine-3-carboxylic acid | 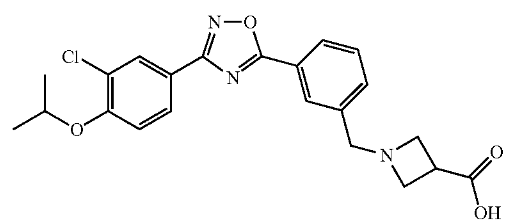 | 1-(3-(3-chloro-4-isopropoxyphenyl)-1,2,4-oxadiazol-5-yl)benzyl)azetidine-3-carboxylic acid | 428.19 (M + H)+ | 1.41 (a) |

TABLE B-continued

Examples made using General Procedures C, D or E, G and H

| Ex # | Nitrile precursor | Acid or acid chloride | Amine | Structure | Name | m/z | Rt/min (method) |
|---|---|---|---|---|---|---|---|
| B.3 | 3-chloro-4-isopropoxybenzonitrile | 2-chloro-4-cyanobenzoic acid | azetidine-3-carboxylic acid | 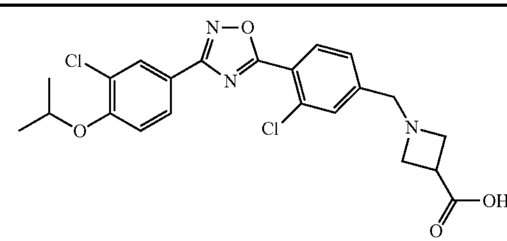 | 1-(3-chloro-4-(3-chloro-4-isopropoxyphenyl)-1,2,4-oxadiazol-5-yl)benzyl)azetidine-3-carboxylic acid | 462.16 (M + H)+ | 2.05 (a) |
| B.4 | 4-isopropoxy-3-(trifluoromethyl)benzonitrile | 4-cyanobenzoic acid | azetidine-3-carboxylic acid | 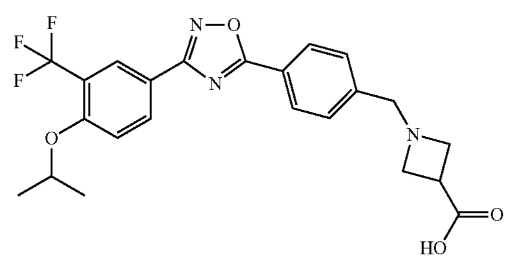 | 1-(4-(3-(4-isopropoxy-3-(trifluoromethyl)phenyl)-1,2,4-oxadiazol-5-yl)benzyl)azetidine-3-carboxylic acid | 462.25 (M + H)+ | 1.42 (a) |

TABLE B-continued

Examples made using General Procedures C, D or E, G and H

| Ex # | Nitrile precursor | Acid or acid chloride | Amine | Structure Name | m/z | Rt/min (method) |
|---|---|---|---|---|---|---|
| B.5 | 3-ethoxy-4-isopropoxybenzonitrile | 4-cyanobenzoic acid | azetidine-3-carboxylic acid | 1-(4-(3-(3-ethoxy-4-isopropoxyphenyl)-1,2,4-oxadiazol-5-yl)benzyl)azetidine-3-carboxylic acid | 438.30 (M + H)+ | 1.19 (a) |
| B.6 | 3-chloro-4-isopropoxybenzonitrile | 4-cyanobenzoic acid | 3-aminopropanoic acid | 3-(4-(3-(3-chloro-4-isopropoxyphenyl)-1,2,4-oxadiazol-5-yl)benzyl)aminopropanoic acid | 416.50 (M + H)+ | 1.82 (c) |

TABLE B-continued

Examples made using General Procedures C, D or E, G and H

| Ex # | Nitrile precursor | Acid or acid chloride | Amine | Structure | Name | m/z | Rt/min (method) |
|---|---|---|---|---|---|---|---|
| B.7 | 4-morpholino-3-(trifluoromethyl)benzonitrile | 4-cyanobenzoic acid | azetidine-3-carboxylic acid | 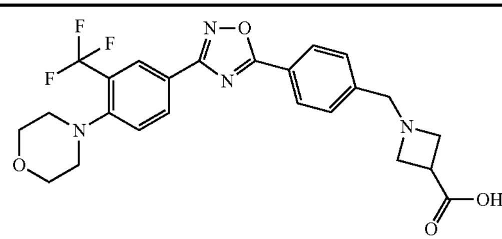 | 1-(4-(3-(4-morpholino-3-(trifluoromethyl)phenyl)-1,2,4-oxadiazol-5-yl)benzyl)azetidine-3-carboxylic acid | 489.22 (M + H)+ | 2.18 (a) |
| B.8 | 4-isopropoxy-3-methoxybenzonitrile | 4-cyanobenzoic acid | azetidine-3-carboxylic acid | 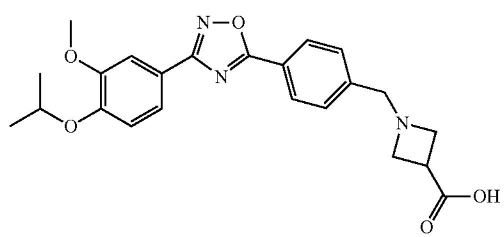 | 1-(4-(3-(4-isopropoxy-3-methoxyphenyl)-1,2,4-oxadiazol-5-yl)benzyl)azetidine-3-carboxylic acid | 424.37 (M + H)+ | 1.41 (a) |

TABLE B-continued

Examples made using General Procedures C, D or E, G and H

| Ex # | Nitrile precursor | Acid or acid chloride | Amine | Structure | Name | m/z | Rt/min (method) |
|---|---|---|---|---|---|---|---|
| B.9 | 3-chloro-4-isopropoxybenzonitrile | 4-cyano-2-methoxybenzoic acid | azetidine-3-carboxylic acid | 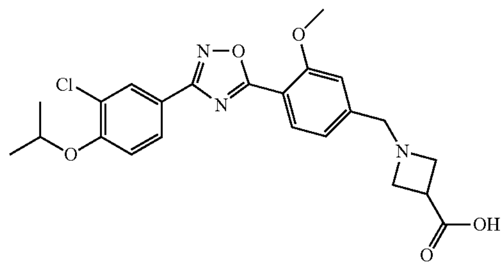 | 1-(4-(3-chloro-4-isopropoxyphenyl)-1,2,4-oxadiazol-5-yl)-3-methoxybenzyl)azetidine-3-carboxylic acid | 458.19 (M + H)+ | 2.05 (a) |
| B.10 | 4-morpholino-3-(trifluoromethyl)benzonitrile | 2-chloro-4-cyanobenzoic acid | azetidine-3-carboxylic acid | 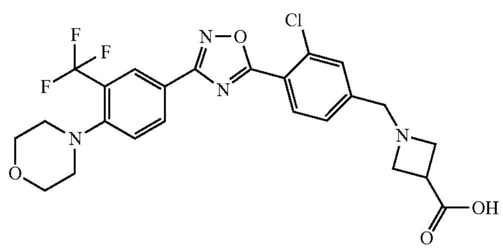 | 1-(3-chloro-4-(3-(4-morpholino-3-(trifluoromethyl)phenyl)-1,2,4-oxadiazol-5-yl)benzyl)azetidine-3-carboxylic acid | 523.21 (M + H)+ | 2.23 (a) |

TABLE B-continued

Examples made using General Procedures C, D or E, G and H

| Ex # | Nitrile precursor | Acid or acid chloride | Amine | Structure | Name | m/z | Rt/min (method) |
|---|---|---|---|---|---|---|---|
| B.11 | (R)-3-chloro-4-(tetrahydrofuran-3-yloxy)benzonitrile | 4-cyanobenzoic acid | azetidine-3-carboxylic acid | 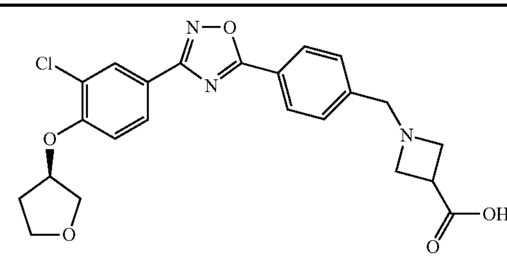 | (R)-1-(4-(3-chloro-4-(tetrahydrofuran-3-yloxy)phenyl)-1,2,4-oxadiazol-5-yl)benzyl)azetidine-3-carboxylic acid | 454.19 (M − H)⁻ | 1.98 (a) |
| B.12 | 4-(tetrahydrofuran-3-yloxy)-3-(trifluoromethyl)benzonitrile | 4-cyanobenzoic acid | azetidine-3-carboxylic acid | 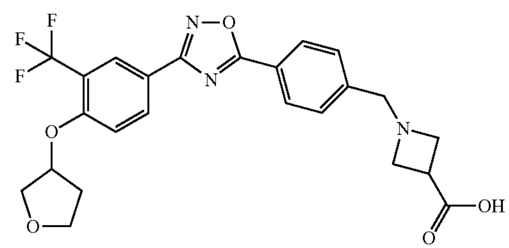 | 1-(4-(3-(4-(tetrahydrofuran-3-yloxy)-3-(trifluoromethyl)phenyl)-1,2,4-oxadiazol-5-yl)benzyl)azetidine-3-carboxylic acid | 490.29 (M + H)⁺ | 2.67 (a) |

TABLE B-continued

Examples made using General Procedures C, D or E, G and H

| Ex # | Nitrile precursor | Acid or acid chloride | Amine | Structure | Name | m/z | Rt/min (method) |
|---|---|---|---|---|---|---|---|
| B.13 | 3-chloro-4-isopropoxybenzonitrile | 4-cyanobenzoic acid | 2-aminoacetic acid | 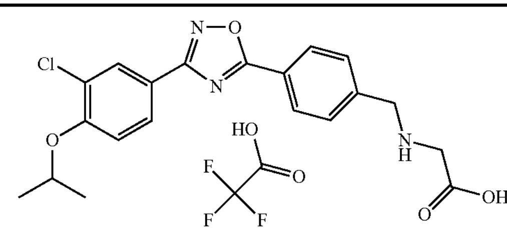 | 2-(4-(3-(3-chloro-4-isopropoxyphenyl)-1,2,4-oxadiazol-5-yl)benzylamino)acetic acid TFA salt | 400.14 (M + H)+ | 1.55 (c) |
| B.14 | 3-chloro-4-isopropoxybenzonitrile | 4-cyanobenzoic acid | piperidine-4-carboxylic acid | 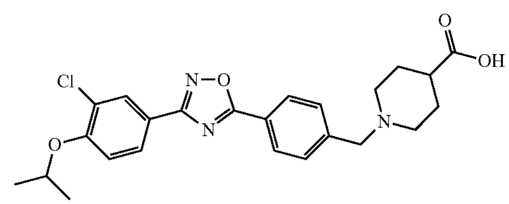 | 1-(4-(3-(3-chloro-4-isopropoxyphenyl)-1,2,4-oxadiazol-5-yl)benzyl)piperidine-4-carboxylic acid | 456.61 (M + H)+ | 1.95 (c) |
| B.15 | 3-chloro-4-isopropoxybenzonitrile | 4-cyanobenzoic acid | 1-aminocyclopropanecarboxylic acid | 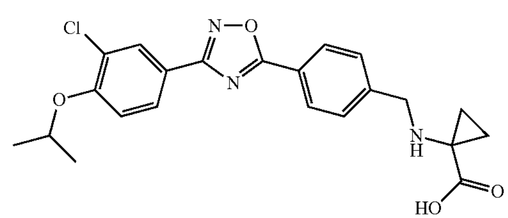 | 1-(4-(3-(3-chloro-4-isopropoxyphenyl)-1,2,4-oxadiazol-5-yl)benzylamino)cyclopropanecarboxylic acid | 426.37 (M − H)− | 1.92 (c) |

TABLE B-continued

Examples made using General Procedures C, D or E, G and H

| Ex # | Nitrile precursor | Acid or acid chloride | Amine | Structure | Name | m/z | Rt/min (method) |
|---|---|---|---|---|---|---|---|
| B.16 | 3-chloro-4-isopropoxybenzonitrile | 2-chloro-5-cyanobenzoic acid | azetidine-3-carboxylic acid | 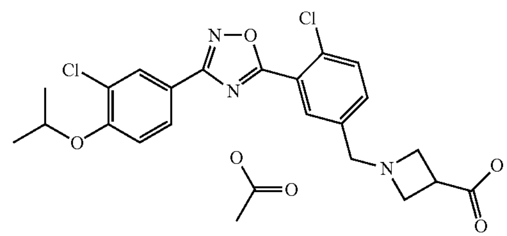 | 1-(4-chloro-3-(3-(3-chloro-4-isopropoxyphenyl)-1,2,4-oxadiazol-5-yl)benzyl)azetidine-3-carboxylic acid acetate salt | 462.49 (M + H)+ | 2.29 (b) |
| B.17 | benzonitrile | 4-cyanobenzoic acid | azetidine-3-carboxylic acid | 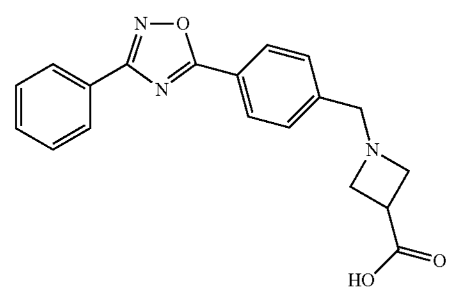 | 1-(4-(3-phenyl-1,2,4-oxadiazol-5-yl)benzyl)azetidine-3-carboxylic acid | 336.23 (M + H) | 2.01 (b) |

TABLE B-continued

Examples made using General Procedures C, D or E, G and H

| Ex # | Nitrile precursor | Acid or acid chloride | Amine | Structure | Name | m/z | Rt/min (method) |
|---|---|---|---|---|---|---|---|
| B.18 | 3-chloro-4-isopropoxybenzonitrile | 3-cyanobenzoic acid | 2-aminoacetic acid | 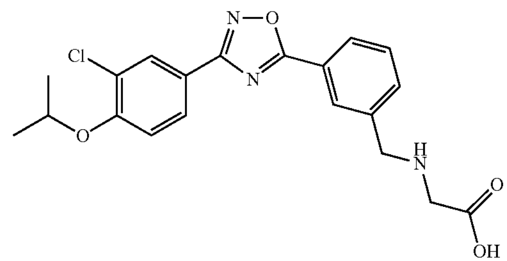 | 2-(3-(3-chloro-4-isopropoxyphenyl)-1,2,4-oxadiazol-5-yl)benzylamino)acetic acid | 402.16 (M + H)+ | 1.85 (f) |
| B.19 | 4-isopropoxy-3-(trifluoromethyl)benzonitrile | 4-cyanobenzoic acid | azetidine-3-carboxylic acid | 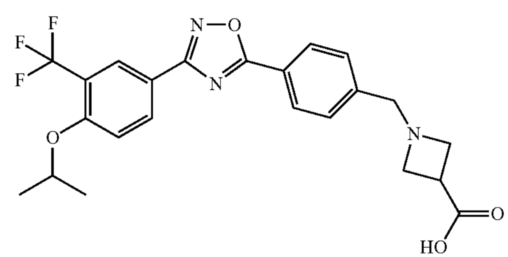 | 1-(4-(3-(4-isopropoxy-3-(trifluoromethyl)phenyl)-1,2,4-oxadiazol-5-yl)benzyl)azetidine-3-carboxylic acid | 462.25 (M + H)+ | 1.42 (f) |

TABLE B-continued

Examples made using General Procedures C, D or E, G and H

| Ex # | Nitrile precursor | Acid or acid chloride | Amine | Structure | Name | m/z | Rt/min (method) |
|---|---|---|---|---|---|---|---|
| B.20 | (S)-3-chloro-4-(tetrahydrofuran-3-yloxy)benzonitrile | 4-cyanobenzoic acid | azetidine-3-carboxylic acid | 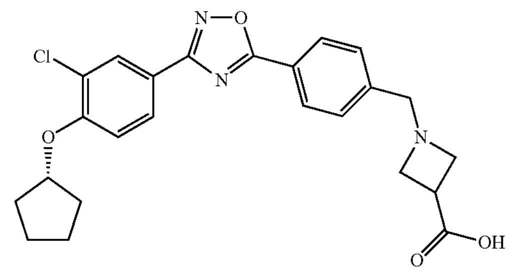 | (S)-1-(4-(3-chloro-4-(tetrahydrofuran-3-yloxy)phenyl)-1,2,4-oxadiazol-5-yl)benzyl)azetidine-3-carboxylic acid | 456.22 (M + H)+ | 1.99 (a) |
| B.21 | benzonitrile | 4-cyanobenzoic acid | (1R,3S)-3-aminocyclopentanecarboxylic acid | 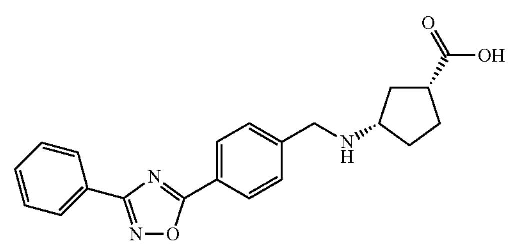 | (1R,3S)-3-(4-(3-phenyl-1,2,4-oxadiazol-5-yl)benzylamino)cyclopentanecarboxylic acid | 364.72 (M + H) | 2.03 (b) |

TABLE B-continued

Examples made using General Procedures C, D or E, G and H

| Ex # | Nitrile precursor | Acid or acid chloride | Amine | Structure | Name | m/z | Rt/min (method) |
|---|---|---|---|---|---|---|---|
| B.22 | benzonitrile | 4-cyanobenzoic acid | (1R,3R)-3-aminocyclopentanecarboxylic acid | 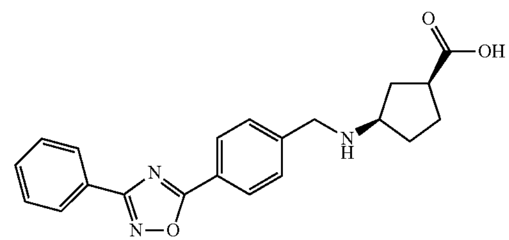 | (1S,3R)-3-(4-(3-phenyl-1,2,4-oxadiazol-5-yl)benzylamino)cyclopentanecarboxylic acid | 364.22 (M + H) | 2.04 (b) |

TABLE C

Examples made using General Procedures C, D or E, I or J and K

| Ex # | Nitrile precursor | Acid or acid chloride | tert-butyl ester | Structure | Name | m/z | Rt/min (method) |
|---|---|---|---|---|---|---|---|
| C.1 | (Z)-N'-hydroxy-1H-indole-4-carboximid-amide | 3-chloro-4-isopropoxy-benzoic acid | tert-butyl acrylate | 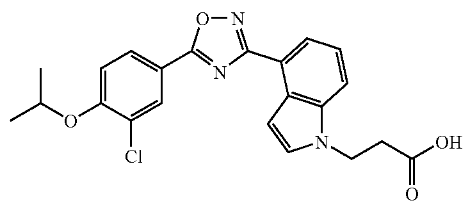 | 3-(4-(5-(3-chloro-4-isopropoxyphenyl)-1,2,4-oxadiazol-3-yl)-1H-indol-1-yl)propanoic acid | 424.14 (M − H)− | 2.41 (c) |
| C.2 | 3-chloro-4-isopropoxy-benzonitrile | 1H-indole-4-carboxylic acid | tert-butyl 2-fluoro-acrylate | 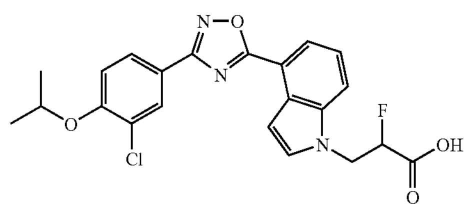 | 3-(4-(3-(3-chloro-4-isopropoxyphenyl)-1,2,4-oxadiazol-5-yl)-1H-indol-1-yl)-2-fluoropropanoic acid | 444.14 (M + H)+ | 2.20 (c) |
| C.3 | 3-chloro-4-isopropoxy-benzonitrile | 1H-indole-4-carboxylic acid | tert-butyl 4-bromo-butanoate | 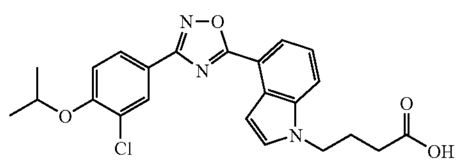 | 4-(4-(3-(3-chloro-4-isopropoxyphenyl)-1,2,4-oxadiazol-5-yl)-1H-indol-1-yl)butanoic acid | 440.21 (M + H)+ | 2.95 (c) |
| C.4 | 3-chloro-4-isopropoxy-benzonitrile | 1H-indole-4-carboxylic acid | tert-butyl meth-acrylate | 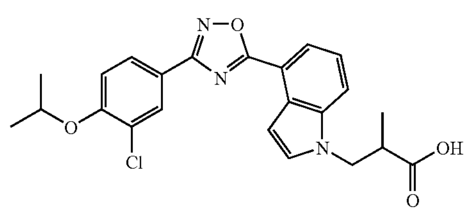 | 3-(4-(3-(3-chloro-4-isopropoxyphenyl)-1,2,4-oxadiazol-5-yl)-1H-indol-1-yl)-2-methylpropanoic acid | 438.17 (M − H)− | 2.47 (c) |
| C.5 | 4-morpholino-3-(trifluoro-methyl)ben-zonitrile | 1H-indole-4-carboxylic acid | tert-butyl acrylate | 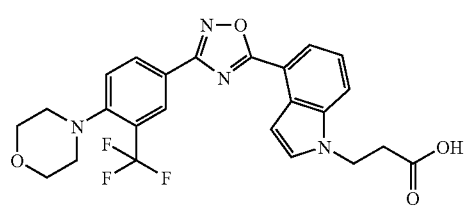 | 3-(4-(3-(4-morpholino-3-(trifluoro-methyl)phenyl)-1,2,4-oxadiazol-5-yl)-1H-indol-1-yl)propanoic acid | 487.56 (M + H)+ | 2.79 (c) |

TABLE C-continued

Examples made using General Procedures C, D or E, I or J and K

| Ex # | Nitrile precursor | Acid or acid chloride | tert-butyl ester | Structure | Name | m/z | Rt/min (method) |
|---|---|---|---|---|---|---|---|
| C.6 | 3-chloro-4-isopropoxy-benzonitrile | 1H-indole-4-carboxylic acid | tert-butyl bromo-acetate | 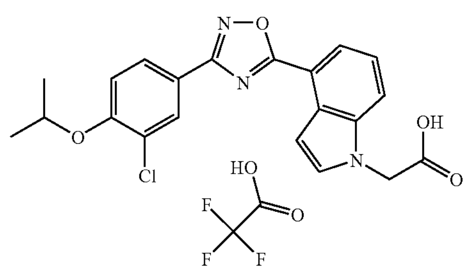 | 2-(4-(3-(3-chloro-4-isopropoxyphenyl)-1,2,4-oxadiazol-5-yl)-1H-indol-1-yl)acetic acid TFA salt | 412.18 (M + H)+ | 2.38 (c) |
| C.7 | 3-chloro-4-isopropoxy-benzonitrile | 1H-indole-4-carboxylic acid | ethyl 3-chloro-2,2-dimethyl-propanoate | 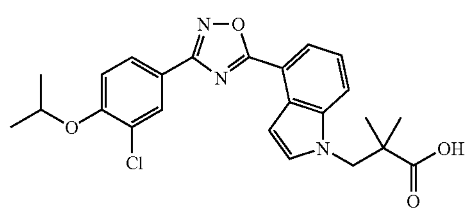 | 3-(4-(3-(3-chloro-4-isopropoxyphenyl)-1,2,4-oxadiazol-5-yl)-1H-indol-1-yl)-2,2-dimethylpropanoic acid | 454.25 (M + H)+ | 3.11 (c) |
| C.8 | 3-chloro-4-isopropoxy-benzonitrile | 1H-pyrrolo[2,3-b]pyridine-4-carboxylic acid | tert-butyl acrylate | 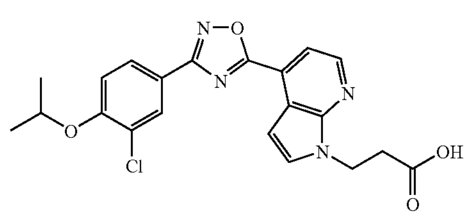 | 3-(4-(3-(3-chloro-4-isopropoxyphenyl)-1,2,4-oxadiazol-5-yl)-1H-pyrrolo[2,3-b]pyridin-1-yl)propanoic acid | 427.17 (M + H)+ | 2.84 (c) |

TABLE D

Examples made using General Procedures C, D or E and L

| Ex # | Nitrile precursor | Acid chloride | Amine | Structure |
|---|---|---|---|---|
| D.1 | 4-morpholino-3-(trifluoromethyl)benzonitrile | 4-fluorobenzoyl chloride | (1R,3S)-3-amino-cyclo-pentane-carboxylic acid | 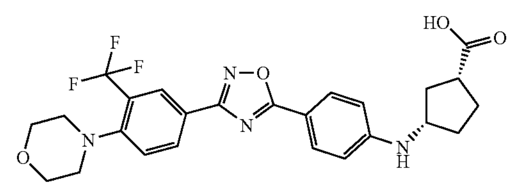 |
| D.2 | 3-chloro-4-isopropoxybenzonitrile | 4-bromobenzoyl chloride | (1R,3R)-3-amino-cyclo-pentane-carboxylic acid | 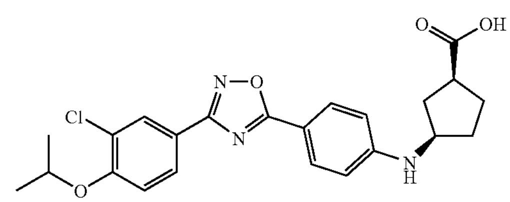 |
| D.3 | benzonitrile | 4-fluorobenzoyl chloride | (1R,3S)-3-amino-cyclo-pentane-carboxylic acid | 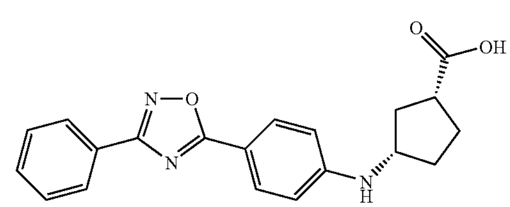 |

| Ex # | Name | m/z | Rt/min (method) |
|---|---|---|---|
| D.1 | (1R,3S)-3-(4-(3-(4-morpholino-3-(trifluoromethyl)phenyl)-1,2,4-oxadiazol-5-yl)phenylamino)cyclopentanecarboxylic acid | 503.21 (M − H)+ | 3.31 (a) |
| D.2 | (1S,3R)-3-(4-(3-(3-chloro-4-isopropoxyphenyl)-1,2,4-oxadiazol-5-yl)phenylamino)cyclopentanecarboxylic acid | 442.05 (M + H) | 2.97 (b) |
| D.3 | (1R,3S)-3-(4-(3-phenyl-1,2,4-oxadiazol-5-yl)phenylamino)cyclopentanecarboxylic acid | 350.16 (M − H)+ | 2.99 (a) |

TABLE E

Examples made using General Procedures M, N, D and O

| Ex # | Nitrile precursor | Phenol | Alcohol | Structure | Name | m/z | Rt/min (method) |
|---|---|---|---|---|---|---|---|
| E.1 | 3-chloro-4-isopropoxy-benzonitrile | benzyl 4-hydroxy-benzoate | (S)-(2,2-dimethyl-1,3-dioxolan-4-yl)methanol | 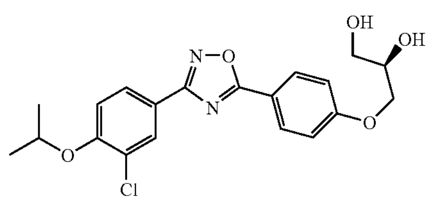 | (R)-3-(4-(3-(3-chloro-4-isopropoxyphenyl)-1,2,4-oxadiazol-5-yl)phenoxy)propane-1,2-diol | 405.25 (M + H)+ | 2.72 (b) |
| E.2 | 3-chloro-4-isopropoxy-benzonitrile | benzyl 4-hydroxy-benzoate | (2,2-dimethyl-1,3-dioxan-5-yl)methanol | 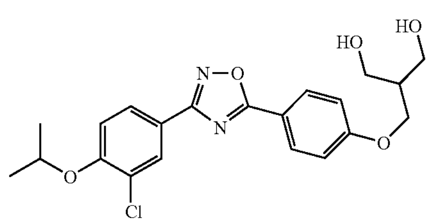 | 2-((4-(3-(3-chloro-4-isopropoxyphenyl)-1,2,4-oxadiazol-5-yl)phenoxy)methyl)propane-1,3-diol | 419.23 (M + H)+ | 3.08 (g) |
| E.3 | 3-chloro-4-isopropoxy-benzonitrile | methyl 2-chloro-4-hydroxy-benzoate | (S)-(2,2-dimethyl-1,3-dioxolan-4-yl)methanol | 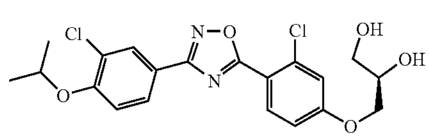 | (R)-3-(3-chloro-4-(3-(3-chloro-4-isopropoxyphenyl)-1,2,4-oxadiazol-5-yl)phenoxy)propane-1,2-diol | 439.16 (M + H)+ | 2.83 (a) |

Preparation of Additional Examples

Example #:1

Preparation of 3-chloro-4-isopropoxy-benzoic Acid

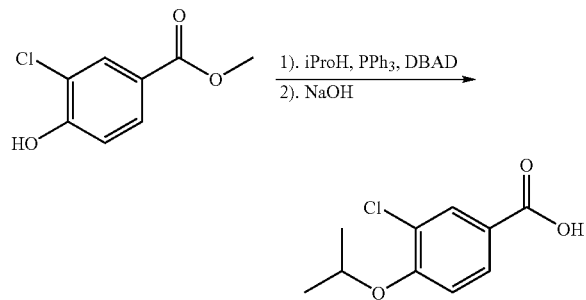

Into a round bottom flask was added triphenylphosphine (62 g, 0.263 mol), 3-chloro-4-hydroxy-benzoic acid methyl ester (10 g, 0.0535 mol) and anhydrous THF (500 mL). The mixture was briefly stirred under nitrogen, then DBAD (19.75 g, 0.0858 mol) was added. The mixture was stirred for a few minutes before adding anhydrous isopropanol (5.125 mL, 0.067 mol). After the reaction mixture was stirred at room temperature under an atmosphere of nitrogen for about 3 hours, DBAD (19.75 g, 0.0858 mol) and anhydrous isopropanol (5.125 mL, 0.067 mol) were added and the mixture was left to stir at room temperature overnight. The solvent was removed under reduced pressure. The residue was dissolved in minimum amount of ethyl acetate. Heptane was added and the precipitate was removed by filtration. The filtrate was brought up in methanol. Water was added until cloudy. Precipitate was filtered off. The methanol/water precipitation procedure was repeated two more times. The filtrate was taken up in THF (200 mL) and 5 M NaOH (200 mL). The mixture was stirred at room temperature overnight. The organic solvent was removed under reduced pressure. The aqueous layer was extracted three times with ethyl acetate. The aqueous layer was further acidified to pH 1-2 with 2 M HCl. The cloudy suspension was then extracted with ethyl acetate three times. The organic layers were combined, dried over magnesium sulfate, and concentrated to dryness to give 3-chloro-4-isopropoxy-benzoic acid (8.4 g, 71.4%) as a white solid.

LC/MS (Table 1, Method b) $R_f$=2.42 min, m/z (M–H)- 213; $^1$H NMR (400 MHz, DMSO-$d_6$) δ12.95 (s, 1H), 7.87 (m, 2H), 7.25 (d, 1H), 4.79 (m, 1H), 1.32 (d, 6H)

Example #2

4-(3-(3-chloro-4-isopropoxyphenyl)-1,2,4-oxadiazol-5-yl)benzonitrile

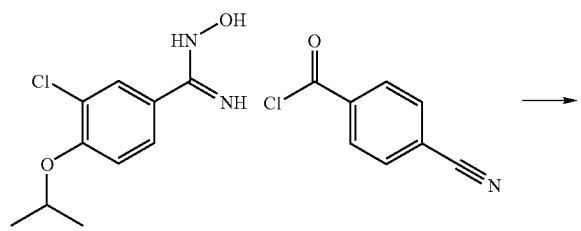

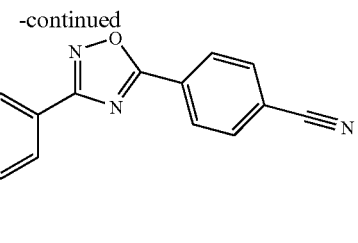

3-Chloro-N-hydroxy-4-isopropoxybenzimidamide (10 g, 43.7 mmol) was dissolved in DMF (219 ml) under nitrogen. The mixture was heated at about 110° C. for about 10 min. A solution of 4-cyanobenzoyl chloride (7.24 g, 43.7 mmol) dissolved in DMF (30 mL) was added dropwise over about 20 min and the reaction heated at about 110° C. for about 4 h. until LCMS shows reaction complete. The reaction was cooled in an ice bath and poured into rapidly stirred water (1000 mL). The resulting white precipitate was collected by vacuum filtration and washed with water. The precipitate was dissolved in methylene chloride and washed with 1 N HCl and then brine. The methylene chloride was dried over sodium sulfate, filtered, and evaporated. Heptane and DCM were added to the residue and the mixture heated until the DCM had boiled off after which the mixture was allowed to cool. Solids did not dissolve in hot heptane. The resulting solid was collected by vacuum filtration and washed with heptane to provide 4-(3-(3-chloro-4-isopropoxyphenyl)-1,2, 4-oxadiazol-5-yl)benzonitrile (12.568 g, 37.0 mmol, 85% yield) as a tan solid: LCMS (Table 1, Method a) $R_t$=4.58 min.; MS m/z: 340.20 (M+H)$^+$.

Example #3

4-(3-(3-chloro-4-isopropoxyphenyl)-1,2,4-oxadiazol-5-yl)benzaldehyde

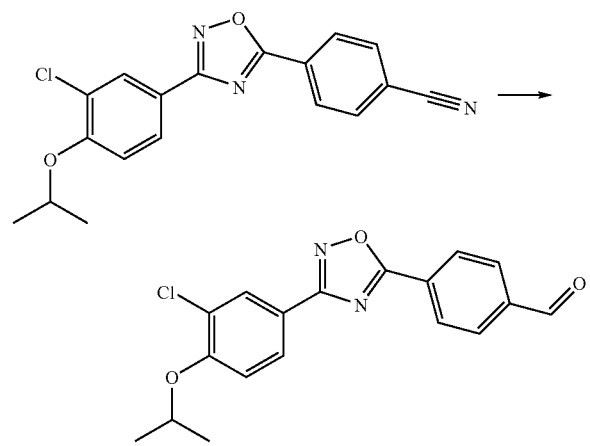

4-(3-(3-Chloro-4-isopropoxyphenyl)-1,2,4-oxadiazol-5-yl)benzonitrile (10 g, 29.4 mmol) was dissolved in dichloromethane (535 ml) under nitrogen. The reaction was cooled to about –40° C. in a dry ice/acetonitrile bath measuring the temperature internally. A solution of Dibal-H (58.9 ml, 58.9 mmol) was added dropwise and the reaction stirred for about 30 min. and then quenched with methanol. The mixture was stirred until the bubbles subsided. The mixture was then warmed to room temp. and stirred rapidly with a 10% solution of Rochelle's salt. The separated layers were extracted with DCM (3×100 mL). The combined extracts were stirred rapidly with about 100 mL of 1 N HCl and the solution turned from orange to colorless. TLC indicated the mixture had been cleaned up to just one spot with some baseline material. The layers were separated and the aqueous layer extracted with DCM (2×100 mL). The combined organic extracts were washed with brine, dried over sodium sulfate, filtered, and evaporated to dryness to afford an off white solid. The solid was stirred with heptane and the solvent removed carefully via pipette. The solid was dried under vacuum to afford 4-(3-(3-chloro-4-isopropoxyphenyl)-1,2,4-oxadiazol-5-yl)benzaldehyde (9.15 g, 26.7 mmol, 91% yield) as white solid: LCMS (Table 1, Method a) $R_t$=4.59 min.; MS m/z: 343.26, 345.18 (M+H)$^+$.

Example #4

1-(4-(3-(3-chloro-4-isopropoxyphenyl)-1,2,4-oxadiazol-5-yl)benzyl)azetidine-3-carboxylic acid

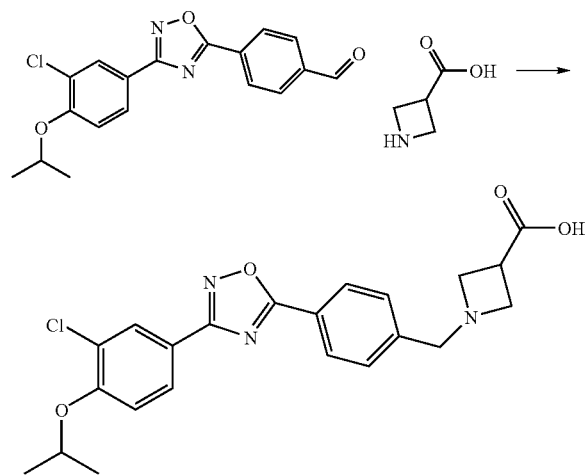

Azetidine-3-carboxylic acid (3.72 g, 36.8 mmol) (Synchem) was dissolved in acetic acid (16.03 ml, 280 mmol) and methanol (2 ml). This was added to a stirred suspension of 4-(3-(3-chloro-4-isopropoxyphenyl)-1,2,4-oxadiazol-5-yl)benzaldehyde (12 g, 35.0 mmol) in MeOH (600 ml). The reaction was stirred for about 18 h. Sodium cyanoborohydride (5.50 g, 88 mmol) was added and the reaction stirred for about 4 h. The reaction was cooled with an ice bath and the precipitate was collected by vacuum filtration and washed with ice cold methanol and then ether. TLC showed impurities still present. The solid was dissolved in 1:1 EtOAc/(6:3:1 CHCl$_3$/MeOH/NH$_4$OH) with a little extra added NH$_4$OH. Chromatography over silica gel in a mixture of 1:1 EtOAc/(6:3:1 CHCl$_3$/MeOH/NH$_4$OH) increasing to all 6:3:1 CHCl$_3$/MeOH/NH$_4$OH eluted the product. The fractions were evaporated to dryness to afford a colorless film/oil. Methanol was added and the mixture swirled but this gave low recovery on filtration. The mixture was dissolved in methanol. and the filtrate evaporated to dryness. The residue was resuspended in the minimum amount of methanol, water was added and the mixture filtered, washed with water and then ether. The residue was dried under vacuum at ambient temperature and then under vacuum at about 60° C. to remove trace methanol to afford 1-(4-(3-(3-chloro-4-isopropoxyphenyl)-1,2,4-oxadiazol-5-yl)benzyl)azetidine-3-carboxylic acid (8.3 g, 19.40 mmol, 55.4% yield) as a white solid: LCMS (Table 1, Method a) $R_t$=2.94 min.; MS m/z: 428.31, 430.27 (M+H)$^+$; mp 194.8-195.9° C.; $^1$H NMR (400 MHz, DMSO) δ ppm 8.12 (d, J=8.34 Hz, 2H), 8.06 (d, J=2.13 Hz, 1H), 8.00 (dd, J=8.67, 2.15 Hz, 1H), 7.54 (d, J=8.36 Hz, 2H), 7.39 (d, J=9.06 Hz, 1H), 4.88-4.77 (m, 1H), 3.67 (s, 2H), 3.48-3.38 (m, 2H), 3.29-3.19 (m, 3H), 1.35 (d, J=6.02 Hz, 6H).

Example #5

Preparation of 3-(3-chloro-4-isopropoxyphenyl)-5-(4-fluorophenyl)-1,2,4-oxadiazole

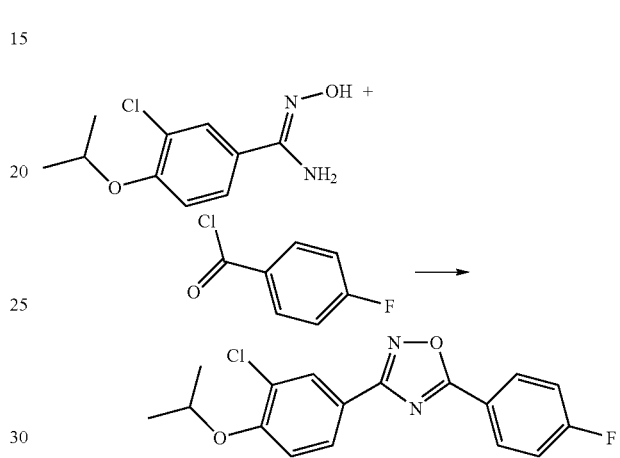

(Z)-3-Chloro-N'-hydroxy-4-isopropoxybenzimidamide (2.0 g. 8.75 mmol), 4-fluorobenzoyl chloride (2.1 g, 13.12 mmol) and pyridine (12 ml) are loaded into a 20 mL microwave vial equipped with a stir bar. The vessel is sealed and the reaction heated to 200° C. with cooling for 25 min. The mixture was purified using normal phase chromatography to afford a pale brown solid. Analysis by LCMS showed this to be a 35:30:21 mixture of 3-(3-chloro-4-isopropoxyphenyl)-5-(4-fluorophenyl)-1,2,4-oxadiazole, 2-chloro-4-(5-(4-fluorophenyl)-1,2,4-oxadiazol-3-yl)phenol and 4-fluorobenzoic acid. The mixture was purified a second time using normal phase chromatography to afford 5 fractions. Fractions 1, 2 and 3 were combined and evaporated to dryness to afford 3-(3-chloro-4-isopropoxyphenyl)-5-(4-fluorophenyl)-1,2,4-oxadiazole (420 mg, 14%) 10023683-145-P1 as a white solid. LCMS (Table 1, Method a) $R_t$, =2.85 min, m/z 333.10 (M+H)$^+$.

Example #6

Preparation of 3-chloro-4-(3-(3-chloro-4-isopropoxyphenyl)-1,2,4-oxadiazol-5-yl)benzonitrile

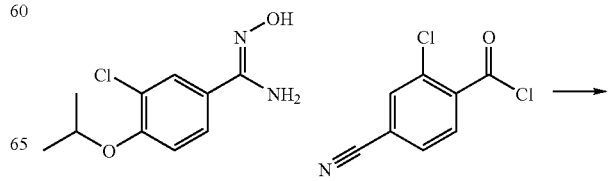

-continued

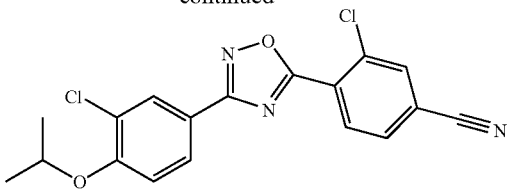

To a 250 mL RBF equipped with a stir bar was charged with 2-chloro-4-cyanobenzoic acid (3.0 g, 16.52 mmol), anhydrous DCM (80 mL), and DMF (0.064 mL, 0.826 mmol). Oxalyl chloride (8.26 mL, 16.52 mmol) (2M solution in DCM) was then added slowly and the mixture was stirred under nitrogen at ambient temperature. Upon addition of the oxalyl chloride, gas evolution began and the suspended solid began to dissolve. After about 2-3 hours, the reaction became translucent. The mixture was concentrated in vacuo. The resulting crude material was dissolved in pyridine (50 mL). To this was added (Z)-3-chloro-N'-hydroxy-4-isopropoxybenzimidamide (1.258 g, 5.50 mmol). The mixture was heated to about 100° C. under an atmosphere of nitrogen for about 16 hrs. The resulting mixture was cooled to ambient temperature. Pyridine was removed under reduced pressure and the resulting material was triturated in DCM and MeOH mixture (about 1:1). The resulting precipitate was left standing for a few minutes at ambient temperature then was collected via filtration, washed with a mixture of 1:1 DCM/MeOH, and then with straight MeOH and dried in a vacuum oven for about 48 hrs to yield 3-chloro-4-(3-(3-chloro-4-isopropoxyphenyl)-1,2,4-oxadiazol-5-yl)benzonitrile (1.529 g, 4.09 mmol) as a beige solid. $^1$H NMR (400 MHz, DMSO) δ ppm 8.39 (d, J=1.53 Hz, 1H), 8.35 (d, J=8.15 Hz, 1H), 8.09 (dd, J=8.14, 1.53 Hz, 1H), 8.05 (d, J=2.11 Hz, 1H), 8.00 (dd, J=8.63, 2.12 Hz, 1H), 7.39 (d, J=8.82 Hz, 1H), 4.82 (sept, J=6.04 Hz, 1H), 1.35 (d, J=6.01 Hz, 6H).

Example #7

Preparation of 2-(4-(3-(3-chloro-4-isopropoxyphenyl)-1,2,4-oxadiazol-5-yl)phenyl)propan-2-amine

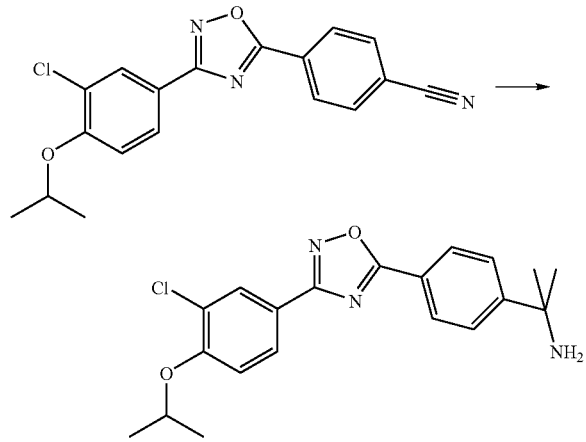

Anhydrous cerium (III) chloride (5.57 g, 22.60 mmol) and anhydrous tetrahydrofuran (20 mL) were added to a dry 2-neck round bottom flask under nitrogen. The resulting suspension was sonicated for a few minutes and then stirred at room temperature for about 90 minutes. The mixture was then cooled to about −50° C., and methyllithium (14.13 mL, 22.60 mmol) was added slowly. After about 60 min, and warming to about 0° C., the reaction was cooled to −50° C. and 4-(3-(3-chloro-4-isopropoxyphenyl)-1,2,4-oxadiazol-5-yl)benzonitrile (2.4 g, 7.06 mmol) in 8 mL of anhydrous THF was added drop-wise, to keep the temperature of the reaction at about −50° C. The reaction was maintained at −50° C. for 1 hr, then left to warm to room temperature overnight. The next day the reaction was cooled to −50° C., and quenched by the addition of 21 mL of 35% NH$_4$OH. The quenched reaction was left to warm to room temperature over two hours. The mixture was filtered through Celite® and washed with DCM (4×60 mL). The filtrate was collected and then washed with water and dried over MgSO$_4$. Solvent was removed under reduced pressure and the crude material was purified by RP-HPLC (A=50 mM ammonium acetate, B=acetonitrile; 30-70% B over 30.0 min (21.0 mL/min flow rate); 21.2×250 mm Thermo Hyperprep C18 column, 8 μm particles) to give 2-(4-(3-(3-chloro-4-isopropoxyphenyl)-1,2,4-oxadiazol-5-yl)phenyl)propan-2-amine as the acetic acid salt (309 mg; 10.1%). LCMS (Table 1, Method a) R$_t$=2.61 min; $^1$H NMR (400 MHz, DMSO-d6) δ ppm 8.14-7.94 (m, 4H), 7.80 (d, J=8.43 Hz, 2H), 7.37 (d, J=8.81 Hz, 1H), 4.80 (sept, J=6.04 Hz, 1H), 1.85 (s, 3H), 1.39 (s, 6H), 1.36-1.31 (d, J=6.04 Hz, 6H)

Example #8

Preparation of Methyl 3-(2-(4-(3-(3-chloro-4-isopropoxyphenyl)-1,2,4-oxadiazol-5-yl)phenyl)propan-2-ylamino)propanoate

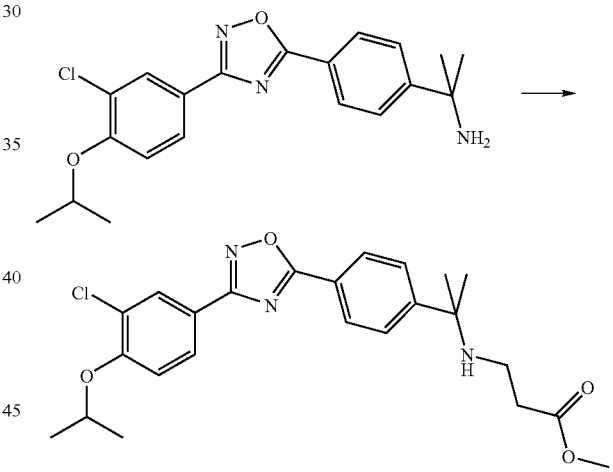

2-(4-(3-(3-Chloro-4-isopropoxyphenyl)-1,2,4-oxadiazol-5-yl)phenyl)propan-2-amine and acetic acid (132 mg, 0.306 mmol) was added to a 5 mL microwave vial equipped with a stirring bar. Methyl acrylate (52.6 mg, 0.611 mmol), and MeOH (3.0 mL) were added, the vial capped, and the reaction heated to about 120° C. for about 90 min under microwave irradiation (Biotage Optimizer, 300 W). After about 90 min another aliquot of methyl acrylate (52.6 mg, 0.611 mmol) was added and the reaction heated for another 60 min at about 120° C.

The reaction was cooled and the solvent removed under reduced pressure. The crude material was purified by RP-HPLC (A=50 mM ammonium acetate, B=acetonitrile; 30-70% B over 30.0 min (21.0 mL/min flow rate); 21.2×250 mm Thermo Hyperprep C18 column, 8 μm particles) to give methyl 3-(2-(4-(3-(3-chloro-4-isopropoxyphenyl)-1,2,4-oxadiazol-5-yl)phenyl)propan-2-ylamino)propanoate (83.5 mg; 59.7%). LCMS (Table 1, Method a) R$_t$=2.78 min, m/z=458.29 (M+H)$^+$.

Example #9

Preparation of 3-(2-(4-(3-(3-chloro-4-isopropoxyphenyl)-1,2,4-oxadiazol-5-yl)phenyl)propan-2-ylamino)propanoic Acid

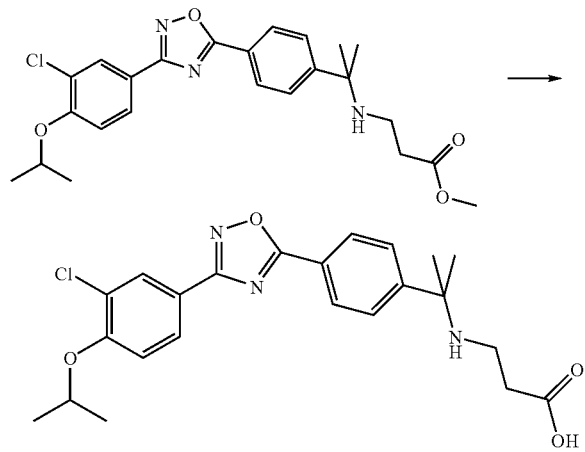

Methyl 3-(2-(4-(3-(3-chloro-4-isopropoxyphenyl)-1,2,4-oxadiazol-5-yl)phenyl)propan-2-ylamino)propanoate (83 mg, 0.181 mmol) was dissolved in ethanol (4 mL) and NaOH (4 mL, 8.00 mmol) was added. The mixture was stirred at room temperature under nitrogen. After about 20 minutes the reaction was neutralized by drop-wise addition of acetic acid. The aqueous mixture was then frozen and lyophilized. DCM was added to the solid, filtered, and washed with DCM. The filtrate was concentrated and ether added to afford a slightly cloudy solution. 1N HCl in ether was added dropwise until white precipitate formed. The material was collected by filtration, washed with ether, and dried in a vacuum oven to give 3-(2-(4-(3-(3-chloro-4-isopropoxyphenyl)-1,2,4-oxadiazol-5-yl)phenyl)propan-2-ylamino)propanoic acid as the hydrochloric acid salt (61.5 mg; 70.6%). LCMS (Table 1, Method a) $R_t$=1.98 min, m/z =444.29 (M+H)$^+$; 1H NMR (400 MHz, DMSO-d6) δ ppm 8.32 (d, J=8.57 Hz, 2H), 8.12 (d, J=2.08 Hz, 1H), 8.03 (dd, J=8.64, 2.10 Hz, 1H), 7.85 (d, J=8.59 Hz, 2H), 7.25 (d, J=8.78 Hz, 1H), 4.79 (sept, J=6.11 Hz, 1H), 2.95 (t, J=6.20 Hz, 2H), 2.44 (t, J=6.17 Hz, 2H), 1.84 (s, 6H), 1.40 (d, J=6.04 Hz, 6H).

Example #10

Preparation of 3-(3-chloro-4-isopropoxyphenyl)-5-(1H-indol-4-yl)-1,2,4-oxadiazole

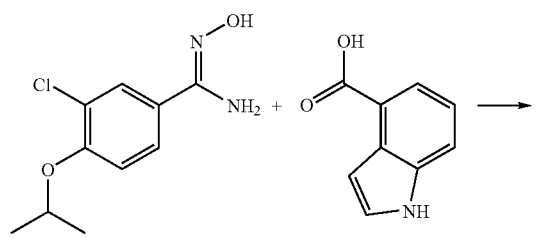

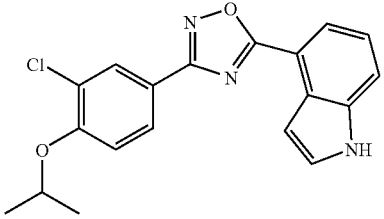

Under an atmosphere of nitrogen a mixture of 1H-indole-4-carboxylic acid (3.88 g, 24.05 mmol), (3-dimethylaminopropyl)-ethyl-carbodiimide hydrochloride (4.61 g, 24.05 mmol) and benzotriazol-1-ol hydrate (3.68 g, 24.05 mmol) in anhydrous DMF (61.4 ml) was stirred at ambient temperature for about 1 h. To the reaction mixture a solution of 3-chloro-N-hydroxy-4-isopropoxybenzamidine (5.0 g, 21.87 mmol) in DMF (11.51 ml) was added. The mixture was stirred and heated at about 140° C. for about 2 h. The mixture was cooled to ambient temperature and poured into water (1L). The product was partitioned between ethyl acetate and the aqueous phase. The organic layer washed with 1N HCl (4×150 mL), 1N NaOH (2×150 mL) and water (2×300 mL), dried over MgSO$_4$ and filtered. The solvent was removed under reduced pressure and the crude product was purified by elution through Florisil with heptane/ethyl acetate (2:1) to give 3-(3-chloro-4-isopropoxyphenyl)-5-(1H-indol-4-yl)-1,2,4-oxadiazole (2.76 g, 35.7%). LCMS (Table 1, Method b) Rt=2.69 min, m/z 354.17 (M+H)$^+$.

Example #11

Preparation of (4-(3-(3-chloro-4-isopropoxyphenyl)-1,2,4-oxadiazol-5-yl)phenyl)methanol

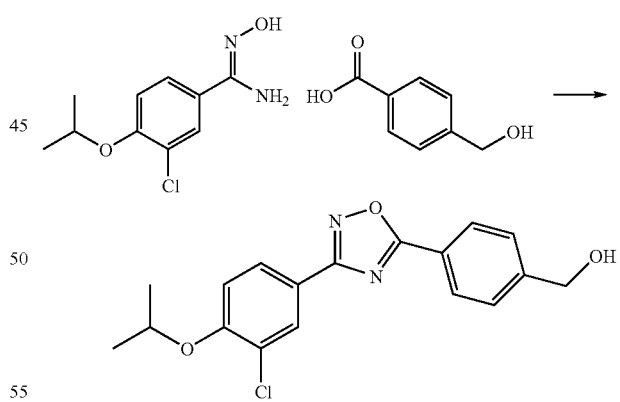

To a slurry of 4-(hydroxymethyl)benzoic acid (0.220 g, 1.443 mmol) in DMF (1.640 ml) was added EDC (0.277 g, 1.443 mmol) followed by HOBT hydrate (0.195 g, 1.443 mmol). After about 45 min. a solution of (Z)-3-chloro-N'-hydroxy-4-isopropoxybenzimidamide (0.300 g, 1.31 mmol) in DMF (1.640 ml) was added and the reaction mixture was heated to about 140° C. for about 2 h. After cooling to room temperature the reaction mixture was concentrated in vacuo and purified by chromatography on silica gel (eluting with EtOAc/Hep) to provide (4-(3-(3-chloro-4-isopropoxyphenyl)-1,2,4-oxadiazol-5-yl)phenyl)methanol (0.336 g, 71%) as an off-white solid. LCMS (Table 1, Method c) R$_t$=2.80 min, m/z 345 (M+H)$^+$.

Example #12

Preparation of 5-(4-(azidomethyl)phenyl)-3-(3-chloro-4-isopropoxyphenyl)-1,2,4-oxadiazole

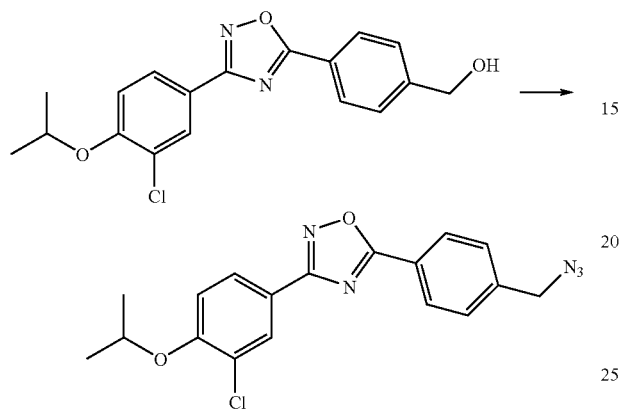

To a solution of (4-(3-(3-chloro-4-isopropoxyphenyl)-1,2,4-oxadiazol-5-yl)phenyl)methanol (0.100 g, 0.290 mmol) in THF (1.5 ml) was added DBU (0.048 ml, 0.319 mmol) followed by diphenyl phosphorazidate (0.069 ml, 0.319 mmol). After about 15 h the reaction mixture was poured into ether and saturated NaHCO$_3$. The organic layer was separated, washed with brine, dried (MgSO$_4$), concentrated in vacuo and purified by chromatography on silica gel (eluting with EtOAc/Hep) to provide 5-(4-(azidomethyl)phenyl)-3-(3-chloro-4-isopropoxyphenyl)-1,2,4-oxadiazole (0.066 g, 60%) as a colorless solid. LCMS (Table 1, Method c) R$_t$=3.22 min, m/z 370 (M+H)$^+$ Example #13

Preparation of (4-(3-(3-chloro-4-isopropoxyphenyl)-1,2,4-oxadiazol-5-yl)phenyl)methanamine

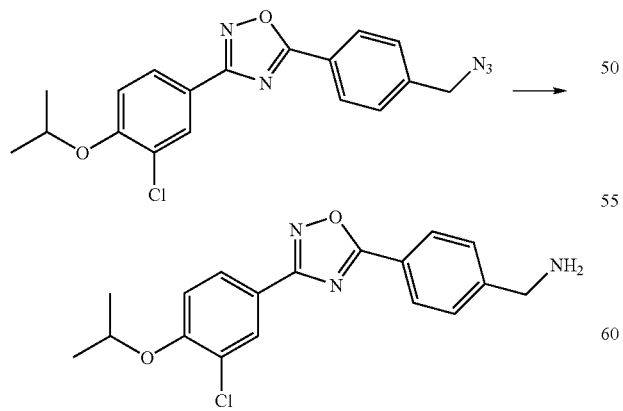

To a solution of 5-(4-(azidomethyl)phenyl)-3-(3-chloro-4-isopropoxyphenyl)-1,2,4-oxadiazole (0.066 g, 0.178 mmol) in THF (3.40 ml) and water (0.170 ml) was added polymer-supported triphenylphosphine (0.237 g, 0.711 mmol). After about 2 h the reaction mixture was heated to about 60° C. After about 1 h the reaction mixture was cooled to room temperature, filtered, concentrated in vacuo and purified by chromatography on silica gel (eluting with MeOH:DCM) to provide (4-(3-(3-chloro-4-isopropoxyphenyl)-1,2,4-oxadiazol-5-yl)phenyl)methanamine (40 mg, 64%) as a colorless solid.

LCMS (Table 1, Method c) R$_t$=1.97 min, m/z 344 (M+H)$^+$.

Preparation #1: 3-(3-(3-chloro-4-isopropoxyphenyl)-1,2,4-oxadiazol-5-yl)cyclopentanone

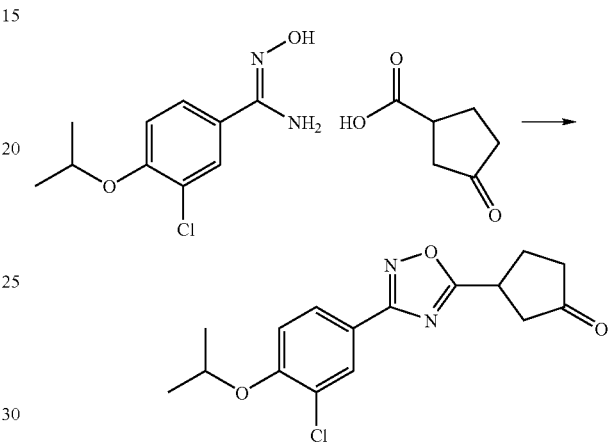

To a slurry of 3-oxocyclopentanecarboxylic acid (0.123 g, 0.962 mmol) in DMF (1.0 ml) was added EDC (0.184 g, 0.962 mmol) followed by HOBT hydrate (0.130 g, 0.962 mmol). After about 1 h a solution of (Z)-3-chloro-N'-hydroxy-4-isopropoxybenzimidamide (0.2 g, 0.875 mmol) in DMF (0.5 ml) was added and the reaction mixture was heated to about 140° C. for about 45 min. After cooling to room temperature the reaction mixture was concentrated in vacuo and purified by chromatography on silica gel (eluting with EtOAc/Hep) to provide 3-(3-(3-chloro-4-isopropoxyphenyl)-1,2,4-oxadiazol-5-yl)cyclopentanone (0.156 g, 56%) as a yellow oil. LCMS (Table 1, Method c) R$_t$=2.75 min, m/z 321 (M+H)$^+$.

Preparation #2: 3-(3-(3-(3-chloro-4-isopropoxyphenyl)-1,2,4-oxadiazol-5-yl)cyclopentylamino)propanoic acid

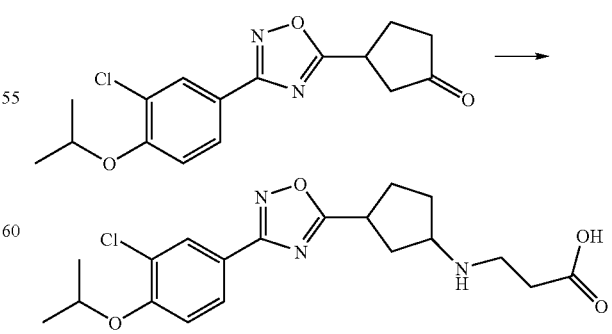

To a slurry of 3-(3-(3-chloro-4-isopropoxyphenyl)-1,2,4-oxadiazol-5-yl)cyclopentanone (0.178 g, 0.555 mmol) in MeOH (6.94 ml) and DCE (6.94 ml) was added acetic acid (0.254 ml, 4.44 mmol) followed by 3-aminopropanoic acid (0.494 g, 5.55 mmol). After about 1 h sodium cyanoborohydride (0.017 g, 0.277 mmol) was added to the reaction mixture. After about 15 h the reaction mixture was filtered, rinsing with MeOH. The filtrate was concentrated in vacuo and purified by RP HPLC to provide 3-(3-(3-(3-chloro-4-isopropoxyphenyl)-1,2,4-oxadiazol-5-yl)cyclopentylamino)propanoic acid. LCMS (Table 1, Method c) Rt=1.64 min, m/z 394 (M+H)+.

Preparation #3: 4-(3-(3-(3-chloro-4-isopropoxyphenyl)-1,2,4-oxadiazol-5-yl)cyclopentylamino)butanoic Acid

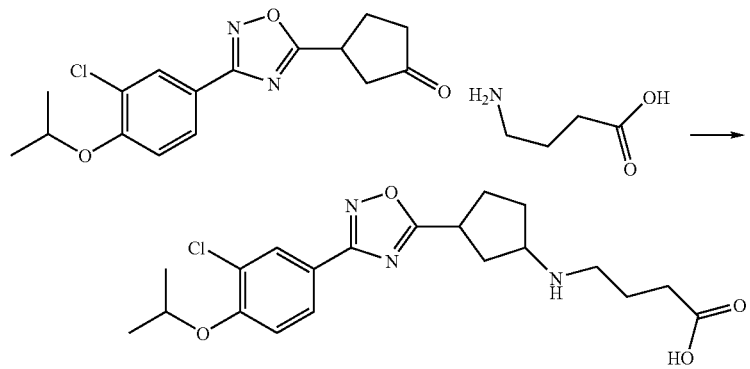

3-(3-(3-chloro-4-isopropoxyphenyl)-1,2,4-oxadiazol-5-yl)cyclopentanone (0.078 g, 0.243 mmol) was suspended in mixture of MeOH (3.04 ml) and DCE (3.04 ml). To this was added acetic acid (0.111 ml, 1.945 mmol) followed by 4-aminobutanoic acid (0.251 g, 2.432 mmol) as solid. The solution was stirred at room temperature for 0.5-1 hr. Sodium cyanoborohydride (7.64 mg, 0.122 mmol) was then added in one portion. The reaction was stirred at room temperature overnight and LCMS indicated reaction was complete. The excess amino acid was filtered off and the filtrate concentrated in vacuo. The crude oil was partitioned between ethyl acetate and brine.

The organic layer was dried (MgSO4) and concentrated to afford a residue that was purified on a Prep HPLC system using 30-100% ACN in 50 mM NH4OAc buffer at 21 mL/min. Fractions 12-14 were combined and concentrated in vacuo. The resulting material was sonicated in MeOH. The suspended precipitate was filtered, rinsed with cold MeOH and dried to yield 4-(3-(3-(3-chloro-4-isopropoxyphenyl )-1, 2,4-oxadiazol-5-yl) cyclopentylamino)butanoic acid, (11 mg, 0.025 mmol) as white solid. LCMS (Table 1, Method c) Rt=1.72 min, m/z 408.22 (M+H)+ 1H NMR (400 MHz, DMSO) δppm 8.06 -7.94 (d, 2H), 7.89 -7.79 (dd, J=1.99, 8.66Hz, 1H), 7.14 -7.06 (d, J=8.68 HZ, 1H), 4.78 -4.65 (td, J=6.08, 12.13 Hz, 1H), 4.09 -3.96 (dd, J. =5.94, 10.14 Hz, 1H), 3.91 -3.79 (m, 1H), 3.38 -3.24 (t, J=7.26 Hz, 2H), 2.73 -2.65 (dd, J =4.81 11.44 Hz, 2H), 2.65 -2.56 (m, 1H). 2.53-2.37 (m, 2H), 2.37-2.28 (m, 1H), 2.28-2.22 (m, 1H), 2.22-2.20 (s, 1H), 2.20-2.10 (m, 2H), [2.10-1.96 (m, 1H) and 1.48-1.38 (d, J=6.05 Hz, 6H)

Preparation #4: (R)-benzyl 4-((2,2-dimethyl-1,3-dioxolan-4-yl)methoxy)benzoate

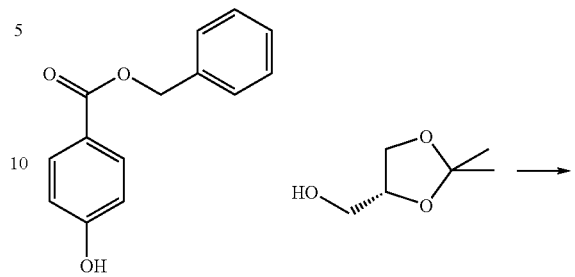

-continued

In a 250 mL round-bottomed flask was added triphenylphosphine (6.54 g, 24.92 mmol) in THF (79 ml) to give a colorless clear solution. The solution was cooled to 0° C. by ice-bath. After stirring for 15 min, diisopropyl azodicarboxylate (5.11 ml, 24.96 mmol) (orange liquid) was added dropwise over 5 min. The reaction mixture turned into off-white suspension in the process. The reaction mixture was stirred at 0° C. for 30 min. Then a colorless solution of benzyl 4-hydroxybenzoate (5.69 g, 24.92 mmol) and (R)-(2,2-dimethyl-1,3-dioxolan-4-yl)methanol (3.00 ml, 23.73 mmol) in THF (39.5 ml) was added to the mixture, keeping the temperature at or below 0° C. The solution turned clear light yellow. The solution was stirred for 2 hr at 0° C. then slowly warmed to ambient temperature and stirred over the weekend. The mixture was concentrated in vacuo to give crude yellow oil (~27 g). The crude oil was dissolved in ether. Then heptane was added. The resultant precipitate was sonicated and filtered. The filtrate was concentrated and purified via Analogix system using RediSep RS 120 g column, with a gradient of 0-20% EtOAc/Heptane over 10 min at 50 mL/min then hold at 20% ethyl acetate for 20 min. Fractions containing product were combined and concentrated to afford (R)-benzyl 4-((2,2-dimethyl-1,3-dioxolan-4-yl)methoxy)benzoate as white solid (6.17 g, 23.73 mmol). LCMS (Table 1, Method c) R$_t$=2.89 min, m/z 343.20 (M+H)$^+$ Preparation #5: (R)-4-((2,2-dimethyl-1,3-dioxolan-4-yl)methoxy)benzoic acid

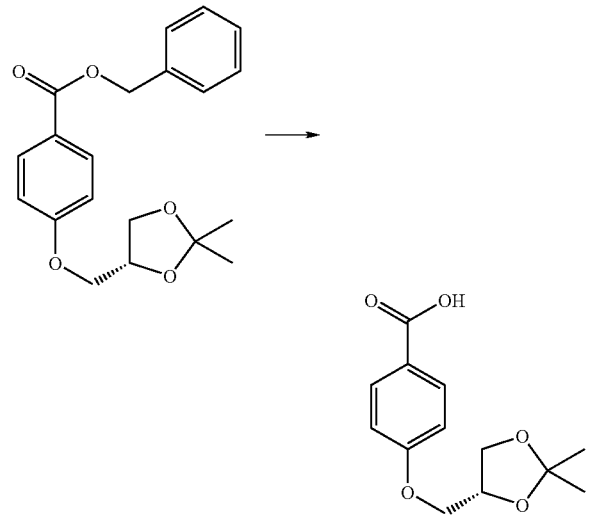

A 500 mL high-pressure flask was charged with palladium on carbon (0.300 g, 0.282 mmol), then MeOH (200 ml) was added, followed by (R)-benzyl 4-((2,2-dimethyl-1,3-dioxolan-4-yl)methoxy)benzoate (6.17 g, 18.02 mmol). The resulting suspension was allowed to shake under an atmosphere of hydrogen (35 Psi) at ambient temperature for 2 hrs. The mixture was filtered through Celite® and the colorless filtrate was concentrated to afford (R)-4-((2,2-dimethyl-1,3-dioxolan-4-yl)methoxy)benzoic acid as white solid (4.45 g, 17.64 mmol).

LCMS (Table 1, Method c) R$_t$=2.15 min, m/z 253.14 (M+H)$^+$

Preparation #6: (R)-3-(3-chloro-4-isopropoxyphenyl)-5-(4-((2,2-dimethyl-1,3-dioxolan-4-yl)methoxy)phenyl)-1,2,4-oxadiazole

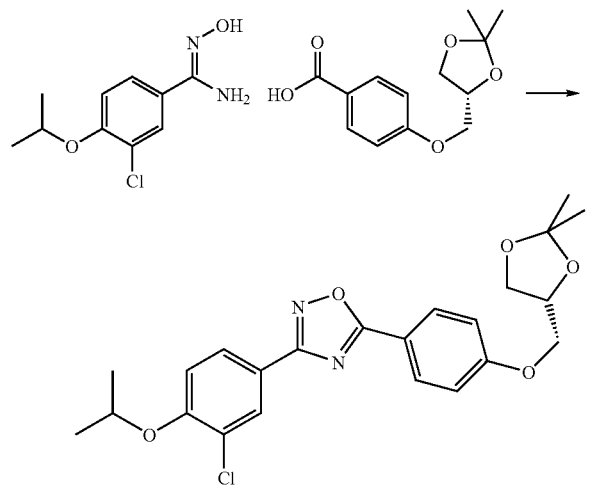

To a slurry of (R)-4-((2,2-dimethyl-1,3-dioxolan-4-yl)methoxy)benzoic acid (0.303 g, 1.203 mmol) in DMF (1.367 ml) was added EDC (0.231 g, 1.203 mmol) followed by HOBT hydrate (0.163 g, 1.203 mmol). After about 1.5 h a solution of (Z)-3-chloro-N'-hydroxy-4-isopropoxybenzimidamide (0.250 g, 1.09 mmol) in DMF (1.367 ml) was added. The reaction mixture was heated to about 140° C. for about 2 hrs. After cooling to room temperature the reaction mixture was concentrated in vacuo and purified by chromatography on silica gel (eluting with EtOAc/Hep) to provide (R)-3-(3-chloro-4-isopropoxyphenyl)-5-(4-((2,2-dimethyl-1,3-dioxolan-4-yl)methoxy)phenyl)-1,2,4-oxadiazole (0.339 g, 70%) as a colorless solid. LCMS (Table 1, Method c) R$_t$=3.36 min, m/z 445 (M+H)$^+$.

Example #14

Preparation of (S)-3-(4-(3-(3-chloro-4-isopropoxyphenyl)-1,2,4-oxadiazol-5-yl)phenoxy)propane-1,2-diol

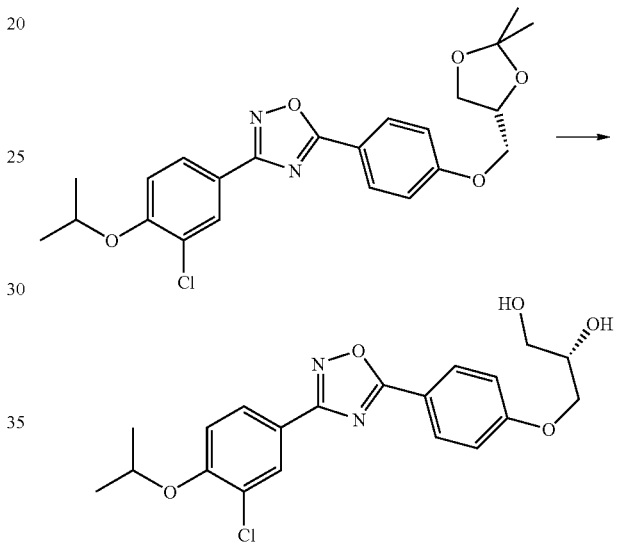

To a solution of (R)-3-(3-chloro-4-isopropoxyphenyl)-5-(4-((2,2-dimethyl-1,3-dioxolan-4-yl)methoxy)phenyl)-1,2,4-oxadiazole (0.339 g, 0.762 mmol) in THF (15.24 ml) was added a solution of 1N HCl (1.524 ml, 1.524 mmol). After 48 h additional 1N HCl (2.286 ml, 2.286 mmol) was added and the reaction mixture was heated to 70° C. for about 2 h. After cooling to ambient temperature a solution of 1N NaOH (3.81 ml, 3.81 mmol) was added and the reaction mixture was concentrated in vacuo. The resulting solid was washed with copious amounts of water and dried in vacuo to provide (S)-3-(4-(3-(3-chloro-4-isopropoxyphenyl)-1,2,4-oxadiazol-5-yl)phenoxy)propane-1,2-diol (0.294 g, 94%) as a colorless solid. LCMS (Table 1, Method c) R$_t$=2.73 min, m/z 405 (M+H)$^+$.

Example #15

Preparation of 4-(3-(3-chloro-4-isopropoxyphenyl)-1,2,4-oxadiazol-5-yl)benzenesulfonamide

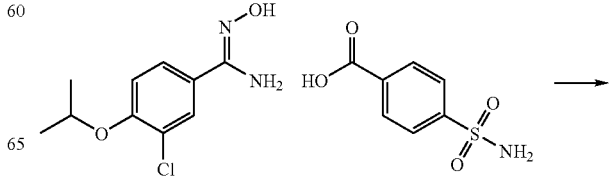

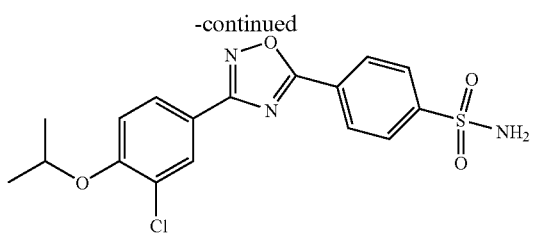

To a slurry of 4-sulfamoylbenzoic acid (1.452 g, 7.22 mmol) in DMF (8.20 ml) was added EDC (1.383 g, 7.22 mmol) followed by HOBT hydrate (0.975 g, 7.22 mmol). After about 30 minutes a solution of (Z)-3-chloro-N'-hydroxy-4-isopropoxybenzimidamide in DMF (8.20 ml) was added. The reaction mixture was heated to about 140° C. for about 2 h. After cooling to room temperature the reaction mixture was concentrated in vacuo and purified by purified by chromatography on silica gel (eluting with EtOAc/Hep) to provide 4-(3-(3-chloro-4-isopropoxyphenyl)-1,2,4-oxadiazol-5-yl)benzenesulfonamide (1.28 g, 50%) as a colorless solid. LCMS (Table 1, Method c) $R_t$=2.74 min, m/z 392 (M−H)⁻.

Example #16

Preparation of tert-butyl 3,3'-(4-(3-(3-chloro-4-isopropoxyphenyl)-1,2,4-oxadiazol-5-yl)phenylsulfonylazanediyl)dipropanoate and tert-butyl 3-(4-(3-(3-chloro-4-isopropoxyphenyl)-1,2,4-oxadiazol-5-yl)phenylsulfonamido)propanoate

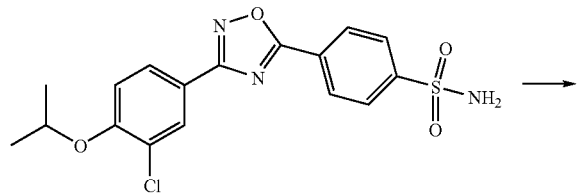

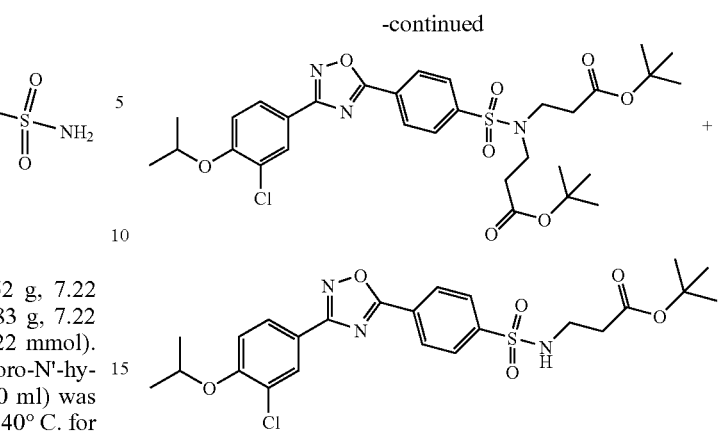

To a solution of 4-(3-(3-chloro-4-isopropoxyphenyl)-1,2,4-oxadiazol-5-yl)benzenesulfonamide (0.500 g, 1.270 mmol) in DMF (3.17 ml) was added NaH (0.056 g, 1.396 mmol). After about 10 min. tert-butyl 3-bromopropanoate (0.233 ml, 1.396 mmol) was added and the reaction mixture was heated to about 60° C. After about 48 h the reaction mixture was cooled to room temperature and purified by chromatography on silica gel (eluting with EtOAc/Hep) to provide tert-butyl 3,3'-(4-(3-(3-chloro-4-isopropoxyphenyl)-1,2,4-oxadiazol-5-yl)phenylsulfonylazanediyl)dipropanoate (0.24 g, 29%) as a colorless solid.

LCMS (Table 1, Method c) $R_t$=3.43 min, m/z 667 (M+NH₄)⁺. In addition to tert-butyl 3-(4-(3-(3-chloro-4-isopropoxyphenyl)-1,2,4-oxadiazol-5-yl)phenylsulfonamido)propanoate (0.28 g, 42%) as a colorless solid. LCMS (Table 1, Method c) $R_t$=3.13 min, m/z 521 (M−H)⁻.

Example #17

Preparation of 3-(4-(3-(3-chloro-4-isopropoxyphenyl)-1,2,4-oxadiazol-5-yl)phenylsulfonamido)propanoic acid

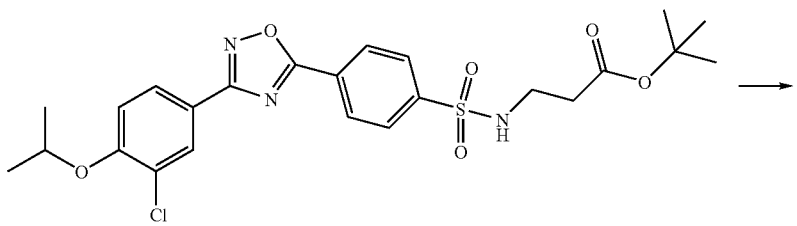

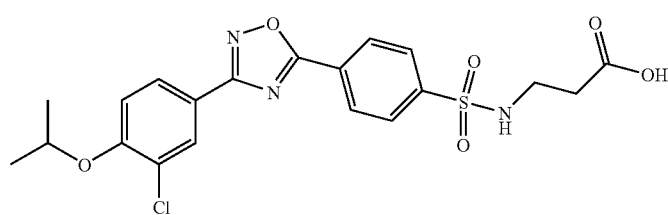

To a solution of tert-butyl 3-(4-(3-(3-chloro-4-isopropoxyphenyl)-1,2,4-oxadiazol-5-yl)phenylsulfonamido)propanoate (0.28 g, 0.536 mmol) in dichloromethane (6.0 ml) was added TFA (2.0 ml, 26.0 mmol). After about 3 h the reaction mixture was concentrated in vacuo and the resulting solid was triturated with ether, filtered and dried to provide 3-(4-(3-(3-chloro-4-isopropoxyphenyl)-1,2,4-oxadiazol-5-yl)phenylsulfonamido)propanoic acid (0.176 g, 70%) as a colorless solid. LCMS (Table 1, Method c) $R_t$=2.54 min, m/z 466 (M+H)$^+$.

Example #18

Preparation of 2,2'-(4-(3-(3-chloro-4-isopropoxyphenyl)-1,2,4-oxadiazol-5-yl)phenylsulfonylazanediyl) diacetic acid TFA (1.0 ml, 12.98 mmol) was added to a stirred mixture of tert-butyl 2,2'-(4-(3-(3-chloro-4-isopropoxyphenyl)-1,2,4-oxadiazol-5-yl)phenylsulfonylazanediyl)diacetate (0.106 g, 0.170 mmol), dichloromethane and TFA (3.10 ml). The mixture was stirred at ambient temperature for 2 hours and then concentrated in vacuo. The resulting residue was triturated with diethyl ether, filtered and dried to give 2,2'-(4-(3-(3-chloro-4-isopropoxyphenyl)-1,2,4-oxadiazol-5-yl)phenylsulfonylazanediyl)diacetic acid (63 mg, 0.122 mmol) as a white solid. LCMS (Table 1, Method c) $R_t$=1.84 min, m/z 508.38 (M−H)$^-$.

Example #19

Preparation of tert-butyl 2,2'-(4-(3-(3-chloro-4-isopropoxyphenyl)-1,2,4-oxadiazol-5-yl)phenylsulfonylazanediyl)diacetate and tert-butyl 2-(4-(3-(3-chloro-4-isopropoxyphenyl)-1,2,4-oxadiazol-5-yl)phenylsulfonamido)acetate Powdered K$_2$CO$_3$ (0.190 g, 1.374 mmol) was added dropwise to a stirred mixture of 4-(3-(3-chloro-4-isopropoxyphenyl)-1,2,4-oxadiazol-5-yl)benzenesulfonamide (0.492 g, 1.249 mmol) in anhydrous acetonitrile (6.25 ml) under N$_2$. Tert-butyl 2-bromoacetate (0.203 ml, 1.374 mmol) was then added and the mixture heated to 80° C. for 3 hrs. The reaction mixture (suspension) was concentrated in vacuo and the resulting material triturated in DCM and filtered. The filtrate was concentrated and purified directly via Analogix system using RediSep RS 40 g column, with a gradient of 0-40% EtOAc/Heptane over 40 min. at 30 mL/min. Fractions containing product were combined and concentrated. This gave tert-butyl 2,2'-(4-(3-(3-chloro-4-isopropoxyphenyl)-1,2,4-oxadiazol-5-yl)phenylsulfonylazanediyl)diacetate (249 mg, 0.400 mmol) as a sticky white solid LCMS (Table 1, Method c) $R_t$=3.17 min, m/z 639 (M+NH$_4$)$^+$ and tert-butyl 2-(4-(3-(3-chloro-4-isopropoxyphenyl)-1,2,4-oxadiazol-5-yl)phenylsulfonamido)acetate (121 mg, 0.238 mmol) as a white solid LCMS (Table 1, Method c) $R_t$=2.81 min, m/z 508 (M+H)$^+$.

Example #20

Preparation of 2-(4-(3-(3-chloro-4-isopropoxyphenyl)-1,2,4-oxadiazol-5-yl)phenylsulfonamido)acetic acid

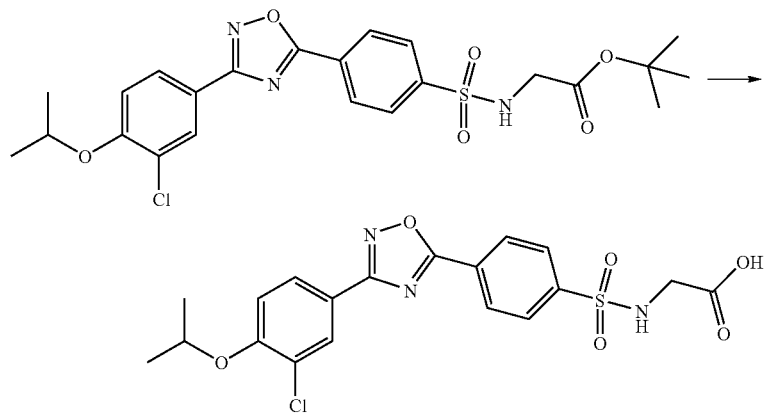

TFA (2.0 ml, 26.0 mmol) was added dropwise to a stirred mixture of tert-butyl 2-(4-(3-(3-chloro-4-isopropoxyphenyl)-1,2,4-oxadiazol-5-yl)phenylsulfonamido)acetate (0.121 g, 0.238 mmol), DCM (5.0 ml) under $N_2$. The mixture was stirred at ambient temperature for 3 hrs then concentrated in vacuo. The resulting solid was triturated in ether, filtered and dried to yield 2-(4-(3-(3-chloro-4-isopropoxyphenyl)-1,2,4-oxadiazol-5-yl)phenylsulfonamido)acetic acid (46 mg, 0.102 mmol) as a white solid. LCMS (Table 1, Method c) $R_t$=2.14 min, m/z 450.34 (M−H)⁻

Example #21

Preparation of tert-butyl 2-(5-(3-(3-chloro-4-isopropoxyphenyl)-1,2,4-oxadiazol-5-yl)-3,4-dihydroisoquinolin-2(1H)-yl)acetate

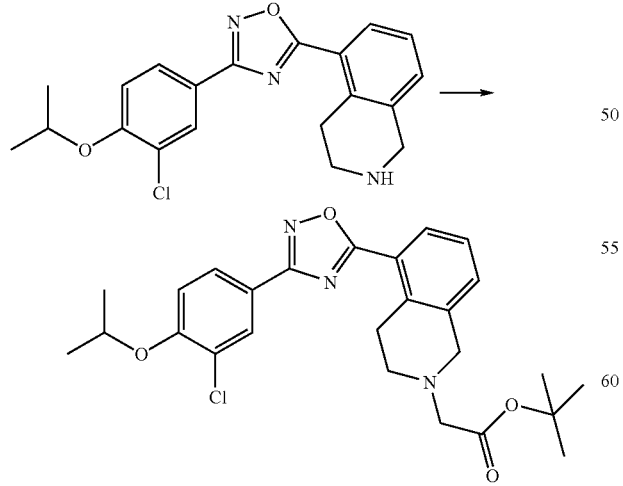

To a solution of 3-(3-chloro-4-isopropoxyphenyl)-5-(1,2,3,4-tetrahydroisoquinolin-5-yl)-1,2,4-oxadiazole (0.0726 g, 0.196 mmol) in DMF (1.963 ml) was added $K_2CO_3$ (0.054 g, 0.393 mmol) followed by tert-butyl bromoacetate (0.030 ml, 0.206 mmol). After about 48 h the reaction mixture was filtered, concentrated in vacuo and purified by chromatography to provide tert-butyl 2-(5-(3-(3-chloro-4-isopropoxyphenyl)-1,2,4-oxadiazol-5-yl)-3,4-dihydroisoquinolin-2(1H)-yl)acetate as a colorless oil that solidified on standing. LCMS (Table 1, Method c) $R_t$=3.41 min, m/z 486 (M+H)⁺.

Example #22

Preparation of tert-butyl 5-(3-(3-chloro-4-isopropoxyphenyl)-1,2,4-oxadiazol-5-yl)-3,4-dihydroisoquinoline-2(1H)-carboxylate

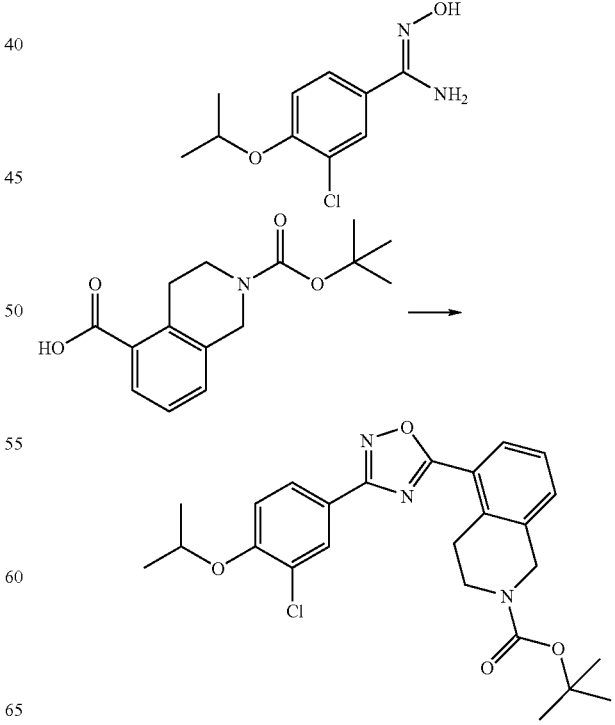

To a slurry of 2-(tert-butoxycarbonyl)-1,2,3,4-tetrahydroisoquinoline-5-carboxylic acid (0.380 g, 1.371 mmol) in DMF (1.662 ml) was added EDC (0.263 g, 1.371 mmol) followed by HOBT hydrate. After about 1 h a solution of (Z)-3-chloro-N'-hydroxy-4-isopropoxybenzimidamide (0.285 g, 1.246 mmol) in DMF (0.831 ml) was added and the reaction mixture was heated to 140° C. for about 1 hr. The reaction mixture was concentrated in vacuo and purified by chromatography on silica gel to provide tert-butyl 5-(3-(3-chloro-4-isopropoxyphenyl)-1,2,4-oxadiazol-5-yl)-3,4-dihydroisoquinoline-2(1H)-carboxylate (0.403 g, 69%) as a colorless oil. LCMS (Table 1, Method c) $R_t$=3.43 min, m/z 471 (M+H)+.

Example #23

Preparation of 3-(3-chloro-4-isopropoxyphenyl)-5-(1,2,3,4-tetrahydroisoquinolin-5-yl)-1,2,4-oxadiazole

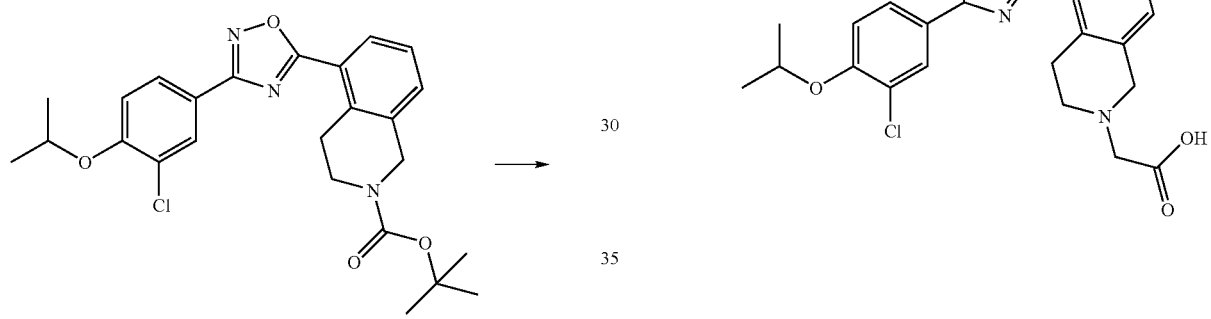

To a solution of tert-butyl 5-(3-(3-chloro-4-isopropoxyphenyl)-1,2,4-oxadiazol-5-yl)-3,4-dihydroisoquinoline-2(1H)-carboxylate (0.403 g, 0.858 mmol) in dioxane (17.15 ml) was added a 4N solution of HCl in dioxane (3.86 ml, 15.44 mmol). After about 15 h the reaction mixture was filtered. The resulting solid was partitioned between EtOAc and sat NaHCO₃. The organic layer was separated, dried (MgSO₄) filtered and concentrated in vacuo to provide 3-(3-chloro-4-isopropoxyphenyl)-5-(1,2,3,4-tetrahydroisoquinolin-5-yl)-1,2,4-oxadiazole (0.230 g, 73%) as a colorless solid. LCMS (Table 1, Method c) $R_t$=2.00 min, m/z 372 (M+H)+.

Example #24

Preparation of 2-(5-(3-(3-chloro-4-isopropoxyphenyl)-1,2,4-oxadiazol-5-yl)-3,4-dihydroisoquinolin-2(1H)-yl)acetic acid

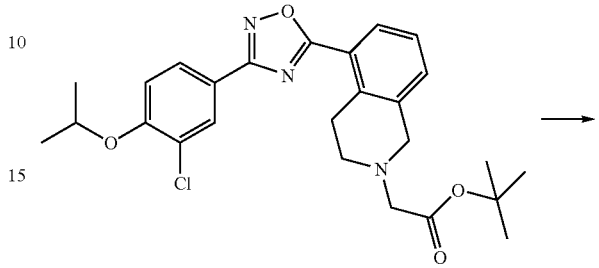

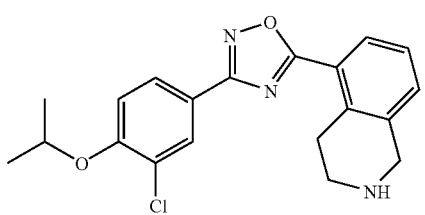

To a solution of tert-butyl 2-(5-(3-(3-chloro-4-isopropoxyphenyl)-1,2,4-oxadiazol-5-yl)-3,4-dihydroisoquinolin-2(1H)-yl)acetate (0.1319 g, 0.273 mmol) in dichloromethane (10 ml) was added triisopropylsilane (0.056 ml, 0.273 mmol) followed by TFA (2 ml). After about 15 h reaction mixture was concentrated in vacuo. The resulting solid was triturated in ether, filtered and dried to provide 2-(5-(3-(3-chloro-4-isopropoxyphenyl)-1,2,4-oxadiazol-5-yl)-3,4-dihydroisoquinolin-2(1H)-yl)acetic acid (0.138 g, 93%) as an off-white solid. LCMS (Table 1, Method c) $R_t$=2.00 min, m/z 428 (M+H)+.

Example #25

Preparation of tert-butyl 3-(5-(3-(3-chloro-4-isopropoxyphenyl)-1,2,4-oxadiazol-5-yl)-3,4-dihydroisoquinolin-2(1H)-yl)propanoate

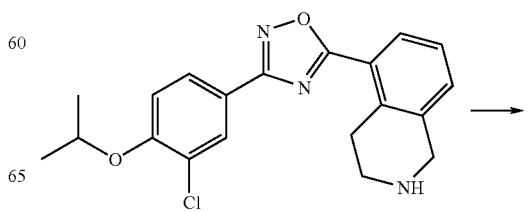

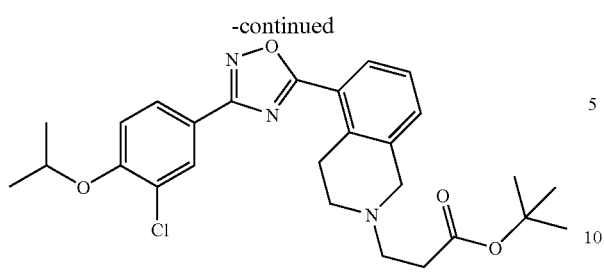

3-(3-chloro-4-isopropoxyphenyl)-5-(1,2,3,4-tetrahydroisoquinolin-5-yl)-1,2,4-oxadiazole (0.1088 g, 0.294 mmol) in DMF (2.94 ml) (briefly heated to 40° C. for complete dissolution). $K_2CO_3$ (0.081 g, 0.588 mmol) and tert-butyl 3-bromopropanoate (0.046 ml, 0.276 mmol) was added and the mixture stirred at ambient temperature for 2 hrs. Additional tert-butyl 3-bromopropanoate (0.053 ml, 0.315 mmol) was added and the reaction was stirred at 60° C. over the weekend. Additional tert-butyl 3-bromopropanoate (0.053 ml, 0.315 mmol) was added and the reaction continued heated at 60° C. overnight. Additional $K_2CO_3$ (0.041 g, 0.294 mmol) was added, followed by tert-butyl 3-bromopropanoate (0.053 ml, 0.315 mmol). The reaction was heated at 60° C. overnight. The reaction mixture was filtered and the filtrate concentrated in vacuo to give ~179 mg of crude yellow oil. The crude residue was purified via Analogix system using RediSep RS 12 g column, with a gradient of 0-45% EtOAc/Heptane over 35 min. at 15 mL/min. Fractions 23-28 were combined and concentrated to yield tert-butyl 3-(5-(3-(3-chloro-4-isopropoxyphenyl)-1,2,4-oxadiazol-5-yl)-3,4-dihydroisoquinolin-2(1H)-yl)propanoate (91 mg, 0.183 mmol) as light yellow oil. LCMS (Table 1, Method c) $R_t$=3.39 min, m/z 500.72 (M+H)$^+$.

Example #26

Preparation of 3-(5-(3-(3-chloro-4-isopropoxyphenyl)-1,2,4-oxadiazol-5-yl)-3,4-dihydroisoquinolin-2(1H)-yl)propanoic acid, TFA salt

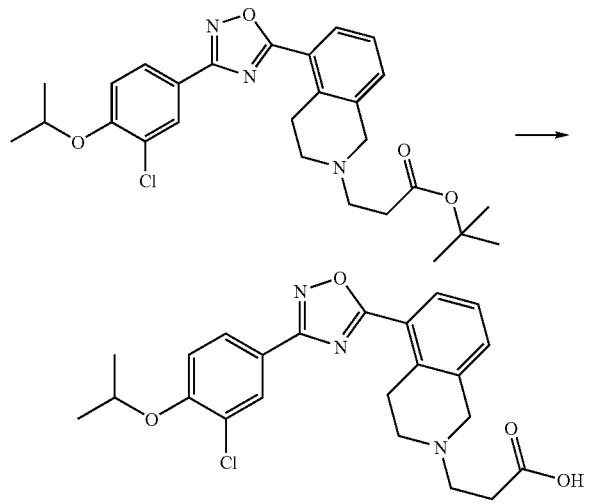

To tert-butyl 3-(5-(3-(3-chloro-4-isopropoxyphenyl)-1,2,4-oxadiazol-5-yl)-3,4-dihydroisoquinolin-2(1H)-yl)propanoate (0.091 g, 0.183 mmol) in dichloromethane (6.0 ml) TFA (1.5 ml) was added and the mixture stirred at ambient temperature overnight. The reaction mixture was concentrated in vacuo and the resulting crude product was dissolved in small amount of DCM. Ether was added until a solid precipitated out. The mixture was filtered, rinsed with ether and dried to give 3-(5-(3-(3-chloro-4-isopropoxyphenyl)-1,2,4-oxadiazol-5-yl)-3,4-dihydroisoquinolin-2(1H)-yl)propanoic acid, TFA salt (74.7 mg, 0.134 mmol) as light yellow solid. LCMS (Table 1, Method c) $R_t$=2.04 min, m/z 442.25 (M+H)$^+$. $^1$H NMR (400 MHz, DMSO) δ ppm 8.18-8.11 (dd, J=2.07 6.76 Hz, 1H), 8.11-8.06 (d, J=2.01 Hz, 1H), 8.06-7.99 (J=2.02, 8.64 Hz, 1H), 7.61-7.53 (J=6.58, 6.58 Hz, 1H), 7.45-7.37 (J=8.8 Hz, 1H), 4.90-4.78 (m, 1H), 4.65-4.46 (s, 2H), 3.71-3.51 (s, 3H), 3.51-3.38 (J=6.87, 6.87 Hz, 3H), 2.91-2.81 (t, J=7.32, 7.32 Hz, 2H) and 1.39-1.33 (d, 6H)

Preparation #7: 4-isopropoxy-3-(trifluoromethyl)benzonitrile.

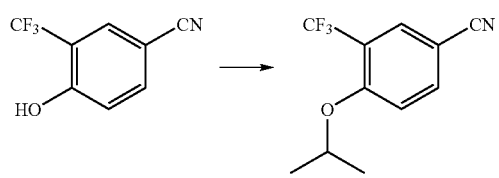

Under an atmosphere of nitrogen a mixture of 4-hydroxy-3-(trifluoromethyl)benzonitrile (5.89 g, 31.5 mmol) and triphenylphosphine (13.21 g, 50.4 mmol) in anhydrous THF (200 mL) was stirred for 5 min. at ambient temperature. To the solution DBAD (11.60 g, 50.4 mmol) was added, stirred 5 min before the addition of 2-propanol (3.03 mL, 39.3 mmol). The mixture was stirred at ambient temperature for 72 hr. The solvent was removed under reduced pressure. The resulting oil was triturated with 30-60° C. pet/ether (200 mL), filtered to remove phosphine oxide and the crude product was purified further by elution through silica with heptane/ethyl acetate (4:1). The isolated oil was dissolved in dichloromethane (200 mL) and stirred with TFA (4.85 mL, 63.0 mmol) for 90 min. at ambient temperature. The solution was basified with 2.5N NaOH (30 mL) and the product was partitioned between DCM and the basic aqueous phase to give the crude 4-isopropoxy-3-(trifluoromethyl)benzonitrile (6.56, 91%). LCMS (Table 1, Method a) Rt=2.32 min, $^1$H NMR (400 MHz, CDCl$_3$) 7.85 (d, 1H), 7.75 (dd, 1H), 7.06 (d, 1H), 4.73 (m, 1H), 1.41 (dd, 6H).

Preparation #8: (Z)-N'-hydroxy-4-isopropoxy-3-(trifluoromethyl)benzimidamide

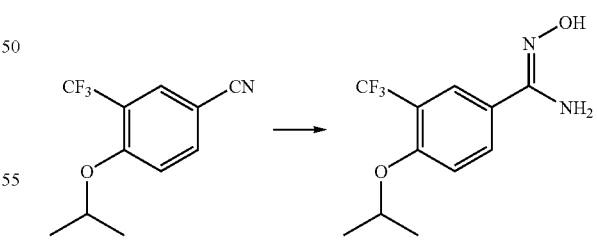

Under an atmosphere of nitrogen, 4-isopropoxy-3-(trifluoromethyl)benzonitrile (6.5 g, 28.4 mmol) and 50% aqueous hyroxylamine (5.21 mL, 85 mmol) in EtOH (20.0 mL) was heated at 60° C. for 18 hr. Solvents removed in vacuo and the residue was azeotroped with MeOH. The residual solid was purified by precipitation from an ethyl acetate/30-600 C pet/ether mixture (1:2) to give (Z)-N'-hydroxy-4-isopropoxy-3-(trifluoromethyl)benzimidamide (2.51 g, 33.8%) LCMS (Table 1, Method b) Rt=1.89 min, m/z 263.13 (M+H)$^+$.

Preparation #9: (S)-3-chloro-4-(tetrahydrofuran-3-yloxy)benzonitrile.

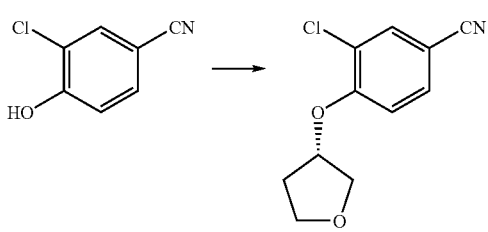

Under an atmosphere of nitrogen a mixture of 3-chloro-4-hydroxybenzonitrile (8.70 g, 56.7 mmol) and triphenylphosphine (23.77 g, 91 mmol) in anhydrous THF (218 mL) was stirred for min. at ambient temperature. To the solution DBAD (20.87 g, 91 mmol) was added, stirred 5 minutes before the addition of (S)-(+)-3-hydroxytetrahydrofuran (3.87 ml, 56.7 mmol) in THF (10 mL). The mixture was stirred at ambient temperature for 24 hr. The solvent was removed under reduced pressure. The residue was dissolved in dichloromethane (200 mL) and stirred with TFA (21.82 ml, 283 mmol) for 90 min. at ambient temperature. The solution was basified with aqueous sodium hydroxide and the product was partitioned between DCM and the basic aqueous phase. The DCM was dried over magnesium sulphate, filtered and solvent removed under reduced pressure to give an oil. The oil was stirred with hot 30-60° C. pet/ether (200 mL), cooled and filtered. Solvent removed under reduced pressure to give the crude (S)-3-chloro-4-(tetrahydrofuran-3-yloxy)benzonitrile (11.2 g). $R_t$ 2.06 min, m/z 378.2 (M+H)$^+$.

Preparation #10: (S,Z)-3-chloro-N'-hydroxy-4-(tetrahydrofuran-3-yloxy)benzimidamide

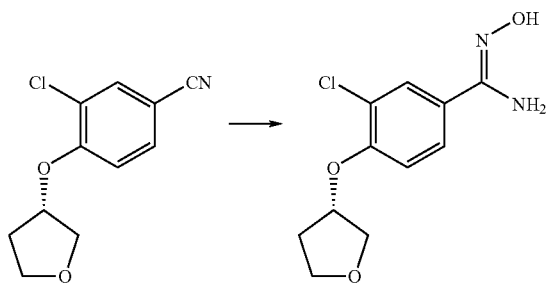

Under an atmosphere of nitrogen, (S)-3-chloro-4-(tetrahydrofuran-3-yloxy)benzonitrile (11.2 g, 50.1 mmol) and 50% aqueous hydroxylamine (3.31 g, 50.1 mmol) in EtOH (150.0 mL) was heated at 60° C. for 18 hr. Solvents removed in vacuo and the residue was azeotroped with MeOH. The residual solid was purified by precipitation from an ethyl acetate/30-60° C. pet/ether mixture (1:2) to give (S,Z)-3-chloro-N'-hydroxy-4-(tetrahydrofuran-3-yloxy)benzimidamide (5.3 g) LCMS (Table 1, Method b) Rt=1.52 min, m/z 257.09 (M+H)$^+$.

Preparation #11: 4-morpholino-3-(trifluoromethyl)benzonitrile

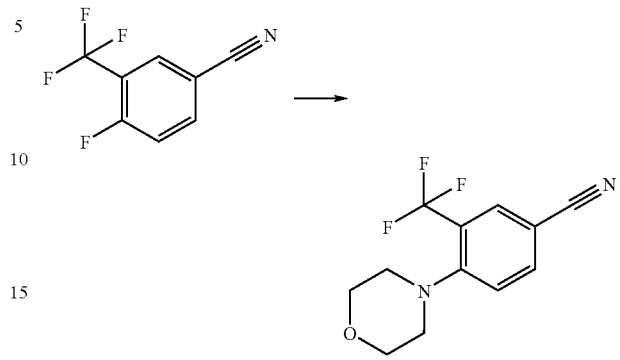

To a solution of 4-fluoro-3-(trifluoromethyl)benzonitrile (15 g, 79 mmol) in dimethylsulfoxide (160 mL) was added morpholine (13.8 mL, 159 mmol) and potassium carbonate (16.4 g, 119 mmol). The mixture was heated at about 90° C. for 18 hours. The mixture was cooled to ambient temperature and the solid was removed by filtration. The fitrate was partitioned between ethyl acetate (1.8 L) and water (1.5 L). The organic layer was washed with water (1.0 L) and brine (1.0 L) and dried over anhydrous magnesium sulphate. The solvent was removed in vacuo to give 4-morpholino-3-(trifluoromethyl)benzonitrile (17.25 g, 85%). $^1$H NMR (DMSO-d$_6$, 400 MHz) δ 8.18 (d, J=2.05 Hz, 1H), 8.09 (dd, J=8.51, 2.06 Hz, 1H), 7.60 (d, J=8.52 Hz, 1H), 3.69-3.75 (m, 4H), 2.97-3.04 (m, 4H).

Preparation #12: N'-hydroxy-4-morpholino-3-(trifluoromethyl)benzimidamide

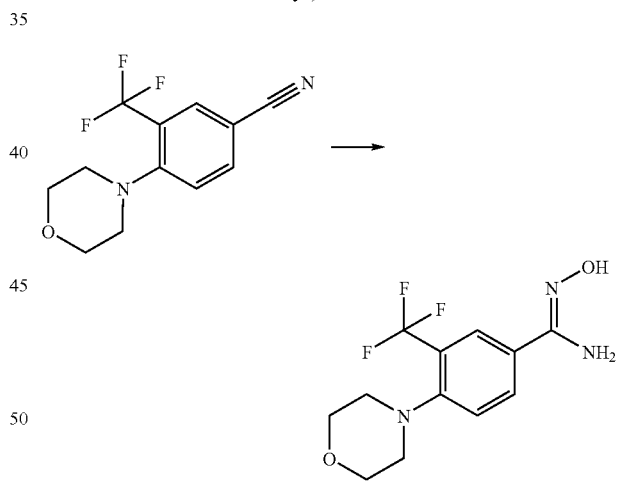

To a solution of 4-morpholino-3-(trifluoromethyl)benzonitrile (17.3 g, 67.3 mmol) in ethanol (400 mL) was added a 50% aqueous solution of hydroxylamine (4.9 mL, 74.1 mmol) dropwise. The mixture was heated at about 65° C. for 24 hours. The mixture was cooled to ambient temperature and the solid was removed by filtration. The fitrate was partitioned between ethyl acetate (1.8 L) and water (1.5 L). The organic layer was washed with water (1.0 L) and brine (1.0 L) and dried over anhydrous magnesium sulphate. The solvent was removed in vacuo to give N'-hydroxy-4-morpholino-3-(trifluoromethyl)benzimidamide (18.6 g, 91%) as a mixture of syn/anti isomers. LCMS (Table 1, Method b) $R_t$=1.85 min, m/z 290.15 (M+H)$^+$; $^1$H NMR (DMSO-d6, 400 MHz) 9.75 (s, 1H), 8.09-8.16 (m, 1H), 7.89-7.96 (m, 1H), 7.52-7.58 (m, 1H), 3.66-3.72 (m, 4H), 2.83-2.93 (m, 4H).

Preparation #13: 5-Methoxy-3,6-dihydro-2H-pyrazine-1-carboxylic Acid Benzyl Ester

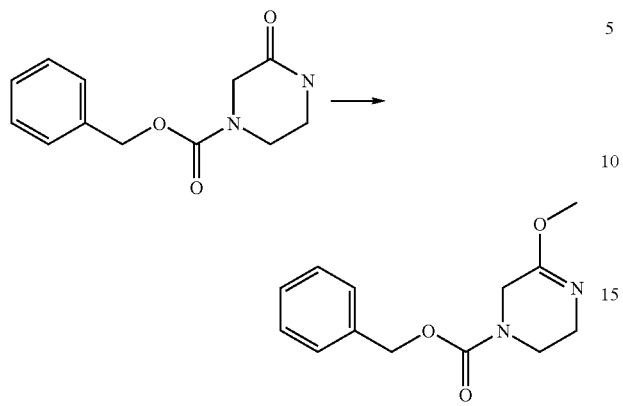

A solution of benzyl 3-oxopiperazine-1-carboxylate (20.50 g, 10.67 mmol) in $CH_2Cl_2$ (100 ml) was cooled to 0° C. and treated with $Na_2CO_3$ (23.0 g, 217 mmol) for 10 minutes. Neat trimethyloxonium tetrafluoroborate (5.50 g, 37.2 mmol) was added in one portion, then the reaction is allowed to warm to room temperature for 6 hours. The reaction was poured into water (100 ml), and the layers were separated. The aqueous layer was re-extracted aqueous with 50 ml $CH_2Cl_2$ and the combined organic layers were washed with brine (100 ml). The organic layer was dried over sodium sulfate, filtered and concentrated to yield 5-methoxy-3,6-dihydro-2H-pyrazine-1-carboxylic acid benzyl ester (2.51 g, 95%) as an oil. LCMS (Table 1, Method a) $R_t$=3.00 min, m/z 249.24 (M+H)+−; $^1$H NMR (400 MHz, DMSO-d6) δ 7.36 (m, 5H), 5.16 (s, 2H), 3.96 (s, 2H), 3.68 (s, 3H), 3.54 (s, 2H), 3.47 (m, 2H)

Preparation #14: 3-Methyl-5,6-dihydro-8H-imidazo[1,2-a]pyrazine-7-carboxylic Acid Benzyl Ester

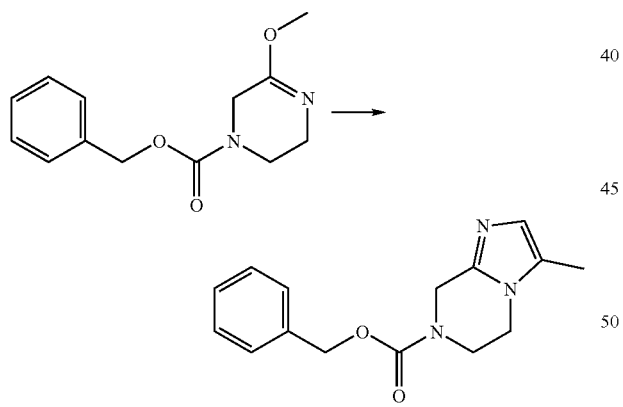

To a solution of 3-methoxy-5,6-dihydropyrazine-1(2H)-carboxylate (4.48 g, 18.03 mmol) in MeOH (200 ml) was added propargylamine (6.18 ml, 90 mmol) at room temperature. The mixture was heated at reflux for 5 hours, then cooled to room temperature and concentrated. The residue was dissolved in 1N HCl (100 ml) and washed 3×75 ml ethyl acetate. The aqueous solution was neutralized with solid $Na_2CO_3$ and extracted with 2×100 ml ethyl acetate. The combined extracts were washed with 100 ml saturated NaCl solution, filtered and concentrated. The residue was triturate with ether, filtered and dried under reduced pressure to yield 3-Methyl-5,6-dihydro-8H-imidazo[1,2-a]pyrazine-7-carboxylic acid benzyl ester (2.91 g, 60%) as an off-white solid. LCMS (Table 1, Method a) $R_t$=3.07 min, m/z 272.11 (M+H)+−; $^1$H NMR (400 MHz, DMSO-d$_6$) δ 7.30 (m, 5H), 6.58 (q, 1H), 5.13 (s, 2H), 4.55 (s,broad, 2H), 3.84 (s, 4H), 2.10 (s, 3H).

Preparation #15: 2-Iodo-3-methyl-5,6-dihydro-8H-imidazo[1,2-a]pyrazine-7-carboxylic Acid Benzyl Ester

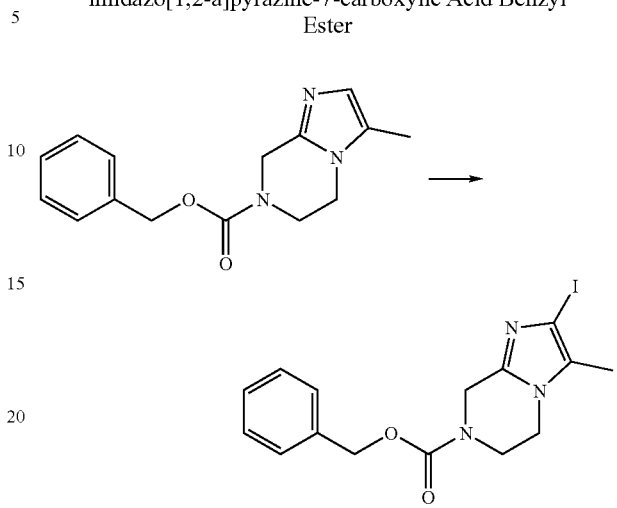

To a solution of benzyl 3-methyl-5,6-dihydroimidazo[1,2-a]pyrazine-7(8H)-carboxylate (1.085 g, 4.00 mmol) in 1,2-dichloroethane (60 ml) was added NIS (4.50 g, 20.00 mmol) and the reaction was heated at reflux for one hour. The reaction was cooled to room temperature and poured into 100 ml of saturated 5% sodium thiosulfate solution. The layers were separated and the aqueous layer was re-extracted with 1,2-dichloroethane (40 ml). The combined organic layers were washed with water (100 ml), dried over sodium sulfate, filtered and concentrated. Product was extracted from the residue by trituration with 3×50 ml portions of ether. The extract was filtered and concentrated to yield 2-Iodo-3-methyl-5,6-dihydro-8H-imidazo[1,2-a] pyrazine-7-carboxylic acid benzyl ester (1.42 g, 89%) as a pale yellow oil. LCMS (Table 1, Method a) $R_t$=3.32 min, m/z 398.59 (M+H)+; $^1$H NMR (400 MHz, CHCl$_3$) δ 7.35 (m, 5H), 5.13 (s, 2H), 4.56 (s,broad, 2H), 4.38 (t, 2H), 3.82 (s, broad, 2H), 2.09 (s, 3H).

Preparation #16: 3-Methyl-5,6-dihydro-8H-imidazo[1,2-a]pyrazine-2,7-dicarboxylic acid 7-benzyl ester

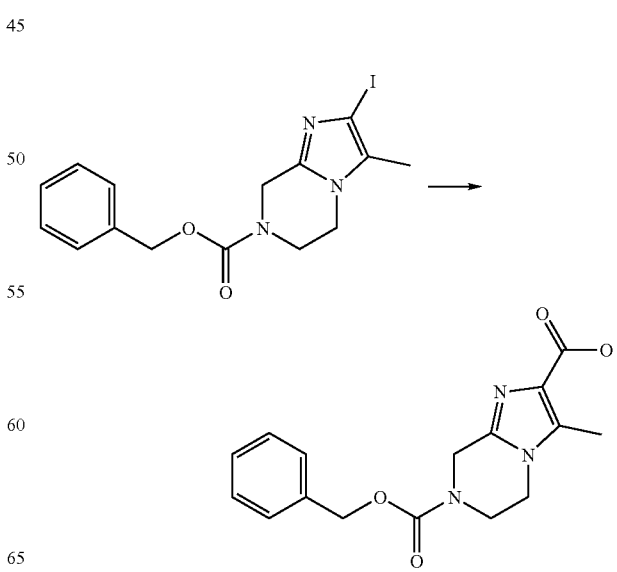

A solution of benzyl 2-iodo-3-methyl-5,6-dihydroimidazo[1,2-a]pyrazine-7(8H)-carboxylate (900mg, 2.266 mmol) in dry THF (25 ml) was cooled to 0 ° C. and ethyl magnesiumbromide (1.888 ml, 5.66 mmol) was added at such a rate as to maintain the reaction temperature below 2.5° C. The reaction was stirred under Nitrogen at 0 ° C. for 15 minutes, then the reaction was quenched with a stream of carbon dioxide. The reaction was concentrated to solids and acetic acid (0.60 ml, 10.48 mmol) ethyl acetate (50 ml) were added and the suspension was stirred vigorously at room temperature for 15 minutes. The resulting solid was filtered and washed with an additional 15 ml ethyl acetate. The residue was dissolved in 10 ml water plus 2N HCl to pH 4, then washed 2 times 10 ml ether then extract with 4×20 ml $CH_2Cl_2$. Dry the combined organic extracts over sodium sulfate, filtered and dried under reduced pressure to yield 3-Methy-5,6-dihydro -8H-imidazo[1,2-a] pyrazine-2,7-dicarboxylic acid 7-benzyl ester (374 mg, 52%) as a foam. LCMS (Table 1, Method a) $R_t$=2.28 min, m/z 316.10 (M+H)+; $^1$H NMR (400 MHz, DMSO-d6)δ 7.35 (m, 5H), 5.11 (s, 2H), 4.56 (s,broad, 2H), 3.88 (m, 2H), 3.83 (s, broad, 2H), 2.36 (s, 3H).

Example #27

Preparation of 2-[3-(3-Chloro-4-isopropoxy-phenyl)-[1,2,4]oxadiazol-5-yl]-3-methyl-5,6-dihydro-8H-imidazo[1,2-a]pyrazine-7-carboxylic acid benzyl ester

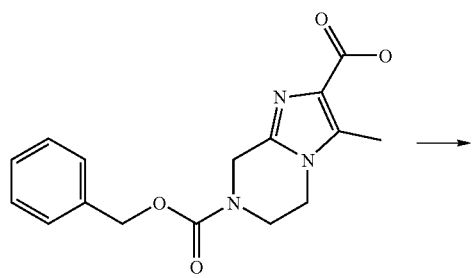

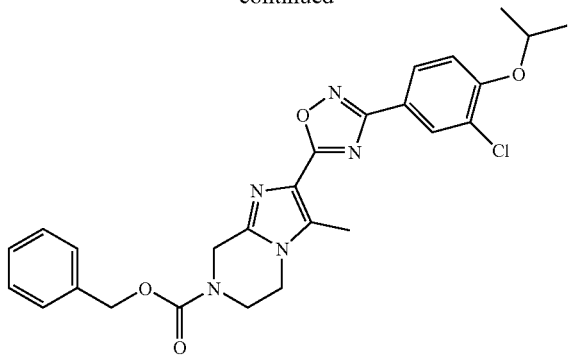

To a solution of 7-(benzyloxycarbony)-3-methy-5,6,7,8-tetrahydroimidazo[1,2-a] pyrazine-2-carboxylic acid (370 mg, 1.173 mmol) in DCM (10m1) was added oxalyl chloride (2.054 ml, 23.47 mmol) and DMF (5 uL). The reaction was stirred for one hour and concentrated. A solution of (E)-3-chloro-N'-hydroxy-4-isopropoxybenzimidamide (268 mg, 1.173 mmol) in pyridine (10.00 ml) was added and the reaction was stirred at room temperature for 30 minutes. The reaction was treated with acetyl chloride (0.092 ml, 1.291 mmol) and then was heated at 115° C. under nitrogen for 4 hours. The reaction was cooled, concentrated and partitioned between saturated $Na_2CO_3$ and methylene chloride. The organic layer was washed with water, dried (sodium sulfate), filtered and concentrated under reduced pressure. The residue was purified on silica gel using 80:20/methylene chloride: ethyl acetate as the eluant to yield 2-[3-(3-Chloro-4-isopropoxy -phenyl)-[1,2,4] oxadiazol-5-yl] -3-methyl-5,6-dihydro-8H-imidazo[1,2-a] pyrazine-7-carboxylic acid benzyl ester (173 mg, 29%) as an off-white solid. LCMS (Table 1, Method a) $R_f$=4.34 min, m/z 508.24 (M+H)+; $^1$H NMR (400 MHz, DMSO-d6)δ 7.98 (d, 1 H), 7.93 (d,d, 1 H), 7.35 (m, 6H), 5.12 (s, 2H), 4.78 (m, 1 H), 4.66 (s,broad, 2H), 3.99 (m, 2H), 3.88 (s, broad, 2H), 2.57 (s, 3H), 1.31 (d, 6H).

Example #28

Preparation of 2-[3-(3-Chloro-4-isopropoxy-phenyl)-[1,2,4]oxadiazol-5-yl]-3-methyl-5,6,7,8-tetrahydro-imidazo[1,2-a]pyrazine

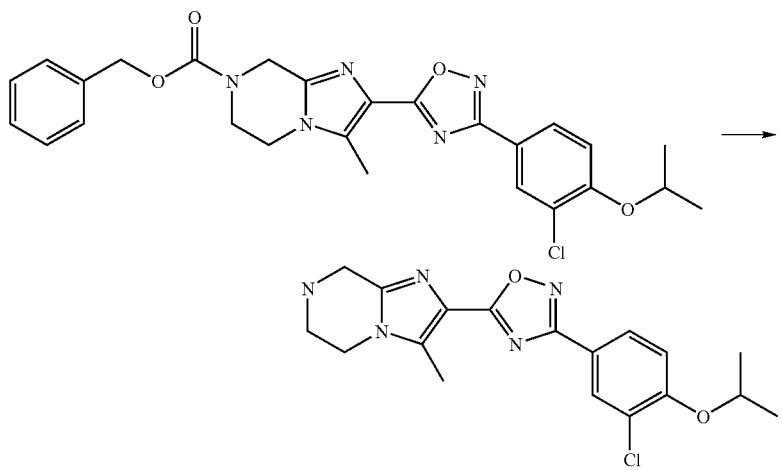

A solution of benzyl 2-(3-(3-chloro-4-isopropoxypheny)-1,2,4-oxadiazol-5-yl)-3-methy-5,6-dihydroimidazo[1,2-a]pyrazine-7(8H)-carboxylate (160 mg, 0.315 mmol) in 33% HBr solution in acetic acid (2.00 mL) containing triisopropylsilane (0.065 mL, 0.315 mmol)) was stirred at room temperature under nitrogen for 10 minutes. Ether (20 ml) was added to precipitate the product. The resulting solid was filtered off, treated with saturated bicarbonate solution (10 ml) and extracted with methylene chloride (2×10 ml). The combined organic layers were dried over sodium sulfate, filtered, concentrated to solids and dried under reduced pressure to yield 2-[3-(3-Chloro -4-isopropoxy-phenyl)-[1,2,4]oxadiazol-5-yl]-3-methyl-5,6,7,8-tetrahydro-imidazo[1,2-a] pyrazine (113 mg, 96%) as an off-white solid. LCMS (Table 1, Method a) $R_t$=3.14 min, m/z 374.24 (M+H)+; $^1$H NMR (400 MHz, DMSO-d6) δ 8.01 (d, 1H), 7.97 (d,d, 1H), 7.36 (d, 1H), 4.81 (m, 1H), 4.66 (s, 2H), 3.90 (s, 2H), 3.87 (t, 2H), 3.12 (t, 2H), 2.60 (s, 3H), 1.34 (d, 6H).

Example #29

Preparation of 1-{2-[3-(3-Chloro-4-isopropoxy-phenyl)-[1,2,4]oxadiazol-5-yl]-3-methyl-5,6-dihydro-8H-imidazo[1,2-a]pyrazin-7-yl}-ethanone

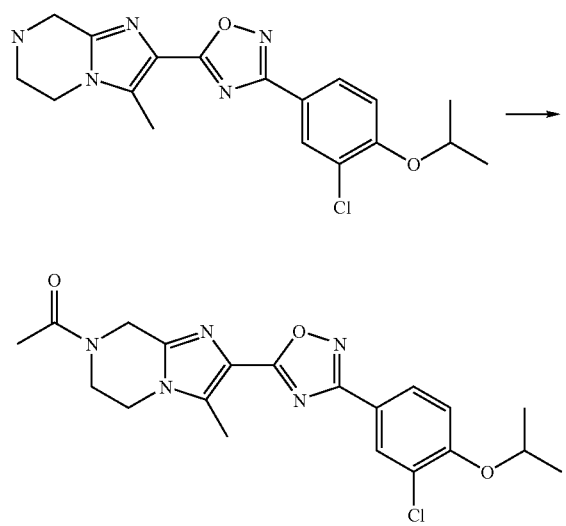

To a solution of 2-(3-chloro-4-isopropoxyphenyl)-3-methyl-5,6,7,8-tetrahydroimidazo[1,2-a]pyrazine (32 mg, 0.105 mmol) in methylene chloride (2.0 ml) was added acetyl chloride (7.50 uL, 0.105 mmol) at room temperature. The mixture was stirred at room temperature for 4 hours and concentrated. The residue was purified by reverse phase HPLC to yield 1-[(2-[3-(3-Chloro-4-isopropoxy-phenyl)-[1,2,4]oxadiazol-5-yl]-3-methyl-5,6-dihydro-8H-imidazo[1,2-a]pyrazin-7-yl]-ethanone (31 mg, 86%) as an off-white solid. LCMS (Table 1, Method a) $R_t$=3.46 min, m/z 416.20 (M+H)+; $^1$H NMR (400 MHz, DMSO-d6) δ 8.02 (d, 1H), 8.97 (d,d, 1H), 7.37 (d, 1H), 4.81 (m, 2H), 4.70 (s, 2H), 3.90 (s, 2H), 4.07 (t0m, 1H), 3.95 (m, 3H), 2.62 (s, 3H), 2.14 (m, 3H), 1.34 (d, 6H).

Example #30

Preparation of {2-[3-(3-Chloro-4-isopropoxy-phenyl)-[1,2,4]oxadiazol-5-yl]-3-methyl-5,6-dihydro-8H-imidazo[1,2-a]pyrazin-7-yl}-acetic acid tert-butyl ester

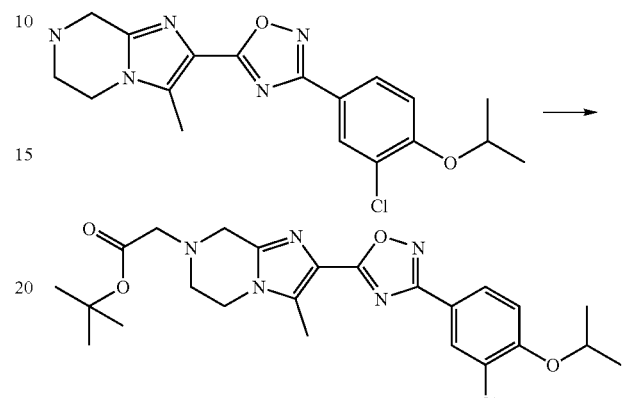

To a solution of 3-(3-chloro-4-isopropoxyphenyl)-5-(3-methyl-5,6,7,8-tetrahydroimldazo[1,2-a]pyrazin-2-yl)-1,2,4-oxadiazole (50.0 mg, 0.134 mmol) in DMF (11.0 ml) at room temperature was added sodium carbonate (28.4 mg, 0.267 mmol) and tert-butyl bromoacetate (0.021 ml, 0.140 mmol) at room temperature. The reaction was continued overnight. The reaction was filtered and concentrated. The residue was dissolved in ethyl acetate (10 ml), washed with brine (10 ml), dried over sodium sulphate, filtered and concentrated to yield {2-[3-(3-Chloro-4-isopropoxy-phenyl)-[1,2,4]oxadiazol-5-yl]-3-methyl-5,6-dihydro-8H-imidazo[1,2-a]pyrazin-7-yl}-acetic acid tert-butyl ester (35 mg, 54%) as an off-white foam which was used in the next step without further purification. LCMS (Table 1, Method a) $R_t$=4.32 min, m/z 488.29 (M+H)+

Example #31

Preparation of {2-[3-(3-Chloro-4-isopropoxy-phenyl)-[1,2,4]oxadiazol-5-yl]-3-methyl-5,6-dihydro-8H-imidazo[1,2-a]pyrazin-7-yl}-acetic acid, trifluoroacetic acid salt

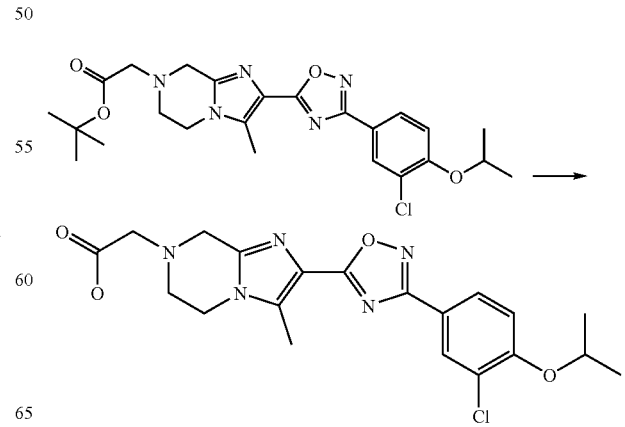

To a solution of tert-butyl 2-(2-(3-(3-chloro-4-isopropoxyphenyl)-1,2,4-oxadiazol-5-yl)-3-methyl-5,6-dihydroimidazo[1,2-a]pyrazin-7(8H)-yl)acetate (32 mg, 0.066 mmol) and Triisopropylsilane (0.013 ml, 0.066 mmol) in methylene chloride (20 ml) was added TFA (2.0 ml) at room temperature for 3 hours. The reaction was diluted with ether (20 ml) and the product was filtered off and dried under reduced pressure. LCMS (Table 1, Method a) $R_t$=2.99 min, m/z 432.23 (M+H)+; $^1$H NMR (400 MHz, DMSO-d6) δ 8.0 (m, 2H), 7.36 (m, 1H), 4.81 (m, 1 H), 3.97 (m, 2H), 3.84 (m, 2H), 3.46 (m, 2H), 3.09 (m, 2H), 2.59 (s, 3H), 1.33 (d, 6H).

Preparation #17:
2-Methyl-imidazo[1,2-a]pyrazine-3-carboxylic acid ethyl ester

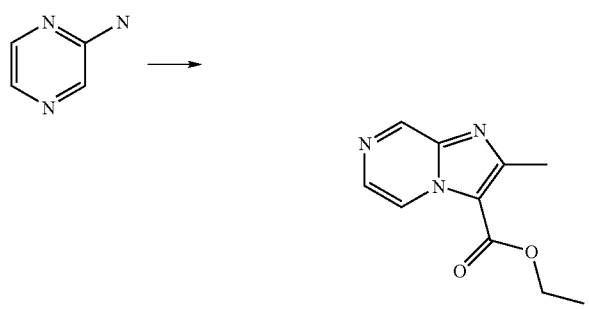

A solution of pyrazin-2-amine (3.6 g, 37.9 mmol) and ethyl 2-chloro-3-oxobutanoate (5.24 ml, 37.9 mmol) in ethanol (30 ml) was heated at reflux for 9 hours. A 1N solution of HCl in ether was added and the mixture was concentrated under reduced pressure. The residue was triturated with 3×50 ml acetonitrile and filtered to yield crude 2-Methyl-imidazo[1,2-a]pyrazine-3-carboxylic acid ethyl ester (4.5 g, 58%) as an amorphous solid which was used in the next step without further purification.

Preparation #18:
2-Methyl-imidazo[1,2-a]pyrazine-3-carboxylic acid

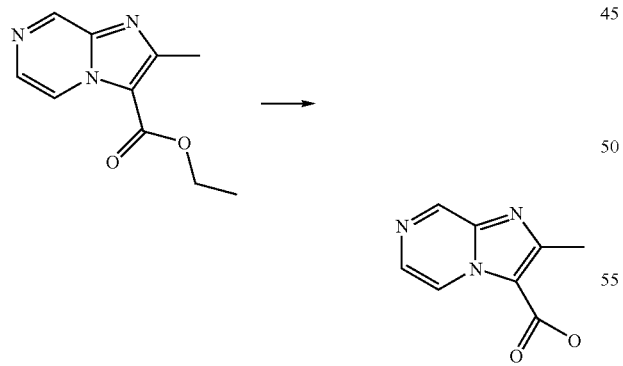

A solution of sodium hydroxide (1.754 g, 43.9 mmol) in water (25 ml) was added to crude ethyl 2-methylimidazo[1,2-a]pyrazine-3-carboxylate (4.5 g, 21.93 mmol). The reaction is exothermic and goes to completion in minutes without additional heating. The mixture was acidified with concentrated HCl to pH 5. The solution was injected onto a preparative C18 column and washed with water and then eluted with 20% CH3CN/water. The product fractions were combined and concentrate to yield 2-Methyl-imidazo[1,2-a]pyrazine-3-carboxylic acid (250 mg, 6%) as a tan solid. LCMS (Table 1, Method a) $R_t$=0.84 min, m/z 176.18 (M−H)⁻; $^1$H NMR (400 MHz, DMSO-d6) δ 9.12 (m, 2H), 8.12 (m, 1H), 2.66 (s, 3H).

Example #32

Preparation of 3-[3-(3-Chloro-4-isopropoxy-phenyl)-[1,2,4]oxadiazol-5-yl]-2-methyl-imidazo[1,2-a]pyrazine

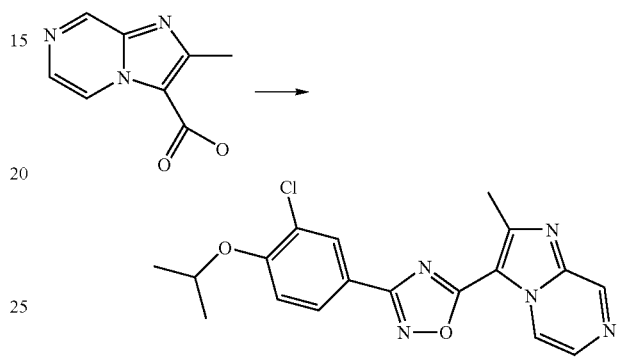

A solution of 2-methylimidazo[1,2-a]pyrazine-3-carboxylic acid (250 mg, 1.411 mmol) in DCE (5 ml) was treated with Hunig's Base (0.542 ml, 3.10 mmol) and HATU (590 mg, 1.552 mmol) at room temperature for 15 minutes and 40 C for 30 min. The reaction was concentrated and the residue was dissolved in acetic acid (10 ml) and heated at 100° C. for 45 minutes. The reaction was cooled to room temperature and concentrated under reduced pressure. The residue was partitioned between saturated sodium carbonate solution (10 ml) and methylene chloride (2×10 ml). The organic layers were dried with sodium sulfate, filtered and concentrated under reduced pressure. The residue was purified on silica gel using 9:1/CH₂Cl₂:MeOH. The product fractions were combined and concentrated under reduced pressure to yield 3-[3-(3-Chloro-4-isopropoxy-phenyl)-[1,2,4]oxadiazol-5-yl]-2-methyl-imidazo[1,2-a]pyrazine (133 mg, 25%) as a tan solid.

LCMS (Table 1, Method a) $R_t$=4.31 min, m/z 370.25 (M+H)⁺; $^1$H NMR (400 MHz, DMSO-d₆) δ 9.43 (d,d, 1H), 9.26 (d, 1H), 8.30 (d, 1H), 8.21 (d, 1H), 8.10 (d,d, 1H), 7.40 (d, 1H), 4.84 (m, 1H), 2.84 (s, 3H), 1.36 (d, 6H)

Example #33

Preparation of 3-(3-chloro-4-isopropoxyphenyl)-5-(4-((2,2-dimethyl-1,3-dioxolan-4-yl)methoxy)phenyl)-1,2,4-oxadiazole

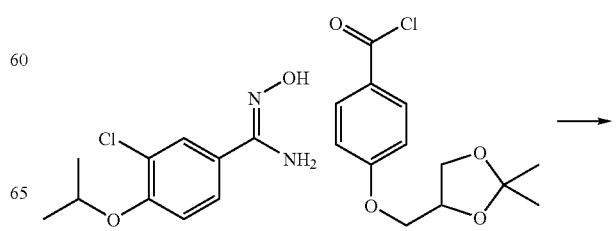

-continued

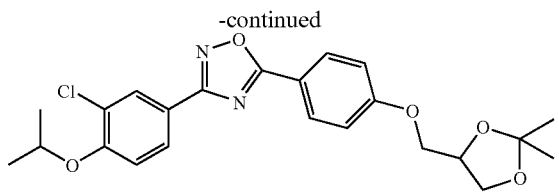

In a 25 mL microwave tube 4-((2,2-dimethyl-1,3-dioxolan-4-yl)methoxy)benzoyl chloride (0.483 g, 1.784 mmol) and (Z)-3-chloro-N'-hydroxy-4-isopropoxybenzimidamide (0.272 g, 1.189 mmol) in pyridine (15 mL) were combined to give an orange solution. The vessel was capped and the reaction heated at 200° C. for 20 min under microwave irradiation (Biotage Optimizer, 300 W). The mixture was cooled, the solvent was removed to afford a yellow solid, which was partitioned between water (100 mL) and EtOAc (50 mL), extracted by EtOAc (2×30 mL), the combined EtOAC layer was washed by water (2×30 mL), and concentrated to afford a yellow solid, which was purified via silica gel chromatography (40 g, 30% EtOAc:Heptane) to afford 3-(3-chloro-4-isopropoxyphenyl)-5-(4-((2,2-dimethyl-1,3-dioxolan-4-yl)methoxy)phenyl)-1,2,4-oxadiazole (0.3 g, 0.674 mmol, 56.7% yield) as white solid. LC/MS (30_95 NH$_4$OAc 4m GC8.olp) R$_f$=3.22 min.; MS m/z: 445.31 (M+H)$^+$. $^1$H NMR (400 MHz, Solvent d-DMSOδ ppm 8.17-8.09 (m, 2H), 8.05 (d, J=2.13 Hz, 1H), 7.99 (dd, J=8.64, 2.15 Hz, 1H), 7.38 (d, J=9.01 Hz, 1H), 7.26-7.19 (m, 2H), 4.88-4.77 (m, 1H), 4.45 (s, 1H), 4.23-4.07 (m, 3H), 3.79 (dd, J=8.42, 6.29 Hz, 1H), 1.35 (m, 12H).

Preparation #19: tert-butyl 2-(4-(chlorocarbonyl)phenoxy)acetate

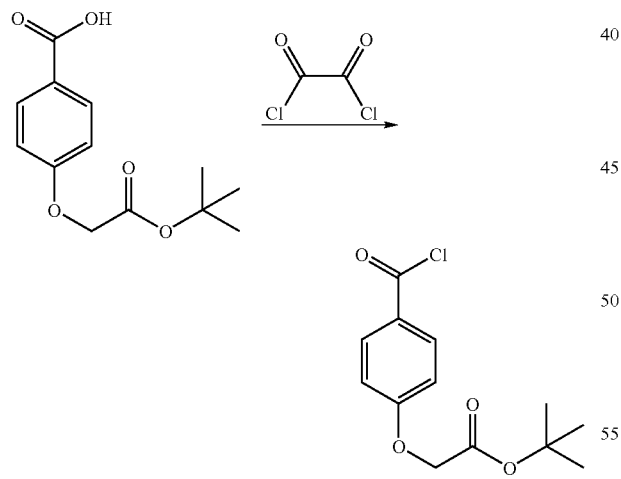

In a 100 mL round bottomed flask was 4-(2-tert-butoxy-2-oxoethoxy)benzoic acid (0.76 g, 3.01 mmol) in Dichloromethane (30.1 ml) to give a colorless suspension. Five drops DMF was added to the solution. The reaction mixture was cooled by ice-bath. Oxalyl chloride (0.396 ml, 4.52 mmol) was added dropwise. The ice-bath was removed, and the solution was stirred at room temperature for 40 min. The reaction mixture was concentrated to afford tert-butyl 2-(4-(chlorocarbonyl)phenoxy)acetate (0.86 g, 3.18 mmol, 105% yield) as colorless oil. $^1$H NMR (400 MHz, CDCl$_3$) d ppm 8.10 (d, 2H), 6.95 (d, 2H), 4.61 (s, 2H), 1.49 (s, 9H)

Example #34

Preparation of 2-(4-(3-(3-chloro-4-isopropoxyphenyl)-1,2,4-oxadiazol-5-yl)phenoxy)acetic Acid

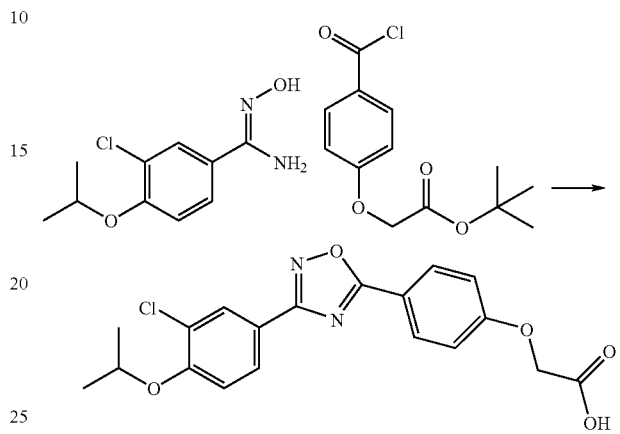

A 25 mL microwave reaction vial was charged with tert-butyl 2-(4-(chlorocarbonyl)phenoxy)acetate (0.815 g, 3.01 mmol) and pyridine (15 mL), (Z)-3-chloro-N'-hydroxy-4-isopropoxybenzimidamide (0.459 g, 2.007 mmol) was added. The vessel was capped and the reaction heated at 200° C. for 20 min under microwave irradiation (Biotage Optimizer, 300 W). The mixture was cooled, the reaction mixture was poured into stirring HCl (10%, 100 mL), the resulting suspension was filtered, the solid was washed by HCl (5%, 2×10 mL) and dried to afford grey solid, which was purified by RP-HPLC (A=50 mM ammonium acetate, B=acetonitrile; 30-95% B over 25.0 min (21.0 mL/min flow rate); 21.2×250 mm Thermo Hyperprep C18 column, 8 μm particles) to give 2-(4-(3-(3-chloro-4-isopropoxyphenyl)-1,2,4-oxadiazol-5-yl)phenoxy)acetic acid (0.246 g, 0.633 mmol, 31.5% yield) as white solid. LC/MS (Table 1, Method f) R$_f$=2.08 min.; MS m/z: 389.14 (M+H)$^+$. $^1$H NMR (400 MHz, Solvent d-DMSO δ ppm 13.28-13.07 (m, 1H), 8.13 (d, J=9.03 Hz, 2H), 8.05 (d, J=2.13 Hz, 1H), 7.99 (dd, J=8.64, 2.15 Hz, 1H), 7.38 (d, J=9.04 Hz, 1H), 7.18 (d, J=9.06 Hz, 2H), 4.85 (s, 3H), 1.35 (d, J=6.03 Hz, 6H).

Example #35

Preparation of 5-(6-(1H-benzo[d][1,2,3]triazol-1-yloxy)pyridin-3-yl)-3-(3-chloro-4-isopropoxyphenyl)-1,2,4-oxadiazole

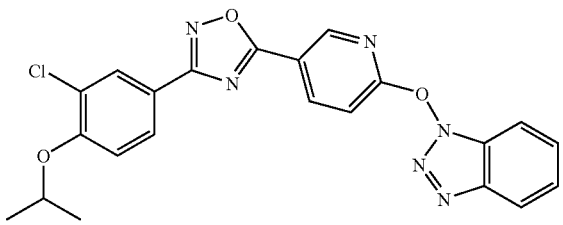

A 25 mL microwave reaction vial was charged with (Z)-3-chloro-N'-hydroxy-4-isopropoxybenzimidamide (0.1 g, 0.437 mmol), 6-bromonicotinic acid (0.097 g, 0.481 mmol), and DCC (0.099 g, 0.481 mmol) in acetonitrile (2.403 ml). HOBT (0.074 g, 0.481 mmol) was added in one portion, the resulting suspension was allowed to stir at room temperature for 10 min. DIEA (0.168 ml, 0.962 mmol) was added dropwise, the reaction mixture was heated at 120° C. for 30 min under microwave irradiation (Biotage Optimizer, 300 W). The solution was cooled, the reaction mixture was partitioned between EtOAc (50 mL) and water (50 mL), the organic layer was washed by water (2×50 mL), and concentrated afforded yellow solid, which was purified via silica gel chromatography (12 g, 20% EtOAc:Heptane) to afford 5-(6-(1H-benzo[d][1,2,3]triazol-1-yloxy)pyridin-3-yl)-3-(3-chloro-4-isopropoxyphenyl)-1,2,4-oxadiazole (0.128 g, 0.285 mmol, 65.2% yield) as a white solid. LC/MS (Table 1, Method a) $R_f$=3.74 min.; MS m/z: 449.18 (M+H)+. 1H NMR (400 MHz, Solvent d-DMSO) ppm 8.88 (dd, J=2.25, 0.65 Hz, 1H), 8.62 (dd, J=8.68, 2.27 Hz, 1H), 8.15 (t, J=5.28 Hz, 2H), 7.97 (dd, J=8.62, 2.14 Hz, 1H), 7.55 (d, J=0.96 Hz, 1H), 7.52-7.44 (m, 2H), 7.36 (dd, J=8.68, 0.70 Hz, 1H), 7.03 (d, J=8.87 Hz, 1H), 4.73-4.61 (m, 1H), 1.46-1.40 (m, 6H).

Preparation #20: (Z)-3-bromo-N'-hydroxy-4-isopropoxybenzimidamide

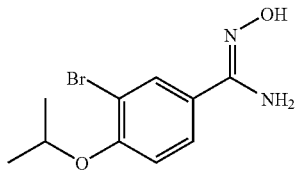

3-bromo-4-isopropoxybenzonitrile (0.68 g, 2.83 mmol) and hydroxylamine (0.208 ml, 3.12 mmol) were combined in EtOH (20 ml). The reaction mixture was heated at 65° C. for 16 hr. The reaction mixture was concentrated to afford (Z)-3-bromo-N'-hydroxy-4-isopropoxybenzimidamide (0.76 g, 2.78 mmol, 98% yield) as pale yellow solid. LC/MS (Table 1, Method a) $R_f$=2.89 min.; MS m/z: 275.00 (M+H)+.

Example #36

Preparation of 4-(3-(3-bromo-4-isopropoxyphenyl)-1,2,4-oxadiazol-5-yl)benzonitrile

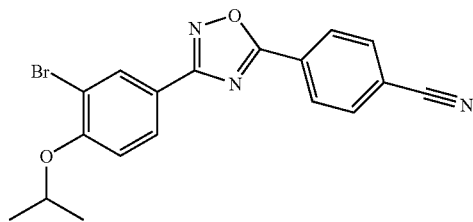

A 25 mL microwave vial equipped with a stirring bar was charged with 4-cyanobenzoyl chloride (0.4 g, 2.416 mmol), (Z)-3-bromo-N'-hydroxy-4-isopropoxybenzimidamide (0.5 g, 1.831 mmol) and pyridine (15 ml) to give an orange solution. The vessel was capped and the reaction heated at 200° C. for 20 min under microwave irradiation (Biotage Optimizer, 300 W). The solution was cooled, the reaction mixture was partitioned between aqueous HCl (10%, 150 mL) and DCM (40 mL) mixture, the DCM layer was drained, and the aqueous layer was extracted by DCM (2×20 mL). The combined DCM layers were washed by water (2×20 mL) and concentrated to afford white solid, which was purified via silica gel chromatography (40 g, 40% EtOAc:Heptane) to afford 4-(3-(3-bromo-4-isopropoxyphenyl)-1,2,4-oxadiazol-5-yl)benzonitrile (0.638 g, 1.660 mmol, 91% yield) as white solid. LC/MS (Method c) $R_f$=3.17 min.; MS m/z: 386.19 (M+H)+. 1H NMR (400 MHz, Solvent d-DMSO) ppm 8.40-8.32 (m, 2H), 8.23 (d, J=2.13 Hz, 1H), 8.14 (dd, J=8.14, 0.61 Hz, 2H), 8.05 (dd, J=8.65, 2.15 Hz, 1H), 7.36 (d, J=9.12 Hz, 1H), 4.89-4.77 (m, 1H), 1.35 (d, J=6.03 Hz, 6H).

Example #37: Preparation of 4-(3-(3-bromo-4-isopropoxyphenyl)-1,2,4-oxadiazol-5-yl)benzaldehyde

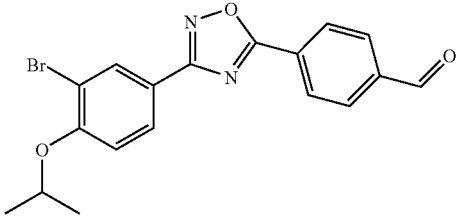

A 100 mL round-bottomed flask equipped with septa cap outfitted with nitrogen inlet needle was charged with 4-(3-(3-bromo-4-isopropoxyphenyl)-1,2,4-oxadiazol-5-yl)benzonitrile (0.64 g, 1.666 mmol) in DCM (33.3 ml) to give a colorless solution. The reaction mixture was cooled to 40° C. by acetonitrile-dry ice bath and it turned into a white suspension. Dibal-H (3.33 ml, 3.33 mmol) was added dropwise over 10 min. It was stirred for extra 60 min at 40° C. Methanol (0.135 ml, 3.33 mmol) was added dropwise to quench the reaction. Then all of the mixture was poured into stirring Rochelle's salt (200 mL). It was stirred at room temperature for 4 hr, then it was partitioned, the aqueous layer was extracted by DCM (2×50 mL), the combined DCM layers were washed by water (60 mL), dried over MgSO4. Filtration and concentration afforded 1.04 g orange oil, which was purified via silica gel chromatography (40 g, 40% EtOAc:Heptane) to afford 4-(3-(3-bromo-4-isopropoxyphenyl)-1,2,4-oxadiazol-5-yl)benzaldehyde (0.551 g, 1.423 mmol, 85% yield) as pale yellow solid. LC/MS (Method c) $R_f$=3.17 min.; MS m/z: 388.94 (M+H)+. 1H NMR (400 MHz, Solvent d-DMSO) ppm 10.15 (s, 1H), 8.41 (d, J=8.20 Hz, 2H), 8.24 (d, J=2.13 Hz, 1H), 8.20-8.14 (m, 2H), 8.06 (dd, J=8.64, 2.15 Hz, 1H), 7.37 (d, J=9.11 Hz, 1H), 4.89-4.78 (m, 1H), 1.36 (d, J=6.03 Hz, 6H).

Example #38

Preparation of 3-(3-bromo-4-isopropoxyphenyl)-5-(4-(dimethoxymethyl)phenyl)-1,2,4-oxadiazole

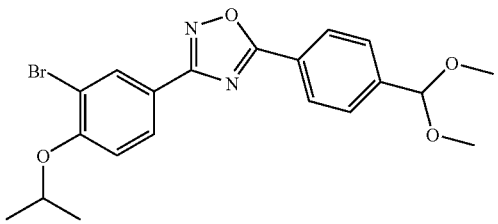

4-(3-(3-bromo-4-isopropoxyphenyl)-1,2,4-oxadiazol-5-yl)benzaldehyde (0.551 g, 1.423 mmol), molecular sieve (4A, 8-12 mesh, 130 mg) and p-toluenesulfonic acid monohydrate (0.037 g, 0.195 mmol) were added in trimethyl orthoformate (4 ml, 36.2 mmol) and methanol (6 ml), the reaction mixture was heated at 80° C. for 16 hr. The solution was cooled, the reaction mixture was concentrated to afford grey solid, which was purified via silica gel chromatography (12 g, 20% EtOAc:Heptane) to afford 3-(3-bromo-4-isopropoxyphenyl)-5-(4-(dimethoxymethyl)phenyl)-1,2,4-oxadiazole (0.61 g, 1.366 mmol, 96% yield) as white solid.

LC/MS (Table 1, Method a) $R_t$=3.31 min.; MS m/z: 435.03 (M+H)$^+$. $^1$H NMR (400 MHz, Solvent d-DMSO) ppm 8.25-8.19 (m, 3H), 8.05 (dd, J=8.63, 2.14 Hz, 1H), 7.67 (d, J=8.18 Hz, 2H), 7.35 (d, J=9.02 Hz, 1H), 5.52 (s, 1H), 4.86-4.78 (m, 1H), 3.30 (s, 6H), 1.35 (d, J=6.02 Hz, 7H).

Example #39

Preparation of 5-(5-(4-(dimethoxymethyl)phenyl)-1,2,4-oxadiazol-3-yl)-2-isopropoxybenzonitrile

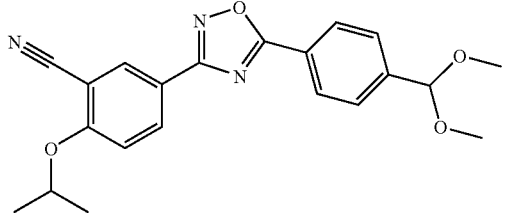

A 25 mL microwave vial equipped with a stirring bar was charged with 3-(3-bromo-4-isopropoxyphenyl)-5-(4-(dimethoxymethyl)phenyl)-1,2,4-oxadiazole (0.25 g, 0.577 mmol), copper(I) cyanide (0.133 g, 1.485 mmol) and pyridine (15 ml). The vessel was capped and the reaction heated to 230° C. for 30 min under microwave irradiation (Biotage Optimizer, 300 W). The solution was cooled, the reaction mixture was concentrated, to the residue was added hydrated ferric chloride (0.8 g), concentrated hydrochloric acid (2 mL) and water (12 mL). The solution was heated at 65° C. for 20 min, the aqueous mixture was extracted by DCM (3×30 mL), the combined DCM layers were washed with FeCl$_3$ solution (2×20 mL), then water (2×20 mL), dried (brine, MgSO$_4$) and concentrated to yield yellow solid, which was purified via silica gel chromatography (40 g, 20% EtOAc:Heptane) to afford 5-(5-(4-(dimethoxymethyl)phenyl)-1,2,4-oxadiazol-3-yl)-2-isopropoxybenzonitrile (0.086 g, 0.227 mmol, 39.3% yield) as pale yellow solid.

Example #40

Preparation of 5-(5-(4-formylphenyl)-1,2,4-oxadiazol-3-yl)-2-isopropoxybenzonitrile

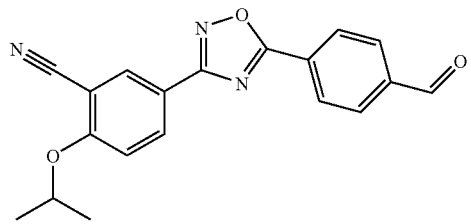

5-(5-(4-(dimethoxymethyl)phenyl)-1,2,4-oxadiazol-3-yl)-2-isopropoxybenzonitrile (0.086 g, 0.227 mmol) and p-toluenesulfonic acid monohydrate (0.043 g, 0.227 mmol) were added in acetone (10 ml) to give a colorless solution. The reaction mixture was heated at 60° C. for 2 hr. The solution was cooled, the reaction mixture was concentrated, the residue was purified via silica gel chromatography (12 g, 50% EtOAc:Heptane) to afford 5-(5-(4-formylphenyl)-1,2,4-oxadiazol-3-yl)-2-isopropoxybenzonitrile (0.077 g, 0.231 mmol, 102% yield) as white solid.

LC/MS (Table 1, Method f) $R_t$=2.88 min.; MS m/z: 334.08 (M+H)$^+$.

Example #41

Preparation of 1-(4-(3-(3-cyano-4-isopropoxyphenyl)-1,2,4-oxadiazol-5-yl)benzyl)azetidine-3-carboxylic Acid

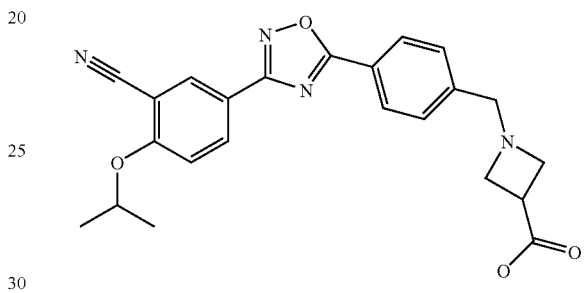

5-(5-(4-formylphenyl)-1,2,4-oxadiazol-3-yl)-2-isopropoxybenzonitrile (0.077 g, 0.231 mmol) and azetidine-3-carboxylic acid (0.028 g, 0.277 mmol) were combined in methanol (11.55 ml) and DCE (11.55 ml) in a sealed vial. Acetic acid (0.066 ml, 1.155 mmol) was added. The reaction mixture was stirred at ambient temperature for 2 hr. MP-cyanoborohydride (0.265 g, 0.570 mmol) was added and the reaction stirred for about 24 h. The solution was filtered, the solid was washed with methylene chloride and methanol, and the filtrate was concentrated to afford a white solid, which was recrystallized by methanol (5 mL) to give 1-(4-(3-(3-cyano-4-isopropoxyphenyl)-1,2,4-oxadiazol-5-yl)benzyl)azetidine-3-carboxylic acid (0.025 g, 0.060 mmol, 25.9% yield) as white solid: LC/MS (Table 1, Method a) $R_t$=2.10 min.; MS m/z: 420.26 (M+H)$^+$. $^1$H NMR (400 MHz, Solvent d-DMSO) ppm 8.35-8.28 (m, 2H), 8.17-8.11 (d, J=8.00 Hz, 2H), 7.56-7.50 (m, 8.69 Hz, 3H), 4.98-4.89 (m, 1H), 3.68 (s, 2H), 3.43 (s, 2H), 3.25-3.23 (m, 3H), 1.38 (d, J=6.03 Hz, 6H).

Example #42

Preparation of 1-(4-(3-(3-chloro-4-isopropoxyphenyl)-1,2,4-oxadiazol-5-yl)phenyl)cyclopropanecarbonitrile

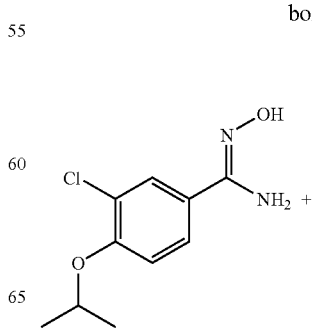

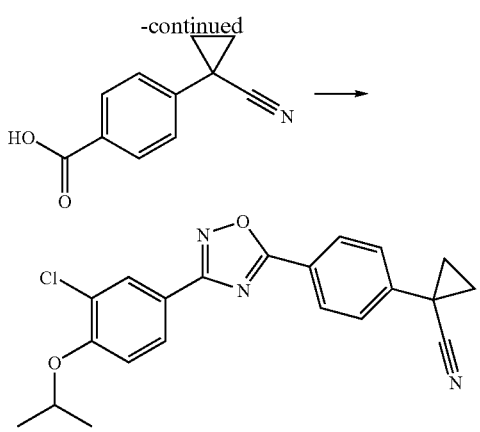

A 20 mL microwave vial was charged with 4-(1-cyanocyclopropyl)benzoic acid (720 mg, 3.85 mmol), (Z)-3-chloro-N'-hydroxy-4-isopropoxybenzimidamide (880 mg, 3.85 mmol), DCC (873 mg, 4.23 mmol), HOBT (648 mg, 4.23 mmol), ACN (10 ml), and DIEA (1.478 ml, 8.46 mmol). The vial was capped and heated to 160° C. via microwave irradiation for 25 minutes (max 300 W). Solvent was removed under reduced pressure and crude oil was purified by flash column chromatography (Analogix system, heptane/ethyl acetate, 0-45% ethyl acetate over 30 min; 80 g column, 60 mL/min flow rate). Fractions containing product were combined, rotovapped, and dried in a vacuum oven overnight to give 1-(4-(3-(3-chloro-4-isopropoxyphenyl)-1,2,4-oxadiazol-5-yl)phenyl)cyclopropanecarbonitrile (347 mg, 23.8%) as a yellow solid. LCMS (Table 1, Method c) R$_f$=3.19 min, m/z 380.43 (M+H)$^+$; $^1$H NMR (400 MHz, DMSO)) δ ppm 8.22-8.12 (m, 2H), 8.05 (d, 1H), 7.99 (dd, 2.14 Hz, 1H), 7.62-7.55 (m, 2H), 7.38 (d, 1H), 4.82 (td, 1H), 1.90 (q, 2H), 1.67 (q, 2H), 1.38-1.33 (m, 6H).

Example #43

Preparation of 1-(4-(3-(3-chloro-4-isopropoxyphenyl)-1,2,4-oxadiazol-5-yl)phenyl)cyclopropanecarbaldehyde

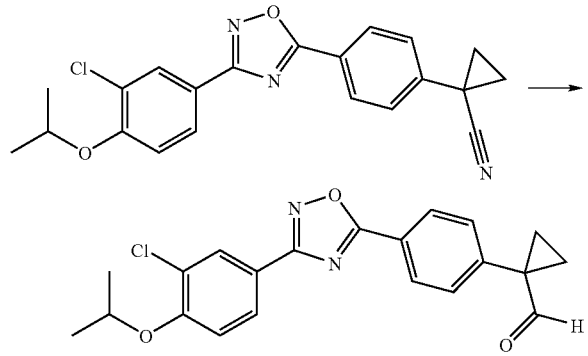

A 100 mL round bottom flask was charged with 1-(4-(3-(3-chloro-4-isopropoxyphenyl)-1,2,4-oxadiazol-5-yl)phenyl)cyclopropanecarbonitrile (300 mg, 0.790 mmol) and Dichloromethane (8 mL) and then cooled to 40° C. DIBAL-H (0.869 mL, 0.869 mmol) was added slowly via syringe and the reaction mixture left to warm to room temperature overnight. Reaction quenched by addition of MeOH (4 mL), and aqueous Rochelle's salt (4 mL). Layers were separated and the aqueous layer was extracted with DCM (3×25 mL). Organics were washed with saturated sodium bicarbonate solution, then dried over MgSO$_4$, and concentrated. To a solution of the crude material in 3 mL of THF was added 3 mL of 1N HCl. The mixture was stirred at room temperature for 1 hr. Mixture was rotovapped to remove THF. Material was then purified via flash column chromatography (Analogix, 40 g column, 0-40% ethyl acetate in heptane over 30 min, 30 ml/min flow rate). Fractions containing product were combined and concentrated to give 1-(4-(3-(3-chloro-4-isopropoxyphenyl)-1,2,4-oxadiazol-5-yl)phenyl)cyclopropanecarbaldehyde (144 mg, 48%) as a tacky yellow solid. LCMS (Table 1, Method c) R$_f$=3.11 min, m/z 383.50 (M+H)$^+$.

Example #44

Preparation of 3-((1-(4-(3-(3-chloro-4-isopropoxyphenyl)-1,2,4-oxadiazol-5-yl)phenyl)cyclopropyl)methylamino)propanoic acid, Trifluoroacetic Acid

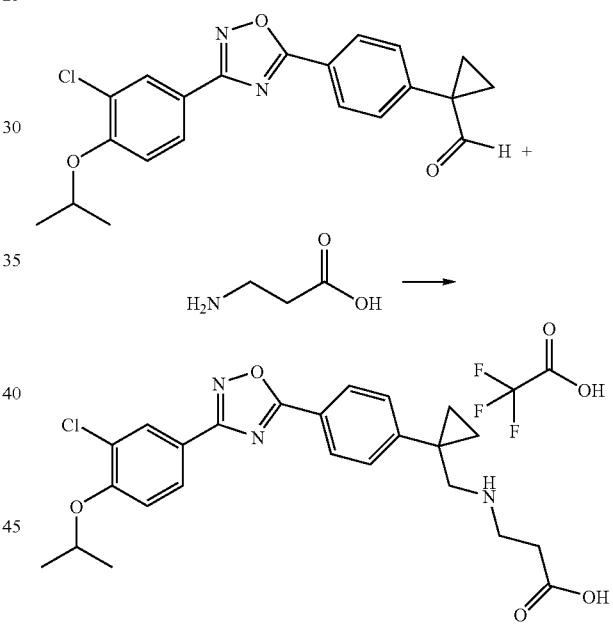

A 20 mL vial was charged with 1-(4-(3-(3-chloro-4-isopropoxyphenyl)-1,2,4-oxadiazol-5-yl)phenyl)cyclopropanecarbaldehyde (46 mg, 0.120 mmol), methanol (2.5 ml), 3-aminopropanoic acid (10.70 mg, 0.120 mmol) and acetic acid (0.034 ml, 0.601 mmol). The vial was capped and the mixture stirred for about 30 min at room temperature. Next, sodium cyanoborohydride (7.55 mg, 0.120 mmol) was added in one aliquot and the reaction was stirred overnight at room temperature. Solvents were removed under reduced pressure and the crude material was purified via RP-HPLC (A=0.1% TFA, B=ACN; 30% to 95% B over 30 min at 21.0 mL/min; UV λ=254 nm; Thermo Hyperprep HS C18, 8 μm, 250×21.2 mm column). Fractions containing product were, rotovapped, and lyophilized to give 3-((1-(4-(3-(3-chloro-4-isopropoxyphenyl)-1 2,4-oxadiazol-5-yl)phenyl)cyclopropyl)methylamino)propanoic acid (27 mg, 40%) as the TFA salt. LCMS (Table 1, Method c) R$_f$=2.07 min, m/z 456.25

(M+H)+; 1H NMR (400 MHz, methanol) δ ppm 8.22 (d, 2H), 8.11 (d, 1H), 8.03 (dd, 1H), 7.69 (d, J=8.19 Hz, 2H), 7.24 (d, 1H), 4.80-4.76 (m, 1H), 3.36 (s, 2H), 3.13 (t, 2H), 2.44 (t, 2H), 1.40 (d, 6H), 1.17 (d, 4H).

Example #45

Preparation N-(4-(3-(3-chloro-4-isopropoxyphenyl)-1,2,4-oxadiazol-5-yl)benzyl)-1-(2,2-dimethyl-1,3-dioxolan-4-yl)methanamine

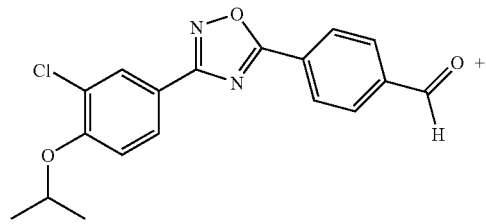

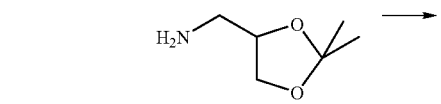

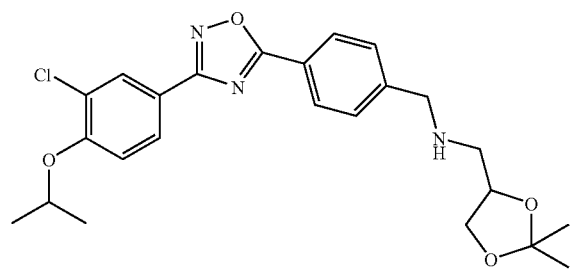

4-(3-(3-chloro-4-isopropoxyphenyl)-1,2,4-oxadiazol-5-yl)benzaldehyde (150 mg, 0.438 mmol), (2,2-dimethyl-1,3-dioxolan-4-yl)methanamine (0.057 mL, 0.438 mmol), methanol (4 mL), and acetic acid (0.125 mL, 2.188 mmol) were loaded into a 25 mL flask equipped with a stirring bar. The mixture was stirred for about 10 minutes at room temperature under nitrogen. Sodium cyanoborohydride (27.5 mg, 0.438 mmol) was added in one portion, and the reaction mixture was stirred at room temperature overnight. Solvent was removed under reduced pressure and crude material was purified by RP-HPLC (A=50 mM ammonium acetate, B=ACN; 40% to 80% B over 30 min at 21.0 mL/min; UV λ=254 nm; Thermo Hyperprep HS C18, 8 μm, 250×21.2 mm column). Fractions containing product were combined, rotovapped and lyophilized to give N-(4-(3-(3-chloro-4-isopropoxyphenyl)-1,2,4-oxadiazol-5-yl)benzyl)-1-(2,2-dimethyl-1,3-dioxolan-4-yl)methanamine (130.9 mg, 64.7%) as a white solid. LCMS (Table 1, Method c) R$_t$=2.59 min, m/z 458.62 (M+H)+; 1H NMR (400 MHz, DMSO) δ ppm 8.13 (d, 2H), 8.06 (d, 1H), 8.00 (dd, 1H), 7.61 (d, 2H), 7.39 (d, 1H), 4.82 (sept, 1H), 4.15 (p, 1H), 3.99 (dd, 1H), 3.84 (s, 2H), 3.63 (dd, 1H), 2.61 (ddd, 2H), 1.86 (s, 4H), 1.35 (d, 6H) 1.26 (s, 3H).

Example #46

Preparation 3-(4-(3-(3-chloro-4-isopropoxyphenyl)-1,2,4-oxadiazol-5-yl)benzylamino)propane-1,2-diol

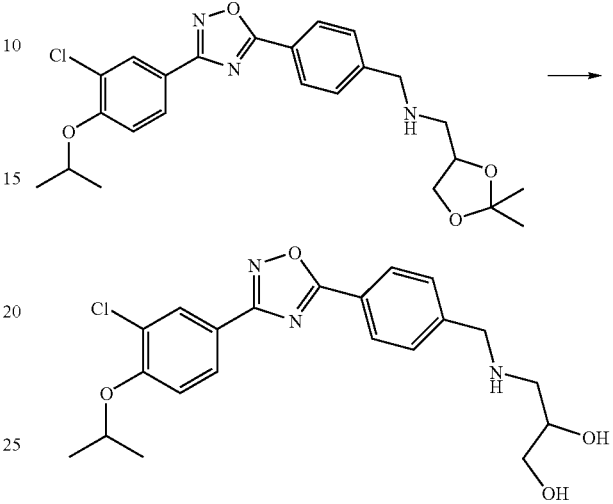

To a solution of N-(4-(3-(3-chloro-4-isopropoxyphenyl)-1,2,4-oxadiazol-5-yl)benzyl)-1-(2,2-dimethyl-1,3-dioxolan-4-yl)methanamine (108 mg, 0.236 mmol) in THF (4 mL) was added 1N aqueous HCl (0.778 mL, 0.778 mmol) The reaction was heated to 65° C. under nitrogen for 90 minutes. Heating was stopped and the reaction was neutralized by addition of 1N aqueous NaOH (0.778 mL, 0.778 mmol). THF was removed under reduced pressure and the remaining aqueous solution was basified (pH approx 9) by the addition of 0.1N NaOH, at which point white precipitate formed. Solid was collected by vacuum filtration, and washed with 0.1N NaOH (3×10 mL). Solid was dried in a vacuum oven overnight to give 3-(4-(3-(3-chloro-4-isopropoxyphenyl)-1,2,4-oxadiazol-5-yl)benzylamino)propane-1,2-diol (31.7 mg, 32%) as an off-white solid. LCMS (Table 1, Method c) R$_t$=1.90 min, m/z 418.47 (M+H)+; 1H NMR (400 MHz, methanol) δ ppm 7.22 (d, J=8.68 Hz, 1H), 7.60 (d, 2H), 8.01 (dd, 1H), 8.10 (d, 1H), 8.16 (d, 2H), 4.78 (sept, 1H), 2.76 (dd, 1H), 2.63 (dd, 1H), 3.52 (d, 2H), 3.90 (d, 2H), 3.78 (m, 1H), 1.40 (d, 6H).

Example #47

Preparation of (Z)-methyl 3-(4-(3-(3-chloro-4-isopropoxyphenyl)-1,2,4-oxadiazol-5-yl)phenyl)acrylate

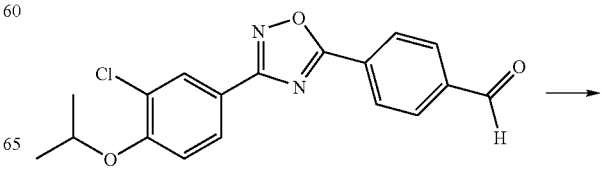

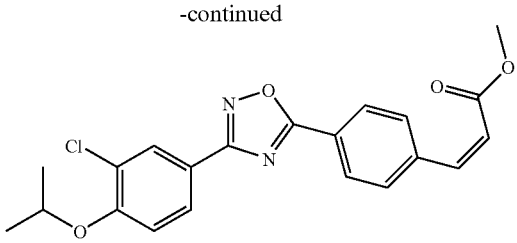

A two-neck round bottom flask was charged with methyl 2-(bis(2,2,2-trifluoroethoxy)phosphoryl)acetate (0.235 ml, 1.109 mmol), 18-crown-6 (1465 mg, 5.54 mmol) and THF (15 ml). The mixture was then cooled to −78° C. under an atmosphere of nitrogen. Potassium bis(trimethylsilyl)amide (221 mg, 1.109 mmol) was added and the mixture stirred for a few minutes. 4-(3-(3-chloro-4-isopropoxyphenyl)-1,2,4-oxadiazol-5-yl)benzaldehyde (380 mg, 1.109 mmol) was added and the mixture stirred at −78° C. for 90 minutes and then left to warm to room temperature overnight. Reaction was quenched by the addition of saturated NH$_4$Cl (aqueous). The mixture was separated and the aqueous layer was extracted with ether (3×10 mL). The combined organics were dried over MgSO$_4$ and concentrated to give an off-white solid. The solid was triturated with MeOH and collected by vacuum filtration and washed with MeOH (3×10 mL). Collected solid was dried overnight in a vacuum oven to give (Z)-methyl 3-(4-(3-(3-chloro-4-isopropoxyphenyl)-1,2,4-oxadiazol-5-yl)phenyl)acrylate (325 mg, 73.5%).

LCMS (Table 1, Method c) R$_t$=3.22 min, m/z 399.16 (M+H)$^+$. $^1$H NMR (400 MHz, DMSO) δ ppm 8.18 (d, 2H), 8.06 (d, 1H), 8.01 (dd, 1H), 7.79 (d, 2H), 7.40 (d, 1H), 7.18 (d, 1H), 6.84 (d, 1H), 6.20 (d, 1H), 4.83 (sept, 1H), 3.67 (s, 3H), 1.35 (d, 6H).

Example #48

Preparation of Trans-methyl 2-(4-(3-(3-chloro-4-isopropoxyphenyl)-1,2,4-oxadiazol-5-yl)phenyl)cyclopropanecarboxylate

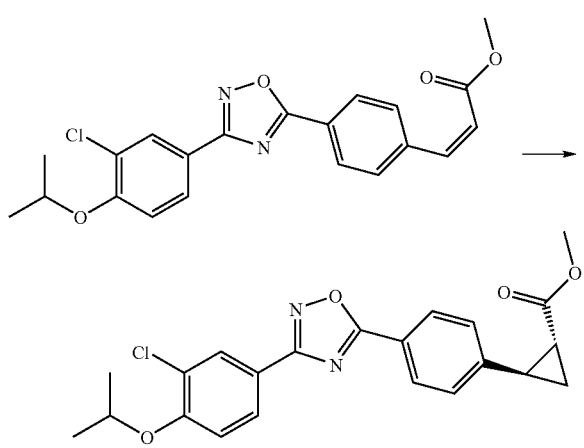

To a stirred suspension of trimethylsulfoxonium iodide (234 mg, 1.065 mmol) in DMSO (5.0 mL) under nitrogen, was added, in portions NaH (42.6 mg, 1.065 mmol), with a water bath in place to keep the reaction between 25-30° C. Upon completion of hydrogen evolution, a solution of (Z)-methyl 3-(4-(3-(3-chloro-4-isopropoxyphenyl)-1,2,4-oxadiazol-5-yl)phenyl)acrylate (386 mg, 0.968 mmol) in DMSO (5.00 mL) was added drop-wise, keeping the reaction temperature at or below 35° C. After addition was complete, the reaction was stirred at room temperature for an hour and a half and then warmed to 50° C. for two hours. 50 ml of water was then added to the reaction, and the reaction left to stir at room temperature overnight. The reaction mixture was diluted with saturated aqueous sodium chloride, and the aqueous layer was extracted 3× with 75 mL EtOAc. Organic layers were combined, dried over MgSO$_4$, and concentrated. The crude material was purified by RP-HPLC (A=50 mM ammonium acetate, B=ACN; 30% to 100% B over 30 min at 21.0 mL/min; UV λ=254 nm; Thermo Hyperprep HS C18, 8 μm, 250×21.2 mm column). Fractions containing product were combined, concentrated and lyophilized to give Trans-methyl 2-(4-(3-(3-chloro-4-isopropoxyphenyl)-1,2,4-oxadiazol-5-yl)phenyl)cyclopropanecarboxylate (155 mg, 39%) as a white solid. LCMS (Table 1, Method c) R$_t$=3.27 min, m/z 413.17 (M+H)$^+$. $^1$H NMR (400 MHz, DMSO) δ ppm 8.08 (d, 2H), 8.06 (d, 1H), 7.99 (dd, 1H), 7.47 (d, 2H), 7.39 (d, 1H), 4.82 (sept, 1H), 3.66 (s, 3H), 2.59 (ddd, 1H), 2.12 (ddd, 1H), 1.58 (ddd, 1H), 1.53 (ddd, 1H), 1.35 (d, 6H).

Example #49

Preparation of Trans-2-(4-(3-(3-chloro-4-isopropoxyphenyl)-1,2,4-oxadiazol-5-yl)phenyl)cyclopropanecarboxylic Acid

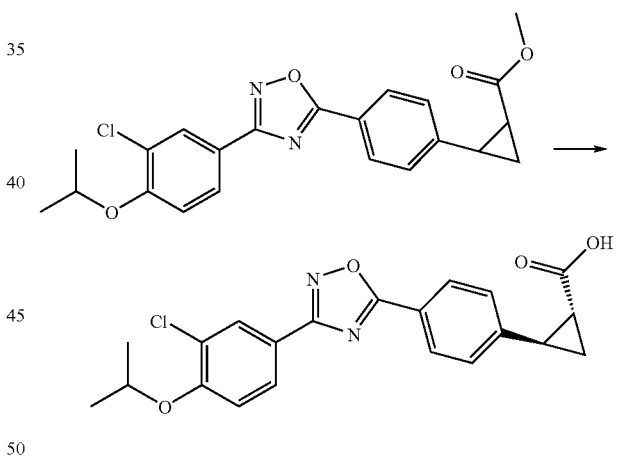

To a suspension of (1S, 2S)-methyl 2-(4-(3-(3-chloro-4-isopropoxyphenyl)-1,2,4-oxadiazol-5-yl)phenyl)cyclopropanecarboxylate (111 mg, 0.269 mmol) in ethanol (5 ml) was added 2 N NaOH (5 ml, 10.00 mmol). The mixture was stirred under nitrogen at room temperature overnight. Reaction mixture was neutralized by addition of acetic acid, and then acidified with a few drops of 1 N aqueous HCl (pH about 2). White solid precipitated and was collected by filtration, washed with 0.1N HCl (3×5 mL), and dried under vacuum to give Trans-2-(4-(3-(3-chloro-4-isopropoxyphenyl)-1,2,4-oxadiazol-5-yl)phenyl)cyclopropanecarboxylic acid (64 mg, 59%). LCMS (Table 1, Method f) R$_t$=2.99 min, m/z 399.16 (M+H)$^+$. $^1$H NMR (400 MHz, DMSO) δ ppm 8.07 (d, 2H), 8.05 (d, 1H), 7.99 (dd, 1H), 7.45 (d, 2H), 7.38 (d, 1H), 4.82 (sept., 1H), 2.54 (m, 1H), 1.97 (m, 1H), 1.53 (td, 1H), 1.46 (ddd, 1H), 1.35 (d, 6H).

Example #50

Preparation of tert-butyl 5-(3-(3-chloro-4-isopropoxyphenyl)-1,2,4-oxadiazol-5-yl)isoindoline-2-carboxylate

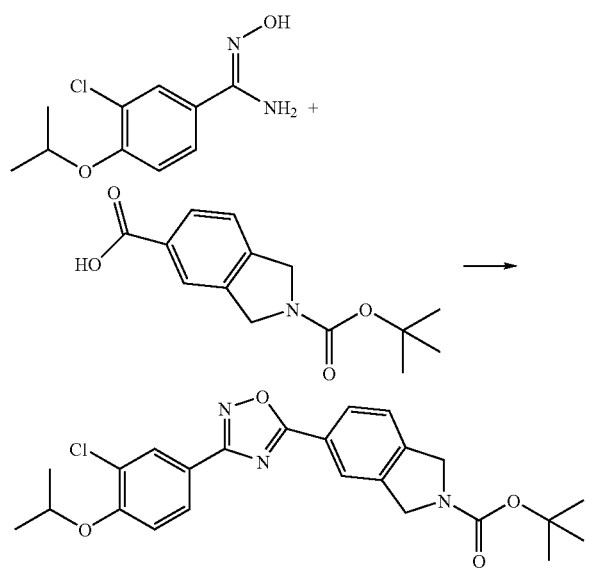

To a solution of 2-(tert-butoxycarbonyl)isoindoline-5-carboxylic acid (190 mg, 0.722 mmol) in acetonitrile (3 mL) in a 5 mL microwave vial was added HOBT (330 mg, 2.16 mmol), DCC (298 mg, 2.16 mmol), and DIEA (0.115 mL, 0.656 mmol). The mixture was stirred at room temperature for approximately 16 hours. Next, (Z)-3-chloro-N'-hydroxy-4-isopropoxybenzimidamide (150 mg, 0.656 mmol) (prepared by General procedure B) was added and the reaction was heated to 150° C. under microwave irradiation (max 300 W) for 20 minutes. After cooling, the reaction mixture was filtered, concentrated, and purified via Analogix system using RediSep 40 g column, with a gradient of 0-40% EtOAc/Heptane over 30 min. at a flow rate of 30 ml/min. Fractions containing product were combined, rotovapped, and dried in a vacuum oven to give tert-butyl 5-(3-(3-chloro-4-isopropoxyphenyl)-1,2,4-oxadiazol-5-yl)isoindoline-2-carboxylate (46.2 mg, 15.5%) LCMS (Table 1, Method c) $R_t$=3.40 min, m/z 456.22 (M+H)+; 1H NMR (400 MHz, DMSO) δ ppm 8.16 (d, 1H), 8.10 (s, 1H), 8.05 (d, 1H), 7.61 (m, 1H), 7.39 (d, 1H), 4.82 (sept, 1H), 4.70 (d, 4H), 1.48 (s, 9H), 1.35 (d, 6H).

Example #51

Preparation of 3-(3-chloro-4-isopropoxyphenyl)-5-(isoindolin-5-yl)-1,2,4-oxadiazole, Trifluoroacetic Acid

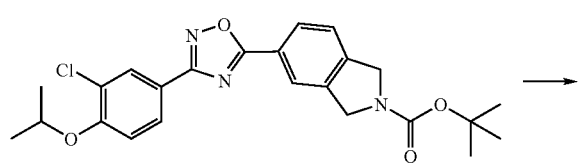

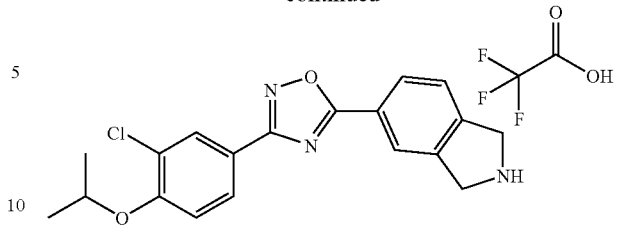

To a solution of tert-butyl 5-(3-(3-chloro-4-isopropoxyphenyl)-1,2,4-oxadiazol-5-yl)isoindoline-2-carboxylate (41 mg, 0.090 mmol) in DCM (2 ml) was added TFA (0.5 mL, 6.49 mmol). The mixture was stirred at room temperature under nitrogen for approximately 30 minutes. After 30 minutes, ether was added slowly to the mixture, until it became cloudy and a white precipitate formed. Solid was collected by filtration and washed with ether (3×10 mL). The collected solid was then dried in vacuum oven to give 3-(3-chloro-4-isopropoxyphenyl)-5-(isoindolin-5-yl)-1,2,4-oxadiazole as the TFA salt (26.7 mg, 62.6%).

LCMS (Table 1, Method c) $R_t$=2.29 min, m/z 356.17 (M+H)+. 1H NMR (400 MHz, DMSO) δ ppm 9.46 (s, 2H), 8.27 (s, 1H), 8.20 (d, 1H), 8.00 (d, 1H), 7.70 (d, 1H), 7.41 (d, 1H), 4.83 (sept, 1H), 4.64 (d, 4H), 1.35 (d, 6H).

Example #52

Preparation of methyl 3-(5-(3-(3-chloro-4-isopropoxyphenyl)-1,2,4-oxadiazol-5-yl)isoindolin-2-yl)propanoate

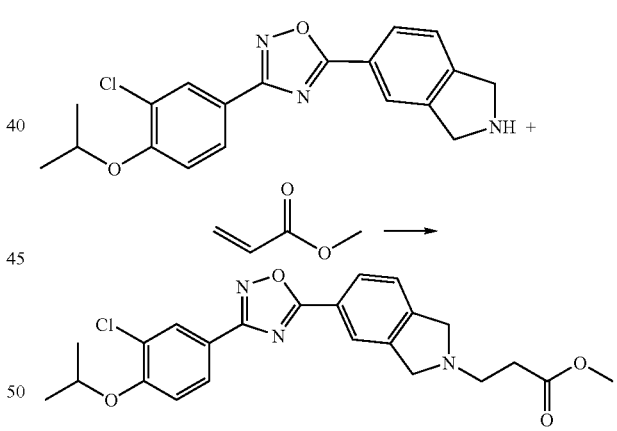

3-(3-chloro-4-isopropoxyphenyl)-5-(isoindolin-5-yl)-1,2,4-oxadiazole (16.7 mg, 0.047 mmol) was added to a 2 mL microwave vial equipped with a stirring bar. Methyl acrylate (8.45 μL, 0.094 mmol), and methanol (1.0 mL) were added, the vial capped, and the reaction heated to 90° C. for 20 min under microwave irradiation (300 W). After 20 minutes, another aliquot of methyl acrylate (8.45 μL, 0.094 mmol) was added, the vial was re-sealed, and heated to 110° C. for 40 min under microwave irradiation (300 W). Reaction was then concentrated and dried under vacuum overnight to give crude methyl 3-(5-(3-(3-chloro-4-isopropoxyphenyl)-1,2,4-oxadiazol-5-yl)isoindolin-2-yl)propanoate as a yellow oil (21.6 mg, 104%). The product was used without further purification. LCMS (Table 1, Method c) $R_t$=2.85 min, m/z 442.45 (M+H)+

Example #53

Preparation of 3-(5-(3-(3-chloro-4-isopropoxyphenyl)-1,2,4-oxadiazol-5-yl)isoindolin-2-yl)propanoic acid, Hydrochloric Acid

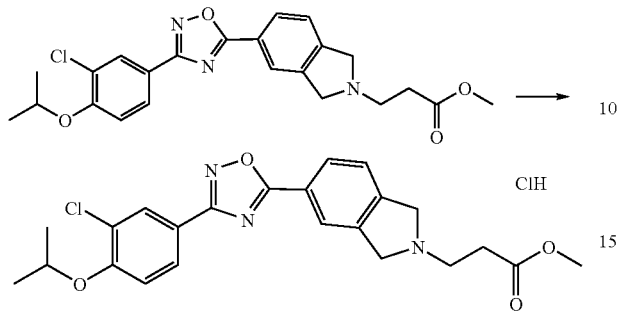

To a solution of methyl 3-(5-(3-(3-chloro-4-isopropoxyphenyl)-1,2,4-oxadiazol-5-yl)isoindolin-2-yl)propanoate (21 mg, 0.048 mmol) in ethanol (1 ml) was added 2M aqueous NaOH (1 ml, 2.000 mmol). The reaction was stirred at room temperature under an atmosphere of nitrogen for approximately 4 hours. Reaction mixture was then acidified to a pH of 1 by addition of 2N HCl, at which time a precipitate formed. The solid was collected by filtration and washed with water (3×5 mL). The solid was then dried in a vacuum oven overnight to give 3-(5-(3-(3-chloro-4-isopropoxyphenyl)-1,2,4-oxadiazol-5-yl)isoindolin-2-yl)propanoic acid as the hydrochloride salt (10.2 mg, 46.2%). LCMS (Table 1, Method c) $R_t$=1.86 min, m/z 428.20 (M+H)$^+$. $^1$H NMR (400 MHz, DMSO) δ ppm 12.12 (m, 1H), 8.23 (s, 1H), 8.19 (d, 1H), 8.07 (dd, 1H), 7.68 (d, 1H), 7.41 (d, 1H), 4.83 (sept, 1H), 4.72 (s, 4H), 3.58 (t, 2H), 2.84 (t, 2H), 1.36 (d, 6H)

Example #54

Preparation of (Z)-methyl 3-(4-(3-(3-chloro-4-isopropoxyphenyl)-1,2,4-oxadiazol-5-yl)phenyl)acrylate

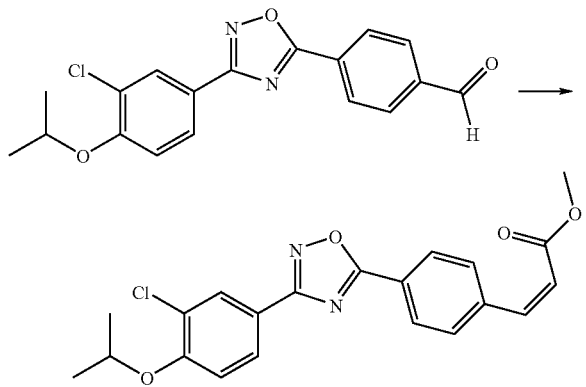

A two-neck round bottom flask was charged with methyl 2-(bis(2,2,2-trifluoroethoxy)phosphoryl)acetate (0.235 ml, 1.109 mmol), 18-crown-6 (1465 mg, 5.54 mmol) and THF (15 ml). The mixture was then cooled to −78° C. under an atmosphere of nitrogen. Potassium bis(trimethylsilyl)amide (221 mg, 1.109 mmol) was added and the mixture stirred for a few minutes. 4-(3-(3-chloro-4-isopropoxyphenyl)-1,2,4-oxadiazol-5-yl)benzaldehyde (380 mg, 1.109 mmol) was added and the mixture stirred at −78° C. for 90 minutes and then left to warm to room temperature overnight. Reaction was quenched by the addition of saturated NH$_4$Cl (aqueous). Mixture was separated and the aqueous layer was extracted with ether (3×10 mL). Combined organics were dried over MgSO$_4$ and concentrated to give an off-white solid. Solid was triturated with MeOH and collected by vacuum filtration and washed with MeOH (3×10 mL). Collected solid was dried overnight in a vacuum oven to give (Z)-methyl 3-(4-(3-(3-chloro-4-isopropoxyphenyl)-1,2,4-oxadiazol-5-yl)phenyl)acrylate (325 mg, 73.5%).

LCMS (Table 1, Method c) $R_t$=3.22 min, m/z 399.16 (M+H)$^+$. $^1$H NMR (400 MHz, DMSO) δ ppm 8.18 (d, 2H), 8.06 (d, 1H), 8.01 (dd, 1H), 7.79 (d, 2H), 7.40 (d, 1H), 7.18 (d, 1H), 6.84 (d, 1H), 6.20 (d, 1H), 4.83 (sept, 1H), 3.67 (s, 3H), 1.35 (d, 6H).

Example #55

Preparation of (Z)-3-(4-(3-(3-chloro-4-isopropoxyphenyl)-1,2,4-oxadiazol-5-yl)phenyl)acrylic Acid

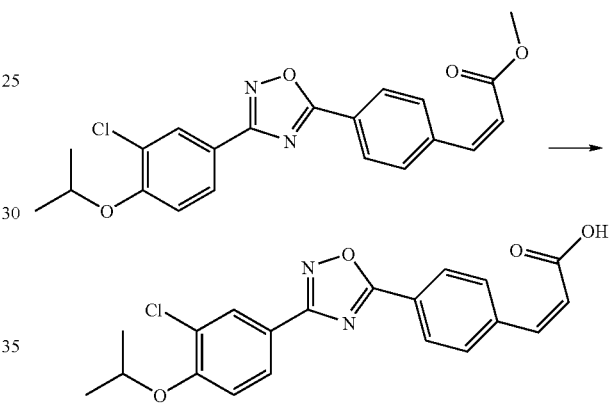

To a solution of (Z)-methyl 3-(4-(3-(3-chloro-4-isopropoxyphenyl)-1,2,4-oxadiazol-5-yl)phenyl)acrylate (30 mg, 0.075 mmol) in EtOH (2 mL) was added 2N aqueous NaOH (2 mL). The reaction was stirred at room temperature, under nitrogen, for 2 hours. Reaction was acidified via addition of 1N HCl, until a precipitate formed. Solid was collected by filtration, washed with 0.2N HCl, and dried in a vac oven to give (Z)-3-(4-(3-(3-chloro-4-isopropoxyphenyl)-1,2,4-oxadiazol-5-yl)phenyl)acrylic acid (8.2 mg, 28.3%). LCMS (Table 1, Method c) $R_t$=2.64 min, m/z 385.12 (M+H)$^+$. $^1$H NMR (400 MHz, DMSO) δ ppm 13.11-12.20 (m, 1H), 8.15 (d, 2H), 8.04 (d, 1H), 7.99 (dd, 1H), 7.78 (d, 2H), 7.37 (d, 1H), 7.03 (d, 1H), 6.12 (d, 1H), 4.81 (sept., 1H), 1.33 (d, 6H)

Example #56

Preparation of 3-chloro-4-(3-(3-chloro-4-isopropoxyphenyl)-1,2,4-oxadiazol-5-yl)aniline

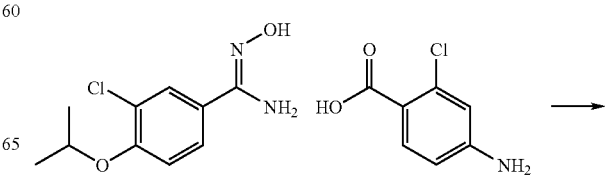

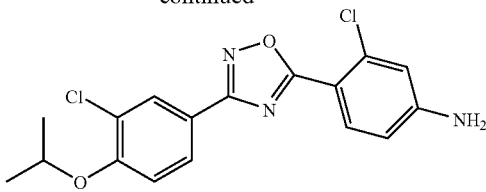

(Z)-3-chloro-N'-hydroxy-4-isopropoxybenzimidamide (0.5 g, 2.187 mmol), 4-amino-2-chlorobenzoic acid (0.413 g, 2.405 mmol), DCC (0.496 g, 2.405 mmol), HOBT (0.368 g, 2.405 mmol) were placed in an 80 ml microwave vial and Acetonitrile (12.01 ml) was added. The reaction mixture was stirred for 5 minutes at room temperature before the addition of DIEA (0.840 ml, 4.81 mmol). The reaction mixture was heated to 120° C. for 30 min in a microwave. TLC (50% EA/Hept) indicated 4 spots Rf 0.8, 0.6, 0.5 and 0.3. LCMS (2007_9349) indicated by UV 16% (2.61 mins) to (M+H) 364.31. The solvent was removed and the crude material purified by FCC (50% EA/Hept) to afford 3-chloro-4-(3-(3-chloro-4-isopropoxyphenyl)-1,2,4-oxadiazol-5-yl)aniline (534 mg, 1.466 mmol, 67.1% yield). LCMS (Table A, Method b) indicated a 99% by UV (3.10 mins) and 92% by ELSD (3.06 mins) to (M+H)+ 364.12.

Example #57

Preparation of 3-(3-chloro-4-(3-(3-chloro-4-isopropoxyphenyl)-1,2,4-oxadiazol-5-yl)phenylamino)cyclobutanecarboxylic Acid

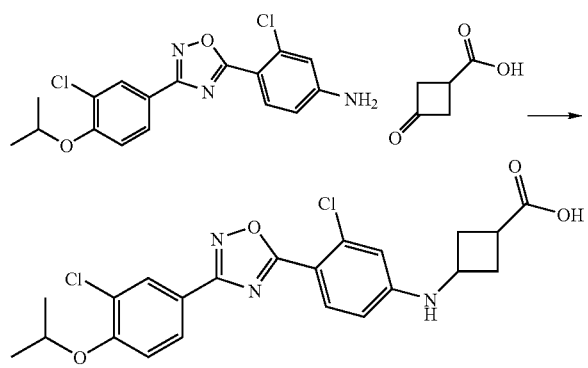

3-chloro-4-(3-(3-chloro-4-isopropoxyphenyl)-1,2,4-oxadiazol-5-yl)aniline (200 mg, 0.549 mmol) and 3-oxocyclobutanecarboxylic acid (62.7 mg, 0.549 mmol) in methanol (1280 μl) at room temperature was added acetic acid (842 μl, 14.72 mmol). The reaction mixture was stirred at room temperature for 10 minutes before addition of sodium cyanoborohydride (17.25 mg, 0.275 mmol) as a single portion. The reaction mixture was stirred at room temperature overnight. LCMS (2007_9476) indicated a 43% by ELSD (2.90 min)s conversion to (M+H) 462.16. The solvent was removed and the crude material purified by FCC (50% EA/Hept) to afford 3-(3-chloro-4-(3-(3-chloro-4-isopropoxyphenyl)-1,2,4-oxadiazol-5-yl)phenylamino)cyclobutanecarboxylic acid (135 mg, 0.292 mmol, 53.2% yield) as a white solid. LCMS (Table A, Method b) indicated 100% by UV (3.06 mins) to (M+H)+ 364.12.

Preparation #21: 4-(3-(3-chloro-4-isopropoxyphenyl)-1,2,4-oxadiazol-5-yl)aniline

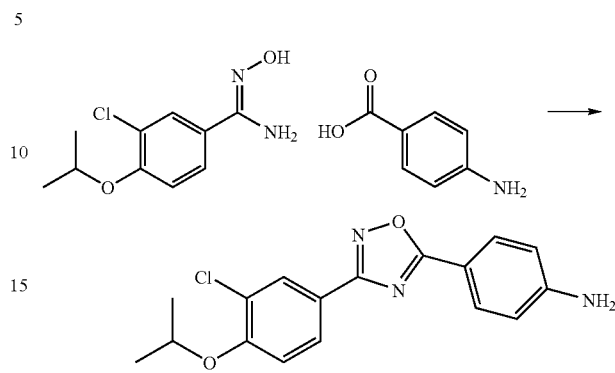

(Z)-3-chloro-N'-hydroxy-4-isopropoxybenzimidamide (1 g, 4.37 mmol), 4-aminobenzoic acid (0.660 g, 4.81 mmol), HOBT (0.737 g, 4.81 mmol), DCC (0.992 g, 4.81 mmol) and DIEA (1.680 ml, 9.62 mmol) were combined in a microwave vial. The reaction mixture was heated in the microwave for 20 minutes at 150° C. The reaction mixture was filtered to remove the urea formed in the reaction and the solvent was removed in vacuo. The crude material was purified by FCC (50% ethyl acetate/heptane) to afford 4-(3-(3-chloro-4-isopropoxyphenyl)-1,2,4-oxadiazol-5-yl)aniline (729 mg, 2.211 mmol, 50.6% yield) as an off white solid: LCMS (Table A, Method b) 3.00 min, (M+H)+ 330.13.

Preparation #22: 3-(4-(3-(3-chloro-4-isopropoxyphenyl)-1,2,4-oxadiazol-5-yl)phenylamino)cyclobutanecarboxylic Acid

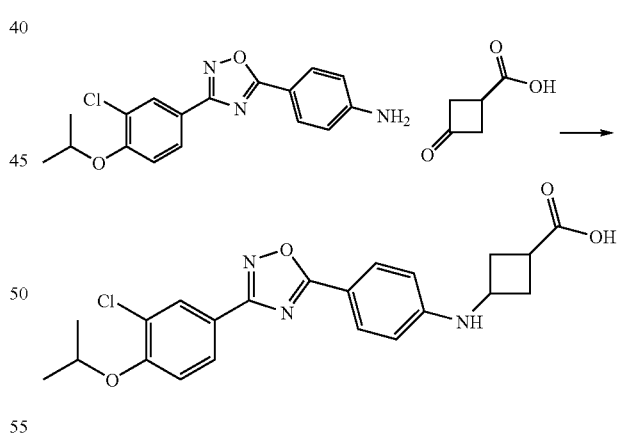

4-(3-(3-chloro-4-isopropoxyphenyl)-1,2,4-oxadiazol-5-yl)aniline (250 mg, 0.531 mmol) in Methanol (1478 μl) at room temperature was added 3-oxocyclobutanecarboxylic acid (60.5 mg, 0.531 mmol) followed by acetic acid (814 μl, 14.22 mmol). The reaction mixture was stirred at room temperature for 5 minutes before the addition of sodium cyanoborohydride (16.67 mg, 0.265 mmol). The reaction mixture was stirred overnight at room temperature. The solvent was removed and the crude material purified by FCC (50% ethyl acetate/heptane) to afford 3-(4-(3-(3-chloro-4-isopropoxyphenyl)-1,2,4-oxadiazol-5-yl)phenylamino)cyclobutanecarboxylic acid (139 mg, 0.302 mmol, 56.9% yield) as a white solid. LCMS (Table A, Method b) 2.89 min, (M+H)+ 428.20.

Example #58

Preparation of 2-(4-(3-(3-chloro-4-isopropoxyphenyl)-1,2,4-oxadiazol-5-yl)phenyl)propan-2-amine

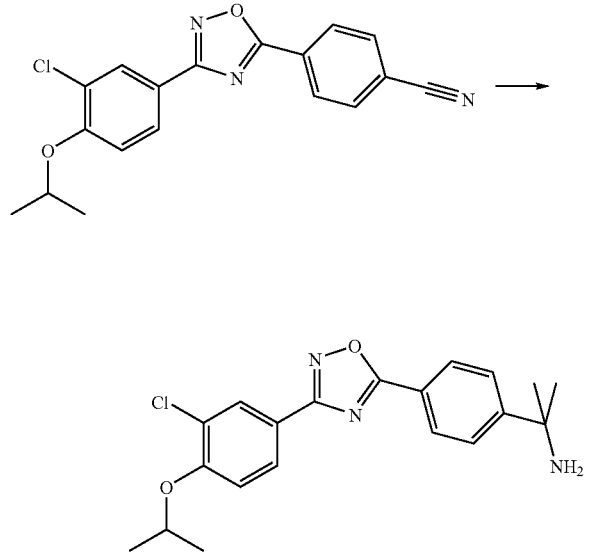

Anhydrous cerium (III) chloride (5.57 g, 22.60 mmol) and anhydrous tetrahydrofuran (20 mL) were added to a dry 2-neck round bottom flask under nitrogen. The resulting suspension was sonicated for a few minutes and then stirred at room temperature for 90 minutes. The mixture was then cooled to −50° C., and methyllithium (14.13 mL, 22.60 mmol) was added slowly. After 60 min, and warming to 0° C., the reaction was cooled to −50° C. and 4-(3-(3-chloro-4-isopropoxyphenyl)-1,2,4-oxadiazol-5-yl)benzonitrile (2.4 g, 7.06 mmol) (prepared by General Procedure X) in 8 mL of anhydrous THF was added drop-wise, to keep the temperature of the reaction at −50° C. The reaction was maintained at −50 C for 1 hr, then left to warm to room temperature overnight. The next day the reaction was cooled to −50° C., and quenched by the addition of 21 mL of 35% NH$_4$OH. The quenched reaction was left to warm to room temperature over two hours. The mixture was filtered through Celite® and washed with DCM (4×60 mL). The filtrate was collected and then washed with water and dried over MgSO$_4$. Solvent was removed under reduced pressure and the crude material was purified by RP-HPLC (A=50 mM ammonium acetate, B=acetonitrile; 30-70% B over 30.0 min (21.0 mL/min flow rate); 21.2×250 mm Thermo Hyperprep C18 column, 8 μm particles) to give 2-(4-(3-(3-chloro-4-isopropoxyphenyl)-1,2,4-oxadiazol-5-yl)phenyl)propan-2-amine as the acetic acid salt (309 mg; 10.1%). LCMS (Table 1, Method a) R$_t$=2.61 min; $^1$H NMR (400 MHz, DMSO-d6) δ ppm 8.14-7.94 (m, 4H), 7.80 (d, J=8.43 Hz, 2H), 7.37 (d, J=8.81 Hz, 1H), 4.80 (sept, J=6.04 Hz, 1H), 1.85 (s, 3H), 1.39 (s, 6H), 1.36-1.31 (d, J=6.04 Hz, 6H)

Preparation #23: methyl 3-(2-(4-(3-(3-chloro-4-isopropoxyphenyl)-1,2,4-oxadiazol-5-yl)phenyl)propan-2-ylamino)propanoate

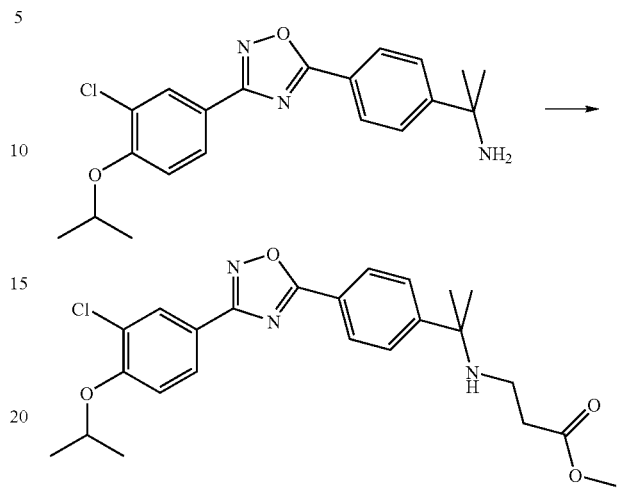

2-(4-(3-(3-chloro-4-isopropoxyphenyl)-1,2,4-oxadiazol-5-yl) phenyl)propan-2-amine, acetic acid (132 mg, 0.306 mmol) was added to a 5 mL microwave vial equipped with a stirring bar. Methyl acrylate (52.6 mg, 0.611 mmol), and MeOH (3.0 mL) were added, the vial capped, and the reaction heated to 120° C. for 90 min under microwave irradiation (Biotage Optimizer, 300 W). After 90 min another aliquot of methyl acrylate (52.6 mg, 0.611 mmol) was added and the reaction submitted for another 60 min at 120° C. Reaction was cooled and the solvent removed under reduced pressure. Crude material was purified by RP-HPLC (A=50 mM ammonium acetate, B=acetonitrile; 30-70% B over 30.0 min (21.0 mL/min flow rate); 21.2×250 mm Thermo Hyperprep C18 column, 8 μm particles) to give methyl 3-(2-(4-(3-(3-chloro-4-isopropoxyphenyl)-1,2,4-oxadiazol-5-yl)phenyl)propan-2-ylamino)propanoate (83.5 mg; 59.7%). LCMS (Table 1, Method f) R$_t$=2.78 min, m/z=458.29 (M+H)+, Example #59

Preparation of 3-(2-(4-(3-(3-chloro-4-isopropoxyphenyl)-1,2,4-oxadiazol-5-yl)phenyl)propan-2-ylamino)propanoic Acid

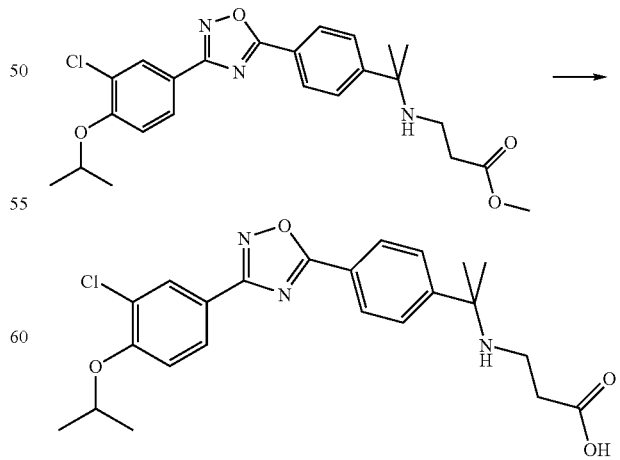

Methyl 3-(2-(4-(3-(3-chloro-4-isopropoxyphenyl)-1,2,4-oxadiazol-5-yl)phenyl)propan-2-ylamino)propanoate (83 mg, 0.181 mmol) was dissolved in ethanol (4mL) and NaOH (4mL, 8.00 mmol) was added. The mixture was stirred at room temperature under nitrogen. After 20 minutes the reaction was neutralized by drop-wise addition of acetic acid. The aqueous mixture was then frozen and lyophilized. The solid obtained after lyophilization was brought up in DCM, filtered, and washed with DCM. The filtrate was concentrated and brought up in ether to provide a slightly cloudy solution. IN HCl in ether was added dropwise until white precipitate formed. Material was collected by filtration, washed with ether, and dried in a vacuum oven to give 3-(2-(4-(3-(3-chloro-4-isopropoxyphenyl)-1,2,4-oxadiazol-5-yl)phenyl) propan-2-ylamino)propanoic acid as the hydrochloric acid salt (61.5 mg; 70.6%). LCMS (Table 1, Method f) $R_t$=1.98 min, m/z=444.29 (M+H)$^+$; 1H NMR (400 MHz, DMSO-d6)δ ppm 8.32 (d, J=8.57 Hz, 2H), 8.12 (d, J=2.08 Hz, 1H), 8.03 (dd, J=8.64, 2.10 Hz, 1H), 7.85 (d, J=8.59 Hz, 2H), 7.25 (d, J=8.78 Hz, 1H), 4.79 (sept, J=6.11 Hz, 1H), 2.95 (t, J=6.20 Hz, 2H), 2.44 (t, J=6.17 Hz, 2H), 1.84 (s, 6H), 1.40 (d, J=6.04 Hz, 6H).

What is claimed is:

1. A compound of Formula I

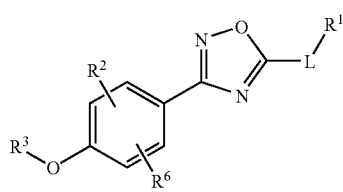

Formula I pharmaceutically acceptable salts, prodrugs, enantiomers or stereoisomers thereof, wherein L is a bond;

$R^1$ is optionally substituted phenyl;

$R^2$ is Br, Cl, $CF_3$, CN, or —O—($C_1$-$C_2$)alkyl;

$R^3$ is optionally substituted—($C_3$-$C_8$)alkyl, ($C_4$-$C_5$)alkenyl, ($C_4$-$C_5$)alkynyl, —($C_2$-$C_3$)alkyl—O—optionally substituted ($C_1$-$C_3$)alkyl, —($C_1$-$C_3$)alkyl-imidazolyl, —($C_1$-$C_3$)alkyl-morpholinyl, —($C_1$-$C_3$)alkyl-optionally substituted phenyl, —($C_1$-$C_3$)alkyl-optionally substituted piperazinyl, —($C_1$-$C_3$)alkyl-pyrrolidinyl, —($C_1$-$C_3$)alkyl-piperidinyl, or —($C_1$-$C_3$)alkyl-thienyl; and $R^6$ is H;

wherein $R^1$ is optionally substituted by one or more substituents independently selected from Br, Cl, F, $CF_3$, CN, oxo, optionally substituted ($C_1$-$C_6$)alkyl, optionally substituted ($C_2$-$C_6$)alkenyl, optionally substituted amino, optionally substituted ($C_3$-$C_6$)cycloalkyl, —$CH_2$-optionally substituted piperidinyl, —C(O)—optionally substituted ($C_1$-$C_6$)alkyl, —C(O)—NR—($C_1$-$C_6$)alkyl, —C(O)—O-optionally substituted($C_1$-$C_6$)alkyl, —O-optionally substituted ($C_1$-$C_6$)alkyl, —NH—($C_3$-$C_6$)cycloalkyl, —NH—C(O)—O—($C_1$-$C_3$) alkyl, —$S(O)_2$-N($R^9$)$_2$, —$S(O)_2$-NH-optionally substituted ($C_1$-$C_4$)alkyl, —NH-optionally substituted($C_1$-$C_6$)alkyl, —NH—C(O)-furanyl, —NH—$S(O)_2$-optionally substituted phenyl, optionally substituted pyridinyl,

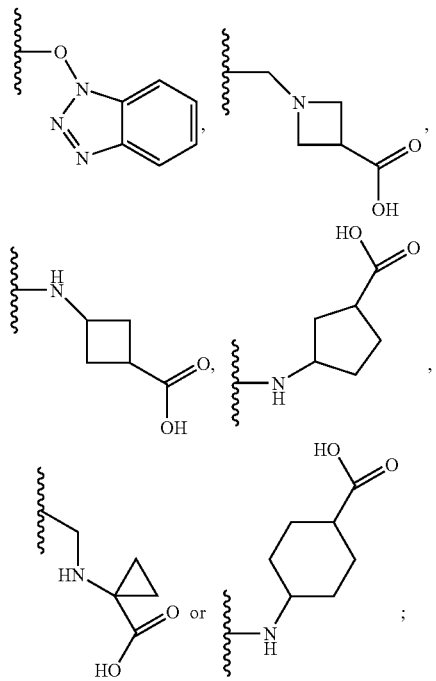

provided that $R^1$ is not substituted by optionally substituted cyclohexyl, —C(O)-cyclohexyl or —NH—cyclohexyl;

when L is ($C_1$-$C_3$)alkyl, $R^1$ is not optionally substituted isoxazolyl;

when $R^3$ is optionally substituted ($C_1$)alkyl, L-$R^1$ is not cyclohexyl or —$CH_2$-cyclohexyl; and provided that the compound is not

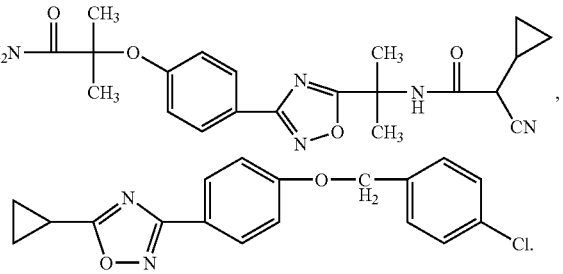

wherein R is H or ($C_1$-$C_3$)alkyl; and wherein each $R^9$ is independently selected from H or optionally substituted ($C_1$-$C_6$)alkyl.

2. The compound of claim 1 wherein the compound is a compound of Formula Ia

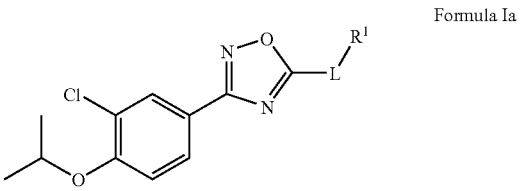

Formula Ia wherein L is a bond.

3. The compound of claim 2 wherein the compound is

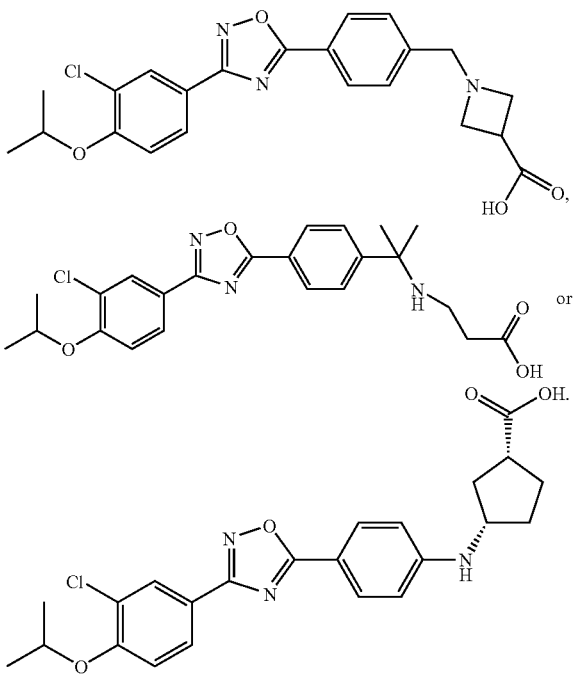

4. A compound having formula (IV):

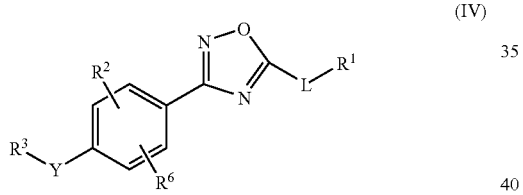

(IV)

or a pharmaceutically acceptable salt, prodrug, enantiomer or stereoisomer thereof,
wherein:
X is $CR^4$;
L is a bond;
Y is —O—;
$R^1$ is optionally substituted phenyl;
$R^2$ is H, —($C_1$-$C_4$)alkyl, —O—($C_1$-$C_3$)alkyl, —$CF_3$, —CN, halo or —COO—($C_1$-$C_4$)alkyl;
$R^6$ is H;
$R^3$ is —$(CH_2)_2$-$R^9$; and when Y is O, $R^3$ is not alkyldiazeapane, —$C(CH_3)_2COOCH_2CH_3$ or —$CH_2CH_2N(CH_2CH_3)_2$, and when Y is —$CH_2$—, $R^3$ is not —$CH_2COOH$;
$R^4$ is H;
$R^5$ is H, O—($C_1$-$C_3$)alkyl or ($C_1$-$C_3$)alkyl;
each occurrence of $R^7$ or $R^{7'}$ is independently H or optionally substituted ($C_1$-$C_3$)alkyl;
$R^8$ is H, optionally substituted $CH_3$, or —$COR^9$;
$R^9$ is hydrogen, optionally substituted ($C_1$-$C_3$)alkyl, optionally substituted alkynyl, optionally substituted aryl, optionally substituted heteroaryl, optionally substituted heterocyclyl or optionally substituted ($C_3$-$C_6$) cycloalkyl; and
n is 1, 2, 3 or 4;

wherein each substituent or optional substituent is independently one or more $R^{10}$ groups wherein $R^{10}$ is optionally substituted alkyl, alkenyl, optionally substituted alkoxy groups, alkoxyalkoxy, alkoxyalkyl, alkoxycarbonyl, alkoxycarbonylheterocycloalkoxy, alkyl, alkylamino, alkylcarbonyl, alkylester, alkyl-O—C(O)—, alkyl-heterocyclyl, alkyl-cycloalkyl, alkyl-nitrile, alkylsulfonyl, alkynyl, amido groups, amino, aminoalkyl, aminocarbonyl, carbonitrile, carbonylalkoxy, carboxamido, $CF_3$, CN, —C(O)OH, —C(O)H, —C(O)—C($CH_3$)$_3$, —OH, —C(O)O-alkyl, —C(O)O-cycloalkyl, —C(O)O-heterocyclyl, —C(O)-alkyl, —C(O)-cycloalkyl, —C(O)-heterocyclyl, CN, dialkylamino, dialkylaminocarbonylalkoxy, dialkylaminocarbonyl, dialkylaminosulfonyl, —C(O)—$OR^a$, halogen, heterocyclyl, heterocyclylalkyl, heterocyclyloxy, hydroxy, hydroxyalkyl, oxo, phenyl, —$SO_2CH_3$, —$SO_2CF_3$, sulfonyl, tetrazolyl, thienylalkoxy, trifluoromethylcarbonylamino, trifluoromethylsulfonamido, heterocyclylalkoxy, heterocyclyl-$S(O)_p$, cycloalkyl-$S(O)_p$, alkyl-S—, heterocyclyl-S, heterocycloalkyl, heterocolthio, cycloalkylthio, N-alkylamino and N,N-dialkylamino where $R^a$ is alkyl, heterocycloalkyl, or heterocyclyl and p is 1 or 2; provided that $R^1$ is not optionally substituted furanyl or —C(O)-optionally substituted furanyl;

$R^3$ is not optionally substituted quinolinyl;

$R^9$ is not optionally substituted cyclopropyl, optionally substituted cyclohexyl, optionally substituted furanyl, optionally substituted imidazolyl, optionally substituted indolyl, optionally substituted naphthyl, optionally substituted piperazinyl, optionally substituted pyrazolyl, optionally substituted pyridazinyl or optionally substituted quinolinyl;

$R^1$ is not substituted by —C(O)-cyclopentyl, optionally substituted cyclopentyl, —C(O)-cyclobutyl, cyclobutyl, —C(O)-cyclohexyl or optionally substituted cyclohexyl;

$R^3$ is not substituted by C(O)-cyclopropyl;

when $R^3$ is $CH_3$ or 4-chlorophenylmethyl, L-$R^1$ is not cyclopropyl, cyclopentyl, optionally substituted cyclohexyl, —$CH_2$-cyclohexyl, —NH-cyclohexyl, —$CH_2CH_2$-cyclohexyl or optionally substituted pyrazolyl;

when Y is O, $R^3$ is not —($C_0$-$C_4$)alkyl-optionally substituted isoxazolyl or optionally substituted pyrazolyl;

when L is ($C_1$-$C_3$)alkyl, $R^1$ is not optionally substituted isoxazolyl;

when L is a bond, $R^1$ is not optionally substituted cyclobutyl, optionally substituted cyclohexyl, optionally substituted naphthyl, —$CH_2$-optionally substituted naphthyl, —$CH_2$—O-optionally substituted naphthyl, optionally substituted pyrazolyl or tetrahydrobenzofuranyl;

the compound is not

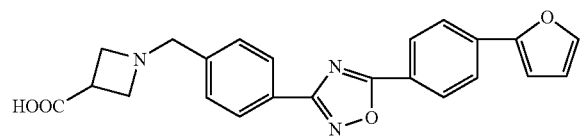

-continued

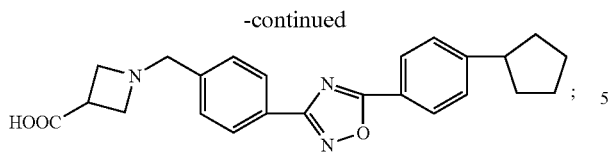

the compound is not

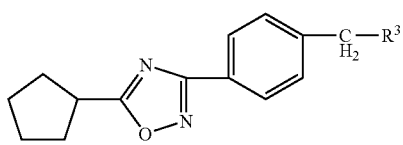

wherein R³ is optionally substituted piperazinyl or optionally substituted phenyl;
the compound is not

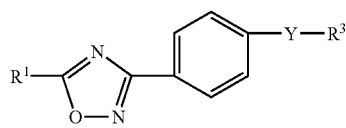

wherein R¹ is optionally substituted pyridine or 3-chlorophenyl and —Y—R³ is
—NH—C(O)-optionally substituted phenyl;
—O-optionally substituted pyridinyl;
—NH—C(O)—OCH₃;
—CH₂-optionally substituted piperazinyl;
—O-optionally substituted (C₁-C₉)alkyl;
—CH₂-morpholinyl; or
—O—C(O)-optionally substituted pyridinyl;
provided the compound is not

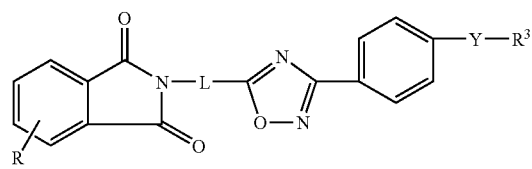

wherein
L is CH₂, CH(CH₃) or CH₂CH₂;
Y is O or CH₂;
R² is H or OCH₃;
R³ is CH₃ or OCF₃; and
R is H or NO₂;
provided the compound is not

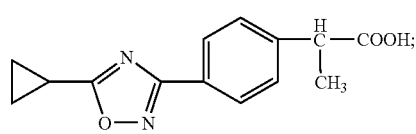

provided the compound is not

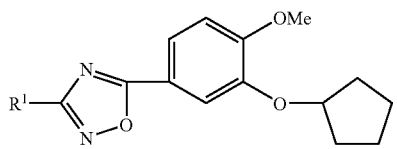

wherein R¹ is phenyl, 4-chlorophenyl, piperidinyl or thienyl.

5. The compound of claim 4 having formula (IVa):

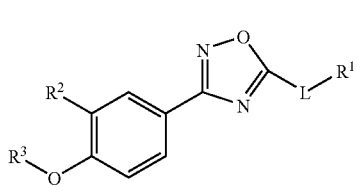

(IVa)

or a physiologically acceptable salt, or stereoisomer thereof, wherein:
L is a bond;
R¹ is optionally substituted phenyl;
R² is Cl or CF₃; and
R³ is straight or branched optionally substituted (C₂-C₈) alkyl.

6. The compound of claim 5 wherein R² is Cl.

7. The compound of claim 4 having formula (IVb):

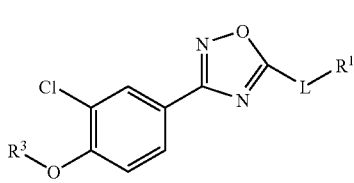

(IVb)

or a physiologically acceptable salt, prodrug, enantiomer or stereoisomer thereof, wherein:
L is a bond;
R¹ is tolyl, ethanonylphenyl, phenyl carbamic acid tert-butyl ester, benzonitrile, or diethylaminophenyl; and
R³ is isobutyl, cyclopropylmethyl, 3-methoxypropyl, 1-ethylpropyl, sec-butyl, isopropyl, tertbutyl, or trifluorethyl.

8. The compound of claim 4 having formula (IVc):

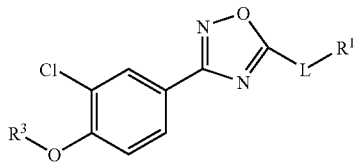

(IVc)

or a physiologically acceptable salt, or stereoisomer thereof, wherein:
L is a bond;
R¹ is tolyl, phenyl carbamic acid tert-butyl ester, or benzonitrile; and
R³ is isobutyl, isopropyl, cyclopropylmethyl, 3-methoxypropyl, 1-ethylpropyl, sec-butyl, or isopropyl.

9. The compound of claim 8, wherein R³ is isopropyl.

10. The compound of claim 9, wherein R¹ is tolyl.

11. A pharmaceutical composition comprising a compound according to claim 1 or a pharmaceutically acceptable salt, prodrug or stereoisomer thereof and a pharmaceutically acceptable diluent or carrier.

12. The compound of claim 1 wherein the compound is
3-[3-chloro-4-(1-ethyl-propoxy)-phenyl]-5-o-tolyl-[1,2,4]oxadiazole;
3-chloro-4-(3-(3-chloro-4-isopropoxyphenyl)-1,2,4-oxadiazol-5-yl)benzonitrile;
1-(3-chloro-4-(3-(3-chloro-4-isopropoxyphenyl)-1,2,4-oxadiazol-5-yl)benzyl)-3-methylazetidine-3-carboxylic acid;
(1R,3S)-3-(4-(3-(3-chloro-4-isopropoxyphenyl)-1,2,4-oxadiazol-5-yl)phenylamino)cyclopentanecarboxylic acid;
3-(4-(3-(3-chloro-4-isopropoxyphenyl)-1,2,4-oxadiazol-5-yl)phenoxy)propane-1,2-diol;
3-(3-Chloro-4-cyclopropylmethoxy-phenyl)-5-o-tolyl-[1,2,4]oxadiazole;
3-(4-Butoxy-3-chloro-phenyl)-5-o-tolyl-[1,2,4]oxadiazole;
3-[3-Chloro-4-(1-methyl-cyclopropylmethoxy)-phenyl]-5-o-tolyl-[1,2,4]oxadiazole;
3-[3-Chloro-4-(1-methyl-cyclopropylmethoxy)-phenyl]-5-o-tolyl-[1,2,4]oxadiazole;
3-(3-Chloro-4-pentyloxy-phenyl)-5-o-tolyl-[1,2,4]oxadiazole;
3-[3-Chloro-4-(3,3-dimethyl-butoxy)-phenyl]-5-o-tolyl-[1,2,4]oxadiazole;
3-[3-Chloro-4-(3,3-dimethyl-butoxy)-phenyl]-5-o-tolyl-[1,2,4]oxadiazole;
3-[3-Chloro-4-(2-ethyl-butoxy)-phenyl]-5-o-tolyl-[1,2,4]oxadiazole;
3-(3-Chloro-4-octyloxy-phenyl)-5-o-tolyl-[1,2,4]oxadiazole;
3-[3-Chloro-4-(3-methoxy-propoxy)-phenyl]-5-o-tolyl-[1,2,4]oxadiazole;
3-[3-Chloro-4-(3-ethoxy-propoxy)-phenyl]-5-o-tolyl-[1,2,4]oxadiazole;
1- {2-[2-Chloro-4-(5-o-tolyl-[1,2,4]oxadiazol-3-yl)-phenoxy]-ethyl} -piperidine;
4- {2-[2-Chloro-4-(5-o-tolyl-[1,2,4]oxadiazol-3-yl)-phenoxy]ethyl} -morpholine;
3-[3-Chloro-4-(1-ethyl-propoxy)-phenyl]-5-o-tolyl-[1,2,4]oxadiazole;
3-[3-Chloro-4-(3-methyl-butoxy)-phenyl]-5-o-tolyl-[1,2,4]oxadiazole;
3-[3-Chloro-4-(2-isopropoxy-ethoxy)-phenyl]-5-o-tolyl-[1,2,4]oxadiazole;
3-(3-Chloro-4-pent-3-ynyloxy-phenyl)-5-o-tolyl-[1,2,4]oxadiazole;
3-(4-sec-Butoxy-3-chloro-phenyl)-5-o-tolyl-[1,2,4]oxadiazole;
{2-[2-Chloro-4-(5-o-tolyl-[1,2,4]oxadiazol-3-yl)-phenoxy]propyl} dimethylamine;
{2-[2-Chloro-4-(5-o-tolyl-[1,2,4]oxadiazol-3-yl)-phenoxy]ethyl} dimethylamine;
3- {4-[-But-2-enyl)oxy]-3-chloro-phenyl} -5-o-tolyl-[1,2,4]oxadiazole;
3-[3-Chloro-4-(4,4,4-trifluoro-butoxy)-phenyl]-5-o-tolyl-[1,2,4]oxadiazole;
3-(3-Chloro-4-isopropoxy-phenyl)-5-o-tolyl-[1,2,4]oxadiazole;
3,5-Bis-(3-chloro-4-isopropoxy-phenyl)-[1,2,4]oxadiazole;
3-(3-Chloro-4-isopropoxy-phenyl)-5-phenyl-[1,2,4]oxadiazole;
3-(3-Chloro-4-isopropoxy-phenyl)-5-(3-trifluoromethyl-phenyl)-[1,2,4]oxadiazole;
1- {4-[3-(3-Chloro-4-isopropoxy-phenyl)-[1,2,4]oxadiazol-5-yl]-phenyl} ethanone;
{4-[3-(3-Chloro-4-isopropoxy-phenyl)-[1,2,4]oxadiazol-5-yl]-phenyl} diethyl-amine;
{4-[3-(3-Chloro-4-isopropoxy-phenyl)-[1,2,4]oxadiazol-5-yl]-phenyl} carbamic acid tert-butyl ester;
3[3-(3-Chloro-4-isopropoxy-phenyl)[1,2,4]oxadiazol-5-yl]benzonitrile;
3[3-(3-Chloro-4-isopropoxy-phenyl)[1,2,4]oxadiazol-5-yl]benzonitrile;
{3-[3-(3-Chloro-4-isopropoxy-phenyl)-[1,2,4]oxadiazol-5-yl]-phenyl} dimethylamine;
3-(3-Chloro-4-isopropoxy-phenyl)-5-(3-chloro-phenyl)-[1,2,4]oxadiazole;
3-(3-Chloro-4-isopropoxy-5-methoxy-phenyl)-5-phenyl-[1,2,4]oxadiazole;
3-(4-Methoxy-3-trifluoromethyl-phenyl)-5-o-tolyl-[1,2,4]oxadiazole;
3-(3-Chloro-4-isopropoxy-phenyl)-5-(2,4-dichloro-phenyl)-[1,2,4]oxadiazole;
3-Chloro-4-(3-(3-chloro-4-isopropoxyphenyl)-1,2,4-oxadiazol-5-yl aniline;
1-(4-(3-(3-Chloro-4-isopropoxyphenyl)-1,2,4-oxadiazol-5-yl)phenyl)cyclopropanecarbonitrile;
4-(3-(3-Chloro-4-isopropoxyphenyl)-1,2,4-oxadiazol-5-yl)benzenesulfonamide;
(4-(3-(3-Chloro-4-isopropoxyphenyl)-1,2,4-oxadiazol-5-yl)phenyl)methanol;
1-(4-(3-(3-Bromo-4-isopropoxyphenyl)-1,2,4-oxadiazol-5-yl)-3-chlorobenzyl)azetidine-3-carboxylic acid;
1-(3-(3-(3-Chloro-4-isopropoxyphenyl)-1,2,4-oxadiazol-5-yl)benzyl)azetidine-3-carboxylic acid;
1-(3-chloro-4-(3-(3-Chloro-4-isopropoxyphenyl)-1,2,4-oxadiazol-5-yl)benzyl)azetidine-3-carboxylic acid;
1 -(4-(3-(4-Isopropoxy-3 -(trifluoromethyl)phenyl)- 1,2,4-oxadiazol-5-yl)benzyl)azetidine-3 -carboxylic acid;
1-(4-(3-(3-Ethoxy-4-isopropoxyphenyl)-1,2,4-oxadiazol-5-yl)benzyl)azetidine-3-carboxylic acid;
3-(4-(3-(3-Chloro-4-isopropoxyphenyl)-1,2,4-oxadiazol-5-yl)benzylamino)propanoic acid;
1-(4-(3-(4-Isopropoxy-3-methoxyphenyl)-1,2,4-oxadiazol-5-yl)benzyl)azetidine-3-carboxylic acid;
1-(4-(3-(3-Chloro-4-isopropoxyphenyl)-1,2,4-oxadiazol-5-yl)-3-methoxybenzyl)azetidine-3-carboxylic acid;
2-(4-(3-(3-Chloro-4-isopropoxyphenyl)-1,2,4-oxadiazol-5-yl)benzylamino)acetic acid;
1-(4-(3-(3-Chloro-4-isopropoxyphenyl)-1,2,4-oxadiazol-5-yl)benzyl)piperidine-4-carboxylic acid;
1-(4-(3-(3-Chloro-4-isopropoxyphenyl)-1,2,4-oxadiazol-5-yl)benzylamino)cyclopropanecarboxylic acid;
1 -(4-Chloro-3 -(3 -(3 -chloro-4-isopropoxyphenyl)- 1,2,4-oxadiazol-5-yl)benzyl)azetidine-3 -carboxylic acid acetate salt;
2-(3-(3-(3-Chloro-4-isopropoxyphenyl)-1,2,4-oxadiazol-5-yl)benzylamino)acetic acid;
1 -(4-(3 -(4-Isopropoxy-3 -(trifluoromethyl)phenyl)- 1,2,4-oxadiazol-5-yl)benzyl)azetidine-3 -carboxylic acid;
(1S,3R)-3-(4-(3-(3-Chloro-4-isopropoxyphenyl)-1,2,4-oxadiazol-5-yl)phenylamino)cyclopentanecarboxylic acid;

(R)-3-(4-(3-(3-Chloro-4-isopropoxyphenyl)-1,2,4-oxadiazol-5-yl)phenoxy)propane-1,2-diol;
2((4-(3-(3-Chloro-4-isopropoxyphenyl)-1,2,4-oxadiazol-5-yl)phenoxy)methyl)propane-1,3-diol;
Chloro-4-(3-(3-chloro-4-isopropoxyphenyl)- 1,2,4-oxadiazol-5-yl)phenoxy)propane- 1,2-diol;
4-(3-(3-Chloro-4-isopropoxyphenyl)-1,2,4-oxadiazol-5-yl)benzonitrile;
4-(3-(3-Chloro-4-isopropoxyphenyl)-1,2,4-oxadiazol-5-yl)benzaldehyde;
1-(4-(3-(3-Chloro-4-isopropoxyphenyl)-1,2,4-oxadiazol-5-yl)benzyl)azetidine-3-carboxylic acid;
3-(3-Chloro-4-isopropoxyphenyl)-5-(4-fluorophenyl)-1,2,4-oxadiazole;
3-Chloro-4-(3-(3-chloro-4-isopropoxyphenyl)-1,2,4-oxadiazol-5-yl)benzonitrile;
2-(4-(3-(3-chloro-4-isopropoxyphenyl)-1,2,4-oxadiazol-5-yl)phenyl)propan-2-amine;
Methyl 3-(2-(4-(3-(3-chloro-4-isopropoxyphenyl)-1,2,4-oxadiazol-5-yl)phenyl)propan-2-ylamino)propanoate;
3-(2-(4-(3-(3-Chloro-4-isopropoxyphenyl)-1,2,4-oxadiazol-5-yl)phenyl)propan-2-ylamino)propanoic acid;
(4-(3-(3-Chloro-4-isopropoxyphenyl)-1,2,4-oxadiazol-5-yl)phenyl)methanol;
5-(4-(Azidomethyl)phenyl)-3-(3-chloro-4-isopropoxyphenyl)- 1,2,4-oxadiazole;
(4-(3-(3-Chloro-4-isopropoxyphenyl)-1,2,4-oxadiazol-5-yl)phenyl)methanamine;
(R)-3-(3-Chloro-4-isopropoxyphenyl)-5-(4-((2,2-dimethyl-1,3-dioxolan-4-yl)methoxy)phenyl)-1,2,4-oxadiazole;
(S)-3-(4-(3-(3-Chloro-4-isopropoxyphenyl)-1,2,4-oxadiazol-5-yl)phenoxy)propane-1,2-diol;
4-(3-(3-Chloro-4-isopropoxyphenyl)-1,2,4-oxadiazol-5-yl)benzenesulfonamide;
Tert-butyl 3,3'-(4-(3-(3-chloro-4-isopropoxyphenyl)-1,2,4-oxadiazol-5-yl)phenylsulfonylazanediyl)dipropanoate;
Tert-butyl 3-(4-(3-(3-chloro-4-isopropoxyphenyl)-1,2,4-oxadiazol-5-yl)phenylsulfonamido)propanoate;
3-(4-(3-(3-cChloro-4-isopropoxyphenyl)-1,2,4-oxadiazol-5-yl)phenylsulfonamido)propanoic acid;
2,2'(4-(3-(3-Chloro-4-isopropoxyphenyl)-1,2,4-oxadiazol-5-yl)phenylsulfonylazanediyl)diacetic acid;
Tert-butyl 2,2'-(4-(3-(3-chloro-4-isopropoxyphenyl)- 1,2,4-oxadiazol-5-yl)phenylsulfonylazanediyl)diacetate;
Tert-butyl 2-(4-(3-(3-chloro-4-isopropoxyphenyl)-1,2,4-oxadiazol-5-yl)phenylsulfonamido)acetate;
2-(4-(3-(3-Chloro-4-isopropoxyphenyl)-1,2,4-oxadiazol-5-yl)phenylsulfonamido)acetic acid;
3-(3-Chloro-4-isopropoxyphenyl)-5-(4((2,2-dimethyl-1,3-dioxolan-4-yl)methoxy)phenyl)-1,2,4-oxadiazole;
2-(4-(3-(3-Chloro-4-isopropoxyphenyl)-1,2,4-oxadiazol-5-yl)phenoxy)acetic acid;
4-(3-(3-Bromo-4-isopropoxyphenyl)-1,2,4-oxadiazol-5-yl)benzonitrile;
4-(3-(3-Bromo-4-isopropoxyphenyl)-1,2,4-oxadiazol-5-yl)benzaldehyde;
3-(3-Bromo-4-isopropoxyphenyl)-5-(4-(dimethoxymethyl)phenyl)-1,2,4-oxadiazole;
5-(5-(4-(Dimethoxymethyl)phenyl)-1,2,4-oxadiazol-3-yl)-2-isopropoxybenzonitrile;
5-(5-(4-Formylphenyl)-1,2,4-oxadiazol-3-yl)-2-isopropoxybenzonitrile;
1-(4-(3-(3-Cyano-4-isopropoxyphenyl)-1,2,4-oxadiazol-5-yl)benzyl)azetidine-3-carboxylic acid;
1-(4-(3-(3-Chloro-4-isopropoxyphenyl)-1,2,4-oxadiazol-5-yl)phenyl)cyclopropanecarbonitrile;
1-(4-(3-(3-Chloro-4-isopropoxyphenyl)-1,2,4-oxadiazol-5-yl)phenyl)cyclopropanecarbaldehyde;
3-((1-(4-(3-(3-Chloro-4-isopropoxyphenyl)-1,2,4-oxadiazol-5-yl)phenyl)cyclopropyl)methylamino)propanoic acid;
N-(4-(3-(3-Chloro-4-isopropoxyphenyl)-1,2,4-oxadiazol-5-yl)benzyl)-1-(2,2-dimethyl-1,3-dioxolan-4-yl)methanamine;
3-(4-(3-(3-Chloro-4-isopropoxyphenyl)-1,2,4-oxadiazol-5-yl)benzylamino)propane-1,2-diol;
(Z)-Methyl 3-(4-(3-(3-chloro-4-isopropoxyphenyl)-1,2,4-oxadiazol-5-yl)phenyl)acrylate;
Trans-methyl 2-(4-(3-(3-chloro-4-isopropoxyphenyl)-1,2,4-oxadiazol-5-yl)phenyl)cyclopropanecarboxylate;
Trans-2-(4-(3-(3-chloro-4-isopropoxyphenyl)-1,2,4-oxadiazol-5-yl)phenyl)cyclopropanecarboxylic acid;
(Z)-Methyl 3-(4-(3-(3-chloro-4-isopropoxyphenyl)-1,2,4-oxadiazol-5-yl)phenyl)acrylate;
(Z)-3-(4-(3-(3-Chloro-4-isopropoxyphenyl)-1,2,4-oxadiazol-5-yl)phenyl)acrylic acid;
3-Chloro-4-(3-(3-chloro-4-isopropoxyphenyl)- 1,2,4-oxadiazol-5-yl)aniline;
3-(3-Chloro-4-(3-(3-chloro-4-isopropoxyphenyl)-1,2,4-oxadiazol-5-yl)phenylamino)cyclobutanecarboxylic acid;
4-(3-(3-Chloro-4-isopropoxyphenyl)- 1,2,4-oxadiazol-5-yl)aniline;
3-(4-(3-(3-Chloro-4-isopropoxyphenyl)-1,2,4-oxadiazol-5-yl)phenylamino)cyclobutanecarboxylic acid;
2-(4-(3-(3-Chloro-4-isopropoxyphenyl)-1,2,4-oxadiazol-5-yl)phenyl)propan-2-amine;
Methyl 3-(2-(4-(3-(3-chloro-4-isopropoxyphenyl)-1,2,4-oxadiazol-5-yl)phenyl)propan-2-ylamino)propanoate; or 3-(2-(4-(3-(3-Chloro-4-isopropoxyphenyl)-1,2,4-oxadiazol-5-yl)phenyl)propan-2-ylamino)propanoic acid.

13. The compound of claim 4 wherein the compound is 3-(3-Chloro-4-cyclopropylmethoxy-phenyl)-5-o-tolyl-[1,2,4]oxadiazole;
3-(3-Chloro-4-cyclopentyloxy-phenyl)-5-o-tolyl-[1,2,4]oxadiazole;
3-(3-Chloro-4-cyclohexyloxy-phenyl)-5-o-tolyl-[1,2,4]oxadiazole;
3-(3-Chloro-4-phenethyloxy-phenyl)-5-o-tolyl-[1,2,4]oxadiazole;
3-(3-Chloro-4-cyclohexylmethoxy-phenyl)-5-o-tolyl-[1,2,4]oxadiazole;
3-[3-Chloro-4-(2-thiophen-2-yl-ethoxy)-phenyl]-5-o-tolyl-[1,2,4]oxadiazole;
3-(3-Chloro-4-cyclobutylmethoxy-phenyl)-5-o-tolyl-[1,2,4]oxadiazole; or 3-[3-Chloro-4-(4-methyl-cyclohexylmethoxy)-phenyl]-5-o-tolyl-[1,2,4]oxadiazole.

* * * * *

UNITED STATES PATENT AND TRADEMARK OFFICE
CERTIFICATE OF CORRECTION

PATENT NO. : 7,834,039 B2  
APPLICATION NO. : 12/002196  
DATED : November 16, 2010  
INVENTOR(S) : Adrian D. Hobson et al.

It is certified that error appears in the above-identified patent and that said Letters Patent is hereby corrected as shown below:

Claim 1, Column 70 line 14

Delete "$R^3$ is -$(CH_2)_2$-$R^9$" and insert -- $R^3$ is -$(CH_2)_n$-$R^9$ --

Claim 7, Column 246 line 49-50

Delete "trifluorethyl" and insert -- trifluoroethyl --

Claim 12 Column 249 line 44

Delete "cChloro" and insert -- Chloro --

Claim 12, Column 247 line 60

Insert -- ((E) -- after "3-{4-["

Signed and Sealed this  
Fifth Day of June, 2012

David J. Kappos  
*Director of the United States Patent and Trademark Office*